United States Patent
Chong et al.

(10) Patent No.: US 10,472,336 B2
(45) Date of Patent: Nov. 12, 2019

(54) MODULATORS OF INDOLEAMINE 2,3-DIOXYGENASE

(71) Applicant: GlaxoSmithKline Intellectual Property (No.2) Limited, Brentford, Middlesex (GB)

(72) Inventors: Pek Yoke Chong, Research Triangle Park, NC (US); Martha Alicia De La Rosa, Research Triangle Park, NC (US); Hamilton D. Dickson, Research Triangle Park, NC (US); Wieslaw Mieczyslaw Kazmierski, Research Triangle Park, NC (US); Vicente Samano, Research Triangle Park, NC (US); Vincent Wing-Fai Tai, Research Triangle Park, NC (US)

(73) Assignee: GLAXOSMITHKLINE INTELLECTUAL PROPERTY DEVELOPMENT LIMITED, Brentford, Middlesex (GB)

( * ) Notice: Subject to any disclaimer, the term of this patent is extended or adjusted under 35 U.S.C. 154(b) by 0 days.

(21) Appl. No.: 15/759,600

(22) PCT Filed: Sep. 22, 2016

(86) PCT No.: PCT/IB2016/055675
§ 371 (c)(1),
(2) Date: Mar. 13, 2018

(65) Prior Publication Data
US 2019/0040023 A1 Feb. 7, 2019

Related U.S. Application Data

(60) Provisional application No. 62/222,862, filed on Sep. 24, 2015.

(51) Int. Cl.
| | | |
|---|---|---|
| C07D 285/08 | (2006.01) |
| C07D 263/58 | (2006.01) |
| C07D 213/74 | (2006.01) |
| C07D 309/14 | (2006.01) |
| C07D 333/20 | (2006.01) |
| C07D 235/30 | (2006.01) |
| C07D 239/42 | (2006.01) |
| C07D 241/20 | (2006.01) |
| C07D 253/06 | (2006.01) |
| C07D 263/48 | (2006.01) |
| C07D 277/82 | (2006.01) |
| C07D 285/00 | (2006.01) |
| C07D 307/66 | (2006.01) |
| C07C 229/42 | (2006.01) |
| C07D 239/47 | (2006.01) |
| C07D 249/14 | (2006.01) |
| C07D 277/28 | (2006.01) |
| C07D 277/42 | (2006.01) |
| C07D 277/593 | (2006.01) |
| C07D 285/135 | (2006.01) |
| C07D 307/52 | (2006.01) |

(52) U.S. Cl.
CPC .......... *C07D 263/58* (2013.01); *C07C 229/42* (2013.01); *C07D 213/74* (2013.01); *C07D 235/30* (2013.01); *C07D 239/42* (2013.01); *C07D 239/47* (2013.01); *C07D 241/20* (2013.01); *C07D 249/14* (2013.01); *C07D 253/06* (2013.01); *C07D 263/48* (2013.01); *C07D 277/28* (2013.01); *C07D 277/42* (2013.01); *C07D 277/593* (2013.01); *C07D 277/82* (2013.01); *C07D 285/00* (2013.01); *C07D 285/08* (2013.01); *C07D 285/135* (2013.01); *C07D 307/52* (2013.01); *C07D 307/66* (2013.01); *C07D 309/14* (2013.01); *C07D 333/20* (2013.01); *C07C 2601/14* (2017.05); *C07C 2601/16* (2017.05)

(58) Field of Classification Search
CPC .................................................. C07D 285/08
See application file for complete search history.

(56) References Cited

U.S. PATENT DOCUMENTS

2019/0040023 A1* 2/2019 Chong ................ C07D 307/66

FOREIGN PATENT DOCUMENTS

| EP | 0 462 808 A2 | 12/1991 | |
|---|---|---|---|
| WO | WO 00/21927 A2 | 4/2000 | |
| WO | WO 2005/016862 A1 | 2/2005 | |
| WO | WO 2014/085284 A1 | 6/2014 | |
| WO | WO 2014/150646 A1 | 9/2014 | |
| WO | WO 2014/150677 A1 | 9/2014 | |
| WO | WO-2016161286 A1 * | 10/2016 | ........... C07D 207/12 |

OTHER PUBLICATIONS

Schmidt et al. "New insights into IDO biology in bacterial and viral infections" Frontiers in Immunology, 2014, vol. 5, Article 384, pp. 1-12. (Year: 2014).*
Maryanoff, et al. "Azepinoindole derivatives with high affinity for brain dopamine and serotonin receptors". Bioorganic & Medicinal Chemistry Letters, 8(8): 983-988 (1998).

* cited by examiner

*Primary Examiner* — Joseph R Kosack
(74) *Attorney, Agent, or Firm* — Robert H. Brink; Kathryn A. Lutomski; Edward R. Gimmi

(57) ABSTRACT

Provided are compounds and pharmaceutically acceptable salts thereof, their pharmaceutical compositions, their methods of preparation, and methods for their use in the prevention and/or treatment of HIV; including the prevention of the progression of AIDS and general immunosuppression.

11 Claims, No Drawings

MODULATORS OF INDOLEAMINE 2,3-DIOXYGENASE

CROSS-REFERENCE TO RELATED APPLICATIONS

This application is a § 371 of International Application No. PCT/IB2016/055675, filed 22 Sep. 2016, which claims the benefit of U.S. Provisional Application No. 62/222,862, filed 24 Sep. 2015.

FIELD OF THE INVENTION

Compounds, methods and pharmaceutical compositions for the prevention and/or treatment of HIV; including the prevention of the progression of AIDS and general immunosuppression, by administering certain indoleamine 2,3-dioxygenase compounds in therapeutically effective amounts are disclosed. Methods for preparing such compounds and methods of using the compounds and pharmaceutical compositions thereof are also disclosed.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required due to a number of issues including but not limited to undesirable drug-drug interactions; drug-food interactions; non-adherence to therapy; drug resistance due to mutation of the enzyme target; and inflammation related to the immunologic damage caused by the HIV infection.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur and the survival and quality of life are not normalized as compared to uninfected persons.[1] Indeed, the incidence of several non-AIDS morbidities and mortalities, such as cardiovascular disease, frailty, and neurocognitive impairment, are increased in HAART-suppressed, HIV-infected subjects.[2] This increased incidence of non-AIDS morbidity/mortality occurs in the context of, and is potentially caused by, elevated systemic inflammation related to the immunologic damage caused by HIV infection.[3,4,5]

Sustained successful treatment of the HIV-1-infected patient population with drugs will therefore require the continued development of new and improved drugs with new targets and mechanisms of action including antiretroviral and/or interventions aimed at restoration of the immune system and decreasing the systemic inflammation.

IDO is a monomeric 45 kDa extrahepatic heme-containing dioxygenase which catalyzes the oxidative pyrrole ring cleavage reaction of l-Trp to N-formylkynurenine utilizing molecular oxygen or reactive oxygen species via three proposed reaction mechanisms.[6] IDO is an enzyme that is the rate limiting step in the kynurenine pathway of tryptophan catabolism. IDO catalyzes the dioxidation of the indole ring of tryptophan (Trp), producing N-formyl-lynurenine (NFK), which is then metabolized by other enzymes into several downstream metabolites such as kynurenine (Kyn) and 3-hydroxy-anthranilate (HAA). The depletion of Trp and accumulation of Kyn and HAA have immunomodulatory activity, typically exemplified by decreased T cell activation and proliferation, enrichment of regulatory CD4+ T cells, and depletion of IL-17-producing CD4+ T cells. IDO activity therefore has a general immunosuppressive impact.

IDO is expressed in response to inflammation and is considered an important counter balance to prevent collateral tissue damaged during prolonged inflammation. IDO expression and activity are elevated during chronic viral infections such as HIV and HCV, chronic bacterial infections, as well as acute conditions such as sepsis. The IDO-mediated shift of Th17 to Treg differentiation of helper T cells likely plays a role in the intestinal immune dysfunction during HIV infection, likely related to the observed elevated systemic inflammation and increased incidence of non-AIDS morbidity/mortality. In addition, IDO activity likely also plays a role in the persistence of pathogens and cancer, and inhibition of IDO may improve clearance mechanism, potentially leading to cure of these chronic diseases. IDO may also play a role in neurological or neuropsychiatric diseases or disorders such as depression by modulating serotonin synthesis or production of excitatory neurotoxins such as kynurenine. As such, pharmacologic inhibition of IDO has application in a broad range of applications from neurology, oncology, and infectious diseases.

It would therefore be an advance in the art to discover IDO inhibitors that effective the balance of the aforementioned properties as a disease modifying therapy in chronic HIV infections to decrease the incidence of non-AIDS morbidity/mortality; and/or an immunotherapy to enhance the immune response to HIV, HBV, HCV and other chronic viral infections, chronic bacterial infections, chronic fungal infections, and to tumors; and/or for the treatment of depression or other neurological/neuropsychiatric disorders.

SUMMARY OF THE INVENTION

In accordance with one embodiment of the present invention, there is provided a compound having the structure of Formula (I):

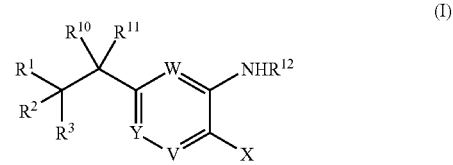

or a pharmaceutically acceptable salt thereof, wherein:
X is

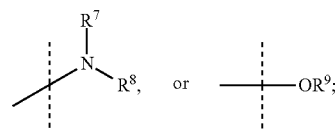

W is $CR^4$ or N;
Y is $CR^5$ or N;
V is $CR^6$ or N;
$R^1$ is selected from the group consisting of —$CO_2H$, heteroaryl, heterocyclyl, —$NHSO_2R^{13}$, —$CONHSO_2R^{14}$, —$CONHCOOR^{15}$, —$SO_2NHCOR^{16}$, —$CONHCOR^{17}$ and

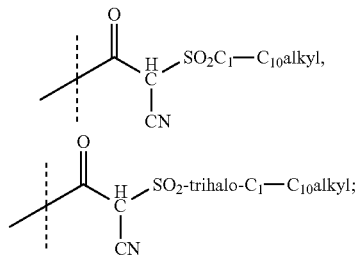

$R^2$ and $R^3$ are independently selected from the group consisting of —H, hydroxyl, halo, —CN, —$CF_3$, $(C_1-C_6)$alkyl, $(C_1-C_6)$alkoxy, —$N((C_1-C_6)$alkyl$)_2$, $(C_3-C_8)$cycloalkyl, $(C_2-C_{10})$alkenyl, and $(C_2-C_{10})$alkynyl;

$R^4$, $R^5$, and $R^6$ are independently selected from the group consisting of —H, —CN, —OH, halo, $(C_1-C_6)$alkyl, aryl, $(C_1-C_6)$alkoxy, $(C_2-C_6)$alkenyl, $(C_2-C_6)$alkynyl, $(C_3-C_8)$cycloalkyl, $(C_2-C_6)$-alken-dienyl, dihydroindenyl, and $(C_1-C_6)$alkanoyl;

$R^7$ and $R^8$ are independently selected from the group consisting of —H, $(C_1-C_6)$alkyl, $(C_1-C_6)$alkoxy, $(C_3-C_8)$cycloalkyl, $(C_2-C_6)$alkynyl, heteroaryl, bicyclic heteroaryl, $(C_2-C_6)$alkenyl, $(C_3-C_8)$cycloalkenyl, $(C_1-C_{10})$-alkoxy-$(C_1-C_{10})$-alkyl, $(C_3-C_8)$-cycloalkyl-$(C_1-C_6)$-alkyl, aryl, 5- to 7-membered monocyclic heteroaryl-$(C_1-C_6)$-alkyl, aryl-$(C_1-C_6)$-alkyl, arylsufonyl, $(C_3-C_8)$cycloalkyl-$(C_1-C_6)$alkyl, 5- to 7-membered monocyclic heterocyclic ring, and 7- to 10-membered bicyclic heterocyclic ring, Provided that only one of $R^7$ or $R^8$ is H, Or $R^7$ and $R^8$ are taken together with the nitrogen to which they are attached to form a group consisting of an 4- to 10-membered monocyclic, bicyclic or tricyclic heterocyclic ring, and an 5- to 7-membered monocyclic heteroaryl ring, And each $R^7$ and $R^8$ group being optionally substituted, where possible, with 1 or 2 groups independently selected from —OH, $(C_1-C_6)$alkyl, $(C_1-C_6)$alkoxy, $(C_1-C_6)$alkenyl, halo, aryl, —CN, $(C_3-C_8)$cycloalkyl, 5- to 7-membered monocyclic heteroaryl, 5- to 7-membered monocyclic heterocyclic, $(C_3-C_8)$-cycloalkyl-$(C_1-C_6)$-alkyl, —H, $(C_1-C_6)$-alkyl-substituted 5- to 7-membered monocyclic heteroaryl, —$OR^{20}$, and —$CF_3$;

$R^9$ is selected from the group consisting of —H, aryl, bicyclic carbocyclyl, aryl-$(C_1-C_{10})$-alkyl, $(C_1-C_{10})$alkyl, 5 to 7-membered monocyclic heteroaryl, 5 to 7-membered monocyclic heterocyclic, $(C_1-C_6)$-alkoxy, $(C_2-C_6)$-alkenyl, $(C_2-C_6)$-alkynyl, $(C_3-C_8)$cycloalkyl, and $(C_5-C_8)$cycloalkenyl, and $R^9$ being optionally substituted, where possible, with 1-3 groups selected from —H, $(C_1-C_6)$alkyl, aryl, $(C_2-C_6)$alkenyl, $(C_2-C_6)$alkynyl, $(C_3-C_8)$cycloalkyl, 5- to 7-membered monocyclic heterocyclic, $(C_2-C_6)$alkynyloxy$(C_1-C_6)$alkyl$_{0-1}$, halo, halo-substituted aryl, oxo, trihalo-$(C_1-C_6)$alkyl, and —$OR^{19}$;

$R^{10}$ and $R^{11}$ are independently selected from the group consisting of —H, $(C_1-C_{10})$alkyl, —$CF_3$, and —OH, Or $R^{10}$ and $R^{11}$ are taken together with the carbon to which they are attached to form a group consisting of the following structures:

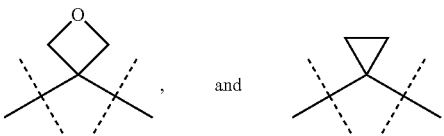

$R^{12}$ is selected from the group consisting of monocyclic and bicyclic heteroaryl ring, monocyclic and bicyclic heterocyclic ring, monocyclic and bicyclic aryl ring, $(C_3-C_8)$ cycloalkyl, $(C_1-C_6)$alkyl, $(C_1-C_6)$alkyl-Q, wherein $R^{12}$ can be optionally substituted by one or more $R^{18}$ groups;

Q is selected from the group consisting of monocyclic and bicyclic aryl ring, monocyclic and bicyclic heterocyclic ring, monocyclic and bicyclic heteroaryl ring, —$O(C_1-C_6)$alkyl, —CN, and $(C_3-C_8)$cycloalkyl;

$R^{13}$ is selected from the group consisting of $(C_1-C_{10})$alkyl, phenyl, —$CF_3$, —$CF_2CF_3$, and —$CH_2CF_3$;

$R^{14}$ is selected from the group consisting of —$CF_3$, $(C_1-C_{10})$alkyl, and $(C_3-C_8)$cycloalkyl;

$R^{15}$ is selected from the group consisting of $(C_1-C_6)$alkyl, $(C_3-C_8)$cycloalkyl, $(C_2-C_6)$alkenyl, and $(C_2-C_6)$alkynyl;

$R^{16}$ is selected from the group consisting of $(C_1-C_6)$alkyl, $(C_3-C_8)$cycloalkyl, $(C_2-C_6)$alkenyl, and $(C_2-C_6)$alkynyl;

$R^{17}$ is selected from the group consisting of $(C_1-C_{10})$alkyl, $(C_3-C_8)$cycloalkyl, $(C_2-C_{10})$alkenyl, and $(C_2-C_{10})$alkynyl;

$R^{18}$ is independently selected from the group consisting of —H, aryl ring, heteroaryl ring, heterocycle, heterocycle-$R^{20}$, $(C_1-C_6)$alkyl, $(C_3-C_8)$cycloalkyl, halo, —CN, —OH, trihaloalkyl, —$O(C_1-C_6)$alkyl, and —$CO_2(C_1-C_6)$alkyl;

$R^{19}$ is selected from the group consisting of —H, $(C_1-C_6)$alkyl, $(C_2-C_6)$alkenyl, and $(C_2-C_6)$alkynyl;

$R^{20}$ is selected from the group consisting of —H, $(C_1-C_6)$alkyl, halo, and trihaloalkyl.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to to a monovalent saturated aliphatic hydrocarbyl group having from 1 to 14 carbon atoms and, in some embodiments, from 1 to 6 carbon atoms. "$(C_x-C_y)$alkyl" refers to alkyl groups having from x to y carbon atoms. The term "alkyl" includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2$CH—), n-butyl ($CH_3CH_2CH_2CH_2$—), isobutyl (($CH_3)_2$CHCH_2$—), sec-butyl (($CH_3)(CH_3CH_2)$CH—), t-butyl (($CH_3)_3$C—), n-pentyl ($CH_3CH_2CH_2CH_2CH_2$—), and neopentyl (($CH_3)_3CCH_2$—).

"Alkylene" or "alkylene" refers to divalent saturated aliphatic hydrocarbyl groups having from 1 to 10 carbon atoms and, in some embodiments, from 1 to 6 carbon atoms. "($C_u$-$C_v$)alkylene" refers to alkylene groups having from u to v carbon atoms. The alkylene groups include branched and straight chain hydrocarbyl groups. For example, "($C_1$-$C_6$)alkylene" is meant to include methylene, ethylene, propylene, 2-methypropylene, dimethylethylene, pentylene, and so forth. As such, the term "propylene" could be exemplified by the following structure:

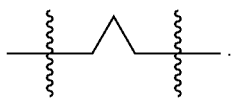

Likewise, the term "dimethylbutylene" could be exemplified, for example, by any of the following structures:

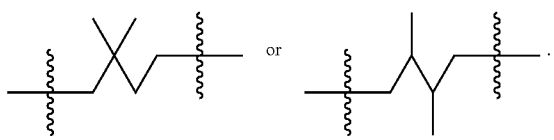

Furthermore, the term "($C_1$-$C_6$)alkylene" is meant to include such branched chain hydrocarbyl groups as cyclopropylmethylene, which could be exemplified by the following structure:

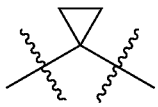

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, ($C_x$-$C_y$)alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, ($C_2$-$C_6$)alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclic-C(O)—. Acyl includes the "acetyl" group $CH_3C(O)$—.

"Acylamino" refers to the groups —$NR^{20}$C(O)alkyl, —$NR^{20}$C(O)cycloalkyl, —$NR^{20}$C(O)alkenyl, —$NR^{20}$C(O)alkynyl, —$NR^{20}$C(O)aryl, —$NR^{20}$C(O)heteroaryl, and —$NR^{20}$C(O)heterocyclic, wherein $R^{20}$ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —$NR^{21}R^{22}$, where $R^{21}$ and $R^{22}$ are independently selected from hydrogen, alkyl, alkenyl, alkynyl, aryl, cycloalkyl, heteroaryl, heterocyclic, —$SO_2$-alkyl, —$SO_2$-alkenyl, —$SO_2$-cycloalkyl, —$SO_2$-aryl, —$SO_2$-heteroaryl, and —$SO_2$-heterocyclic, and wherein $R^{21}$ and $R^{22}$ are optionally joined together with the nitrogen bound thereto to form a heterocyclic group. When $R^{21}$ is hydrogen and $R^{22}$ is alkyl, the amino group is sometimes referred to herein as alkylamino. When $R^{21}$ and $R^{22}$ are alkyl, the amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)$NR^{26}R^{27}$ where $R^{26}$ and $R^{27}$ are independently selected from hydrogen, alkyl, alkenyl, alkynyl, aryl, cycloalkyl, heteroaryl, heterocyclic, hydroxy, alkoxy, amino, and acylamino, and where $R^{26}$ and $R^{27}$ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"AUC" refers to the area under the plot of plasma concentration of drug (not logarithm of the concentration) against time after drug administration.

"$EC_{50}$" refers to the concentration of a drug that gives half-maximal response.

"$IC_{50}$" refers to the half-maximal inhibitory concentration of a drug. Sometimes, it is also converted to the $pIC_{50}$ scale ($-\log IC_{50}$), in which higher values indicate exponentially greater potency.

"Clade" refers to a hypothetical construct based on experimental data. Clades are found using multiple (sometimes hundreds) of traits from a number of species (or specimens) and analyzing them statistically to find the most likely phylogenetic tree for the group.

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below:

bicyclohexyl, and

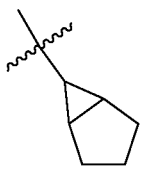 [SMILES: *C1C2CCCC12]

bicyclohexyl.

"(C$_u$-C$_v$)cycloalkyl" refers to cycloalkyl groups having u to v carbon atoms.

"Spiro cycloalkyl" refers to a 3 to 10 member cyclic substituent formed by replacement of two hydrogen atoms at a common carbon atom in a cyclic ring structure or in an alkylene group having 2 to 9 carbon atoms, as exemplified by the following structure wherein the group shown here attached to bonds marked with wavy lines is substituted with a spiro cycloalkyl group:

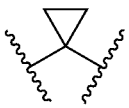

"Fused cycloalkyl" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused cycloalkyl group:

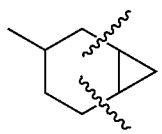

"Carboxy" or "carboxyl" refers interchangeably to the groups

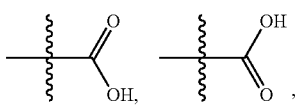

—C(O)O, —COOH, or, —CO$_2$H, —CO$_2$.

"Halo" or "halogen" refers to fluoro, chloro, bromo, and iodo.

"Haloalkyl" refers to substitution of an alkyl group with 1 to 3 halo groups (e.g., bifluoromethyl or trifluoromethyl).

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy).

"Human Serum Protein Shift Assay" refers to an HIV assay using a Luciferase Reporter to determine percent inhibition—pIC$_{50}$. The HIV assay makes use of a two-cell co-culture system. In this assay, an infected cell line J4HxB2 and an indicator cell line HOS (delta LTR+luciferase) are co-cultured in the presence and absence of compound. The assay is designed to find inhibitors that prevent the infection of HOS cells by the J4HxB2 cell line. The assay can detect inhibitors of any stage of the HIV infection cycle.

"Hydroxy" or "hydroxyl" refers to the group —OH.

"Heteroaryl" refers to an aromatic group of from 1 to 14 carbon atoms and 1 to 6 heteroatoms selected from, for example, oxygen, boron, phosphorous, silicon, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, for example, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from, for example, boron, silicon, nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, for example, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., C$_3$-C$_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" or "fused heterocycle" refer to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

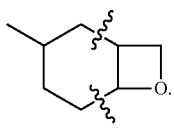

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means such atoms as, for example, boron, silicon, nitrogen, oxygen, phosphorous, or sulfur and includes any oxidized form of nitrogen, such as $N(O)$ $\{N^+—O^-\}$, phosphorous, and sulfur such as $S(O)$ and $S(O)_2$, and the quaternized form of any basic nitrogen.

"Oxazolidinone" refers to a 5-membered heterocyclic ring containing one nitrogen and one oxygen as heteroatoms and also contains two carbons and is substituted at one of the two carbons by a carbonyl group as exemplified by any of the following structures, wherein the oxazolidinone groups shown here are bonded to a parent molecule, which is indicated by a wavy line in the bond to the parent molecule:

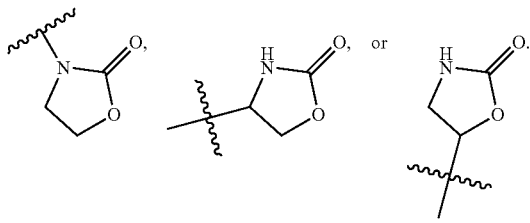 [SMILES: *N1CCOC1=O ; *C1COC(=O)N1 ; "or" ; *C1CNC(=O)O1]

"Oxo" refers to a (=O) group.

"Polymorphism" refers to when two or more clearly different phenotypes exist in the same population of a species where the occurrence of more than one form or morph. In order to be classified as such, morphs must occupy the same habitat at the same time and belong to a panmictic population (one with random mating).

"Protein binding" refers to the binding of a drug to proteins in blood plasma, tissue membranes, red blood cells and other components of blood.

"Protein shift" refers to determining a binding shift by comparing the $EC_{50}$ values determined in the absence and presence of human serum.

"QVT" refers to the amino acids at positions 369, 370, and 371, respectively in the Sp1 fragment of HIV-1 Gag.

"Racemates" refers to a mixture of enantiomers. In an embodiment of the invention, the compounds recited within, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" or "subject" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Wherever dashed lines occur adjacent to single bonds denoted by solid lines, then the dashed line represents an optional double bond at that position. Likewise, wherever dashed circles appear within ring structures denoted by solid lines or solid circles, then the dashed circles represent one to three optional double bonds arranged according to their proper valence taking into account whether the ring has any optional substitutions around the ring as will be known by one of skill in the art. For example, the dashed line in the structure below could either indicate a double bond at that position or a single bond at that position:

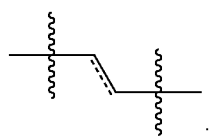

Similarly, ring A below could be a cyclohexyl ring without any double bonds or it could also be a phenyl ring having three double bonds arranged in any position that still depicts the proper valence for a phenyl ring. Likewise, in ring B below, any of $X^1$-$X^5$ could be selected from: C, CH, or $CH_2$, N, or NH, and the dashed circle means that ring B could be a cyclohexyl or phenyl ring or a N-containing heterocycle with no double bonds or a N-containing heteroaryl ring with one to three double bonds arranged in any position that still depicts the proper valence:

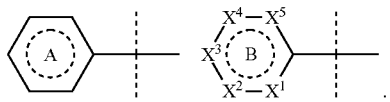

Where specific compounds or generic formulas are drawn that have aromatic rings, such as aryl or heteroaryl rings, then it will understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

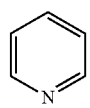
A

-continued

B

The present invention includes compounds as well as their pharmaceutically acceptable salts. Accordingly, the word "or" in the context of "a compound or a pharmaceutically acceptable salt thereof" is understood to refer to either: 1) a compound alone or a compound and a pharmaceutically acceptable salt thereof (alternative), or 2) a compound and a pharmaceutically acceptable salt thereof (in combination).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C(R)$_2$", it should be understood that the two $R^x$ groups can be the same, or they can be different if $R^x$ is defined as having more than one possible identity. In addition, certain substituents are drawn as —$R^xR^y$, where the "-" indicates a bond adjacent to the parent molecule and $R^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or ACN are preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes isomers, or mixed isomers, which by definition are the molecules of identical atomic compositions, but with different bonding arrangements of atoms or orientations of their atoms in space i.e., isomers are two or more different substances with the same molecular formula. Cis and trans geometric isomers of the compound of the present invention are described and may be isolated as a mixture of isomers or as separated isomeric forms. A bond in a structure diagram represented by a wavy line " ⌇ " or a crossed line " ⋈ " is intended to indicate that the structure represents the cis or the trans isomer, or a mixture of the cis and trans isomer in any proportion. Isomerism, in the field of clinical pharmacology and pharmacotherapeutics, can differ in their pharmacokinetic and pharmacodynamic which may provide introducing safer and more effective drug alternatives of newer as well as existing drugs.

In accordance with one embodiment of the present invention, there is provided a compound having the structure of Formula (I):

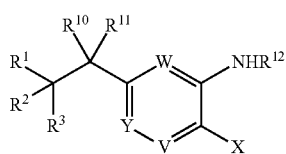

or a pharmaceutically acceptable salt thereof, wherein:
X is

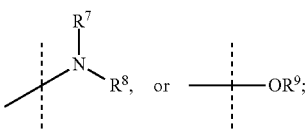

W is $CR^4$ or N;
Y is $CR^5$ or N;
V is $CR^6$ or N;
$R^1$ is selected from the group consisting of —$CO_2H$, heteroaryl, heterocyclyl, —$NHSO_2R^{13}$, —$CONHSO_2R^{14}$, —$CONHCOOR^{15}$, —$SO_2NHCOR^{16}$, —$CONHCOR^{17}$ and

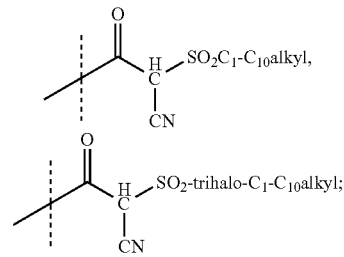

$R^2$ and $R^3$ are independently selected from the group consisting of —H, hydroxyl, halo, —CN, —$CF_3$, ($C_1$-$C_6$) alkyl, ($C_1$-$C_6$)alkoxy, —N(($C_1$-$C_6$)alkyl)$_2$, ($C_3$-$C_8$)cycloalkyl, ($C_2$-$C_{10}$)alkenyl, and ($C_2$-$C_{10}$)alkynyl;

$R^4$, $R^5$, and $R^6$ are independently selected from the group consisting of —H, —CN, —OH, halo, ($C_1$-$C_6$)alkyl, aryl, ($C_1$-$C_6$)alkoxy, ($C_2$-$C_6$)alkenyl, ($C_2$-$C_6$)alkynyl, ($C_3$-$C_8$)cycloalkyl, ($C_2$-$C_6$)-alken-dienyl, dihydroindenyl, and ($C_1$-$C_6$) alkanoyl;

$R^7$ and $R^8$ are independently selected from the group consisting of —H, ($C_1$-$C_6$)alkyl, ($C_1$-$C_6$)alkoxy, ($C_3$-$C_8$) cycloalkyl, ($C_2$-$C_6$)alkynyl, heteroaryl, bicyclic heteroaryl, ($C_2$-$C_6$)alkenyl, ($C_3$-$C_8$)cycloalkenyl, ($C_1$-$C_{10}$)-alkoxy-($C_1$-$C_{10}$)-alkyl, ($C_3$-$C_8$)-cycloalkyl-($C_1$-$C_6$)-alkyl, aryl, 5- to 7-membered monocyclic heteroaryl-($C_1$-$C_6$)-alkyl, aryl-($C_1$-$C_6$)-alkyl, arylsufonyl, ($C_3$-$C_8$)cycloalkyl-($C_1$-$C_6$)alkyl, 5- to 7-membered monocyclic heterocyclic ring, and 7- to 10-membered bicyclic heterocyclic ring, Provided that only one of $R^7$ or $R^8$ is H, Or $R^7$ and $R^8$ are taken together with the nitrogen to which they are attached to form a group consisting of a 4- to 10-membered monocyclic, bicyclic or tricyclic heterocyclic ring, and a 5- to 7-membered monocyclic heteroaryl ring, And each $R^7$ and $R^8$ group being optionally substituted, where possible, with 1 or 2 groups independently selected from —OH, ($C_1$-$C_6$)alkyl, ($C_1$-$C_6$)alkoxy, ($C_1$-$C_6$)alkenyl, halo, aryl, —CN, ($C_3$-$C_8$)cycloalkyl, 5- to 7-membered monocyclic heteroaryl, 5- to 7-membered monocyclic heterocyclic, ($C_3$-$C_8$)-cycloalkyl-($C_1$-$C_6$)-alkyl, —H, ($C_1$-$C_6$)-alkyl-substituted 5- to 7-membered monocyclic heteroaryl, —$OR^{20}$, and —$CF_3$;

$R^9$ is selected from the group consisting of —H, aryl, bicyclic carbocyclyl, aryl-($C_1$-$C_{10}$)-alkyl, ($C_1$-$C_{10}$)alkyl, 5 to 7-membered monocyclic heteroaryl, 5 to 7-membered monocyclic heterocyclic, ($C_1$-$C_6$)-alkoxy, ($C_2$-$C_6$)-alkenyl, ($C_2$-$C_6$)-alkynyl, ($C_3$-$C_8$)cycloalkyl, and ($C_5$-$C_8$)cycloalkenyl, and $R^9$ being optionally substituted, where possible, with 1-3 groups selected from —H, ($C_1$-$C_6$)alkyl, aryl, ($C_2$-$C_6$) alkenyl, ($C_2$-$C_6$)alkynyl, ($C_3$-$C_8$)cycloalkyl, 5- to 7-membered monocyclic heterocyclic, ($C_2$-$C_6$)alkynyloxy($C_1$—C) alkyl$_{0-1}$, halo, halo-substituted aryl, oxo, trihalo-($C_1$-$C_6$) alkyl, and —$OR^{19}$;

$R^{10}$ and $R^{11}$ are independently selected from the group consisting of —H, ($C_1$-$C_{10}$)alkyl, —$CF_3$, and —OH, Or $R^{10}$ and $R^{11}$ are taken together with the carbon to which they are attached to form a group consisting of the following structures:

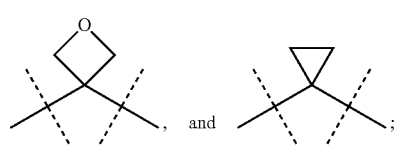

$R^{12}$ is selected from the group consisting of monocyclic and bicyclic heteroaryl ring, monocyclic and bicyclic heterocyclic ring, monocyclic and bicyclic aryl ring, ($C_3$-$C_8$)cycloalkyl, ($C_1$-$C_6$)alkyl, ($C_1$-$C_6$)alkyl-Q, wherein $R^{12}$ can be optionally substituted by one or more $R^{18}$ groups;

Q is selected from the group consisting of monocyclic and bicyclic aryl ring, monocyclic and bicyclic heterocyclic ring, monocyclic and bicyclic heteroaryl ring, —O($C_1$-$C_6$)alkyl, —CN, and ($C_3$-$C_8$)cycloalkyl;

$R^{13}$ is selected from the group consisting of ($C_1$-$C_{10}$)alkyl, phenyl, —$CF_3$, —$CF_2CF_3$, and —$CH_2CF_3$;

$R^{14}$ is selected from the group consisting of —$CF_3$, ($C_1$-$C_{10}$)alkyl, and ($C_3$-$C_8$)cycloalkyl;

$R^{15}$ is selected from the group consisting of ($C_1$-$C_6$)alkyl, ($C_3$-$C_8$)cycloalkyl, ($C_2$-$C_6$)alkenyl, and ($C_2$-$C_6$)alkynyl;

$R^{16}$ is selected from the group consisting of ($C_1$-$C_6$)alkyl, ($C_3$-$C_8$)cycloalkyl, ($C_2$-$C_6$)alkenyl, and ($C_2$-$C_6$)alkynyl;

$R^{17}$ is selected from the group consisting of ($C_1$-$C_{10}$)alkyl, ($C_3$-$C_8$)cycloalkyl, ($C_2$-$C_{10}$)alkenyl, and ($C_2$-$C_{10}$)alkynyl;

$R^{18}$ is independently selected from the group consisting of —H, aryl ring, heteroaryl ring, heterocycle, heterocycle-$R^{20}$, ($C_1$-$C_6$)alkyl, ($C_3$-$C_8$)cycloalkyl, halo, —CN, —OH, trihaloalkyl, —O($C_1$-$C_6$)alkyl, and —$CO_2$($C_1$-$C_6$)alkyl;

$R^{19}$ is selected from the group consisting of —H, ($C_1$-$C_6$)alkyl, ($C_2$-$C_6$)alkenyl, and ($C_2$-$C_6$)alkynyl;

$R^{20}$ is selected from the group consisting of —H, ($C_1$-$C_6$)alkyl, halo, and trihaloalkyl.

In accordance with one embodiment of the present invention, there is provided a compound having the structure of Formula (I):

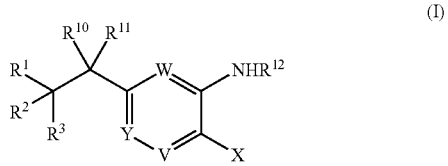

(I)

or a pharmaceutically acceptable salt thereof, wherein:
X is

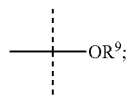

W is $CR^4$;
Y is $CR^5$;
V is $CR^6$ or N;
$R^1$ is selected from the group consisting of —$CO_2H$, tetrazol-5-yl, —$NHSO_2R^{13}$, —$CONHSO_2R^{14}$,

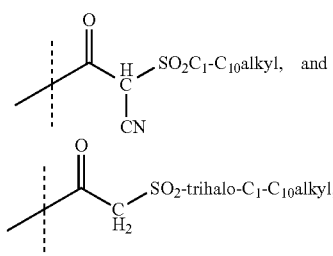

$R^2$ is selected from the group consisting of —H, hydroxyl, halo, ($C_1$-$C_6$)alkyl, and ($C_1$-$C_6$)alkoxy;

$R^3$ is selected from the group consisting of —H, halo, ($C_1$-$C_6$)alkyl, and ($C_1$-$C_6$)alkoxy;

$R^4$ and $R^5$ are independently selected from the group consisting of —H, —CN, —OH, and -halo;

$R^6$ is selected from the group consisting of —H, halo, ($C_1$-$C_6$)alkyl, ($C_2$-$C_6$)alkenyl, ($C_3$-$C_8$)cycloalkyl, ($C_2$-$C_6$)-alken-dienyl, ($C_3$-$C_8$)cycloalkyl-($C_1$-$C_6$)-alkyl, aryl ($C_1$-$C_6$)-alkyl, and aryl-($C_2$-$C_6$)-alkenyl;

$R^9$ is selected from the group consisting of aryl, ($C_1$-$C_{10}$)alkyl, 5 to 7-membered monocyclic heterocyclic, ($C_3$-$C_8$)cycloalkyl, ($C_3$-$C_8$)cycloalkyl-($C_1$-$C_6$)-alkyl, ($C_3$-$C_8$)cycloalkylaryl, ($C_1$-$C_6$)alkylaryl, aryl ($C_1$-$C_6$)-alkyl, ($C_1$-$C_6$)-alkyl(aryl)-($C_1$-$C_6$)-alkyl, and ($C_2$-$C_6$)alkynyloxy(($C_1$-$C_6$)alkyl)aryl, and $R^9$ being optionally substituted, where possible, with 1-3 groups selected from —H, ($C_1$-$C_6$)alkyl, aryl, ($C_2$-$C_6$)alkenyl, ($C_2$-$C_6$)alkynyl, ($C_3$-$C_8$)cycloalkyl, 5- to 7-membered monocyclic heterocyclic, ($C_2$-$C_6$)alkynyloxy($C_1$-$C_6$)alkyl$_{0-1}$, halo, halo-substituted aryl, oxo, trihalo-($C_1$-$C_6$)alkyl, and —$OR^{19}$;

$R^{10}$ and $R^{11}$ are independently selected from the group consisting of —H, ($C_1$-$C_{10}$)alkyl, —$CF_3$, and —OH, Or $R^{10}$ and $R^{11}$ are taken together with the carbon to which they are attached to form a group selected from the following structures:

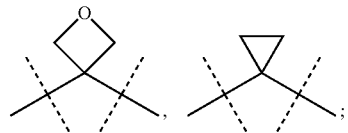

$R^{12}$ is selected from the group consisting of a 5- or 6-membered heteroaryl ring, a [5,6]-bicyclic heteroaryl ring, a 4- to 6-membered heterocylic ring, 6-membered aryl ring, ($C_3$-$C_6$)cycloalkyl, ($C_1$-$C_6$)alkyl, and ($C_1$-$C_6$)alkyl-Q, wherein $R^{12}$ can be optionally substituted by one or more $R^{18}$;

Q is selected from the group consisting of 5- or 6-membered aryl ring, 4- to 6-membered heterocyclic ring, 5- or 6-membered heteroaryl ring, —O($C_1$-$C_6$)alkyl, —CN, and ($C_3$-$C_8$)cycloalkyl;

$R^{13}$ is selected from the group consisting of ($C_1$-$C_{10}$)alkyl, phenyl, —$CF_3$, —$CF_2CF_3$, and —$CH_2CF_3$;

$R^{14}$ is selected from the group consisting of —$CF_3$, ($C_1$-$C_{10}$)alkyl, and ($C_3$-$C_8$)cycloalkyl;

$R^{18}$ is independently selected from the group consisting of —H, aryl ring, heteroaryl ring, heterocycle, heterocycle-$R^{20}$, ($C_1$-$C_6$)alkyl, ($C_3$-$C_8$)cycloalkyl, halo, —CN, —OH, —$CF_3$, —O($C_1$-$C_6$)alkyl, and —$CO_2$($C_1$-$C_6$)alkyl;

$R^{19}$ is selected from the group consisting of —H, ($C_1$-$C_6$)alkyl, ($C_2$-$C_6$)alkenyl, and ($C_2$-$C_6$)alkynyl.

$R^{20}$ is selected from the group consisting of —H, ($C_1$-$C_6$)alkyl, halo, and trihaloalkyl.

In accordance with one embodiment of the present invention, there is provided a compound having the structure of Formula (I):

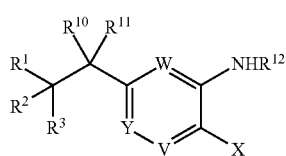

or a pharmaceutically acceptable salt thereof, wherein:
X is

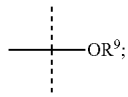

W is CR$^4$;
Y is CR$^5$;
V is CR$^6$;
R$^1$ is selected from the group consisting of —CO$_2$H, tetrazol-5-yl, —NHSO$_2$R$^{13}$, —CONHSO$_2$R$^{14}$, and

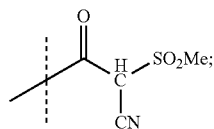

R$^2$ is selected from the group consisting of —H, —OH, —Cl, —F, —OCH$_3$, —OCF$_3$, —CH$_3$, and —C$_2$C$_5$;
R$^3$ is selected from the group consisting of —H, —OCH$_3$, —F, —CH$_3$, and —C$_2$C$_5$;
R$^4$ is —H;
R$^5$ is selected from the group consisting of —H and halo;
R$^6$ is selected from the group consisting of —H, halo, (C$_1$-C$_6$)alkyl, (C$_2$-C$_6$)alkenyl, (C$_3$-C$_8$)cycloalkyl, (C$_2$-C$_6$)-alken-dienyl, (C$_3$-C$_8$)cycloalkyl-(C$_1$-C$_6$)-alkyl, aryl (C$_1$-C$_6$)-alkyl, and aryl-(C$_2$-C$_6$)-alkenyl;
R$^9$ is selected from the group consisting of aryl, (C$_1$-C$_{10}$) alkyl, 5 to 7-membered monocyclic heterocyclic, (C$_3$-C$_8$) cycloalkyl, (C$_3$-C$_8$)cycloalkyl-(C$_1$-C$_6$)-alkyl, (C$_3$-C$_8$)cycloalkylaryl, (C$_1$-C$_6$)alkylaryl, aryl (C$_1$-C$_6$)-alkyl, (C$_1$-C$_6$)-alkyl(aryl)-(C$_1$-C$_6$)-alkyl, (C$_2$-C$_6$)alkynyloxy((C$_1$-C$_6$)alkyl) aryl,
and R$^9$ being optionally substituted, where possible, with 1-3 groups selected from —H, (C$_1$-C$_6$)alkyl, aryl, (C$_2$-C$_6$) alkenyl, (C$_2$-C$_6$)alkynyl, (C$_3$-C$_8$)cycloalkyl, 5- to 7-membered monocyclic heterocyclic, (C$_2$-C$_6$)alkynyloxy(C$_1$-C$_6$) alkyl$_{0-1}$, halo, halo-substituted aryl, oxo, trihalo-(C$_1$-C$_6$) alkyl, and —OR$^{19}$;
R$^{10}$ and R$^{11}$ are independently selected from the group consisting of —H, —CH$_3$, —CF$_3$, and —OH,
Or R$^{10}$ and R$^{11}$ are taken together with the carbon to which they are attached to form a group selected from the following structures:

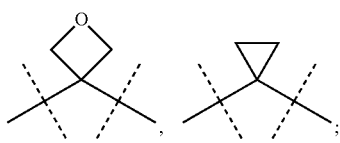

R$^{12}$ is selected from the group consisting of benzimidazole ring, benzoxazole ring, benzothiazole ring, triazolopyridine ring, thiazole ring, oxazole ring, thiadiazole ring, pyrimidine ring, pyridine ring, isoxazole ring, triazole ring, oxadiazole ring, tetrahydropyran, thiazoline ring, oxazoline ring, cyclohexane ring, phenyl, pyrazine, and (C$_1$-C$_6$)alkyl-Q, wherein R$^{12}$ can be optionally substituted by one or more R$^{18}$;
Q is selected from the group consisting of phenyl ring, thiazole ring, thiophene ring, and furan ring;
R$^{13}$ is selected from the group consisting of (C$_1$-C$_{10}$)alkyl and —CF$_3$;
R$^{14}$ is selected from the group consisting of (C$_1$-C$_{10}$) alkyl, (C$_3$-C$_8$)cycloalkyl, and —CF$_3$;
R$^{18}$ is independently selected from the group consisting of phenyl, -iPr, —Cl, —Br, —CF$_3$, —H, —OCH$_3$, —CH$_3$, —CN, —CO$_2$Et, and -cPr;
R$^{19}$ is selected from the group consisting of —H, (C$_1$-C$_6$)alkyl, (C$_2$-C$_6$)alkenyl, and (C$_2$-C$_6$)alkynyl.

In accordance with one embodiment of the present invention, there is provided a compound having the structure of Formula (I):

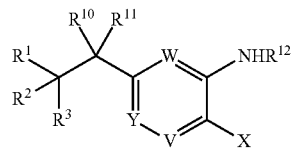

(I)

or a pharmaceutically acceptable salt thereof, wherein:
X is

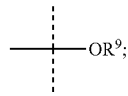

W is CR$^4$;
Y is CR$^5$;
V is CR$^6$;
R$^1$ is selected from the group consisting of —CO$_2$H, tetrazol-5-yl, —NHSO$_2$R$^{13}$, and —CONHSO$_2$R$^{14}$;
R$^2$ is selected from the group consisting of —H, —OH, —Cl, —F, and —OCH$_3$;
R$^3$ is —H;
R$^4$ is —H;
R$^5$ is-H;
R$^6$ is selected from the group consisting of the following structures:

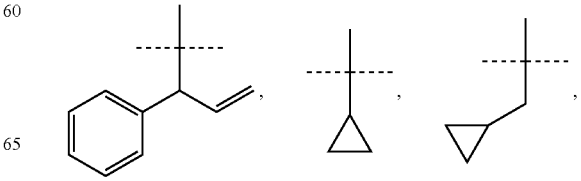

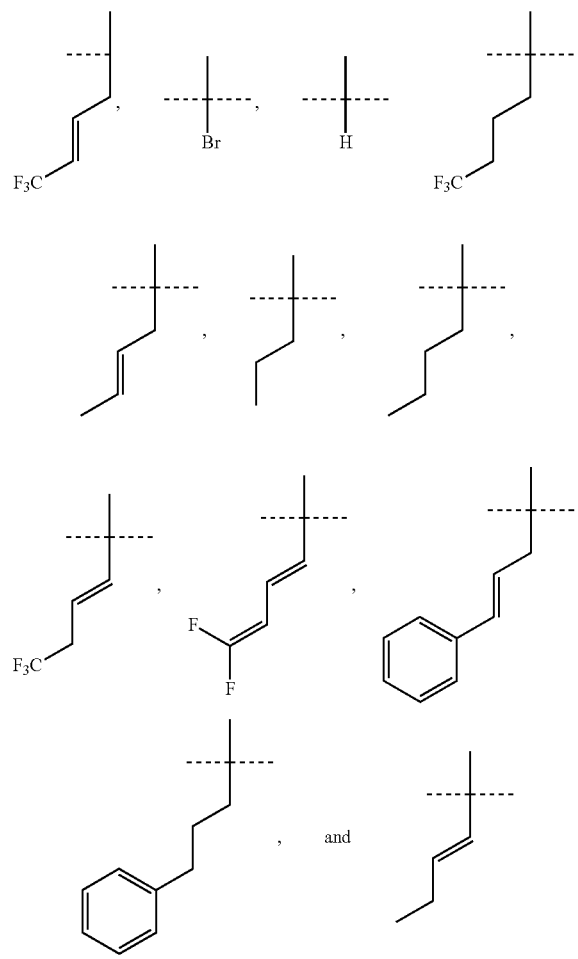
$R^9$ is selected from the group consisting of the following structures:
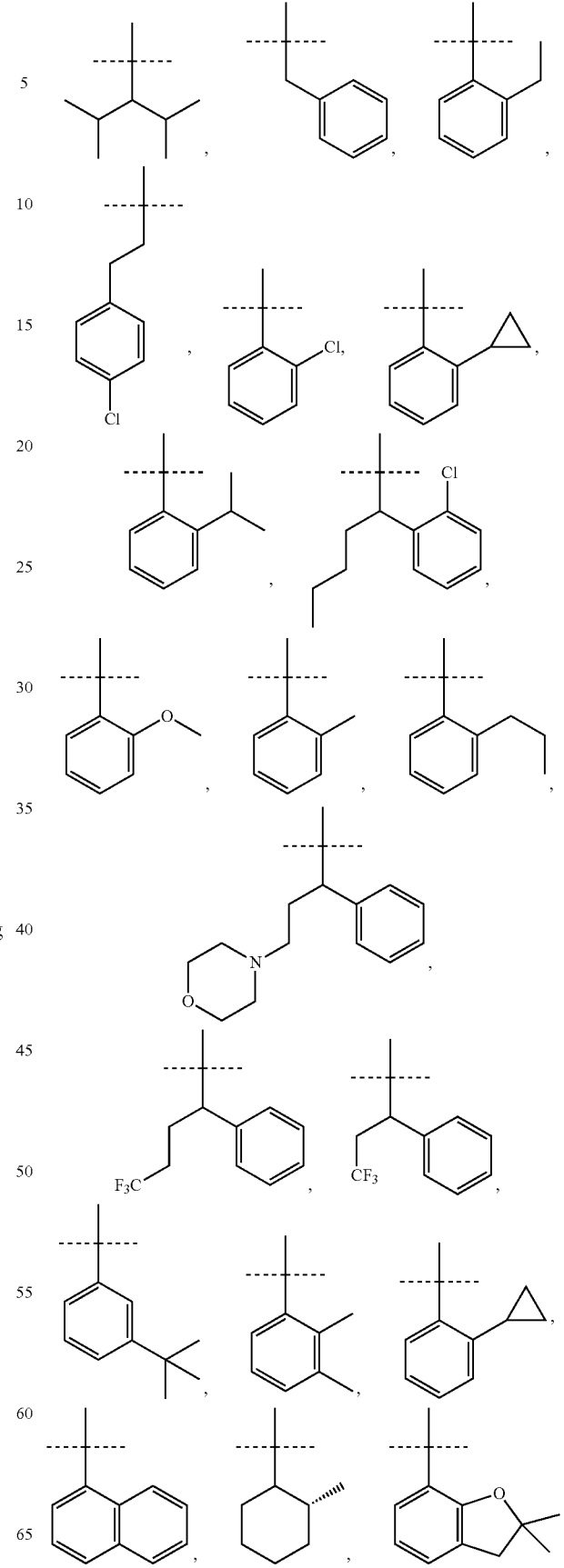

-continued
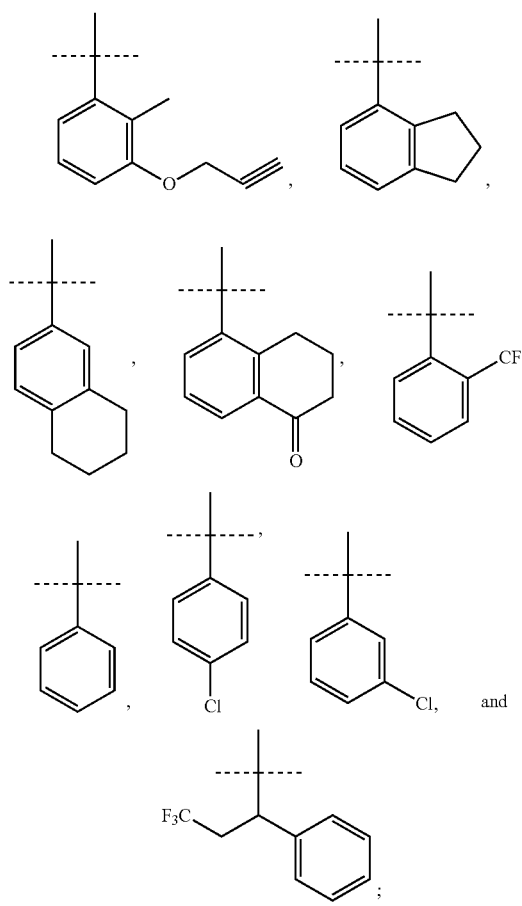
$R^{10}$ and $R^{11}$ are independently selected from the group consisting of —H, —CH$_3$, and —CHF$_2$;
$R^{12}$ is selected from the group consisting of the following structures:
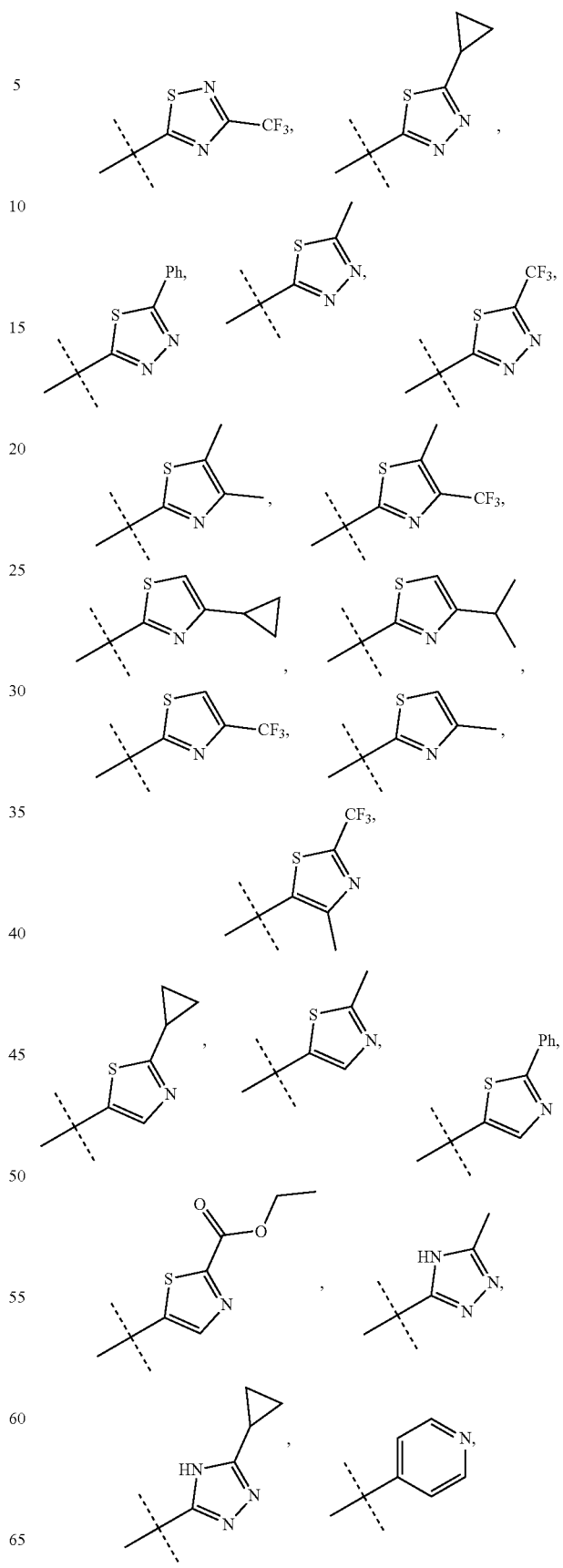

-continued

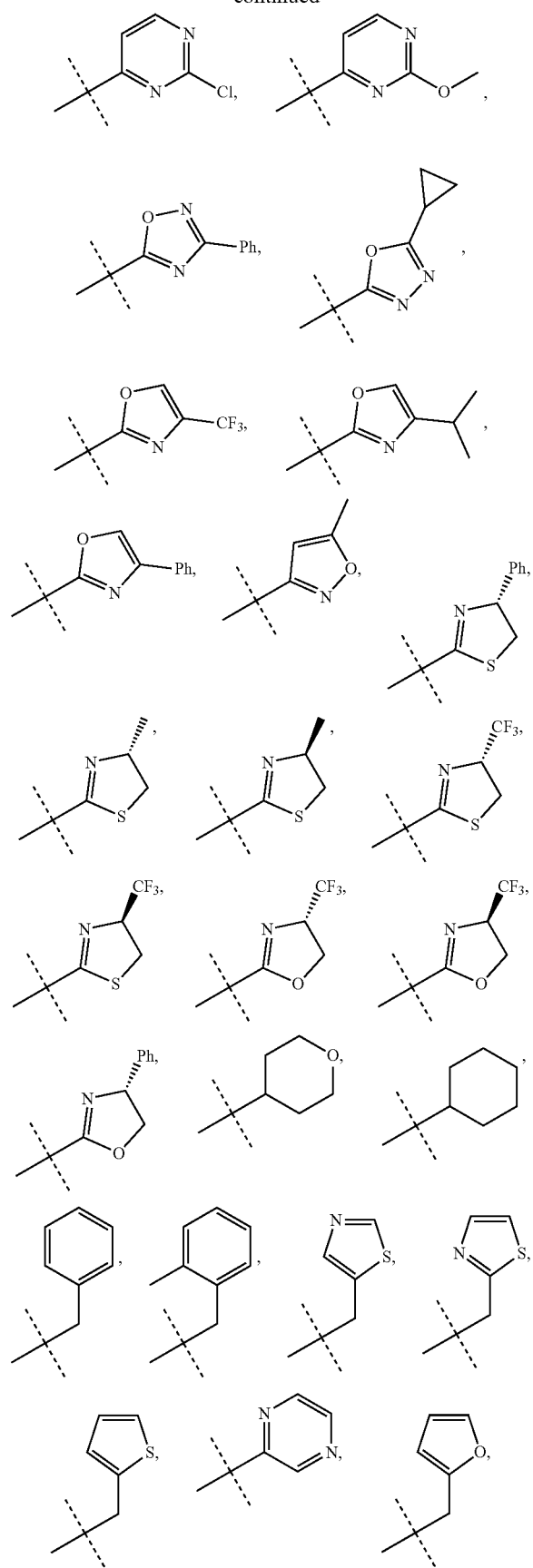

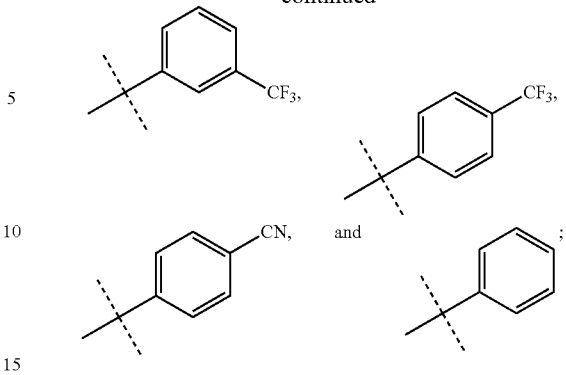

R$^{13}$ is -Me;
R$^{14}$ is selected from the group consisting of -Me, —CF$_3$, and -cC$_3$H$_5$;

In accordance with one embodiment of the present invention, there is provided a compound having the structure of Formula (I):

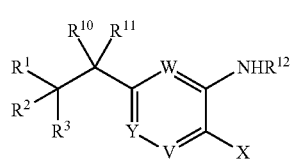

(I)

or a pharmaceutically acceptable salt thereof, wherein:
X is

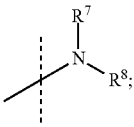

W is CR$^4$;
Y is CR$^5$;
V is CR$^6$ or N;
R$^1$ is selected from the group consisting of —CO$_2$H, tetrazol-5-yl, —NHSO$_2$R$^{13}$, —CONHSO$_2$R$^{14}$, and

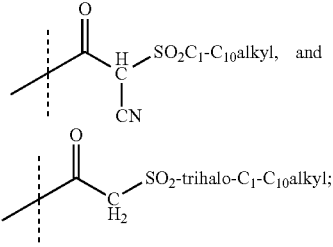

R$^2$ is selected from the group consisting of —H, hydroxyl, halo, (C$_1$-C$_6$)alkyl, and (C$_1$-C$_6$)alkoxy;
R$^3$ is selected from the group consisting of —H, halo, (C$_1$-C$_6$)alkyl, and (C$_1$-C$_6$)alkoxy;
R$^4$, R$^5$, and R$^6$ are independently selected from a group consisting of —H, halo, —CN, —OH, (C$_1$-C$_6$)alkyl, (C$_1$-C$_6$)alkoxy, and (C$_2$-C$_6$)alkenyl;

$R^7$ and $R^8$ are independently selected from the group consisting of $(C_1$-$C_6)$alkyl, $(C_1$-$C_6)$alkoxy, $(C_3$-$C_8)$cycloalkyl, $(C_2$-$C_6)$alkynyl, 7 to 10-membered bicyclic heteroaryl, 5- to 6-membered monocyclic heteroaryl, $(C_2$-$C_6)$alkenyl, $(C_3$-$C_8)$cycloalkenyl, $(C_1$-$C_6)$-alkoxy-$(C_1$-$C_6)$-alkyl, $(C_3$-$C_8)$-cycloalkyl-$(C_1$-$C_6)$-alkyl, aryl, 5- to 6-membered monocyclic heteroaryl-$(C_1$-$C_6)$-alkyl, aryl-$(C_1$-$C_6)$-alkyl, phenylsufonyl, $(C_1$-$C_6)$alkoxy-$(C_1$-$C_6)$alkyl, $(C_1$-$C_6)$alky aryl $(C_1$-$C_6)$-alkyl, $(C_1$-$C_6)$alkoxy aryl $(C_1$-$C_6)$-alkyl, and $(C_1$-$C_6)$alkylphenyl-$(C_1$-$C_6)$alkyl, Wherein the optional substituent on $R^7$ and $R^8$, where possible, are 1 or 2 groups independently selected from —OH, $(C_1$-$C_6)$alkyl, $(C_2$-$C_6)$alkoxy, halo, aryl, $(C_3$-$C_8)$cycloalkyl, 5- to 7-membered monocyclic heteroaryl, 5- to 7-membered monocyclic heterocyclic, cyano, $(C_2$-$C_6)$alkenyl, and —O$(C_1$-$C_6)$alkyl, Or $R^7$ and $R^8$ are taken together with the nitrogen to which they are attached to form a group consisting of a 7- to 10-membered bicyclic heterocyclic ring, a 5- to 7-membered monocyclic heterocyclic, and a 5- to 7-membered monocyclic heteroaryl, and each $R^7$ and $R^8$ group being optionally substituted, where possible, with 1 or 2 groups independently selected from —OH, $(C_1$-$C_6)$alkyl, $(C_1$-$C_6)$alkoxy, $(C_1$-$C_6)$alkenyl, halo, aryl, —CN, $(C_3$-$C_8)$cycloalkyl, 5- to 7-membered monocyclic heteroaryl, 5- to 7-membered monocyclic heterocyclic, $(C_3$-$C_8)$-cycloalkyl-$(C_1$-$C_6)$-alkyl, —H, $(C_1$-$C_6)$-alkyl-substituted 5- to 7-membered monocyclic heteroaryl, —OR$^{20}$, and —CF$_3$;

$R^{10}$ and $R^{11}$ are independently selected from the group consisting of —H, $(C_1$-$C_{10})$alkyl, —CF$_3$, and —OH, Or $R^{10}$ and $R^{11}$ are taken together with the carbon to which they are attached to form a group from the following structures:

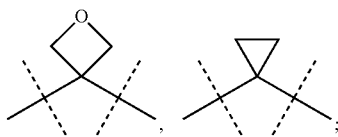

$R^{12}$ is selected from the group consisting of a 5- or 6-membered heteroaryl ring, a [5,6]-bicyclic heteroaryl ring, a 4- to 6-membered heterocylic ring, 6-membered aryl ring, $(C_3$-$C_6)$cycloalkyl, $(C_1$-$C_6)$alkyl, and $(C_1$-$C_6)$alkyl-Q, wherein $R^{12}$ can be optionally substituted by one or more $R^{18}$;

Q is selected from the group consisting of 5- or 6-membered aryl ring, 4- to 6-membered heterocyclic ring, 5- or 6-membered heteroaryl ring, —O$(C_1$-$C_6)$alkyl, —CN, and $(C_3$-$C_8)$cycloalkyl;

$R^{13}$ is selected from the group consisting of $(C_1$-$C_{10})$ alkyl, phenyl, —CF$_3$, —CF$_2$CF$_3$, and —CH$_2$CF$_3$;

$R^{14}$ is selected from the group consisting of —CF$_3$, $(C_1$-$C_{10})$alkyl, and $(C_3$-$C_8)$cycloalkyl;

$R^{18}$ is independently selected from the group consisting of —H, aryl ring, heteroaryl ring, heterocycle, heterocycle-$R^{20}$, $(C_1$-$C_6)$alkyl, $(C_3$-$C_8)$cycloalkyl, halo, —CN, —OH, —CF$_3$, —O$(C_1$-$C_6)$alkyl, and —CO$_2(C_1$-$C_6)$alkyl;

$R^{20}$ is selected from the group consisting of —H, $(C_1$-$C_6)$alkyl, halo, and trihaloalkyl.

In accordance with one embodiment of the present invention, there is provided a compound having the structure of Formula (I):

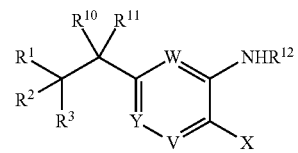

or a pharmaceutically acceptable salt thereof, wherein:

X is

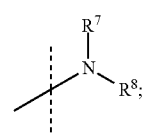

W is CR$^4$;
Y is CR$^5$;
V is CR$^6$;

$R^1$ is selected from the group consisting of —CO$_2$H, tetrazol-5-yl, —NHSO$_2$R$^{13}$, —CONHSO$_2$R$^{14}$, and

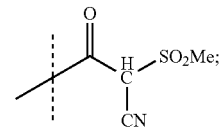

$R^2$ is selected from the group consisting of —H, —OH, —Cl, —F, —OCH$_3$, —OCF$_3$, —CH$_3$, and —C$_2$C$_5$;

$R^3$ is selected from the group consisting of —H, —OCH$_3$, —F, —CH$_3$, and —C$_2$C$_5$;

$R^4$ is selected from the group consisting of —H, halo, and $(C_1$-$C_6)$alkyl;

$R^5$ is selected from the group consisting of —H, halo, and $(C_1$-$C_6)$alkyl;

$R^6$ is selected from the group consisting of —H and halo;

$R^7$ and $R^8$ are independently selected from the group consisting of the following structures:

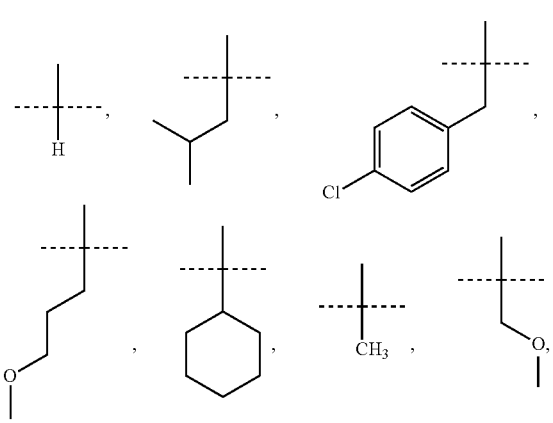

-continued
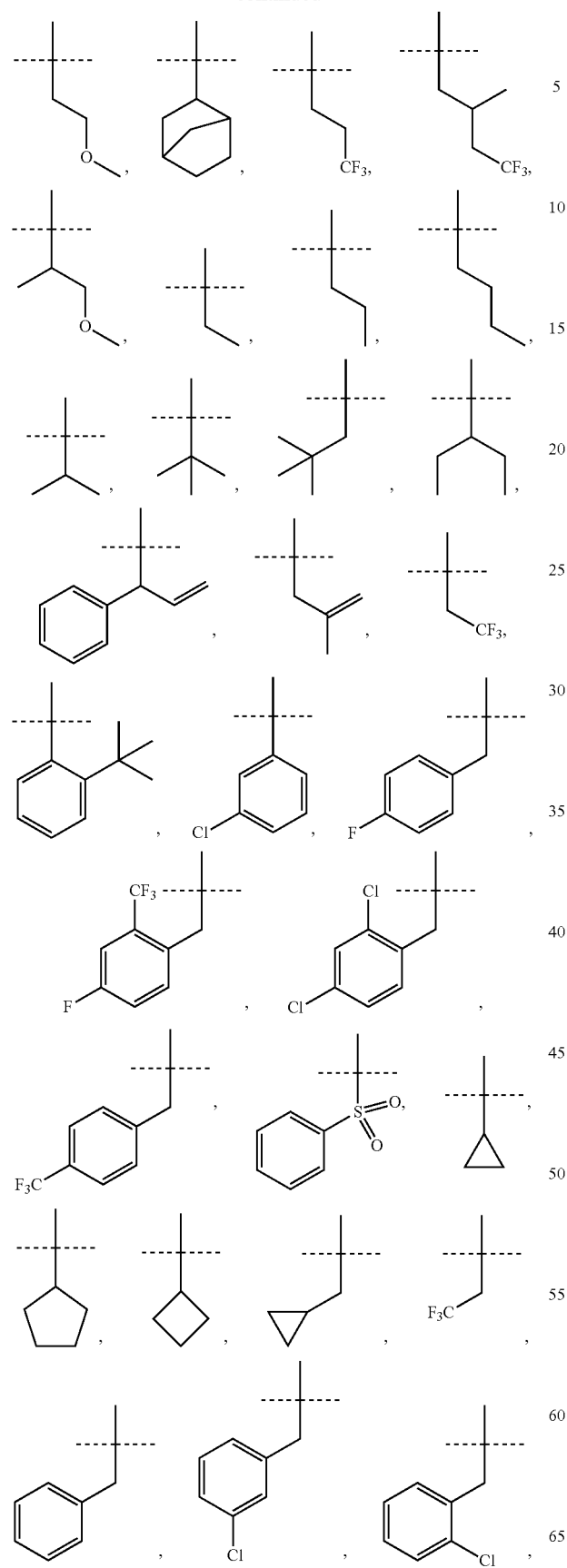
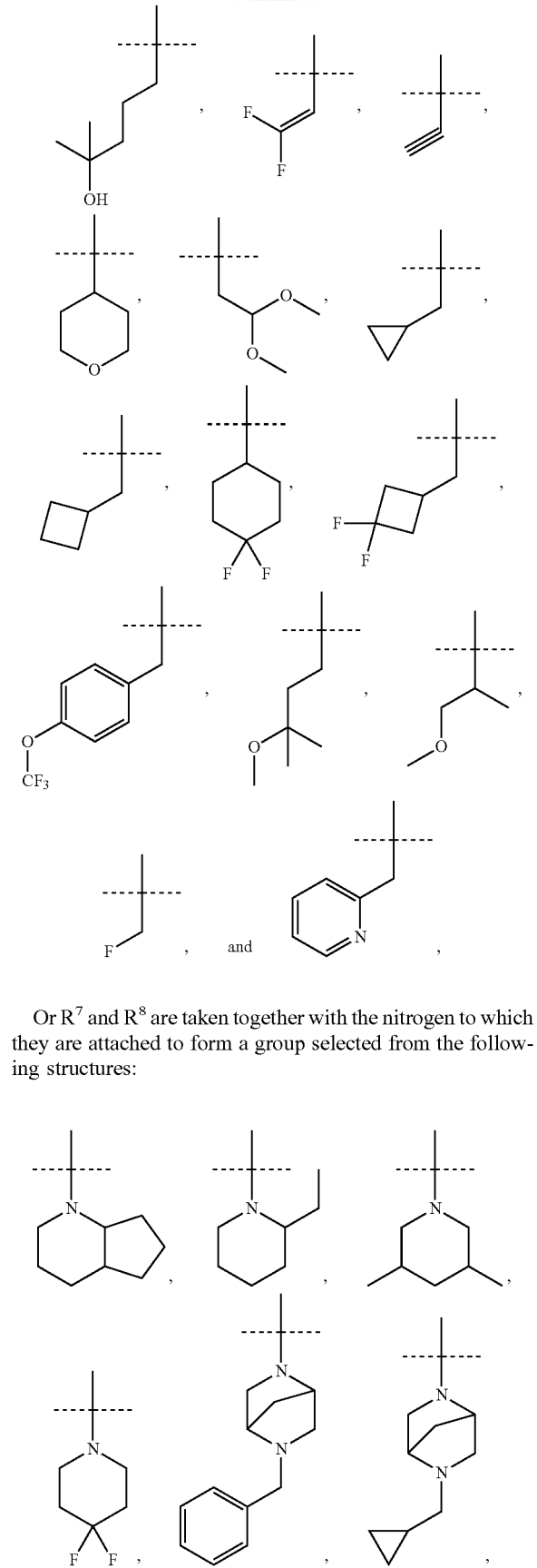
Or $R^7$ and $R^8$ are taken together with the nitrogen to which they are attached to form a group selected from the following structures:
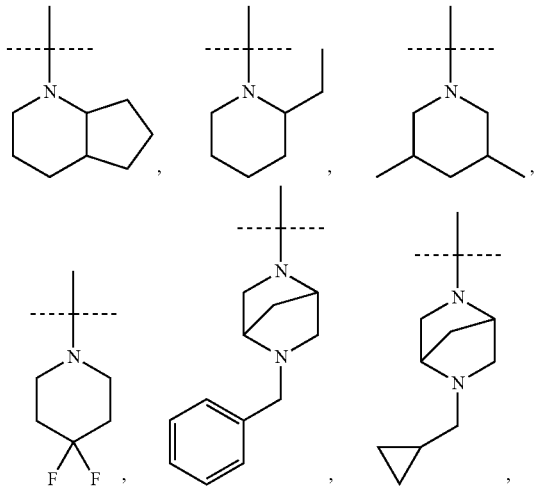

-continued

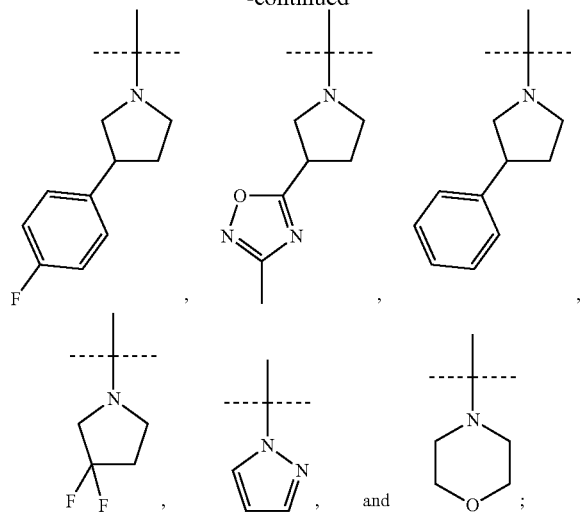

R[10] and R[11] are independently selected from the group consisting of —H, —CH$_3$, —CF$_3$, and —OH, Or R[10] and R[11] are taken together with the carbon to which they are attached to form a group selected from the following structures:

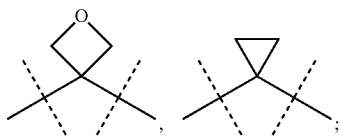

R[12] is selected from the group consisting of benzimidazole ring, benzoxazole ring, benzothiazole ring, triazolopyridine ring, thiazole ring, oxazole ring, thiadiazole ring, pyrimidine ring, pyridine ring, isoxazole ring, triazole ring, oxadiazole ring, tetrahydropyran, thiazoline ring, oxazoline ring, cyclohexane ring, phenyl, pyrazine, and (C$_1$-C$_6$)alkyl-Q, wherein R[12] can be optionally substituted by one or more R[18];

Q is selected from the group consisting of phenyl ring, thiazole ring, thiophene ring, and furan ring;

R[13] is selected from the group consisting of (C$_1$-C$_{10}$)alkyl and —CF$_3$;

R[14] is selected from the group consisting of (C$_1$-C$_{10}$) alkyl, (C$_3$-C$_8$)cycloalkyl, and —CF$_3$;

R[18] is independently selected from the group consisting of phenyl, -iPr, —Cl, —Br, —CF$_3$, —H, —OCH$_3$, —CH$_3$, —CN, —CO$_2$Et, and -cPr.

In accordance with one embodiment of the present invention, there is provided a compound having the structure of Formula (I):

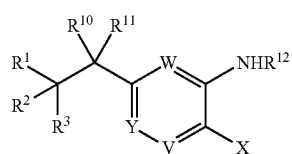

(I)

or a pharmaceutically acceptable salt thereof, wherein:

X is

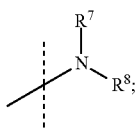

W is CR[4];
Y is CR[5];
V is CR[6];
R[1] is selected from the group consisting of —CO$_2$H, tetrazol-5-yl, —NHSO$_2$R[13], and —CONHSO$_2$R[14];
R[2] is selected from the group consisting of —H, —OH, —Cl, —F, and —OCH$_3$;
R[3] is —H;
R[4] is selected from the group consisting of —H and —F;
R[5] is selected from the group consisting of —H and —F;
R[6] is selected from the group consisting of —H, —F, and —Cl;
R[7] and R[8] are independently selected from the group consisting of the following structures:

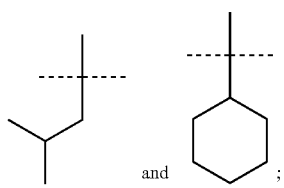

R[10] and R[11] are independently selected from the group consisting of —H, —CH$_3$, and —CHF$_2$;
R[12] is selected from the group consisting of the following structures:

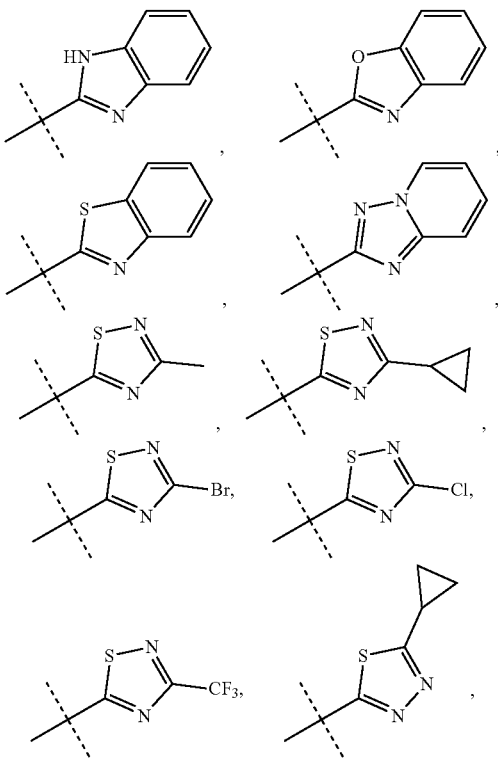

-continued
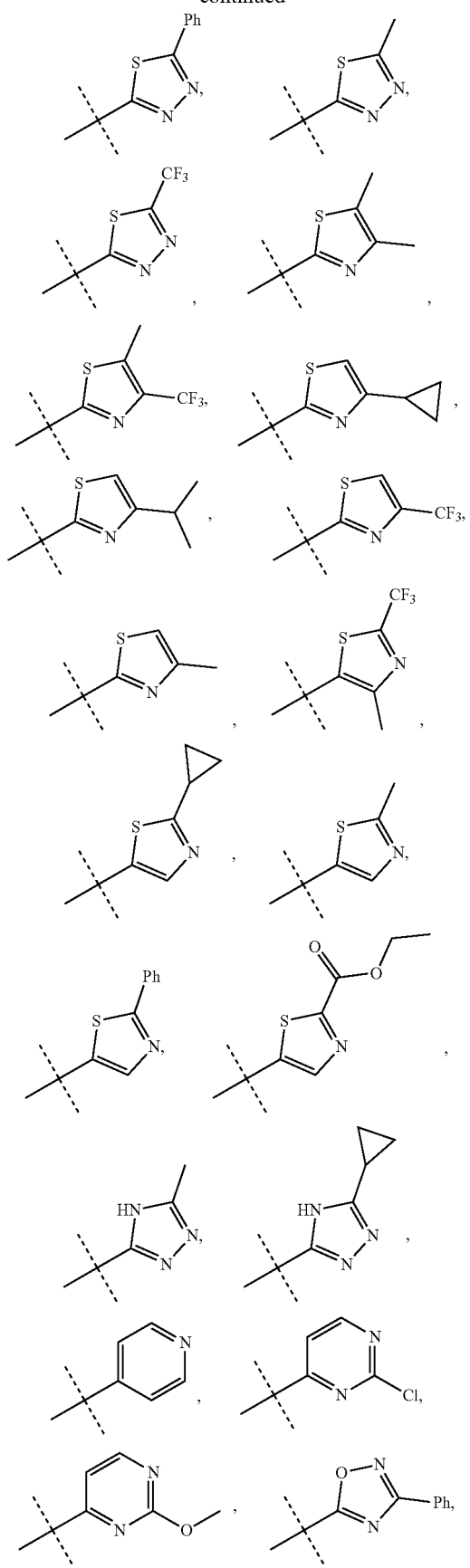
-continued
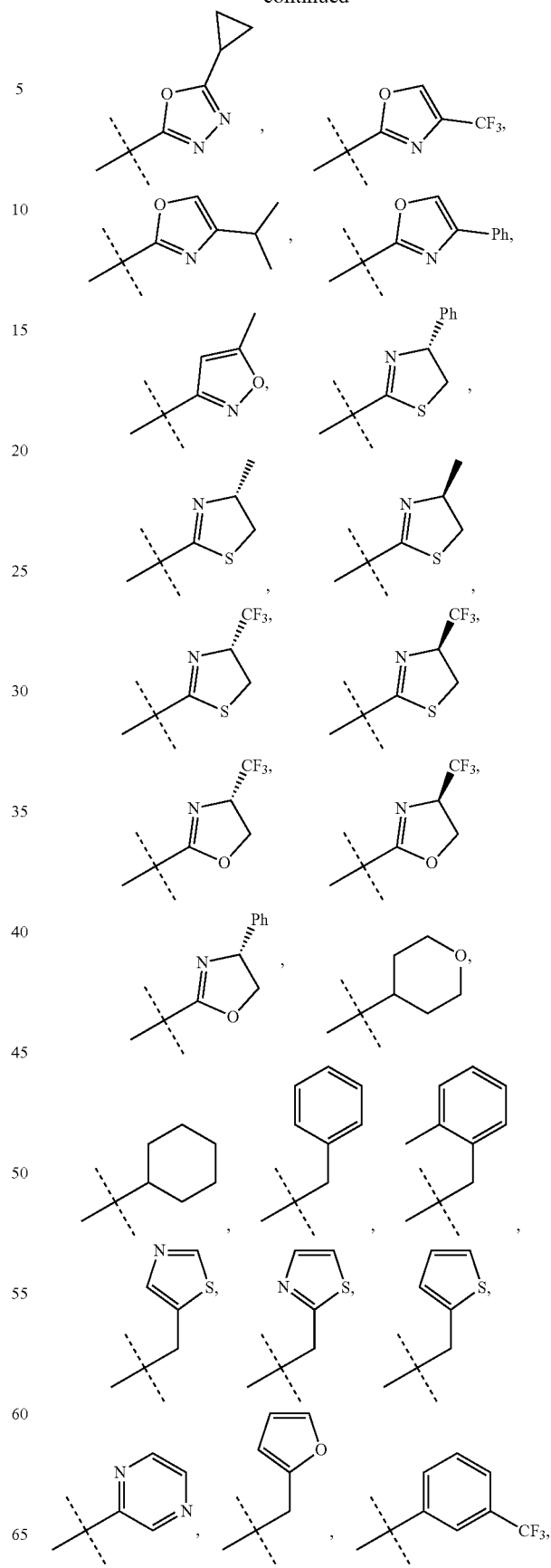

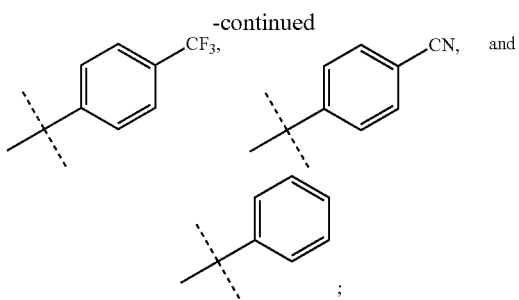

$R^{13}$ is —$CH_3$;

$R^{14}$ is selected from the group consisting of —$CH_3$, —$CF_3$, and -$cC_3H_5$;

In accordance with one embodiment of the present invention, there is provided a compound having the structure of Formula I above, wherein $R^1$ is selected from —$CO_2H$ or tetrazol-5-yl.

In accordance with one embodiment of the present invention, there is provided a compound having the structure of Formula I above, wherein $R^1$ is —$CO_2H$ In accordance with one embodiment of the present invention, there is provided a compound having the structure of Formula I above, wherein $R^1$ is tetrazol-5-yl.

In accordance with one embodiment of the present invention, there is provided a compound having the structure of Formula I above, wherein $R^2$ is selected from —H, hydroxyl, halo, ($C_1$-$C_6$)alkyl, or ($C_1$-$C_6$)alkoxy.

In accordance with one embodiment of the present invention, there is provided a compound having the structure of Formula I above, wherein $R^2$ is selected from —H, —OH, —Cl, —F, —$OCH_3$, —$OCF_3$, —$CH_3$, or —$C_2C_5$.

In accordance with one embodiment of the present invention, there is provided a compound having the structure of Formula I above, wherein $R^2$ is selected from —H, —OH, —Cl, —F, or —$OCH_3$.

In accordance with one embodiment of the present invention, there is provided a compound having the structure of Formula I above, wherein $R^2$ is —H.

In accordance with one embodiment of the present invention, there is provided a compound having the structure of Formula I above, wherein $R^3$ is selected from —H, halo, ($C_1$-$C_6$)alkyl, or ($C_1$-$C_6$)alkoxy.

In accordance with one embodiment of the present invention, there is provided a compound having the structure of Formula I above, wherein $R^3$ is selected from —H, —$OCH_3$, —F, —$CH_3$, or —$C_2C_5$.

In accordance with one embodiment of the present invention, there is provided a compound having the structure of Formula I above, wherein $R^3$ is —H.

In accordance with one embodiment of the present invention, there is provided a compound having the structure of Formula I above, wherein $R^{10}$ and $R^{11}$ are independently selected from —H, —$CF_3$, or ($C_1$-$C_6$)alkyl.

In accordance with one embodiment of the present invention, there is provided a compound having the structure of Formula I above, wherein $R^{10}$ and $R^{11}$ are independently selected from —H, —$CF_3$, or —$CH_3$.

In accordance with one embodiment of the present invention, there is provided a compound having the structure of Formula I above, wherein $R^{10}$ is —H.

In accordance with one embodiment of the present invention, there is provided a compound having the structure of Formula I above, wherein $R^{11}$ is —$CH_3$.

In accordance with one embodiment of the present invention, there is provided a compound having the structure of Formula I above, wherein $R^{11}$ is —$CF_3$.

In accordance with one embodiment of the present invention, there is provided a compound having the structure of Formula I above, wherein

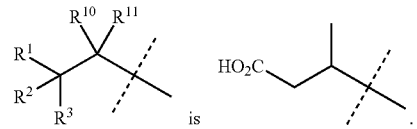

In accordance with one embodiment of the present invention, there is provided a compound having the structure of Formula I above, wherein

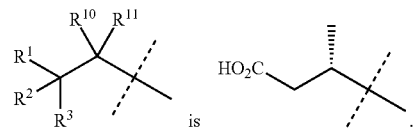

In accordance with one embodiment of the present invention, there is provided a compound having the structure of Formula I above, wherein

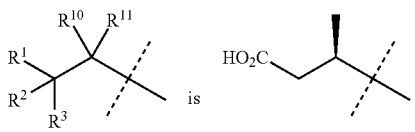

In accordance with one embodiment of the present invention, there is provided a compound having the structure of Formula I above, wherein W is $CR^4$.

In accordance with one embodiment of the present invention, there is provided a compound having the structure of Formula I above, wherein $R^4$ is selected from —H or halo.

In accordance with one embodiment of the present invention, there is provided a compound having the structure of Formula I above, wherein $R^4$ is selected from —H or —F.

In accordance with one embodiment of the present invention, there is provided a compound having the structure of Formula I above, wherein $R^4$ is —H.

In accordance with one embodiment of the present invention, there is provided a compound having the structure of Formula I above, wherein $R^4$ is —F.

In accordance with one embodiment of the present invention, there is provided a compound having the structure of Formula I above, wherein W is C—F.

In accordance with one embodiment of the present invention, there is provided a compound having the structure of Formula I above, wherein W is C—H.

In accordance with one embodiment of the present invention, there is provided a compound having the structure of Formula I above, wherein Y is $CR^5$.

In accordance with one embodiment of the present invention, there is provided a compound having the structure of Formula I above, wherein $R^5$ is selected from —H or halo.

In accordance with one embodiment of the present invention, there is provided a compound having the structure of Formula I above, wherein $R^5$ is selected from —H or —F.

In accordance with one embodiment of the present invention, there is provided a compound having the structure of Formula I above, wherein $R^5$ is —H.

In accordance with one embodiment of the present invention, there is provided a compound having the structure of Formula I above, wherein $R^5$ is —F.

In accordance with one embodiment of the present invention, there is provided a compound having the structure of Formula I above, wherein Y is C—H.

In accordance with one embodiment of the present invention, there is provided a compound having the structure of Formula I above, wherein Y is C—F.

In accordance with one embodiment of the present invention, there is provided a compound having the structure of Formula I above, wherein V is $CR^6$.

In accordance with one embodiment of the present invention, there is provided a compound having the structure of Formula I above, wherein $R^6$ is selected from —H, $(C_1-C_6)$alkyl, or $(C_2-C_6)$alkenyl.

In accordance with one embodiment of the present invention, there is provided a compound having the structure of Formula I above, wherein $R^6$ is selected from —H, -$nC_4H_9$, —$CH_2CHCHCH_3$ or —$CHCHCH_2CH_2CH_3$.

In accordance with one embodiment of the present invention, there is provided a compound having the structure of Formula I above, wherein $R^6$ is —H.

In accordance with one embodiment of the present invention, there is provided a compound having the structure of Formula I above, wherein $R^6$ is -$nC_4H_9$.

In accordance with one embodiment of the present invention, there is provided a compound having the structure of Formula I above, wherein $R^6$ is —$CH_2CHCHCH_3$.

In accordance with one embodiment of the present invention, there is provided a compound having the structure of Formula I above, wherein $R^6$ is —$CHCHCH_2CH_2CH_3$.

In accordance with one embodiment of the present invention, there is provided a compound having the structure of Formula I above, wherein V is C—H.

In accordance with one embodiment of the present invention, there is provided a compound having the structure of Formula I above, wherein V is C-$nC_4H_9$.

In accordance with one embodiment of the present invention, there is provided a compound having the structure of Formula I above, wherein V is C—$CH_2CHCHCH_3$.

In accordance with one embodiment of the present invention, there is provided a compound having the structure of Formula I above, wherein V is C—$CHCHCH_2CH_2CH_3$.

In accordance with one embodiment of the present invention, there is provided a compound having the structure of Formula I above, wherein X is selected from

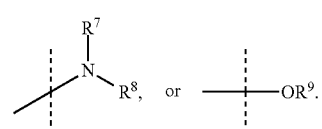

In accordance with one embodiment of the present invention, there is provided a compound having the structure of Formula I above, wherein X is

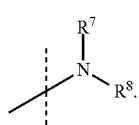

In accordance with one embodiment of the present invention, there is provided a compound having the structure of Formula I above, wherein $R^7$ and $R^8$ are independently selected from $(C_1-C_6)$alkyl, or $(C_3-C_8)$cycloalkyl.

In accordance with one embodiment of the present invention, there is provided a compound having the structure of Formula I above, wherein $R^7$ and $R^8$ are independently selected from

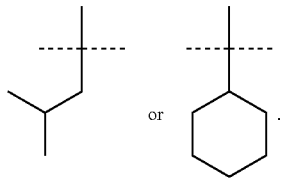

In accordance with one embodiment of the present invention, there is provided a compound having the structure of Formula I above, wherein $R^7$ is

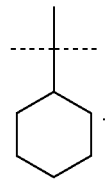

In accordance with one embodiment of the present invention, there is provided a compound having the structure of Formula I above, wherein $R^7$ is

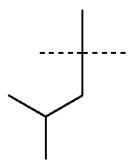

In accordance with one embodiment of the present invention, there is provided a compound having the structure of Formula I above, wherein $R^8$ is

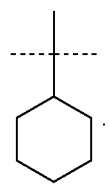

In accordance with one embodiment of the present invention, there is provided a compound having the structure of Formula I above, wherein $R^8$ is

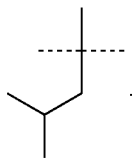

In accordance with one embodiment of the present invention, there is provided a compound having the structure of Formula I above, wherein $R^7$ and $R^8$ are both

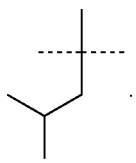

In accordance with one embodiment of the present invention, there is provided a compound having the structure of Formula I above, wherein X is

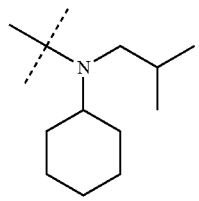

In accordance with one embodiment of the present invention, there is provided a compound having the structure of Formula I above, wherein X is

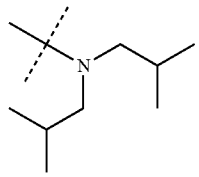

In accordance with one embodiment of the present invention, there is provided a compound having the structure of Formula I above, wherein X

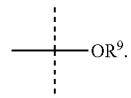

In accordance with one embodiment of the present invention, there is provided a compound having the structure of Formula I above, wherein $R^9$ is $(C_1-C_{10})$alkyl.

In accordance with one embodiment of the present invention, there is provided a compound having the structure of Formula I above, wherein $R^9$ is —$CH_2CH_2CH_3$.

In accordance with one embodiment of the present invention, there is provided a compound having the structure of Formula I above, wherein $R^9$ is —$CH(CH_2CH_2CH_3)_2$.

In accordance with one embodiment of the present invention, there is provided a compound having the structure of Formula I above, wherein X is —$OCH_2CH_2CH_3$.

In accordance with one embodiment of the present invention, there is provided a compound having the structure of Formula I above, wherein X is —$OCH(CH_2CH_2CH_3)_2$.

In accordance with one embodiment of the present invention, there is provided a compound having the structure of Formula I above, wherein $R^{12}$ is selected from

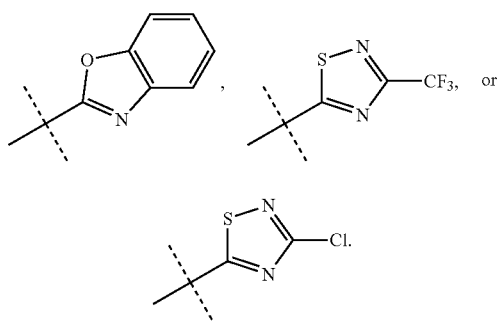

In accordance with one embodiment of the present invention, there is provided a compound having the structure of Formula I above, wherein $R^{12}$ is

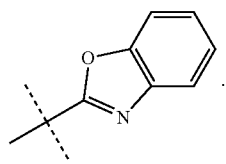

In accordance with one embodiment of the present invention, there is provided a compound having the structure of Formula I above, wherein $R^{12}$

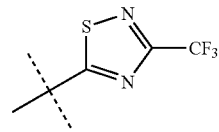

In accordance with one embodiment of the present invention, there is provided a compound having the structure of Formula I above, wherein $R^{12}$ is

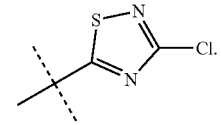

The present invention further provides compositions comprising a compound of the invention, or pharmaceutically acceptable salt thereof, and at least one pharmaceutically acceptable carrier.

The present invention further provides methods of modulating activity of indoleamine 2,3-dioxygenase by contacting the indoleamine 2,3-dioxygenase with a compound of the invention, or pharmaceutically acceptable salt thereof.

The present invention further provides methods for the prevention and/or treatment of HIV; including the prevention of the progression of AIDS and general immunosuppression in a patient by administering to the patient an effective amount of a compound of the invention, or pharmaceutically acceptable salt thereof.

The present invention further provides methods of treating cancer, viral infection, bacterial infection, sepsis, macular degeneration, wounds, depression, a neurodegenerative disorder, trauma, age-related cataracts, organ transplant rejection, an autoimmune disease, or the like, in a patient comprising administering to the patient a therapeutically effective amount of a compound of the invention, or pharmaceutically acceptable salt thereof.

The present invention further provides use of the compounds herein for the production of a medicament for use in therapy.

Such compounds of the present invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formula I, wherein the compound or salt of the compound is used in the manufacture of a medicament for use in the treatment immunosuppression in a human.

In another embodiment of the invention, there is provided a pharmaceutical composition comprising a pharmaceutically acceptable diluent and a therapeutically effective amount of a compound as defined in Formula I.

In one embodiment, the pharmaceutical formulation containing a compound of Formula I or a salt thereof is a formulation adapted for parenteral administration. In another embodiment, the formulation is a long-acting parenteral formulation. In a further embodiment, the formulation is a nano-particle formulation.

The present invention is directed to compounds, compositions and pharmaceutical compositions that have utility as novel treatments for immunosuppresion. While not wanting to be bound by any particular theory, it is thought that the present compounds are able to inhibit the enzyme that catalyzes the oxidative pyrrole ring cleavage reaction of l-Trp to N-formylkynurenine utilizing molecular oxygen or reactive oxygen species.

Therefore, in another embodiment of the present invention, there is provided a method for the prevention and/or treatment of HIV; including the prevention of the progression of AIDS and general immunosuppression.

TABLE 1

| Example No. | Structure | Chemical Name |
|---|---|---|
| 1 | 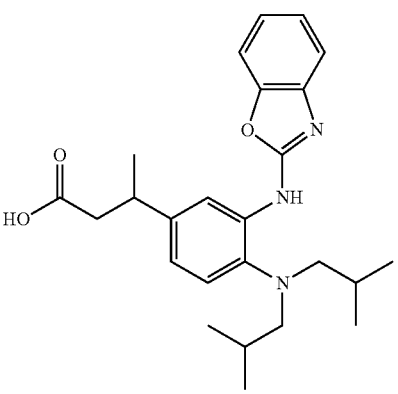 | 3-(3-(benzo[d]oxazol-2-ylamino)-4-(diisobutylamino)phenyl) butanoic acid |

TABLE 1-continued

| Example No. | Structure | Chemical Name |
|---|---|---|
| 2 | 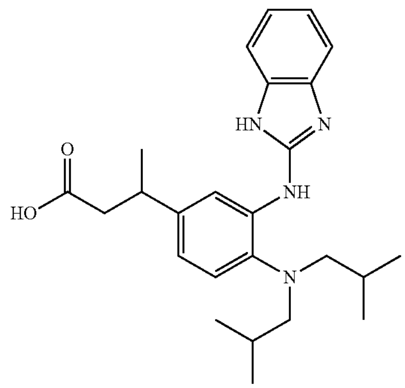 [SMILES: CC(C)CN(CC(C)C)c1ccc(C(C)CC(=O)O)cc1Nc1nc2ccccc2o1] | 3-(3-((1H-benzo[d]imidazol-2-yl)amino)-4-(diisobutylamino)phenyl)butanoic acid |
| 3 | 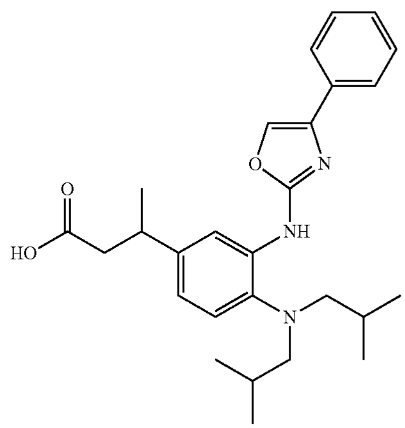 | 3-(4-(diisobutylamino)-3-((4-phenyloxazol-2-yl)amino)phenyl)butanoic acid |
| 4 | 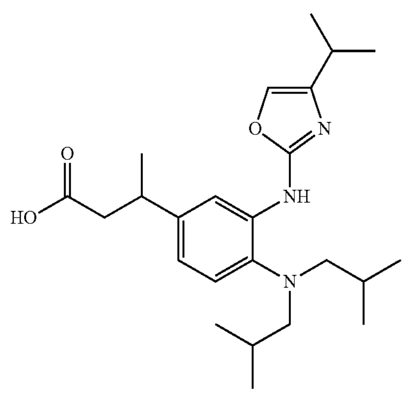 [SMILES: CC(C)CN(CC(C)C)c1ccc(C(C)CC(=O)O)cc1Nc1nc(C(C)C)co1] | 3-(4-(diisobutylamino)-3-((4-isopropyloxazol-2-yl)amino)phenyl)butanoic acid |
| 5 | 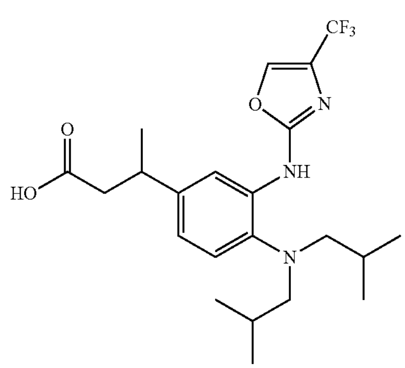 | 3-(4-(diisobutylamino)-3-((4-(trifluoromethyl)oxazol-2-yl)amino)phenyl)butanoic acid |

TABLE 1-continued

| Example No. | Structure | Chemical Name |
|---|---|---|
| 6 | 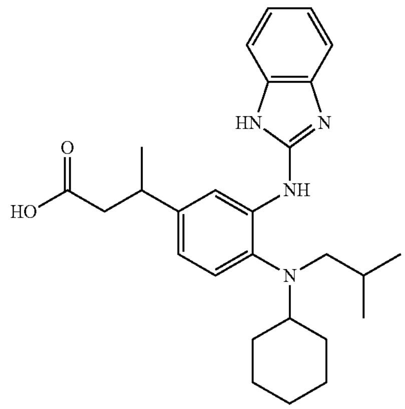 | 3-(3-((1H-benzo[d]imidazol-2-yl)amino)-4-(cyclohexyl(isobutyl)amino)phenyl)butanoic acid |
| 7 | 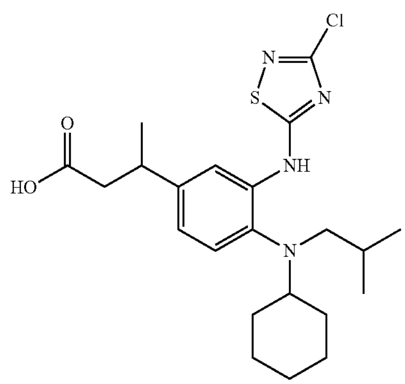 | 3-(3-((3-chloro-1,2,4-thiadiazol-5-yl)amino)-4-(cyclohexyl(isobutyl)amino)phenyl)butanoic acid |
| 8 | 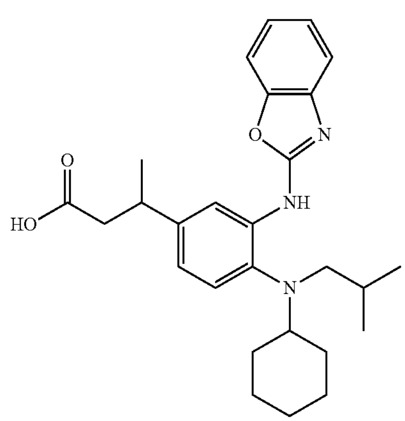 [SMILES: CC(C)CN(c1ccc(C(C)CC(=O)O)cc1Nc1nc2ccccc2o1)C1CCCCC1] | 3-(3-(benzo[d]oxazol-2-ylamino)-4-(cyclohexyl(isobutyl)amino)phenyl)butanoic acid |

TABLE 1-continued

| Example No. | Structure | Chemical Name |
|---|---|---|
| 9 | 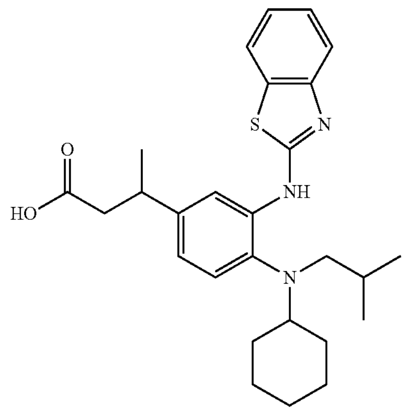 | 3-(3-(benzo[d]thiazol-2-ylamino)-4-(cyclohexyl(isobutyl)amino)phenyl)butanoic acid |
| 10 | 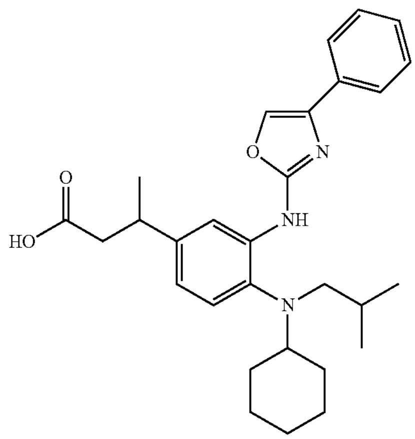 [SMILES: CC(C)CN(c1ccc(C(C)CC(=O)O)cc1Nc1nc(-c2ccccc2)co1)C1CCCCC1] | 3-(4-(cyclohexyl(isobutyl)amino)-3-((4-phenyloxazol-2-yl)amino)phenyl)butanoic acid |
| 11 | 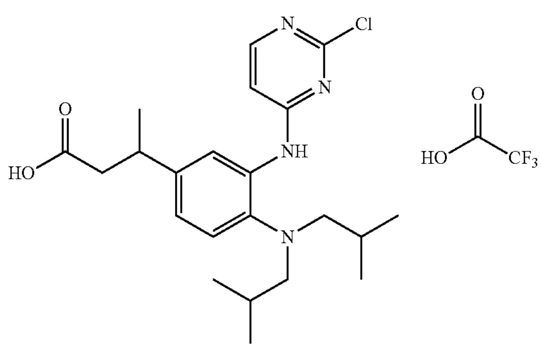 [SMILES: CC(C)CN(CC(C)C)c1ccc(C(C)CC(=O)O)cc1Nc1ccnc(Cl)n1 ; O=C(O)C(F)(F)F] | 3-(3-((2-chloropyrimidin-4-yl)amino)-4-(diisobutylamino)phenyl)butanoic acid, 2,2,2-trifluoroacetic acid salt |
| 12 | 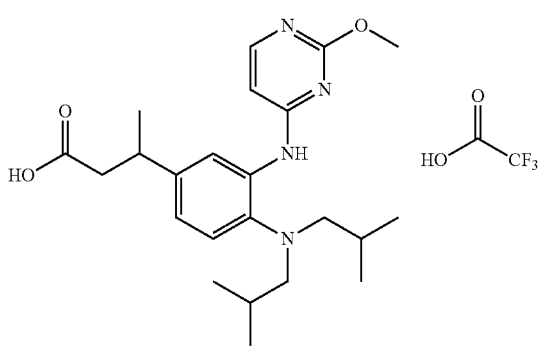 [SMILES: COc1nccc(Nc2cc(C(C)CC(=O)O)ccc2N(CC(C)C)CC(C)C)n1 ; O=C(O)C(F)(F)F] | 3-(4-(diisobutylamino)-3-((2-methoxypyrimidin-4-yl)amino)phenyl)butanoic acid, 2,2,2-trifluoroacetic acid salt |

TABLE 1-continued

| Example No. | Structure | Chemical Name |
|---|---|---|
| 13 | 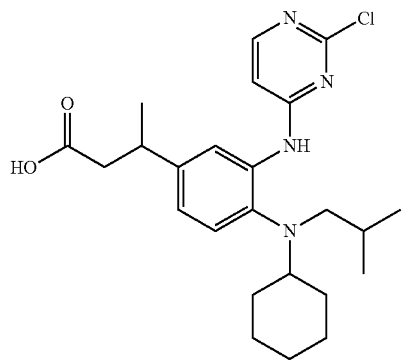 | 3-(3-((2-chloropyrimidin-4-yl)amino)-4-(cyclohexyl(isobutyl)amino)phenyl)butanoic acid |
| 14 | 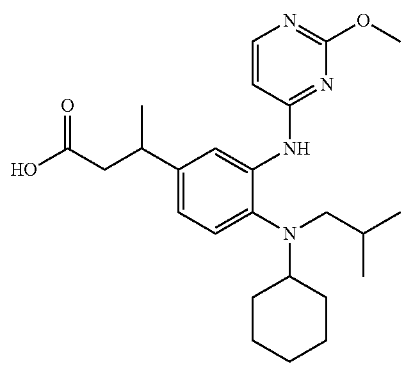 [SMILES: COc1nccc(Nc2cc(C(C)CC(=O)O)ccc2N(CC(C)C)C2CCCCC2)n1] | 3-(4-(cyclohexyl(isobutyl)amino)-3-((2-methoxypyrimidin-4-yl)amino)phenyl)butanoic acid |
| 15 | 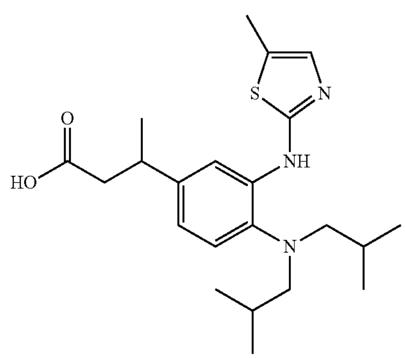 | 3-(4-(diisobutylamino)-3-((5-methylthiazol-2-yl)amino)phenyl)butanoic acid |
| 16 | 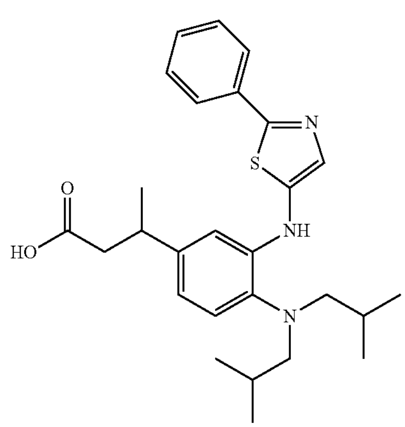 [SMILES: CC(C)CN(CC(C)C)c1ccc(C(C)CC(=O)O)cc1Nc1cnc(-c2ccccc2)s1] | 3-(4-(diisobutylamino)-3-((2-phenylthiazol-5-yl)amino)phenyl)butanoic acid |

TABLE 1-continued
| Example No. | Structure | Chemical Name |
|---|---|---|
| 17 | 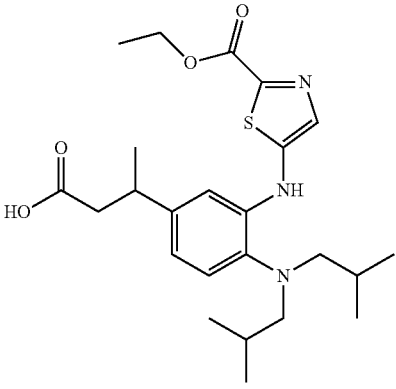 [SMILES: CCOC(=O)c1ncc(Nc2cc(C(C)CC(=O)O)ccc2N(CC(C)C)CC(C)C)s1] | 3-(4-(diisobutylamino)-3-((2-(ethoxycarbonyl)thiazol-5-yl)amino)phenyl)butanoic acid |
| 18 | 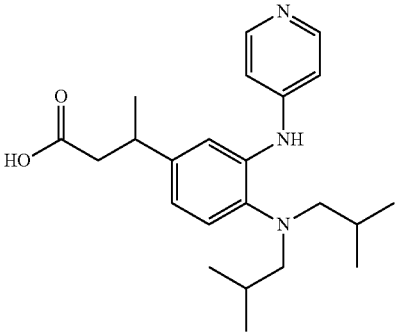 [SMILES: CC(C)CN(CC(C)C)c1ccc(C(C)CC(=O)O)cc1Nc1ccncc1] | 3-(4-(diisobutylamino)-3-(pyridin-4-ylamino)phenyl)butanoic acid |
| 19 | 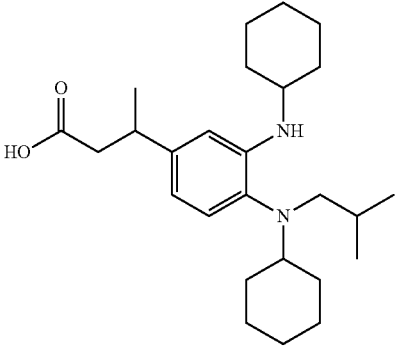 [SMILES: CC(C)CN(c1ccc(C(C)CC(=O)O)cc1NC1CCCCC1)C1CCCCC1] | 3-(4-(cyclohexyl(isobutyl)amino)-3-(cyclohexylamino)phenyl)butanoic acid |
| 20 | 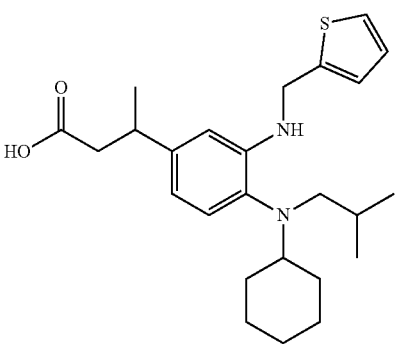 | 3-(4-(cyclohexyl(isobutyl)amino)-3-((thiophen-2-ylmethyl)amino)phenyl)butanoic acid |

TABLE 1-continued

| Example No. | Structure | Chemical Name |
|---|---|---|
| 21 | 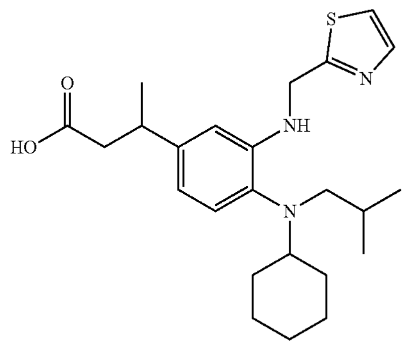 | 3-(4-(cyclohexyl(isobutyl)amino)-3-((thiazol-2-ylmethyl)amino)phenyl)butanoic acid |
| 22 | 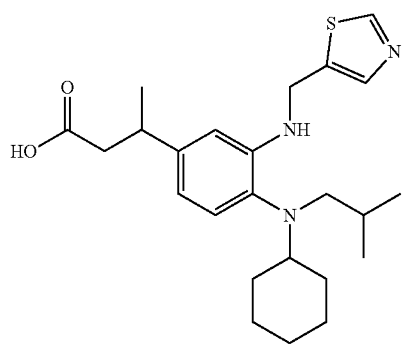 | 3-(4-(cyclohexyl(isobutyl)amino)-3-((thiazol-5-ylmethyl)amino)phenyl)butanoic acid |
| 23 | 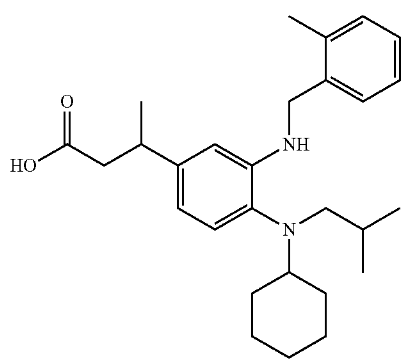 [SMILES: Cc1ccccc1CNc1cc(C(C)CC(=O)O)ccc1N(CC(C)C)C1CCCCC1] | 3-(4-(cyclohexyl(isobutyl)amino)-3-((2-methylbenzyl)amino)phenyl)butanoic acid |
| 24 | 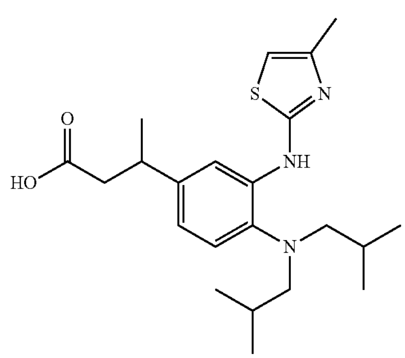 [SMILES: Cc1csc(Nc2cc(C(C)CC(=O)O)ccc2N(CC(C)C)CC(C)C)n1] | 3-(4-(diisobutylamino)-3-((4-methylthiazol-2-yl)amino)phenyl)butanoic acid |

TABLE 1-continued

| Example No. | Structure | Chemical Name |
|---|---|---|
| 25 | 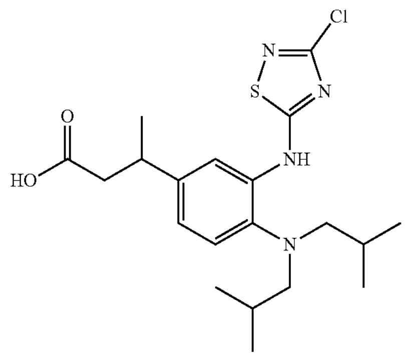 | 3-(3-((3-chloro-1,2,4-thiadiazol-5-yl)amino)-4-(diisobutylamino)phenyl)butanoic acid |
| 26 | 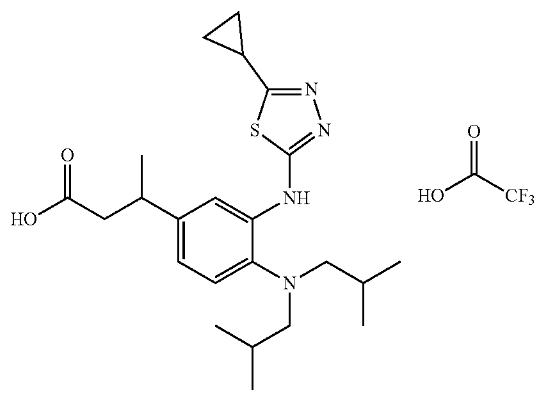 [SMILES: CC(C)CN(CC(C)C)c1ccc(C(C)CC(=O)O)cc1Nc1nnc(C2CC2)s1 ; O=C(O)C(F)(F)F] | 3-(3-((5-cyclopropyl-1,3,4-thiadiazol-2-yl)amino)-4-(diisobutylamino)phenyl)butanoic acid, 2,2,2-trifluoroacetic acid salt |
| 27 | 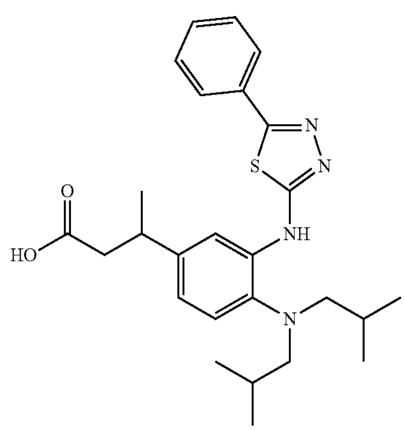 [SMILES: CC(C)CN(CC(C)C)c1ccc(C(C)CC(=O)O)cc1Nc1nnc(-c2ccccc2)s1] | 3-(4-(diisobutylamino)-3-((5-phenyl-1,3,4-thiadiazol-2-yl)amino)phenyl)butanoic acid |
| 28 | 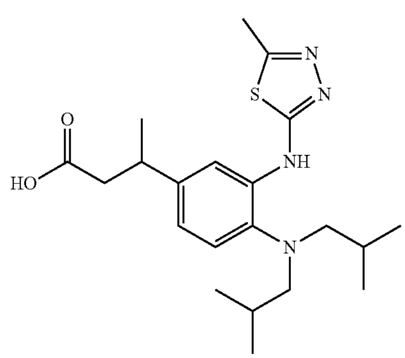 [SMILES: Cc1nnc(Nc2cc(C(C)CC(=O)O)ccc2N(CC(C)C)CC(C)C)s1] | 3-(4-(diisobutylamino)-3-((5-methyl-1,3,4-thiadiazol-2-yl)amino)phenyl)butanoic acid |

TABLE 1-continued

| Example No. | Structure | Chemical Name |
|---|---|---|
| 29 | 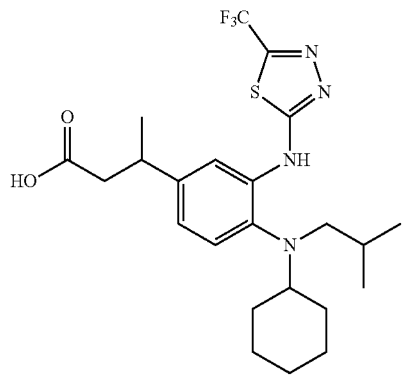 [SMILES: CC(C)CN(c1ccc(C(C)CC(=O)O)cc1Nc1nnc(C(F)(F)F)s1)C1CCCCC1] | 3-(4-(cyclohexyl(isobutyl)amino)-3-((5-(trifluoromethyl)-1,3,4-thiadiazol-2-yl)amino)phenyl)butanoic acid |
| 30 | 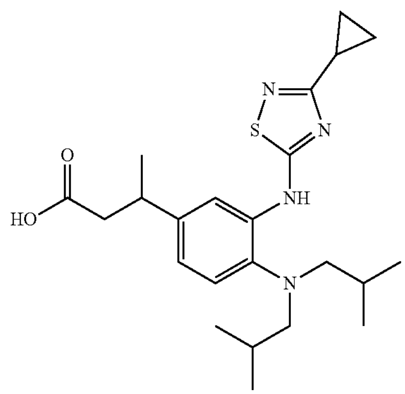 [SMILES: CC(C)CN(CC(C)C)c1ccc(C(C)CC(=O)O)cc1Nc1nc(C2CC2)ns1] | 3-(3-((3-cyclopropyl-1,2,4-thiadiazol-5-yl)amino)-4-(diisobutylamino)phenyl)butanoic acid |
| 31 | 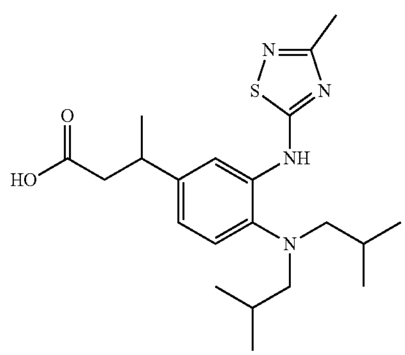 [SMILES: Cc1nsc(Nc2cc(C(C)CC(=O)O)ccc2N(CC(C)C)CC(C)C)n1] | 3-(4-(diisobutylamino)-3-((3-methyl-1,2,4-thiadiazol-5-yl)amino)phenyl)butanoic acid |
| 32 | 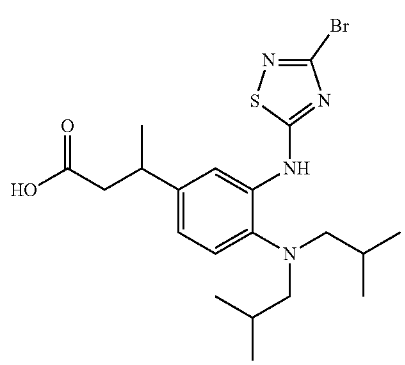 [SMILES: CC(C)CN(CC(C)C)c1ccc(C(C)CC(=O)O)cc1Nc1nc(Br)ns1] | 3-(3-((3-bromo-1,2,4-thiadiazol-5-yl)amino)-4-(diisobutylamino)phenyl)butanoic acid |

TABLE 1-continued

| Example No. | Structure | Chemical Name |
|---|---|---|
| 33 | 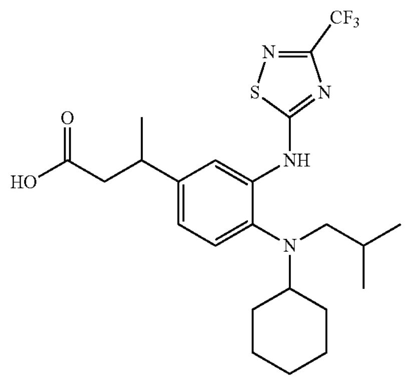 | 3-(4-(cyclohexyl(isobutyl)amino)-3-((3-(trifluoromethyl)-1,2,4-thiadiazol-5-yl)amino)phenyl)butanoic acid |
| 34 | 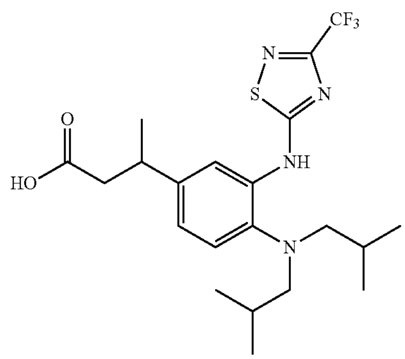 | 3-(4-(diisobutylamino)-3-((3-(trifluoromethyl)-1,2,4-thiadiazol-5-yl)amino)phenyl)butanoic acid |
| 35 | 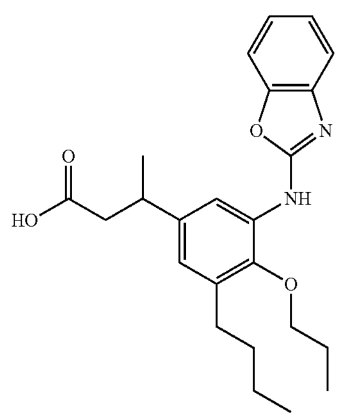 [SMILES: CCCCc1cc(C(C)CC(=O)O)cc(Nc2nc3ccccc3o2)c1OCCC] | 3-(3-(benzo[d]oxazol-2-ylamino)-5-butyl-4-propoxyphenyl)butanoic acid |
| 36 | 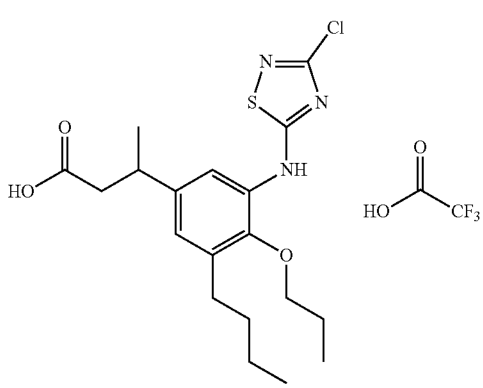 [SMILES: CCCCc1cc(C(C)CC(=O)O)cc(Nc2nc(Cl)ns2)c1OCCC ; O=C(O)C(F)(F)F] | 3-(3-butyl-5-((3-chloro-1,2,4-thiadiazol-5-yl)amino)-4-propoxyphenyl)butanoic acid, 2,2,2-trifluoroacetic acid salt |

TABLE 1-continued

| Example No. | Structure | Chemical Name |
|---|---|---|
| 37 | 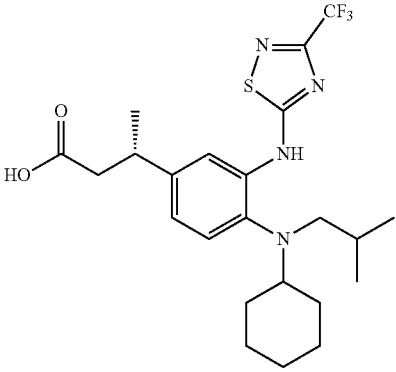 | (S)-3-(4-(cyclohexyl(isobutyl)amino)-3-((3-(trifluoromethyl)-1,2,4-thiadiazol-5-yl)amino)phenyl)butanoic acid |
| 38 | 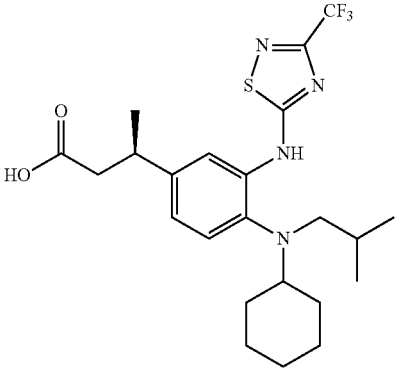 | (R)-3-(4-(cyclohexyl(isobutyl)amino)-3-((3-(trifluoromethyl)-1,2,4-thiadiazol-5-yl)amino)phenyl)butanoic acid |
| 39 | 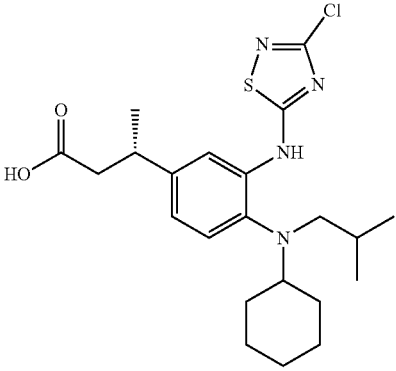 [SMILES: CC(C)CN(c1ccc([C@@H](C)CC(=O)O)cc1Nc1nc(C(F)(F)F)ns1)C1CCCCC1] | (S)-3-(3-((3-chloro-1,2,4-thiadiazol-5-yl)amino)-4-(cyclohexyl(isobutyl)amino)phenyl)butanoic acid |
| 40 | 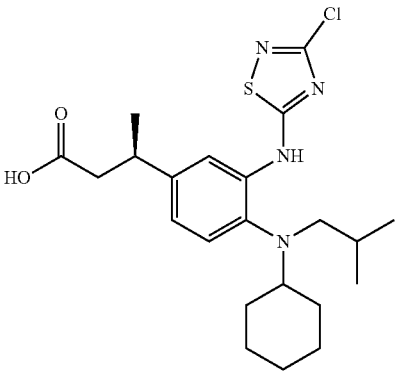 | (R)-3-(3-((3-chloro-1,2,4-thiadiazol-5-yl)amino)-4-(cyclohexyl(isobutyl)amino)phenyl)butanoic acid |

TABLE 1-continued

| Example No. | Structure | Chemical Name |
|---|---|---|
| 41 | 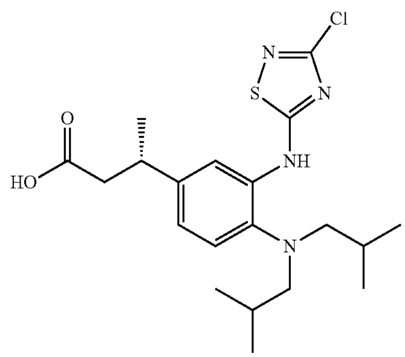 | (S)-3-(3-((3-chloro-1,2,4-thiadiazol-5-yl)amino)-4-(diisobutylamino)phenyl)butanoic acid |
| 42 | 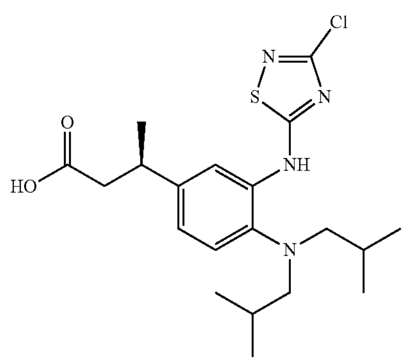 [SMILES: CC(C)CN(CC(C)C)c1ccc([C@H](C)CC(=O)O)cc1Nc1nc(Cl)ns1] | (R)-3-(3-((3-chloro-1,2,4-thiadiazol-5-yl)amino)-4-(diisobutylamino)phenyl)butanoic acid |
| 43 | 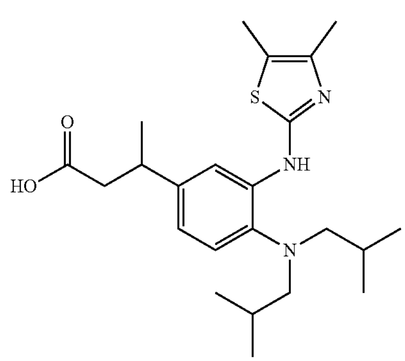 [SMILES: Cc1nc(Nc2cc(C(C)CC(=O)O)ccc2N(CC(C)C)CC(C)C)sc1C] | 3-(4-(diisobutylamino)-3-((4,5-dimethylthiazol-2-yl)amino)phenyl)butanoic acid |
| 44 | 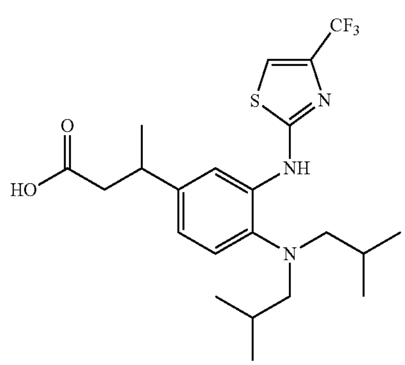 | 3-(4-(diisobutylamino)-3-((4-(trifluoromethyl)thiazol-2-yl)amino)phenyl)butanoic acid |

TABLE 1-continued

| Example No. | Structure | Chemical Name |
|---|---|---|
| 45 | 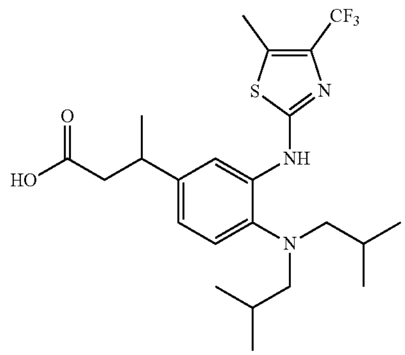 [SMILES: Cc1sc(Nc2cc(C(C)CC(=O)O)ccc2N(CC(C)C)CC(C)C)nc1C(F)(F)F] | 3-(4-(diisobutylamino)-3-((5-methyl-4-(trifluoromethyl)thiazol-2-yl)amino)phenyl)butanoic acid |
| 46 | 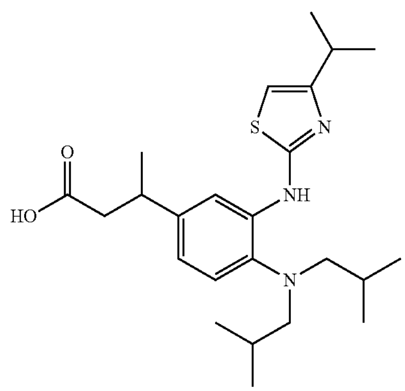 | 3-(4-(diisobutylamino)-3-((4-isopropylthiazol-2-yl)amino)phenyl)butanoic acid |
| 47 | 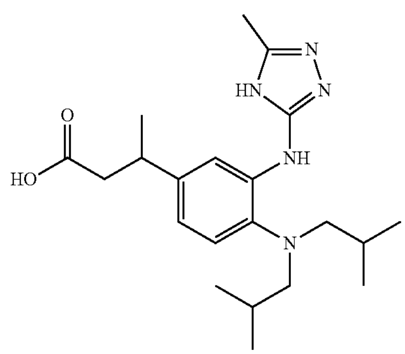 [SMILES: Cc1nnc(Nc2cc(C(C)CC(=O)O)ccc2N(CC(C)C)CC(C)C)[nH]1] | 3-(4-(diisobutylamino)-3-((5-methyl-4H-1,2,4-triazol-3-yl)amino)phenyl)butanoic acid |
| 48 | 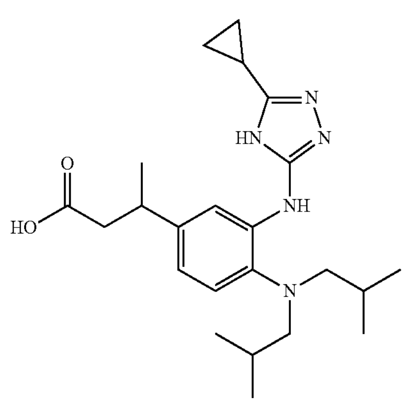 [SMILES: CC(C)CN(CC(C)C)c1ccc(C(C)CC(=O)O)cc1Nc1nnc(C2CC2)[nH]1] | 3-(3-((5-cyclopropyl-4H-1,2,4-triazol-3-yl)amino)-4-(diisobutylamino)phenyl)butanoic acid |

TABLE 1-continued

| Example No. | Structure | Chemical Name |
|---|---|---|
| 49 | 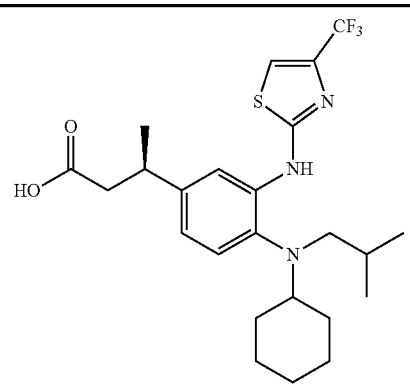 | (R)-3-(4-(cyclohexyl(isobutyl)amino)-3-((4-(trifluoromethyl)thiazol-2-yl)amino)phenyl)butanoic acid |
| 50 | 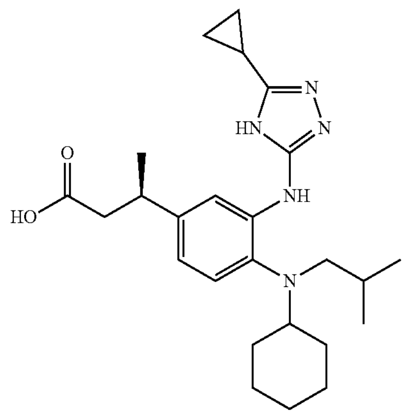 [SMILES: CC(C)CN(c1ccc([C@H](C)CC(=O)O)cc1Nc1nnc(C2CC2)[nH]1)C1CCCCC1] | (R)-3-(4-(cyclohexyl(isobutyl)amino)-3-((5-cyclopropyl-4H-1,2,4-triazol-3-yl)amino)phenyl)butanoic acid |
| 51 | 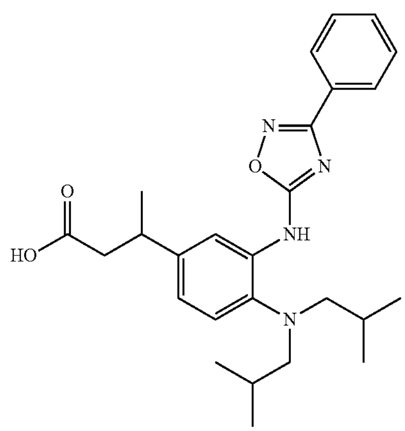 [SMILES: CC(C)CN(CC(C)C)c1ccc(C(C)CC(=O)O)cc1Nc1nc(-c2ccccc2)no1] | 3-(4-(diisobutylamino)-3-((3-phenyl-1,2,4-oxadiazol-5-yl)amino)phenyl)butanoic acid |
| 52 | 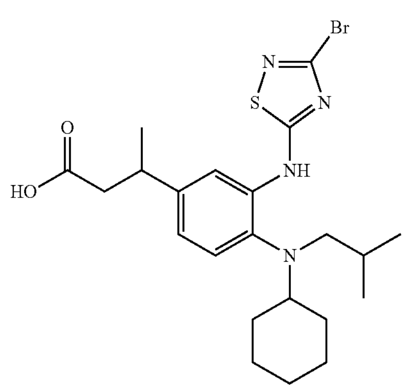 | 3-(3-((3-bromo-1,2,4-thiadiazol-5-yl)amino)-4-(cyclohexyl(isobutyl)amino)phenyl)butanoic acid |

TABLE 1-continued

| Example No. | Structure | Chemical Name |
|---|---|---|
| 53 | 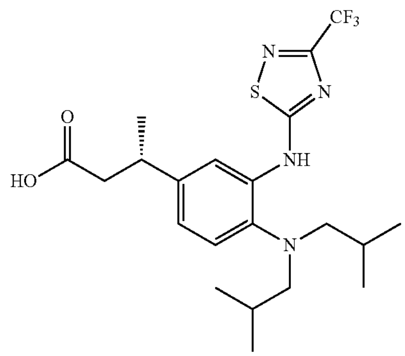 | (S)-3-(4-(diisobutylamino)-3-((3-(trifluoromethyl)-1,2,4-thiadiazol-5-yl)amino)phenyl)butanoic acid |
| 54 | 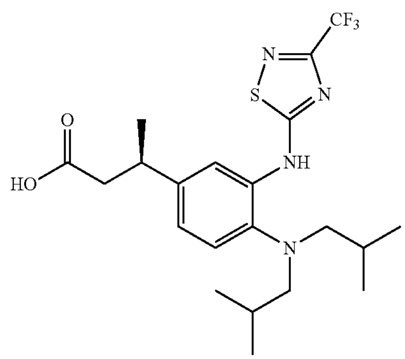 | (R)-3-(4-(diisobutylamino)-3-((3-(trifluoromethyl)-1,2,4-thiadiazol-5-yl)amino)phenyl)butanoic acid |
| 55 | 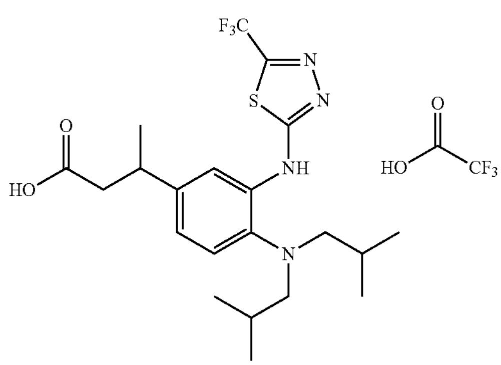 [SMILES: CC(C)CN(CC(C)C)c1ccc(C(C)CC(=O)O)cc1Nc1nnc(C(F)(F)F)s1 ; O=C(O)C(F)(F)F] | 3-(4-(diisobutylamino)-3-((5-(trifluoromethyl)-1,3,4-thiadiazol-2-yl)amino)phenyl)butanoic acid, 2,2,2-trifluoroacetic acid salt |
| 56 | 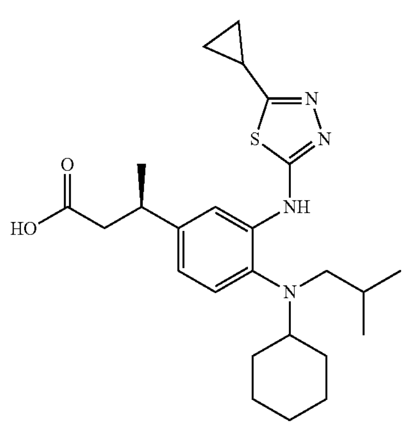 [SMILES: CC(C)CN(c1ccc([C@H](C)CC(=O)O)cc1Nc1nnc(C2CC2)s1)C1CCCCC1] | (R)-3-(4-(cyclohexyl(isobutyl)amino)-3-((5-cyclopropyl-1,3,4-thiadiazol-2-yl)amino)phenyl)butanoic acid |

TABLE 1-continued

| Example No. | Structure | Chemical Name |
|---|---|---|
| 57 | 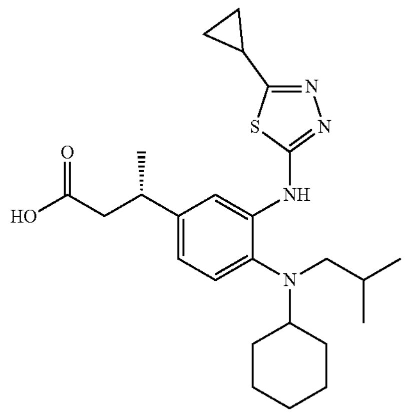 [SMILES: CC(C)CN(c1ccc([C@@H](C)CC(=O)O)cc1Nc1nnc(C2CC2)s1)C1CCCCC1] | (S)-3-(4-(cyclohexyl(isobutyl)amino)-3-((5-cyclopropyl-1,3,4-thiadiazol-2-yl)amino)phenyl)butanoic acid |
| 58 | 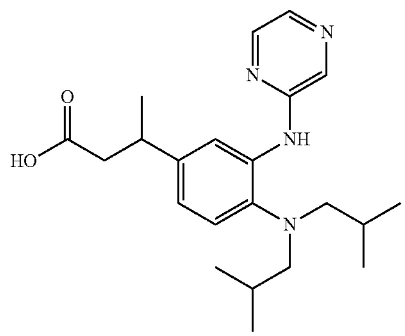 [SMILES: CC(C)CN(CC(C)C)c1ccc(C(C)CC(=O)O)cc1Nc1cnccn1] | 3-(4-(diisobutylamino)-3-(pyrazin-2-ylamino)phenyl)butanoic acid |
| 59 | 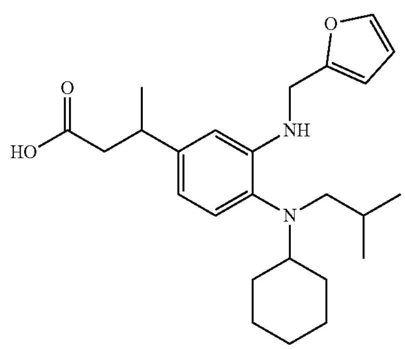 | 3-(4-(cyclohexyl(isobutyl)amino)-3-((furan-2-ylmethyl)amino)phenyl)butanoic acid |
| 60 | 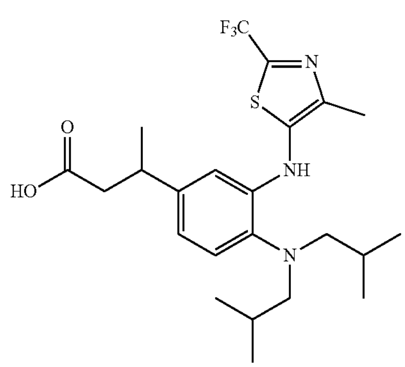 [SMILES: Cc1nc(C(F)(F)F)sc1Nc1cc(C(C)CC(=O)O)ccc1N(CC(C)C)CC(C)C] | 3-(4-(diisobutylamino)-3-((4-methyl-2-(trifluoromethyl)thiazol-5-yl)amino)phenyl)butanoic acid |

TABLE 1-continued

| Example No. | Structure | Chemical Name |
|---|---|---|
| 61 | 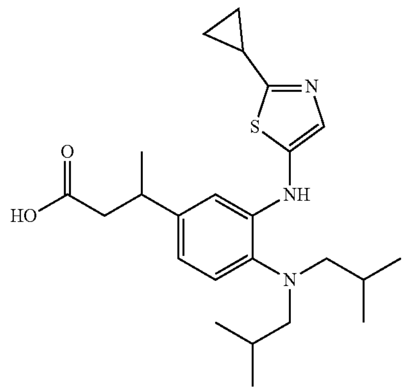 [SMILES: CC(C)CN(CC(C)C)c1ccc(C(C)CC(=O)O)cc1Nc1cnc(C2CC2)s1] | 3-(3-((2-cyclopropylthiazol-5-yl)amino)-4-(diisobutylamino)phenyl) butanoic acid |
| 62 | 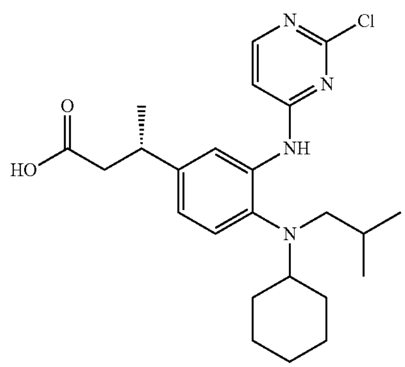 | (S)-3-(3-((2-chloropyrimidin-4-yl)amino)-4-(cyclohexyl(isobutyl)amino) phenyl)butanoic acid |
| 63 | 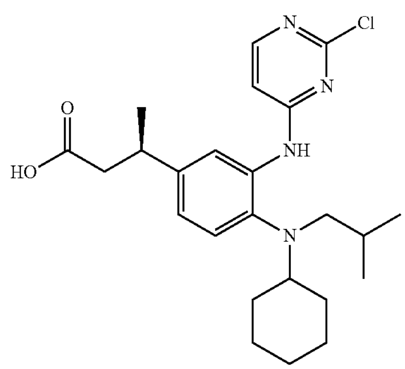 [SMILES: CC(C)CN(c1ccc([C@H](C)CC(=O)O)cc1Nc1ccnc(Cl)n1)C1CCCCC1] | (R)-3-(3-((2-chloropyrimidin-4-yl)amino)-4-(cyclohexyl(isobutyl)amino) phenyl)butanoic acid |
| 64 | 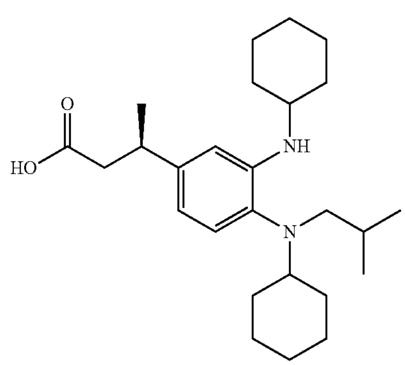 [SMILES: CC(C)CN(c1ccc([C@H](C)CC(=O)O)cc1NC1CCCCC1)C1CCCCC1] | (R)-3-(4-(cyclohexyl(isobutyl)amino)-3-(cyclohexylamino)phenyl) butanoic acid |

TABLE 1-continued

| Example No. | Structure | Chemical Name |
|---|---|---|
| 65 | 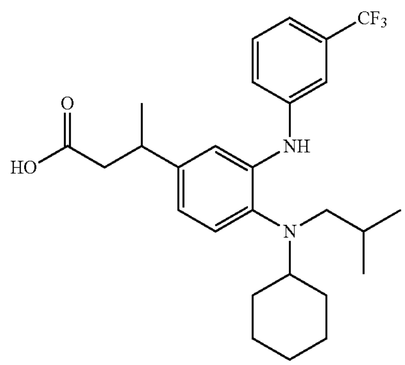 [SMILES: CC(C)CN(c1ccc(C(C)CC(=O)O)cc1Nc1cccc(C(F)(F)F)c1)C1CCCCC1] | 3-(4-(cyclohexyl(isobutyl)amino)-3-((3-(trifluoromethyl)phenyl)amino)phenyl)butanoic acid |
| 66 | 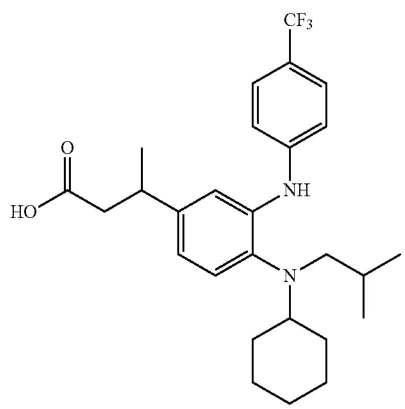 | 3-(4-(cyclohexyl(isobutyl)amino)-3-((4-(trifluoromethyl)phenyl)amino)phenyl)butanoic acid |
| 67 | 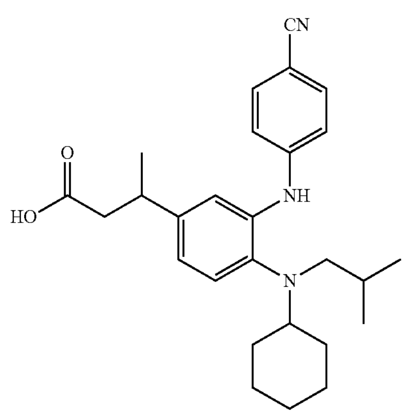 | 3-(3-((4-cyanophenyl)amino)-4-(cyclohexyl(isobutyl)amino)phenyl)butanoic acid |
| 68 | 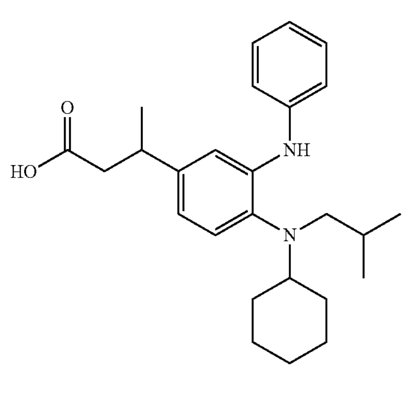 [SMILES: CC(C)CN(c1ccc(C(C)CC(=O)O)cc1Nc1ccccc1)C1CCCCC1] | 3-(4-(cyclohexyl(isobutyl)amino)-3-(phenylamino)phenyl)butanoic acid |

TABLE 1-continued

| Example No. | Structure | Chemical Name |
|---|---|---|
| 69 | 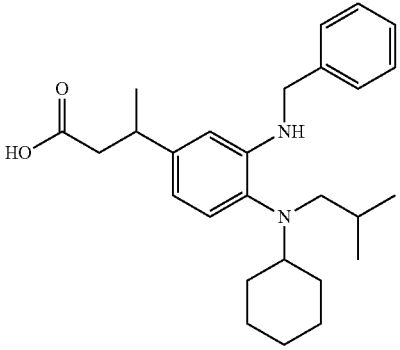 [SMILES: CC(C)CN(c1ccc(C(C)CC(=O)O)cc1NCc1ccccc1)C1CCCCC1] | 3-(3-(benzylamino)-4-(cyclohexyl(isobutyl)amino)phenyl)butanoic acid |
| 70 | 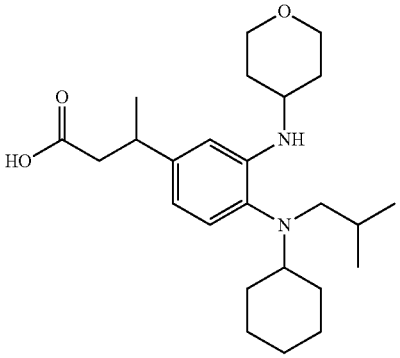 [SMILES: CC(C)CN(c1ccc(C(C)CC(=O)O)cc1NC1CCOCC1)C1CCCCC1] | 3-(4-(cyclohexyl(isobutyl)amino)-3-((tetrahydro-2H-pyran-4-yl)amino)phenyl)butanoic acid |
| 71 | 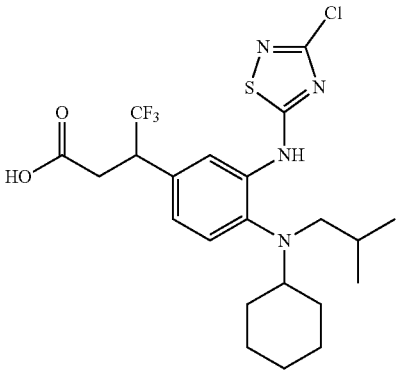 [SMILES: CC(C)CN(c1ccc(C(CC(=O)O)C(F)(F)F)cc1Nc1nc(Cl)ns1)C1CCCCC1] | 3-(3-((3-chloro-1,2,4-thiadiazol-5-yl)amino)-4-(cyclohexyl(isobutyl)amino)phenyl)-4,4,4-trifluorobutanoic acid |
| 72 | 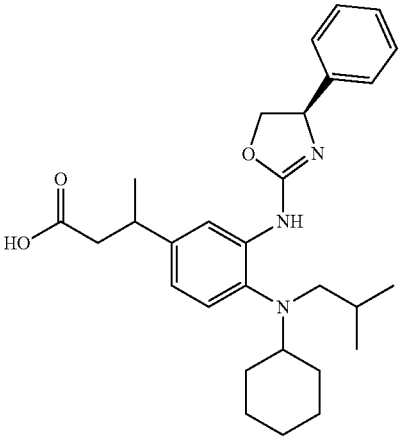 [SMILES: CC(C)CN(c1ccc(C(C)CC(=O)O)cc1NC1=N[C@H](c2ccccc2)CO1)C1CCCCC1] | 3-(4-(cyclohexyl(isobutyl)amino)-3-(((R)-4-phenyl-4,5-dihydrooxazol-2-yl)amino)phenyl)butanoic acid |

TABLE 1-continued

| Example No. | Structure | Chemical Name |
|---|---|---|
| 73 | 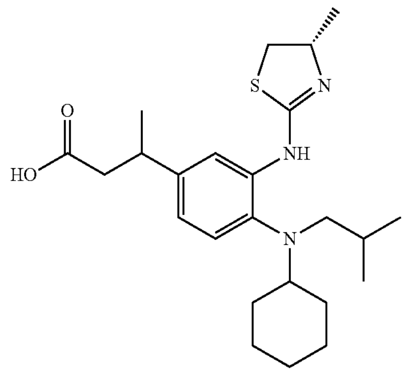 [SMILES: CC(C)CN(c1ccc(C(C)CC(=O)O)cc1NC1=N[C@@H](C)CS1)C1CCCCC1] | 3-(4-(cyclohexyl(isobutyl)amino)-3-(((S)-4-methyl-4,5-dihydrothiazol-2-yl)amino)phenyl)butanoic acid |
| 74 | 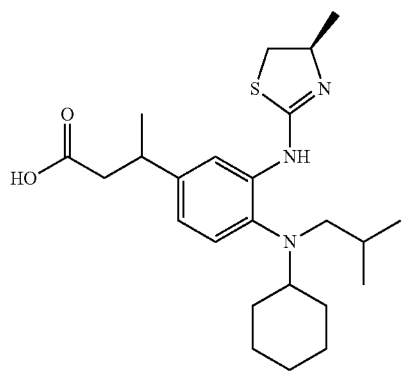 [SMILES: CC(C)CN(c1ccc(C(C)CC(=O)O)cc1NC1=N[C@H](C)CS1)C1CCCCC1] | 3-(4-(cyclohexyl(isobutyl)amino)-3-(((R)-4-methyl-4,5-dihydrothiazol-2-yl)amino)phenyl)butanoic acid |
| 75 | 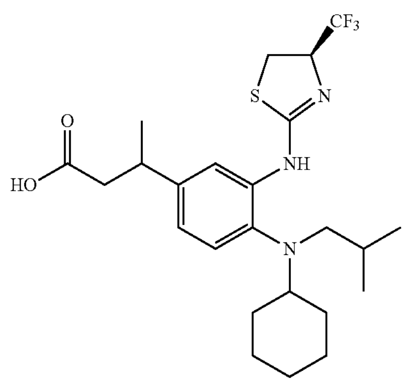 [SMILES: CC(C)CN(c1ccc(C(C)CC(=O)O)cc1NC1=N[C@H](C(F)(F)F)CS1)C1CCCCC1] | 3-(4-(cyclohexyl(isobutyl)amino)-3-(((R)-4-(trifluoromethyl)-4,5-dihydrothiazol-2-yl)amino)phenyl)butanoic acid |
| 76 | 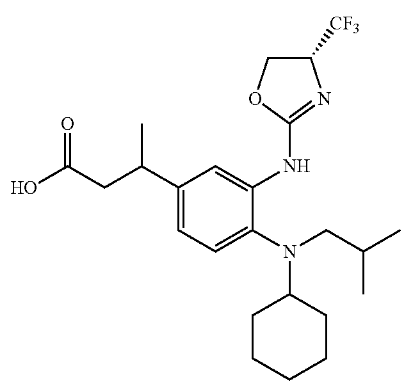 [SMILES: CC(C)CN(c1ccc(C(C)CC(=O)O)cc1NC1=N[C@@H](C(F)(F)F)CO1)C1CCCCC1] | 3-(4-(cyclohexyl(isobutyl)amino)-3-(((R)-4-(trifluoromethyl)-4,5-dihydrooxazol-2-yl)amino)phenyl)butanoic acid |

The compounds of Table 1 were synthesized according to the Synthetic Methods, General Schemes, and the Examples described below. Any chemical not directly described are readily prepared by one skilled in the art using available starting materials.

In certain embodiments, the compound(s) of the present invention, or a pharmaceutically acceptable salt thereof, is chosen from the compounds set forth in Table 1. Wherein a salt is indicated in Table 1, the present invention also encompasses the free base.

Synthetic Methods

The methods of synthesis for the provided chemical entities employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Ernka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, $4^{th}$ Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples and the synthetic schemes below, the following abbreviations have the following meanings. If an abbreviation is not defined, it has its generally accepted meaning.

ACN=acetonitrile
AIBN=azobisisobutyronitrile
aq.=aqueous
μL or uL=microliters
μM or uM=micromolar
NMR=nuclear magnetic resonance
boc=tert-butoxycarbonyl
br=broad
Cbz=Benzyloxycarbonyl
CDI=1,1'-carbonyldiimidazole
d=doublet
δ=chemical shift
° C.=degrees celcius
DCM=dichloromethane
dd=doublet of doublets
DHP=dihydropyran
DIAD=diisopropyl azodicarboxylate DIEA or DIPEA=N,N-diisopropylethylamine
DMAP=4-(dimethylamino)pyridine
DMEM=Dulbeco's Modified Eagle's Medium
EtOAc=ethyl acetate
h or hr=hours
HATU=1-[Bis(dimethylamino)methylene]-1H-1,2,3-triazolo[4,5-b]pyridinium 3-oxid hexafluorophosphate
HCV=hepatitus C virus
HPLC=high performance liquid chromatography
Hz=hertz
IU=International Units
$IC_{50}$=inhibitory concentration at 50% inhibition
J=coupling constant (given in Hz unless otherwise indicated)
LCMS=liquid chromatography-mass spectrometry
m=multiplet
M=molar
M+H⁺=parent mass spectrum peak plus H⁺
MeOH=methanol
mg=milligram
min=minutes
mL=milliliter
mM=millimolar
mmol=millimole
MS=mass spectrum
MTBE=methyl tert-butyl ether
N=normal
NFK=N-formylkynurenine
NBS=N-bromosuccinimide
nm=nanomolar
PE=petroleum ether
ppm=parts per million
q.s.=sufficient amount
s=singlet
RT=room temperature
Rf=retardation factor
sat.=saturated
t=triplet
TEA=triethylamine
TFA=trifluoroacetic acid
TFAA=trifluoroacetic anhydride
THF=tetrahydrofuran Equipment Description ¹H NMR spectra were recorded on a Bruker Ascend 400 spectrometer or a Varian 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).
The analytical low-resolution mass spectra (MS) were recorded on Waters ACQUITY UPLC with SQ Detectors using a Waters BEH C18, 2.1×50 mm, 1.7 μm using a gradient elution method.
Solvent A: 0.1% formic acid (FA) in water;
Solvent B: 0.1% FA in acetonitrile;
30% B for 0.5 min followed by 30-100% B over 2.5 min.

Schemes and Experimental Procedures

The following schemes and procedures illustrate how compounds of the present invention can be prepared. The specific solvents and reaction conditions referred to are also illustrative and are not intended to be limiting. Compounds not described are either commercially available or are readily prepared by one skilled in the art using available starting materials. The Examples disclosed herein are for illustrative purposes only and are not intended to limit the scope of the invention. All examples exhibited IDO $EC_{50}$ values between 700 nM and 1 nM using the assay disclosed herein.

Synthesis of Methyl
3-(3-amino-4-(diisobutylamino)phenyl)butanoate

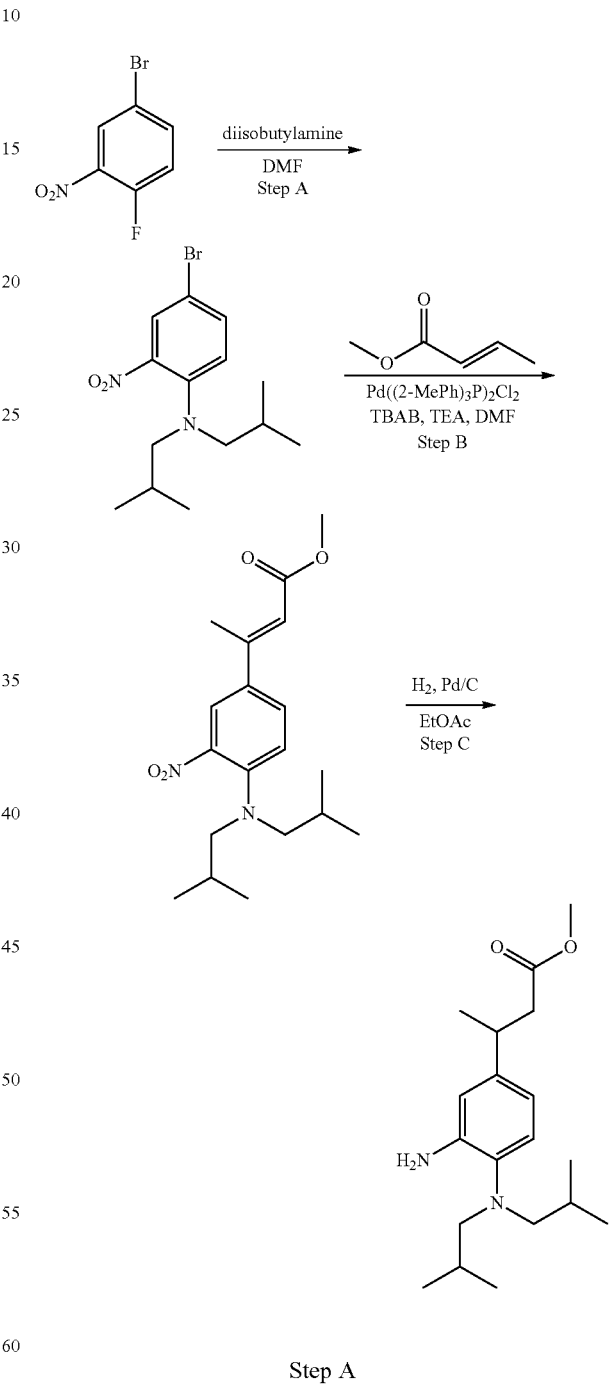

Step A

4-Bromo-N, N-diisobutyl-2-nitroaniline

To a solution of 4-bromo-1-fluoro-2-nitrobenzene (20 g, 0.09 mol) in 1-methyl-2-pyrrolidinone (100 mL) was added DIEA (11.0 g, 0.09 mol) and diisobutylamine (11.0 g, 0.9 mol) at room temperature in one portion. The resulting mixture was stirred at 120° C. for 3 hrs. After the reaction was cooled down to room temperature, it was partitioned between EtOAc (200 mL) and water (60 mL). The layers were separated and the organic layer was washed with brine, dried over Na$_2$SO$_4$ and concentrated to give the red solid which was recrystallized in petroleum ether to give intermediate 4-bromo-N,N-diisobutyl-2-nitroaniline (32 g, 73%) as a red solid.

Step B

Methyl (E)-3-(4-(diisobutylamino)-3-nitrophenyl)but-2-enoate

To a solution of 4-bromo-N,N-diisobutyl-2-nitroaniline (21 g, 63.6 mmol), tetrabutylammonium bromide (4.1 g, 12.7 mmol), methyl (E)-but-2-enoate (12.7 g, 127.2 mol), TEA (18.3 g, 0.18 mol) in DMF (200 mL) was added dichlorobis(tris(2-tolyl)phosphine)palladium (2.5 g, 3.2 mmol) in one portion at room temperature. The resulting mixture was purged with N$_2$ (3×) and stirred at 110° C. overnight. After cooling down to room temperature, the solid was filtered off. The filtrate was concentrated and the residue was partitioned between EtOAc (200 mL) and water (60 mL). The layers were separated and the combined organic layer was washed with brine (60 mL), dried over Na$_2$SO$_4$ and concentrated. The residue was purified by silica gel chromatography (5-20% EtOAc/PE) to give methyl (E)-3-(4-(diisobutylamino)-3-nitrophenyl)but-2-enoate (16.5 g, 71%) as a red oil. LCMS (M+H)$^+$: m/z=349.3.

Step C

Methyl 3-(3-amino-4-(diisobutylamino)phenyl)butanoate

To a solution of methyl (E)-3-(4-(diisobutylamino)-3-nitrophenyl)but-2-enoate (3.0 g, 8.6 mmol) in MeOH (20 mL) was added 10% palladium on carbon (0.6 g) at room temperature. The resulting mixture was purged with N$_2$ (3×) before stirred at 50° C. under H$_2$ atmosphere for 2 hrs. After the reaction was cooled down to room temperature, the palladium catalyst was filtered off. The filtrate was concentrated to give methyl 3-(3-amino-4-(diisobutylamino)phenyl)butanoate (2.75 g, 100%) as a brown oil. LCMS (M+H)$^+$: m/z=321.4.

Example 1

3-(3-(Benzo[d]oxazol-2-ylamino)-4-(diisobutylamino)phenyl)butanoic Acid

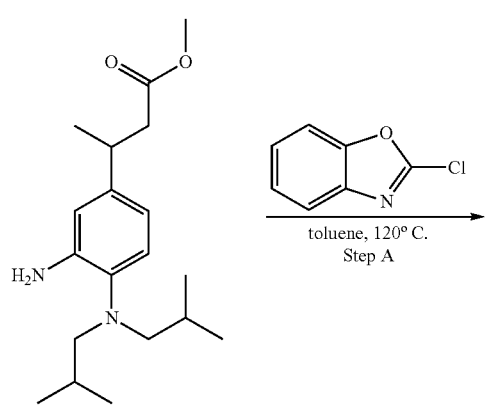

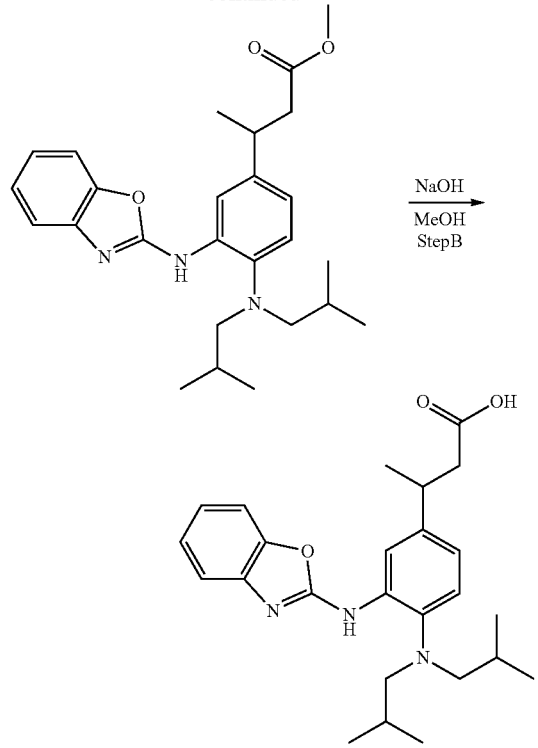

Step A

Methyl 3-(3-(benzo[d]oxazol-2-ylamino)-4-(diisobutylamino)phenyl)butanoate

A mixture of methyl 3-(3-amino-4-(diisobutylamino)phenyl)butanoate (90 mg, 0.28 mmol) and 2-chlorobenzoxazole in toluene (1 mL) was stirred at 120° C. for 16 hrs. After the reaction was cooled down to room temperature, it was partitioned between EtOAc (10 mL) and water (5 mL). The layers were separated and the organic layer was washed with brine, dried over Na$_2$SO$_4$, and concentrated. The residue was purified by preparative TLC (10% EtOAc/PE) to give intermediate methyl 3-(3-(benzo[d]oxazol-2-ylamino)-4-(diisobutylamino)phenyl)butanoate (50 mg, 41% yield). LCMS (M+H)$^+$: m/z=438.4.

Step B 3-(3-(Benzo[d]oxazol-2-ylamino)-4-(diisobutylamino)phenyl)butanoic Acid

A mixture of methyl 3-(3-(benzo[d]oxazol-2-ylamino)-4-(diisobutylamino)phenyl)butanoate (50 mg, 0.11 mmol) and NaOH (1 N, 1.1 mL, 1.1 mmol) in MeOH (1 mL) was stirred at room temperature for 2 hrs before acidified with 1 N HCl to ~pH 7. The resulting reaction mixture was loaded to prep HPLC column and purified by reverse phase chromatography (40-100% ACN in water, 0.1% formic acid) to give 3-(3-(benzo[d]oxazol-2-ylamino)-4-(diisobutylamino)phenyl)butanoic acid (36 mg, 81%) as a white powder. LCMS (M+H)$^+$: m/z=424.3. $^1$H NMR (400 MHz, DMSO) δ 12.08 (s, 1H), 8.94 (s, 1H), 8.21 (d, J=1.9 Hz, 1H), 7.53 (d, J=8.6 Hz, 2H), 7.31 (d, J=8.2 Hz, 1H), 7.25 (dd, J=11.4, 4.8 Hz, 1H), 7.16 (td, J=7.8, 1.1 Hz, 1H), 6.99 (dd, J=8.2, 2.0 Hz, 1H), 3.24-3.13 (m, 1H), 2.62 (d, J=7.2 Hz, 4H), 2.58-2.52 (m, 2H), 1.73-1.59 (m, 2H), 1.26 (d, J=6.9 Hz, 3H), 0.91 (d, J=6.6 Hz, 12H).

Example 2

3-(3-((1H-benzo[d]imidazol-2-yl)amino)-4-(diisobutylamino)phenyl)butanoic Acid

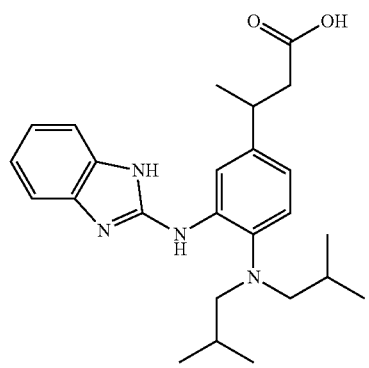 [SMILES: CC(C)CN(CC(C)C)c1ccc(C(C)CC(=O)O)cc1Nc1nc2ccccc2[nH]1]

The title compound, 3-(3-((1H-benzo[d]imidazol-2-yl) amino)-4-(diisobutylamino)phenyl)butanoic acid, was made in a similar manner to example 1 and isolated (20.2 mg, 32% over two steps). LCMS (M+H)$^+$: m/z=423.5. $^1$H NMR (400 MHz, DMSO-d$_6$) δ 12.15 (s, 1H), 11.76 (s, 1H), 8.48 (d, J=1.7 Hz, 1H), 8.32 (s, 1H), 7.34 (d, J=46.5 Hz, 2H), 7.22 (d, J=8.2 Hz, 1H), 7.01 (d, J=4.7 Hz, 2H), 6.84 (dd, J=8.1, 1.8 Hz, 1H), 3.15 (dd, J=14.6, 7.1 Hz, 1H), 2.61 (t, J=9.1 Hz, 4H), 2.58-2.52 (m, 2H), 1.62 (td, J=13.4, 6.8 Hz, 2H), 1.24 (d, J=6.9 Hz, 3H), 0.90 (d, J=6.6 Hz, 12H).

Example 3

3-(4-(Diisobutylamino)-3-((4-phenyloxazol-2-yl)amino)phenyl)butanoic Acid

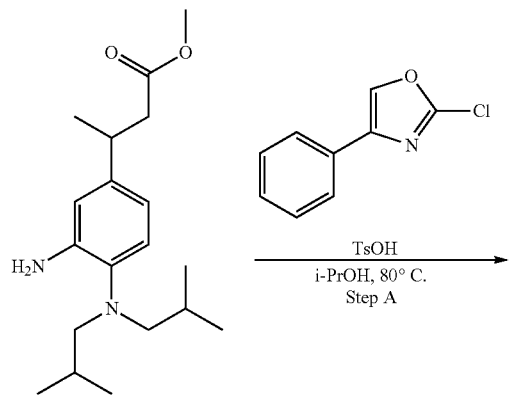

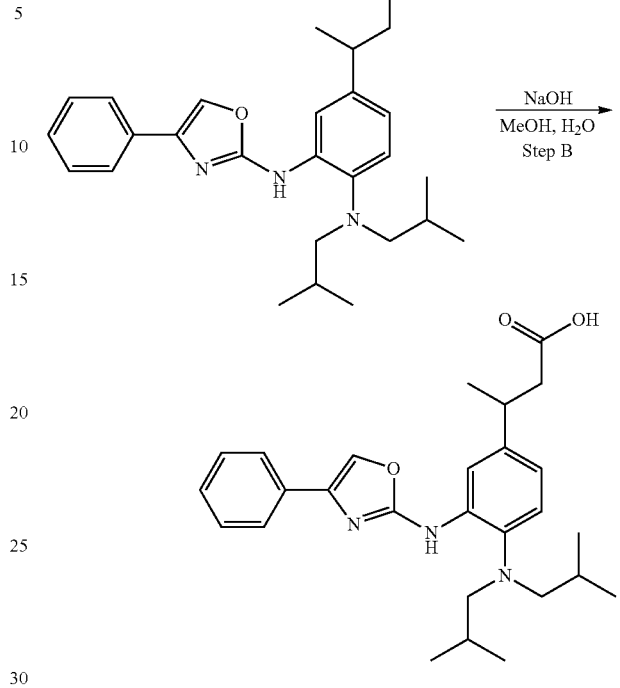

Step A

Methyl 3-(4-(diisobutylamino)-3-((4-phenyloxazol-2-yl)amino)phenyl)butanoate

A mixture of methyl 3-(3-amino-4-(diisobutylamino)phenyl)butanoate (200 mg, 0.625 mmol), 2-chloro-4-phenyloxazole (112 mg, 0.625 mmol) and TsOH (21.5 mg, 0.125 mmol) in i-PrOH (2 mL) was stirred at 80° C. overnight. After the reaction was cooled down to room temperature, it was partitioned between EtOAc (10 mL) and water (5 mL). The layers were separated and the organic layer was washed with brine, dried over Na$_2$SO$_4$, and concentrated. The residue was purified by preparative TLC (10% EtOAc in petroleum ether) to give methyl 3-(4-(diisobutylamino)-3-((4-phenyloxazol-2-yl)amino)phenyl)butanoate (67 mg, 23% yield). LCMS (M+H)$^+$: m/z=464.5.

Step B 3-(4-(Diisobutylamino)-3-((4-phenyloxazol-2-yl)amino)phenyl)butanoic Acid A mixture of methyl 3-(4-(diisobutylamino)-3-((4-phenyloxazol-2-yl)amino)phenyl)butanoate (67 mg, 0.145 mmol) and NaOH (1 N, 1.5 mL, 1.5 mmol) in MeOH (5 mL) was stirred at room temperature for 1 hr before acidified with 1 N HCl to ~pH 7. The resulting mixture was loaded to prep. HPLC column and purified by reverse phase chromatography (40-100% acetonitrile in water, 0.1% formic acid) to give 3-(4-(diisobutylamino)-3-((4-phenyloxazol-2-yl)amino)phenyl)butanoic acid (20.2 mg, 47%) as a white solid. LCMS (M+H)$^+$: m/z=450.2. $^1$H NMR (400 MHz, CDCl$_3$) δ 8.62 (s, 1H), 8.37 (d, J=2.0 Hz, 1H), 7.85-7.74 (m, 2H), 7.56 (s, 1H), 7.42 (t, J=7.7 Hz, 2H), 7.31 (t, J=7.4 Hz, 1H), 7.13 (d, J=8.1 Hz, 1H), 6.83 (dd, J=8.1, 2.0 Hz, 1H), 3.34 (dq, J=13.5, 6.8 Hz, 1H), 2.77 (dd, J=15.5, 6.1 Hz, 1H), 2.68-2.55 (m, 5H), 1.73 (dt, J=13.5, 6.7 Hz, 2H), 1.40 (d, J=6.9 Hz, 3H), 0.94 (d, J=6.6 Hz, 12H).

Example 4

3-(4-(Diisobutylamino)-3-((4-isopropyloxazol-2-yl)amino)phenyl)butanoic Acid

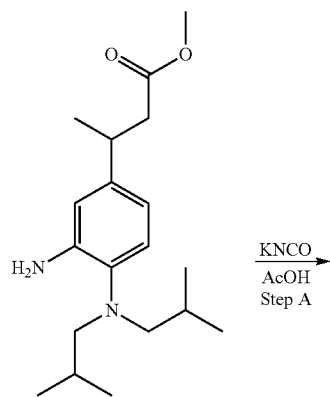

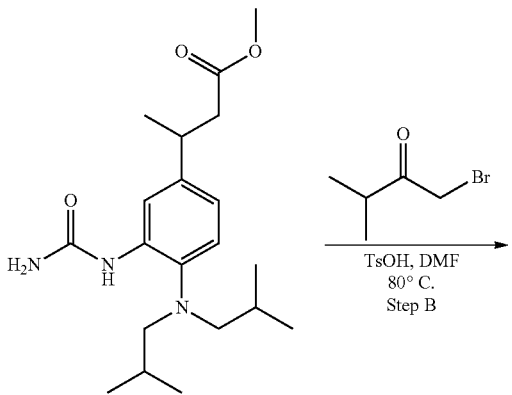

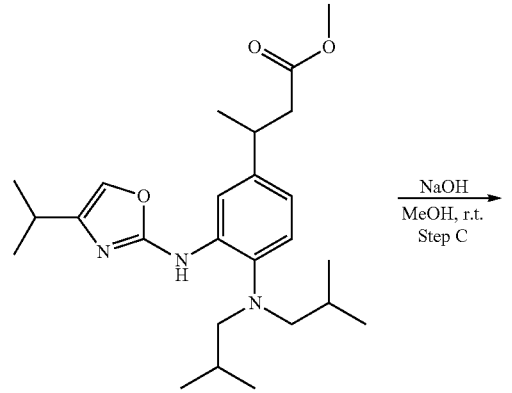

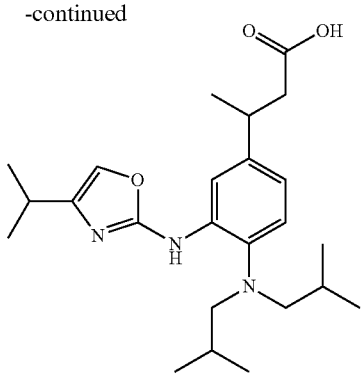

Step A

Methyl 3-(4-(diisobutylamino)-3-ureidophenyl)butanoate

To a solution of methyl 3-(3-amino-4-(diisobutylamino)phenyl)butanoate (1.5 g, 4.7 mmol) in AcOH/water (8 mL/3 mL) was added potassium cyanate (1.9 g, 23 mmol) in one portion. The resulting mixture was stirred at 80° C. for 2 hrs. The reaction was then cooled to room temperature, quenched with water (40 mL) and extracted with EtOAc (100 mL×3). The combined organic layers were washed with brine (100 mL), dried over $Na_2SO_4$, and concentrated. The residue was purified by silica gel chromatography (20% EtOAc/PE) to give methyl 3-(4-(diisobutylamino)-3-ureidophenyl)butanoate (1.2 g, 71%) as a yellow solid. LCMS $(M+H)^+$: m/z=364.0.

Step B

Methyl 3-(4-(diisobutylamino)-3-((4-isopropyloxazol-2-yl)amino)phenyl)butanoate A mixture of methyl 3-(4-(diisobutylamino)-3-ureidophenyl)butanoate (300 mg, 0.89 mmol), 1-bromo-3-methylbutan-2-one (409 mg, 2.48 mmol) and TsOH (32 mg, 0.17 mmol) in DMF was stirred at room temperature for 2 hrs before heated up to 80° C. for further 3 hrs. The mixture was then partitioned between EtOAc (30 mL) and water (10 mL). The layers were separated and the organic layer was washed with brine (10 mL), dried over $Na_2SO_4$, and concentrated. The residue was purified by prep. TLC (10% EtOAc/PE) to give methyl 3-(4-(diisobutylamino)-3-((4-isopropyloxazol-2-yl)amino)phenyl)butanoate (20 mg, 5%). LCMS $(M+H)^+$: m/z=430.5.

Step C

3-(4-(Diisobutylamino)-3-((4-isopropyloxazol-2-yl)amino)phenyl)butanoic Acid A mixture of methyl 3-(4-(diisobutylamino)-3-((4-isopropyloxazol-2-yl)amino)phenyl)butanoate (20 mg, 0.047 mmol) was stirred with NaOH (1 N, 0.5 mL, 0.5 mmol) in MeOH (5 mL) at room temperature for 1 hr before being acidified with 1 N HCl to ~pH 7. The reaction mixture was purified by reverse phase chromatography (40-100% acetonitrile in water, 0.1% formic acid) to give 3-(4-(diisobutylamino)-3-((4-isopropyloxazol-2-yl)amino)phenyl)butanoic acid (9.0 mg, 47%) as a white solid. LCMS (M+H)+: m/z=416.4. ¹H NMR (400 MHz, CDCl₃) δ 8.45 (s, 1H), 8.19 (d, J=2.0 Hz, 1H), 7.09 (d, J=8.1 Hz, 1H), 6.93 (d, J=1.3 Hz, 1H), 6.78 (dd, J=8.1, 2.0 Hz, 1H), 3.32-3.26 (m, 1H), 2.82 (tt, J=8.0, 3.4 Hz, 1H), 2.72 (dd, J=15.4, 5.9 Hz, 1H), 2.63-2.54 (m, 5H), 1.76-1.65 (m, 2H), 1.35 (d, J=6.9 Hz, 3H), 1.26 (d, J=6.9 Hz, 6H), 0.91 (d, J=6.6 Hz, 12H).

Example 5

3-(4-(diisobutylamino)-3-((4-(trifluoromethyl)oxazol-2-yl)amino)phenyl)butanoic Acid

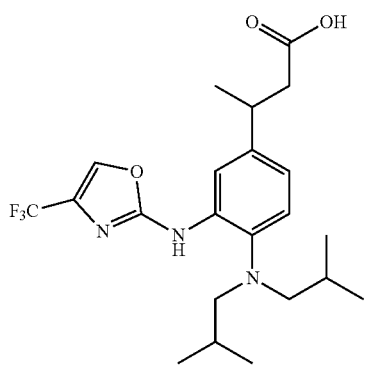 [SMILES: CC(C)CN(CC(C)C)c1ccc(C(C)CC(=O)O)cc1Nc1nc(C(F)(F)F)co1]

The title compound, 3-(4-(diisobutylamino)-3-((4-(trifluoromethyl)oxazol-2-yl)amino)phenyl)butanoic acid, was made in a similar manner to example 4 and isolated (9.9 mg, 2.6% over two steps) as a white powder. LCMS (M+H)*: m/z=442.5. ¹H NMR (400 MHz, CDCl₃) δ 8.80 (s, 1H), 8.11 (d, J=2.0 Hz, 1H), 7.56 (q, J=1.6 Hz, 1H), 7.13 (d, J=8.2 Hz, 1H), 6.86 (dd, J=8.2, 2.0 Hz, 1H), 3.31 (dd, J=15.2, 6.7 Hz, 1H), 2.76-2.53 (m, 6H), 1.69 (td, J=13.5, 6.8 Hz, 2H), 1.35 (d, J=6.9 Hz, 3H), 0.92 (d, J=6.6 Hz, 12H).

Synthesis of Ethyl 3-(3-amino-4-(cyclohexyl(isobutyl)amino)phenyl)butanoate

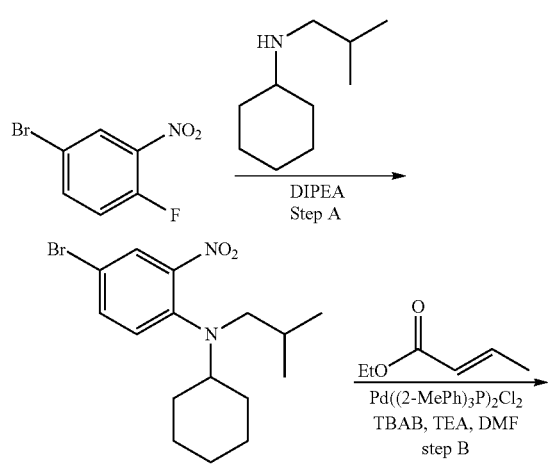

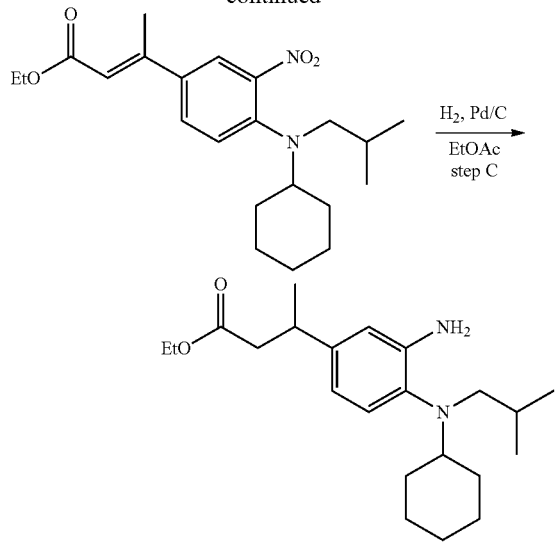

Step A 4-bromo-N-cyclohexyl-N-isobutyl-2-nitroaniline

To a solution of 4-bromo-1-fluoro-2-nitrobenzene (60 g, 0.27 mol), N-isobutylcyclohexanamine (52 g, 0.33 mol) in 1-methyl-2-pyrrolidinone (300 mL) was added DIEA (70 g, 0.55 mol) at room temperature. The resulting mixture was stirred at 120° C. overnight, then cooled down and quenched with water (350 mL). The layers were separated and the aqueous layer was extracted with EtOAc (3×300 mL). The combined organic layers were washed with brine (800 mL), dried over Na₂SO₄ and concentrated under reduced pressure to give a red solid which was subject to trituration with petroleum ether (200 mL). The precipitate was collected by filtration to give 4-bromo-N-cyclohexyl-N-isobutyl-2-nitroaniline (74 g, 77%) as a red solid. LCMS (M+H)+: m/z=355.2. ¹H NMR (400 MHz, CDCl₃) δ 7.78 (d, J=2.4 Hz, 1H), 7.46 (dd, J=8.9, 2.4 Hz, 1H), 7.04 (d, J=8.9 Hz, 1H), 2.91-2.82 (m, 3H), 1.84-1.73 (m, 4H), 1.60 (dd, J=13.5, 6.6 Hz, 2H), 1.43-1.33 (m, 2H), 1.18 (td, J=12.9, 6.5 Hz, 2H), 1.10-1.00 (m, 1H), 0.85 (d, J=6.6 Hz, 6H).

Step B

Ethyl (E)-3-(4-(cyclohexyl(isobutyl)amino)-3-nitrophenyl)but-2-enoate

To a solution of 4-bromo-N-cyclohexyl-N-isobutyl-2-nitroaniline (32 g, 0.09 mol), tetrabutylammonium bromide (5.8 g, 0.018 mol), ethyl (E)-but-2-enoate (30.8 g, 0.27 mol), TEA (18.3 g, 0.18 mol) in DMF (350 mL) was added dichlorobis(tris(2-tolyl) phosphine)palladium (3.54 g, 4.5 mmol) in one portion. The resulting mixture was purged with N₂ (3×), and stirred at 110° C. overnight. The mixture was cooled to room temperature, the solids were filtered, and the filtrate was concentrated under reduced pressure. The residue was partitioned between EtOAc (300 mL) and water (150 mL). The combined organic layers were washed with brine (150 mL), dried over Na₂SO₄, and concentrated. The crude product was purified by silica gel chromatography (5-15% EtOAc/PE) to give (E)-ethyl 3-(4-(cyclohexyl(isobutyl)amino)-3-nitrophenyl)but-2-enoate (18.0 g, 98%)

as a red oil. LCMS (M+H)⁺: m/z=389.1. ¹H NMR (400 MHz, CDCl₃) δ 7.82 (d, J=2.4 Hz, 1H), 7.52 (dd, J=8.8, 2.4 Hz, 1H), 7.10 (d, J=8.8 Hz, 1H), 6.13 (d, J=1.2 Hz, 1H), 4.21 (q, J=7.1 Hz, 2H), 3.00-2.87 (m, 3H), 2.55 (d, J=1.1 Hz, 3H), 1.87-1.57 (m, 6H), 1.41 (qd, J=12.2, 3.0 Hz, 2H), 1.35-1.28 (m, 3H), 1.21 (ddd, J=13.0, 8.1, 3.4 Hz, 2H), 1.06 (ddd, J=12.7, 8.1, 3.3 Hz, 1H), 0.88 (d, J=6.6 Hz, 6H).

Step C

Ethyl 3-(3-amino-4-(cyclohexyl(isobutyl)amino) phenyl)butanoate

To a solution of (E)-ethyl 3-(4-(cyclohexyl(isobutyl) amino)-3-nitrophenyl)but-2-enoate (10 g, 0.026 mol) in EtOAc (250 mL) was added 10% Pd/C (2.0 g) at room temperature. The reaction was purged with N₂ (3×) and stirred at H₂ atmosphere at 50° C. overnight. The reaction was cooled to room temperature and the catalyst was filtered off. The filtrate was concentrated to give ethyl 3-(3-amino-4-(cyclohexyl(isobutyl)amino)phenyl)butanoate (9.6 g, 91%) as a yellow oil. LCMS (M+H)⁺: m/z=361.3. ¹H NMR (400 MHz, CDCl₃) δ 6.95 (d, J=8.1 Hz, 1H), 6.59 (d, J=2.1 Hz, 1H), 6.53 (dd, J=8.1, 2.1 Hz, 1H), 4.23-3.82 (m, 4H), 3.19-3.07 (m, 1H), 2.95-2.40 (m, 5H), 1.82 (d, J=11.5 Hz, 2H), 1.73 (d, J=12.2 Hz, 2H), 1.58 (d, J=12.2 Hz, 1H), 1.49-1.23 (m, 7H), 1.20-1.13 (m, 4H), 1.10-1.02 (m, 1H), 0.81 (d, J=6.6 Hz, 6H).

Example 6

3-(3-((1H-Benzo[d]imidazol-2-yl)amino)-4-(cyclohexyl(isobutyl)amino)phenyl)butanoic acid

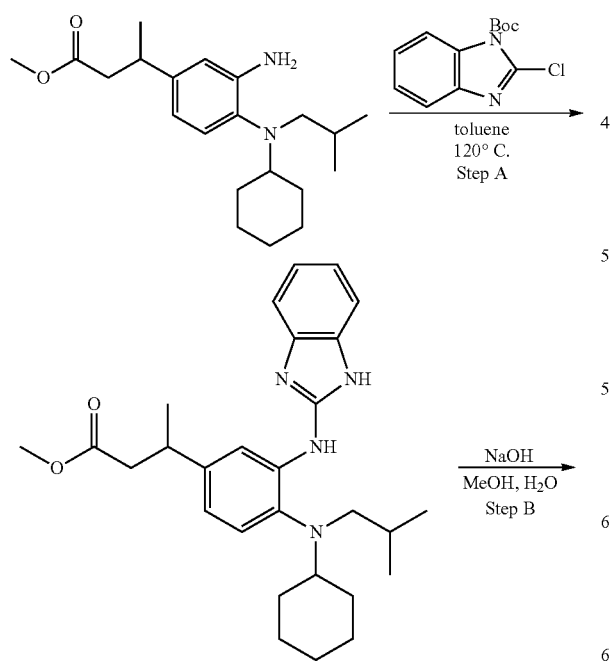

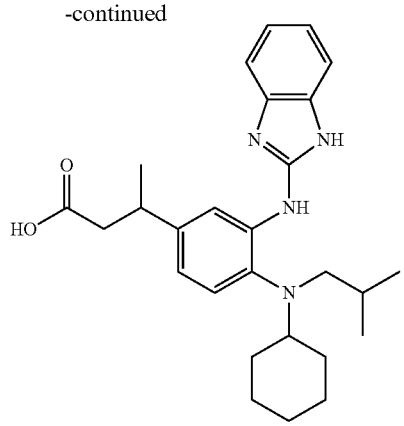

Step A

Methyl 3-(3-((1H-benzo[d]imidazol-2-yl)amino)-4-(cyclohexyl(isobutyl)amino)phenyl)butanoate A mixture of methyl 3-(3-amino-4-(cyclohexyl(isobutyl) amino)phenyl)butanoate (100 mg, 0.29 mmol) and tert-butyl 2-chloro-1H-benzo[d]imidazole-1-carboxylate (109 mg, 0.43 mmol) in toluene (2 mL) was stirred at 110° C. overnight. The mixture was cooled to room temperature, quenched with water (5 mL) and extracted with EtOAc (10 mL×2). The combined organic layers were washed with brine (7 mL), dried over Na₂SO₄, and concentrated. The residue was purified by preparative TLC (20% EtOAc/PE) to give methyl 3-(3-((1H-benzo[d]imidazol-2-yl)amino)-4-(cyclohexyl(isobutyl)amino)phenyl)butanoate (60 mg, 45% yield). LCMS (M+H)⁺: m/z=463.6.

Step B 3-(3-((1H-Benzo[d]imidazol-2-yl)amino)-4-(cyclohexyl(isobutyl)amino)phenyl)butanoic Acid To a solution of methyl 3-(3-((1H-benzo[d]imidazol-2-yl)amino)-4-(cyclohexyl(isobutyl)amino)phenyl)butanoate (60 mg, 0.13 mmol) in MeOH (5 mL) was added NaOH (1 N, 1.3 mL, 1.3 mmol). The resulting mixture was stirred at 50° C. for 2 hrs before acidified with 1 N HCl to ~pH 7. The reaction mixture was purified by reverse phase chromatography (40-100% ACN in water, 0.1% formic acid) to give 3-(3-((1H-benzo[d]imidazol-2-yl)amino)-4-(cyclohexyl(isobutyl)amino)phenyl)butanoic acid (32 mg, 55%) as a white solid. LCMS (M+H)⁺: m/z=449.7. ¹H NMR (400 MHz, DMSO-d₆) δ 11.82 (s, 1H), 8.55 (d, J=1.8 Hz, 1H), 8.33 (s, 1H), 8.18 (s, 1H), 7.34 (s, 2H), 7.17 (d, J=8.1 Hz, 1H), 7.01 (dd, J=5.7, 3.1 Hz, 2H), 6.89-6.77 (m, 1H), 3.15 (m, 1H), 2.82 (s, 2H), 2.56 (dd, J=15.3, 6.3 Hz, 2H), 2.48-2.42 (m, 1H), 1.95 (d, J=11.0 Hz, 2H), 1.70 (d, J=11.6 Hz, 2H), 1.52 (d, J=11.6 Hz, 1H), 1.38-1.21 (m, 6H), 1.19-0.98 (m, 3H), 0.84 (d, J=6.3 Hz, 6H).

Example 7

3-(3-((3-Chloro-1,2,4-thiadiazol-5-yl)amino)-4-(cyclohexyl(isobutyl)amino)phenyl)butanoic Acid

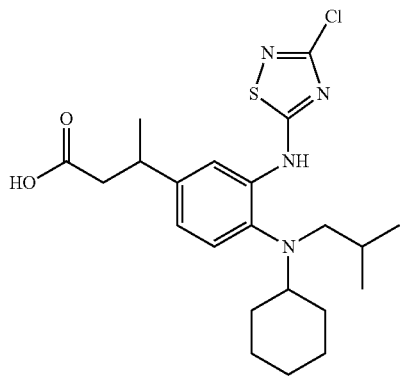

The title compound, 3-(3-((3-chloro-1,2,4-thiadiazol-5-yl)amino)-4-(cyclohexyl(isobutyl)amino)phenyl)butanoic acid, was made in a similar manner to example 6 and isolated (110 mg, 57% over two steps) as white powder. LCMS (M+H)$^+$: m/z=451.6. $^1$H NMR (400 MHz, CDCl$_3$) δ 9.36 (s, 1H), 7.11 (dd, J=11.4, 5.0 Hz, 2H), 6.89 (dd, J=8.2, 1.9 Hz, 1H), 3.29-3.21 (m, 1H), 2.73 (d, J=6.6 Hz, 2H), 2.59 (ddd, J=23.8, 15.7, 7.4 Hz, 2H), 2.46 (ddd, J=11.4, 7.4, 3.4 Hz, 1H), 1.80 (d, J=11.6 Hz, 2H), 1.67 (d, J=12.6 Hz, 2H), 1.51 (d, J=12.3 Hz, 1H), 1.37-1.25 (m, 4H), 1.20-0.91 (m, 5H), 0.76 (d, J=6.6 Hz, 6H).

Example 8

3-(3-(Benzo[d]oxazol-2-ylamino)-4-(cyclohexyl(isobutyl)amino)phenyl)butanoic Acid

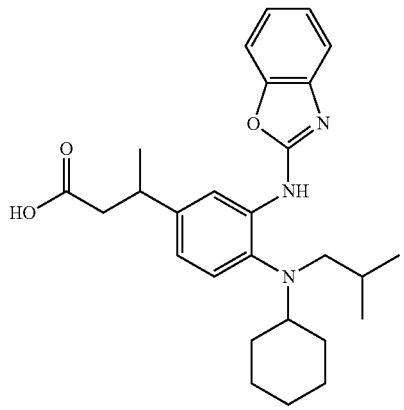 [SMILES: CC(C)CN(c1ccc(C(C)CC(=O)O)cc1Nc1nc2ccccc2o1)C1CCCCC1]

The title compound, 3-(3-(benzo[d]oxazol-2-ylamino)-4-(cyclohexyl(isobutyl)amino)phenyl)butanoic acid, was made in a similar manner to example 7 and isolated (45 mg, 32% yield over two steps) was obtained as a white powder. LCMS (M+H)$^+$: m/z=450.4. $^1$H NMR (400 MHz, CDCl$_3$) δ 8.79 (s, 1H), 8.26 (d, J=2.0 Hz, 1H), 7.55 (d, J=7.5 Hz, 1H), 7.35 (d, J=7.9 Hz, 1H), 7.23 (td, J=7.7, 1.0 Hz, 1H), 7.13 (ddd, J=12.5, 6.5, 2.6 Hz, 2H), 6.87 (dd, J=8.1, 2.0 Hz, 1H), 3.42-3.32 (m, 1H), 2.99-2.53 (m, 5H), 1.92 (d, J=11.4 Hz, 2H), 1.74 (d, J=12.4 Hz, 2H), 1.57 (d, J=12.1 Hz, 1H), 1.51-1.26 (m, 6H), 1.17 (dd, J=25.3, 12.5 Hz, 2H), 1.10-1.01 (m, 1H), 0.87 (d, J=6.4 Hz, 6H).

Example 9

3-(3-(Benzo[d]thiazol-2-ylamino)-4-(cyclohexyl(isobutyl)amino)phenyl)butanoic Acid

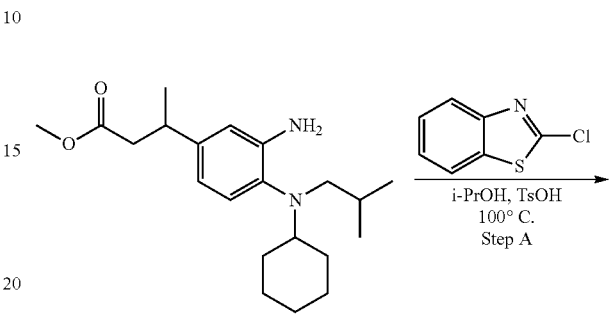

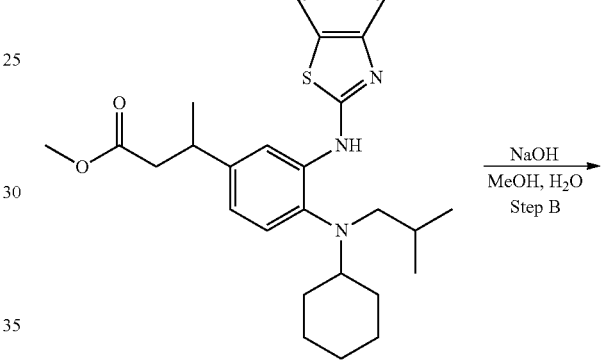

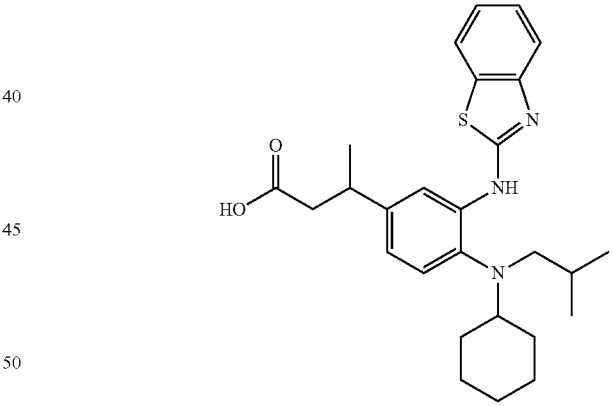

Step A

Methyl 3-(3-(benzo[d]thiazol-2-ylamino)-4-(cyclohexyl(isobutyl)amino)phenyl)butanoate A mixture of methyl 3-(3-amino-4-(cyclohexyl(isobutyl)amino)phenyl)butanoate (100 mg, 0.29 mmol), 2-chlorobenzo[d]thiazole (76 mg, 0.45 mmol) and TsOH (16 mg, 0.09 mmol) in i-PrOH (2 mL) was stirred at 120° C. for 2 hrs, then cooled to room temperature, quenched with water (5 mL) and extracted with EtOAc (10 mL×2). The combined organic layers was washed with brine (7 mL), dried over Na₂SO₄, and concentrated to give intermediate 20, which was used in the next step without purification. LCMS (M+H)⁺: m/z=480.4.

Step B 3-(3-(Benzo[d]thiazol-2-ylamino)-4-(cyclohexyl(isobutyl)amino)phenyl)butanoic Acid Methyl 3-(3-(benzo[d]thiazol-2-ylamino)-4-(cyclohexyl(isobutyl)amino)phenyl)butanoate was hydrolyzed with NaOH (1 N) to give 3-(3-(benzo[d]thiazol-2-ylamino)-4-(cyclohexyl(isobutyl)amino)phenyl)butanoic acid as a white powder (18.4 mg, 11% over 2 steps) after reverse phase chromatography (40-100% ACN/water, 0.1% formic acid). LCMS (M+H)⁺: m/z=466.2. ¹H NMR (400 MHz, CDCl₃) δ 8.10 (d, J=1.8 Hz, 1H), 7.71 (d, J=8.0 Hz, 1H), 7.64 (d, J=7.9 Hz, 1H), 7.38-7.32 (m, 1H), 7.19-7.09 (m, 2H), 6.87 (dd, J=8.1 Hz, 2.0 Hz, 1H), 3.39-3.28 (m, 1H), 2.87-2.69 (m, 3H), 2.60 (ddd, J=12.2 Hz, 11.3 Hz, 6.2 Hz, 2H), 1.89 (d, J=11.0 Hz, 2H), 1.72 (d, J=12.8 Hz, 2H), 1.54 (d, J=11.9 Hz, 1H), 1.49-1.21 (m, 7H), 1.11 (dt, J=19.6 Hz, 9.8 Hz, 2H), 0.86 (d, J=6.6 Hz, 6H).

Example 10

3-(4-(Cyclohexyl(isobutyl)amino)-3-((4-phenyloxazol-2-yl)amino)phenyl)butanoic Acid

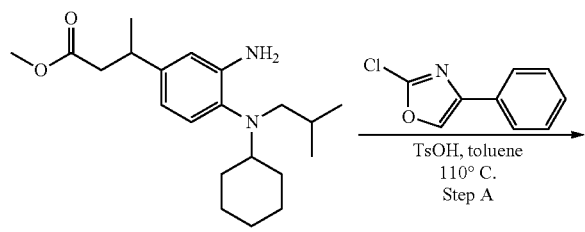

15

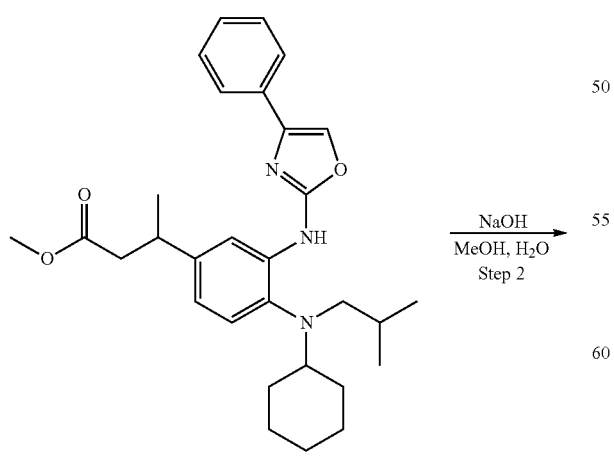

22

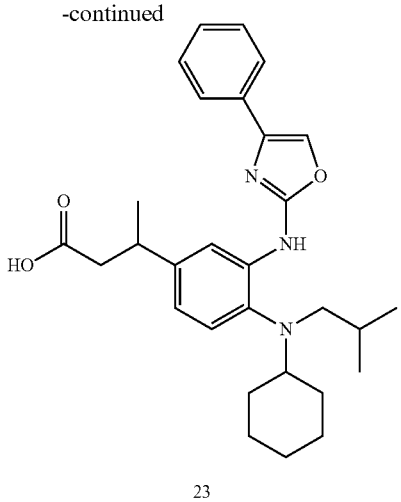

23

Methyl 3-(4-(cyclohexyl(isobutyl)amino)-3-((4-phenyloxazol-2-yl)amino)phenyl)butanoate A mixture of methyl 3-(3-amino-4-(cyclohexyl(isobutyl)amino)phenyl)butanoate (120 mg, 0.35 mmol), 2-chloro-4-phenyloxazole (93 mg, 0.52 mmol) and TsOH (10 mg, 0.06 mmol) in toluene (2 mL) was stirred at 110° C. overnight then cooled to room temperature, quenched with water (5 mL) and extracted with EtOAc (10 mL×2). The combined organic layer was washed with brine, dried over Na₂SO₄, and concentrated. The residue was purified by reverse phase chromatography (40-100% ACN/water, 0.1% formic acid) to give methyl 3-(4-(cyclohexyl(isobutyl)amino)-3-((4-phenyloxazol-2-yl)amino)phenyl)butanoate (60 mg, 40% yield). LCMS (M+H)⁺: m/z=490.4.

Step B 3-(4-(Cyclohexyl(isobutyl)amino)-3-((4-phenyloxazol-2-yl)amino)phenyl)butanoic Acid The title compound, 3-(4-(cyclohexyl(isobutyl)amino)-3-((4-phenyloxazol-2-yl)amino)phenyl)butanoic acid, was prepared in a manner similar to example 6 and was isolated (39 mg, 67%) as white powder. LCMS (M+H)⁺: m/z=476.6. ¹H NMR (400 MHz, CDCl₃) δ 8.43 (s, 1H), 8.26 (d, J=2.0 Hz, 1H), 7.75-7.68 (m, 2H), 7.49 (s, 1H), 7.35 (dd, J=10.5, 4.7 Hz, 2H), 7.23 (t, J=7.4 Hz, 1H), 7.04 (d, J=8.1 Hz, 1H), 6.74 (dd, J=8.1, 2.1 Hz, 1H), 3.27 (dq, J=13.2, 6.7 Hz, 1H), 2.91-2.47 (m, 5H), 1.82 (s, 2H), 1.67 (d, J=12.7 Hz, 2H), 1.51 (d, J=12.2 Hz, 1H), 1.44-1.31 (m, 4H), 1.09 (ddd, J=52.5, 26.5, 12.1 Hz, 5H), 0.79 (d, J=5.8 Hz, 6H).

Synthesis of Ethyl 3-(3-amino-4-(diisobutylamino)phenyl)butanoate

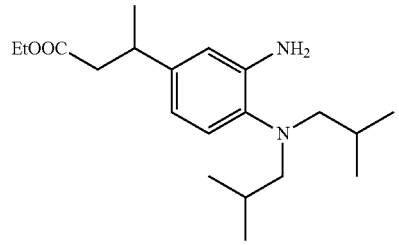 [SMILES: CCOC(=O)CC(C)c1ccc(N(CC(C)C)CC(C)C)c(N)c1]

Intermediate ethyl 3-(3-amino-4-(diisobutylamino)phenyl)butanoate was made in a manner similar to methyl 3-(3-amino-4-(diisobutylamino)phenyl)butanoate. $^1$H NMR (400 MHz, CHLOROFORM-d) δ 6.97 (d, J=8.0 Hz, 1H), 6.59-6.52 (m, 2H), 4.08 (q, J=7.1 Hz, 4H), 3.13 (d, J=8.5 Hz, 1H), 2.60-2.52 (m, 5H), 2.49-2.41 (m, 1H), 1.72 (td, J=6.8, 13.5 Hz, 2H), 1.25 (d, J=6.9 Hz, 3H), 1.17 (t, J=7.1 Hz, 3H), 0.89 (d, J=6.6 Hz, 12H).

Example 11 and Example 12

3-(3-((2-chloropyrimidin-4-yl)amino)-4-(diisobutylamino)phenyl)butanoic Acid and 3-(4-(diisobutylamino)-3-((2-methoxypyrimidin-4-yl)amino)phenyl)butanoic Acid

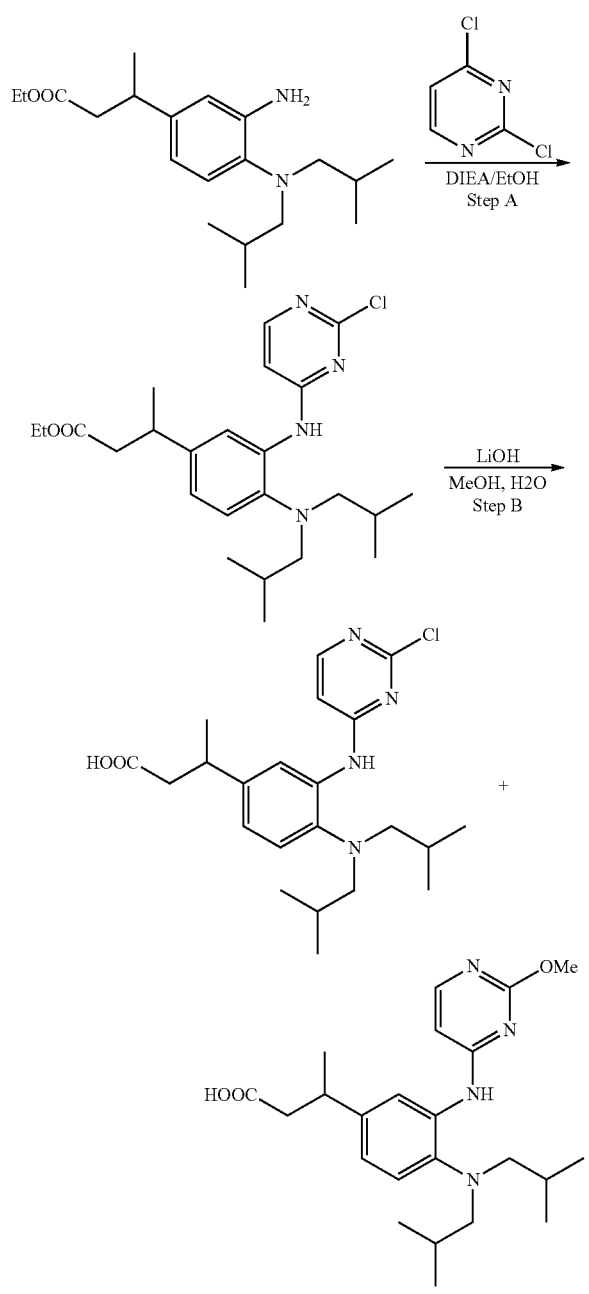

Step A

Ethyl 3-(3-((2-chloropyrimidin-4-yl)amino)-4-(diisobutylamino)phenyl)butanoate

A mixture of ethyl 3-(3-amino-4-(diisobutylamino)phenyl)butanoate (98 mg, 0.293 mmol), 2,4-dichloropyrimidine (43.6 mg, 0.293 mmol), ethanol (2 mL) and DIEA (0.184 mL, 1.055 mmol) was stirred at 95° C. for 24 h. Additional DIEA (0.3 mL) was added and the reaction was stirred at 110° C. for 2.5 h. The mixture was partitioned between EtOAc and water. The organic phase was dried over Na$_2$SO$_4$, concentrated, and purified by silica gel chromatography (EtOAc/hexanes 0-100%), to give ethyl 3-(3-((2-chloropyrimidin-4-yl)amino)-4-(diisobutylamino)phenyl)butanoate (53 mg, 0.116 mmol, 39.7% yield). LCMS (M+1)$^+$: 447.39. $^1$H NMR (400 MHz, CHLOROFORM-d) δ ppm 0.90 (d, J=6.59 Hz, 12H), 1.18 (t, J=7.14 Hz, 3H), 1.35 (d, J=6.96 Hz, 3H), 1.70 (dt, J=13.51, 6.71 Hz, 2H), 2.45-2.72 (m, 6H), 3.23-3.36 (m, 1H), 4.10 (q, J=7.14 Hz, 2H), 6.52 (d, J=5.86 Hz, 1H), 6.93 (dd, J=8.24, 1.83 Hz, 1H), 7.14 (d, J=8.06 Hz, 1H), 8.13 (d, J=5.86 Hz, 1H), 8.22 (br. s., 1H), 8.63 (br. s., 1H).

Step B 3-(3-((2-Chloropyrimidin-4-yl)amino)-4-(diisobutylamino)phenyl)butanoic Acid and 3-(4-(Diisobutylamino)-3-((2-methoxypyrimidin-4-yl)amino)phenyl)butanoic Acid To a solution of ethyl 3-(3-((2-chloropyrimidin-4-yl)amino)-4-(diisobutylamino)phenyl)butanoate (51 mg, 0.112 mmol) in MeOH (1.5 mL) was added LiOH (0.559 mL, 0.559 mmol) (1 M/water) and the mixture was stirred at ambient temperature for 1 h and then at 50° C. for 1.5 h. The mixture was purified by reverse phase chromatography (MeCN/water 10-90%, 0.05% TFA) to provide a late eluting fraction, 3-(3-((2-chloropyrimidin-4-yl)amino)-4-(diisobutylamino)phenyl)butanoic acid, as the trifluoroacetic acid salt (39.4 mg, 0.071 mmol, 63.5% yield) as the as a yellowish solid foam. LCMS (M+1)$^+$: 419.39. $^1$NMR (400 MHz, DMSO-d$_6$) δ ppm 0.80 (d, J=6.59 Hz, 12H), 1.21 (d, J=6.96 Hz, 3H), 1.65 (dt, J=13.37, 6.68 Hz, 2H), 2.45-2.50 (m, 2H), 2.65 (d, J=6.96 Hz, 4H), 3.03-3.22 (m, 1H), 5.2-5.4 (broad s, 1H), 6.58 (d, J=4.94 Hz, 1H), 7.06 (d, J=8.06 Hz, 1H), 7.18 (d, J=8.24 Hz, 1H), 7.57 (br. s., 1H), 8.12 (d, J=5.86 Hz, 1H), 8.95 (s, 1H). And an early eluting fraction provided 3-(4-(diisobutylamino)-3-((2-methoxypyrimidin-4-yl)amino)phenyl)butanoic acid as the trifluoroacetic acid salt (20.8 mg, 0.039 mmol, 35.2% yield) as a sticky foam. LCMS (M+1)$^+$: 415.42. $^1$H NMR (400 MHz, CHLOROFORM-d) δ ppm 0.82-0.95 (m, 12H), 1.35 (d, J=6.96 Hz, 3H), 1.73 (dt, J=13.19, 6.59 Hz, 2H), 2.57-2.78 (m, 6H), 3.24-3.38 (m, 1H), 4.19 (br. s., 3H), 6.36-6.66 (m, 1H), 7.16 (d, J=7.87 Hz, 1H), 7.25-7.33 (m, 2H), 8.27 (br. s., 2H), 11.42-12.09 (m, 1H).

Example 13 and Example 14

3-(3-((2-Chloropyrimidin-4-yl)amino)-4-(cyclohexyl(isobutyl)amino) phenyl)butanoic Acid and 3-(4-(Cyclohexyl(isobutyl)amino)-3-((2-methoxypyrimidin-4-yl)amino)phenyl)butanoic Acid

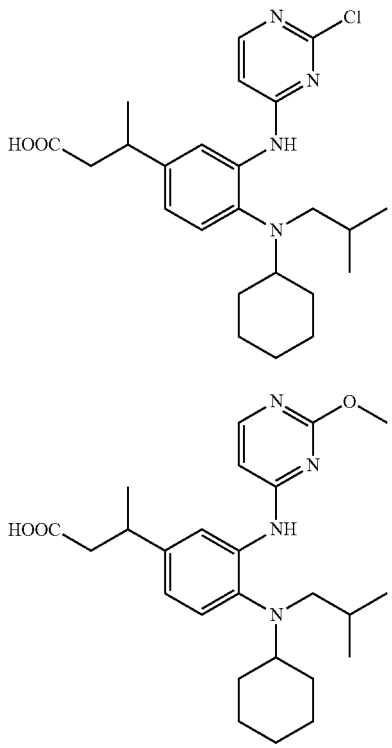

The title compounds, 3-(3-((2-chloropyrimidin-4-yl)amino)-4-(cyclohexyl(isobutyl)amino)phenyl)butanoic acid and 3-(4-(cyclohexyl(isobutyl)amino)-3-((2-methoxypyrimidin-4-yl)amino)phenyl)butanoic acid, were made in a similar manner to example 11/12 using methyl 3-(3-amino-4-(cyclohexyl(isobutyl)amino)phenyl)butanoate. 3-(3-((2-chloropyrimidin-4-yl)amino)-4-(cyclohexyl(isobutyl)amino)phenyl)butanoic acid. LCMS (M+1)$^+$: 445.47. $^1$H NMR (400 MHz, DMSO-$d_6$) δ ppm 0.79 (d, J=6.59 Hz, 6H), 0.98 (br. s., 3H), 1.11-1.41 (m, 7H), 1.47 (br. s., 1H), 1.58-1.76 (m, 4H), 2.47 (s, 1H), 2.54-2.69 (m, 1H), 2.76 (d, J=6.59 Hz, 2H), 3.05-3.18 (m, 1H), 6.75 (d, J=4.21 Hz, 1H), 7.03 (d, J=8.06 Hz, 1H), 7.14 (d, J=8.24 Hz, 1H), 7.61 (br. s., 1H), 8.12 (d, J=5.86 Hz, 1H), 8.80 (s, 1H), 12.08 (br. s., 1H). 3-(4-(cyclohexyl(isobutyl)amino)-3-((2-methoxypyrimidin-4-yl)amino)phenyl)butanoic acid. LCMS (M+1)$^+$: 441.54. $^1$H NMR (400 MHz, DMSO-$d_6$) δ ppm 0.80 (d, J=6.41 Hz, 6H), 0.93-1.10 (m, 3H), 1.22 (d, J=6.96 Hz, 6H), 1.49 (br. s., 1H), 1.58-1.84 (m, 4H), 2.56 (d, J=12.27 Hz, 1H), 2.79 (d, J=6.23 Hz, 2H), 3.04-3.23 (m, 1H), 3.5-3.7 (br s, 2H), 3.95 (s, 3H), 6.69 (br. s., 1H), 7.07 (d, J=7.87 Hz, 2H), 7.18 (d, J=8.24 Hz, 2H), 7.79 (br. s., 1H), 8.13 (d, J=6.59 Hz, 1H).

Example 15

3-(4-(Diisobutylamino)-3-((2-methylthiazol-5-yl)amino)phenyl)butanoic Acid

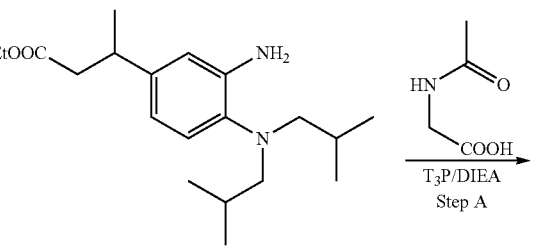

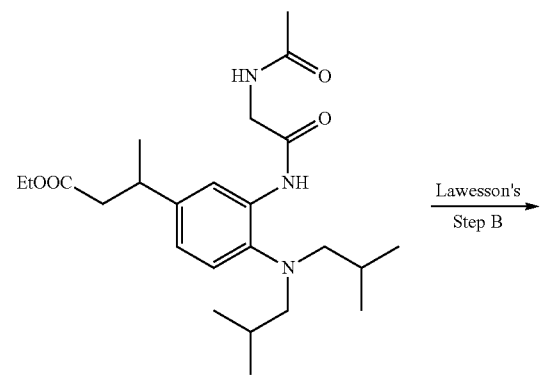

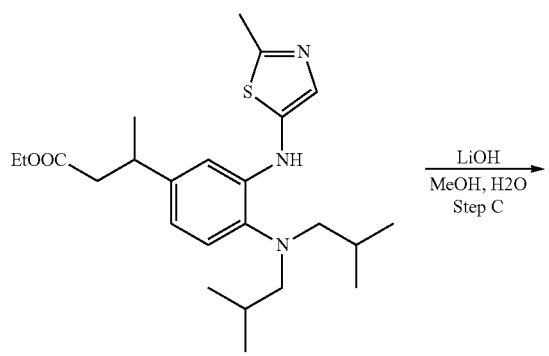

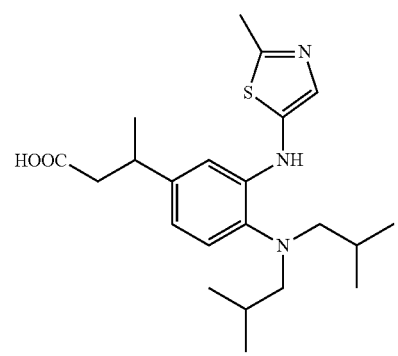

Step A

Ethyl 3-(3-(2-acetamidoacetamido)-4-(diisobutylamino)phenyl)butanoate

To a solution of ethyl 3-(3-amino-4-(diisobutylamino)phenyl)butanoate (147 mg, 0.439 mmol), 2-acetamidoacetic acid (57.2 mg, 0.483 mmol) and DIEA (0.230 mL, 1.318 mmol) in EtOAc (3 mL) was added 2,4,6-tripropyl-1,3,5,2,4,6-trioxatriphosphinane 2,4,6-trioxide (419 mg, 0.659 mmol) (50%/EtOAc) and the mixture was stirred at ambient temperature for 48 h. The mixture was partitioned between EtOAc and water. The organic phase was washed with water, dried over $Na_2SO_4$, concentrated, purified by silica gel chromatography (EtOAc/hexanes 0-50%) to provide ethyl 3-(3-(2-acetamidoacetamido)-4-(diisobutylamino)phenyl)butanoate (197.7 mg, 0.433 mmol, 99% yield). LCMS (M+1)$^+$: 434.46. $^1$H NMR (400 MHz, CHLOROFORM-d) δ ppm 0.91 (d, J=6.41 Hz, 12H), 1.19 (t, J=7.14 Hz, 3H), 1.28-1.34 (m, 3H), 1.66 (dt, J=13.09, 6.64 Hz, 2H), 2.09 (s, 3H), 2.48-2.67 (m, 6H), 3.20-3.35 (m, 1H), 4.02-4.17 (m, 4H), 6.32 (br. s., 1H), 6.94 (d, J=7.69 Hz, 1H), 7.14 (d, J=8.06 Hz, 1H), 8.31 (s, 1H), 9.18 (br. s., 1H).

Step B

Ethyl 3-(4-(diisobutylamino)-3-((2-methylthiazol-5-yl)amino)phenyl)butanoate A mixture of ethyl 3-(3-(2-acetamidoacetamido)-4-(diisobutylamino)phenyl)butanoate (147 mg, 0.322 mmol) and Lawesson's reagent (107 mg, 0.265 mmol) in toluene (3 mL) was heated to 100° C. for 45 min. The mixture was concentrated, purified by silica gel chromatography (EtOAc/hexanes 0-10%) to provide ethyl 3-(4-(diisobutylamino)-3-((2-methylthiazol-5-yl)amino)phenyl)butanoate (92.5 mg, 0.206 mmol, 63.9% yield) as a yellowish thick oil. LCMS (M+1)$^+$: 432.44. $^1$H NMR (400 MHz, CHLOROFORM-d) δ ppm 0.91 (d, J=6.59 Hz, 12H), 1.18 (t, J=7.14 Hz, 3H), 1.25 (d, J=6.96 Hz, 3H), 1.72 (dt, J=13.28, 6.55 Hz, 2H), 2.40-2.50 (m, 1H), 2.52-2.62 (m, 5H), 2.67 (s, 3H), 3.10-3.24 (m, 1H), 4.09 (q, J=7.14 Hz, 2H), 6.68 (dd, J=8.06, 1.65 Hz, 1H), 6.83 (d, J=1.28 Hz, 1H), 7.06 (d, J=8.06 Hz, 1H), 7.14 (br. s., 1H), 7.30 (s, 1H).

Step C

3-(4-(Diisobutylamino)-3-((2-methylthiazol-5-yl)amino)phenyl)butanoic Acid

The title compound, 3-(4-(diisobutylamino)-3-((2-methylthiazol-5-yl)amino)phenyl)butanoic acid, was made in a similar manner to example 11/12 step B. LCMS (M+1)$^+$: 404.44. $^1$H NMR (400 MHz, CHLOROFORM-d) δ ppm 0.91 (d, J=6.59 Hz, 12H), 1.29 (d, J=6.96 Hz, 3H), 1.72 (dt, J=13.14, 6.52 Hz, 2H), 2.46-2.64 (m, 6H), 2.66 (s, 3H), 3.19 (d, J=7.69 Hz, 1H), 6.70 (d, J=7.14 Hz, 1H), 6.86 (s, 1H), 7.07 (d, J=8.06 Hz, 1H), 7.15 (br. s., 1H), 7.32 (s, 1H).

Example 16

3-(4-(Diisobutylamino)-3-((2-phenylthiazol-5-yl)amino)phenyl)butanoic Acid

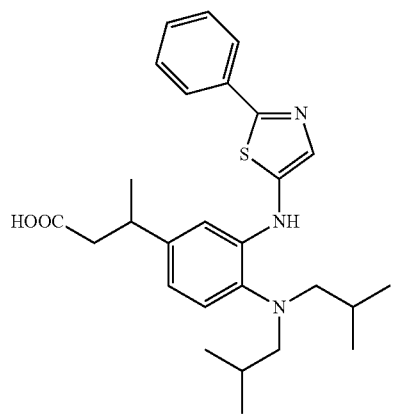 [SMILES: CC(C)CN(CC(C)C)c1ccc(C(C)CC(=O)O)cc1Nc1cnc(-c2ccccc2)s1]

The title compound, 3-(4-(diisobutylamino)-3-((2-phenylthiazol-5-yl)amino)phenyl)butanoic acid, was made in a manner similar to example 15. LCMS (M+1)$^+$: 466.51. $^1$H NMR (400 MHz, DMSO-d$_6$) δ ppm 0.88 (d, J=6.64 Hz, 12H), 1.19 (d, J=6.84 Hz, 3H), 1.66 (dt, J=13.33, 6.71 Hz, 2H), 2.42-2.47 (m, 2H), 2.61 (d, J=7.23 Hz, 4H), 3.02-3.15 (m, 1H), 6.79 (d, J=8.20 Hz, 1H), 7.04 (s, 1H), 7.19 (d, J=8.20 Hz, 1H), 7.36-7.54 (m, 3H), 7.58 (s, 1H), 7.63 (s, 1H), 7.85 (d, J=7.03 Hz, 2H), 12.08 (br. s., 1H).

Example 17

3-(4-(Diisobutylamino)-3-((2-(ethoxycarbonyl)thiazol-5-yl)amino)phenyl)butanoic Acid

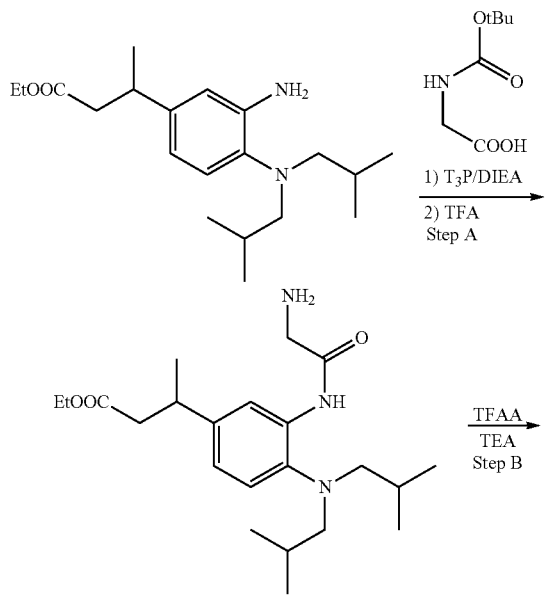

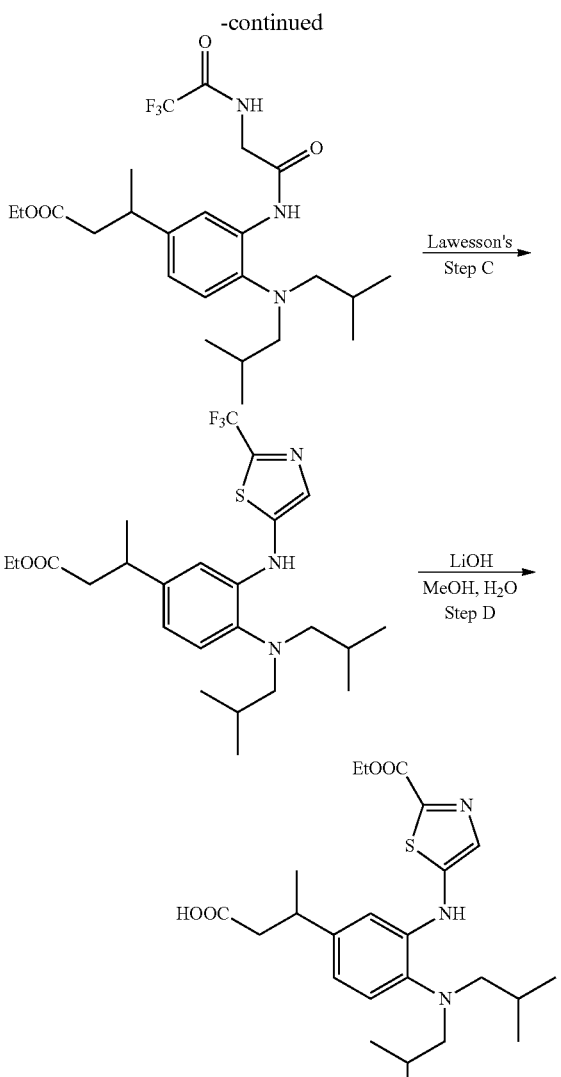

Step A

Ethyl 3-(3-(2-aminoacetamido)-4-(diisobutylamino)phenyl)butanoate

To a solution of ethyl 3-(3-amino-4-(diisobutylamino)phenyl)butanoate (142 mg, 0.425 mmol) in EtOAc (3 mL) was added 2-((tert-butoxycarbonyl)amino)acetic acid (82 mg, 0.467 mmol) and DIEA (0.222 mL, 1.274 mmol) followed by 2,4,6-tripropyl-1,3,5,2,4,6-trioxatriphosphinane 2,4,6-trioxide (405 mg, 0.637 mmol)(50%/EtOAc) and the mixture was stirred at ambient temperature for 18 h. The mixture was washed with water (2×) and the organic phase was dried over $Na_2SO_4$ and concentrated to provide ethyl 3-(3-(2-((tert-butoxycarbonyl)amino)acetamido)-4-(diisobutylamino)phenyl)butanoate (220 mg, 0.447 mmol, 105% yield). This residue was dissolved in dichloromethane (1.5 mL) at 0° C. and TFA (1.5 mL) was added. After stirring for 1 h at ambient temperature, the mixture was concentrated and partitioned between EtOAc and saturated $NaHCO_3$/water. The organic phase was dried over $Na_2SO_4$ and concentrated to provide the ethyl 3-(3-(2-aminoacetamido)-4-(diisobutylamino)phenyl)butanoate (160 mg, 0.409 mmol, 96% yield) as an orange oil. LCMS (M+1)$^+$: 392.52. $^1$H NMR (400 MHz, CHLOROFORM-d) δ ppm 0.90 (d, J=6.44 Hz, 12H), 1.18 (t, J=7.13 Hz, 3H), 1.30 (d, J=7.03 Hz, 3H), 1.65 (dt, J=13.43, 6.66 Hz, 2H), 1.92 (br. s., 3H), 2.46-2.68 (m, 5H), 3.17-3.33 (m, 1H), 3.53 (s, 2H), 4.09 (q, J=7.23 Hz, 2H), 6.91 (dd, J=8.20, 1.95 Hz, 1H), 7.14 (d, J=8.20 Hz, 1H), 8.40 (d, J=1.56 Hz, 1H), 10.01 (br. s., 1H).

Step B

Ethyl 3-(4-(diisobutylamino)-3-(2-(2,2,2-trifluoroacetamido)acetamido)phenyl)butanoate To a solution of ethyl 3-(3-(2-aminoacetamido)-4-(diisobutylamino)phenyl)butanoate (157 mg, 0.401 mmol) in DCM (3 mL) at 0° C. was added TEA (0.140 mL, 1.002 mmol) and TFAA (0.062 mL, 0.441 mmol) and the mixture was stirred at 0° C. for 30 min. The mixture was partitioned between dichloromethane and cold half-saturated $NaHCO_3$/water. The organic phase was concentrated to provide ethyl 3-(4-(diisobutylamino)-3-(2-(2,2,2-trifluoroacetamido)acetamido)phenyl)butanoate (209 mg, 0.386 mmol, 96% yield). LCMS (M+1)$^+$: 488.3. $^1$H NMR (400 MHz, CHLOROFORM-d) δ ppm 0.83-0.97 (m, 12H), 1.18 (t, J=7.14 Hz, 3H), 1.31 (d, J=6.96 Hz, 3H), 1.67 (dt, J=13.41, 6.75 Hz, 2H), 2.49-2.70 (m, 6H), 3.06-3.19 (m, 1H), 4.09 (q, J=7.14 Hz, 2H), 4.17 (d, J=4.21 Hz, 2H), 6.98 (dd, J=8.15, 1.92 Hz, 1H), 7.16 (d, J=8.06 Hz, 1H), 7.33 (br. s., 1H), 8.28 (d, J=1.46 Hz, 1H), 9.30 (br. s., 1H).

Step C

Ethyl 3-(4-(diisobutylamino)-3-((2-(trifluoromethyl)thiazol-5-yl)amino)phenyl)butanoate To a solution of ethyl 3-(4-(diisobutylamino)-3-(2-(2,2,2-trifluoroacetamido)acetamido)phenyl)butanoate (201 mg, 0.371 mmol) in toluene (4 mL) was added Lawesson's reagent (105 mg, 0.260 mmol) and the mixture was stirred at 100° C. under nitrogen atmosphere for 1 h. Additional Lawesson's reagent (70 mg) was added. After 2.5 h the mixture was concentrated and purified by silica gel chromatography (EtOAc/hexanes 0-5%) to provide ethyl 3-(4-(diisobutylamino)-3-((2-(trifluoromethyl)thiazol-5-yl)amino)phenyl)butanoate (143 mg, 0.294 mmol, 79% yield) as a yellow oil. LCMS (M+1)$^+$: 486.2. $^1$H NMR (400 MHz, CHLOROFORM-d) δ ppm 0.82-0.99 (m, 12H), 1.18 (t, J=7.14 Hz, 3H), 1.25-1.35 (m, 3H), 1.71 (d, J=6.04 Hz, 2H), 2.44-2.73 (m, 6H), 3.16-3.34 (m, 1H), 4.09 (q, J=7.14 Hz, 2H), 6.81 (d, J=7.87 Hz, 1H), 7.06 (br. s., 1H), 7.13 (d, J=8.24 Hz, 1H), 7.51 (s, 1H), 7.92 (br. s., 1H).

Step D 3-(4-(Diisobutylamino)-3-((2-(ethoxycarbonyl)thiazol-5-yl)amino)phenyl)butanoic Acid To a solution of ethyl 3-(4-(diisobutylamino)-3-((2-(trifluoromethyl)thiazol-5-yl)amino)phenyl)butanoate (138 mg, 0.284 mmol) in EtOH (3 mL) was added LiOH (1.421 mL, 1.421 mmol)(1 M/water) and the mixture was stirred at ambient temperature for 18 h and then at 60° C. for 18 h. Additional LiOH (1.421 mL, 1.421 mmol) and THF (1 mL) was added and stirring at 70° C. continued for 2 h. The mixture was partitioned between EtOAc and 1N HCl/water. The organic phase was dried over $Na_2SO_4$, concentrated, and purified by silica gel chromatography (EtOAc/hexanes 0-25-100%, product eluted at 25-30%) to provide 3-(4-(diisobutylamino)-3-((2-(ethoxycarbonyl)thiazol-5-yl)amino)phenyl)butanoic acid (35 mg, 0.070 mmol, 24.55% yield) as a yellow oil. LCMS (M+1)$^+$: 462.52. $^1$H NMR (400 MHz, DMSO-d$_6$) δ ppm 0.83 (d, J=6.41 Hz, 12H), 1.21 (d, J=6.96 Hz, 3H), 1.30 (t, J=7.05 Hz, 3H), 1.65 (dt, J=13.19, 6.59 Hz, 2H), 2.47-2.50 (m, 2H), 2.64 (d, J=6.96 Hz, 4H), 3.12 (m, 1H), 4.31 (q, J=7.02 Hz, 2H), 6.90-6.98 (m, 1H), 7.15-7.24 (m, 2H), 7.56 (s, 1H), 8.42 (s, 1H), 12.06 (s, 1H).

Example 18

3-(4-(Diisobutylamino)-3-(pyridin-4-ylamino)phenyl)butanoic Acid

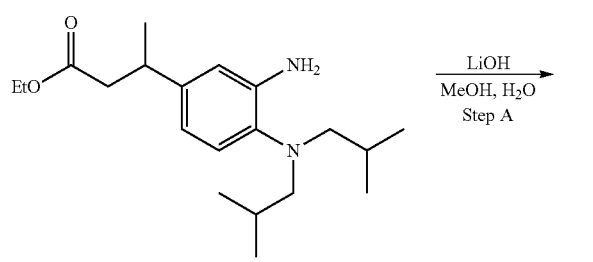

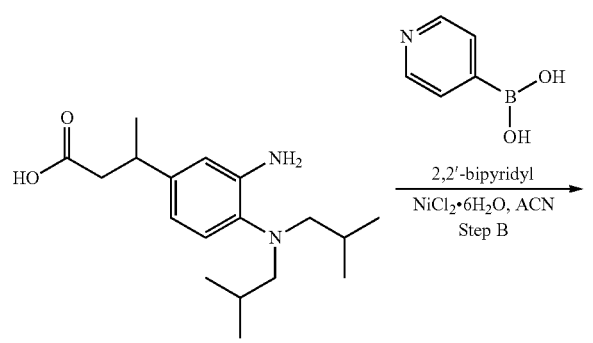

Step A 3-(3-Amino-4-(diisobutylamino)phenyl)butanoic Acid

To a solution of ethyl 3-(3-amino-4-(diisobutylamino)phenyl)butanoate (1.00 g, 2.99 mmol) in water (12 ml) and MeOH (30 ml) was added LiOH (1.016 g, 42.4 mmol) and the reaction mixture was stirred at room temperature for 5 hours. The reaction mixture was acidified to pH 4, most of the methanol was evaporated, the resulting mixture was diluted with EtOAc and the organic layer was separated. The organics were dried over MgSO$_4$ and concentrated to give 3-(3-amino-4-(diisobutylamino)phenyl)butanoic acid (823 mg, 2.69 mmol, 90% yield), which was used directly in the next step without purification. LCMS ESI (M+H)$^+$: m/z=307.3. $^1$H NMR (400 MHz, DMSO-d$_6$) δ ppm 6.92 (d, J=8.06 Hz, 1H) 6.55 (s, 1H) 6.44 (d, J=7.51 Hz, 1H) 2.92-3.01 (m, 1H) 2.31-2.51 (m, 6H) 1.64 (dt, J=13.41, 6.75 Hz, 2H) 1.15 (d, J=6.78 Hz, 3H) 0.85 (d, J=6.59 Hz, 12H).

Step B 3-(4-(Diisobutylamino)-3-(pyridin-4-ylamino)phenyl)butanoic Acid

A solution of 3-(3-amino-4-(diisobutylamino)phenyl)butanoic acid (230 mg, 0.751 mmol), pyridin-4-ylboronic acid (158 mg, 1.285 mmol), 2,2'-bipyridyl (23.42 mg, 0.150 mmol) and NiCl$_2$.6H$_2$O (35.7 mg, 0.150 mmol) in MeCN (3 mL) was stirred at room temperature overnight. The reaction mixture was diluted with EtOAc, washed with water, the organics were separated, concentrated and the residue was purified by reverse phase chromatography (10-90 MeCN/H$_2$O+Formic acid) to give 3-(4-(diisobutylamino)-3-(pyridin-4-ylamino)phenyl)butanoic acid (9 mg, 0.022 mmol, 2.97% yield). LCMS ESI (M+H)$^+$: m/z=384.4. $^1$H NMR (400 MHz, DMSO-d$_6$): δ ppm 8.17 (d, J=6.0 Hz, 2H), 7.58 (s, 1H), 7.10-7.18 (m, 2H), 6.92-6.98 (m, 1H), 6.84 (d, J=6.2 Hz, 2H), 3.05-3.17 (m, 1H), 2.62 (d, J=7.1 Hz, 4H), 2.42-2.51 (m, 2H), 1.65 (dt, J=13.4, 6.7 Hz, 2H), 1.21 (d, J=7.0 Hz, 3H), 0.80 (d, J=6.4 Hz, 12H)

Example 19

3-(4-(Cyclohexyl(isobutyl)amino)-3-(cyclohexylamino)phenyl)butanoic Acid

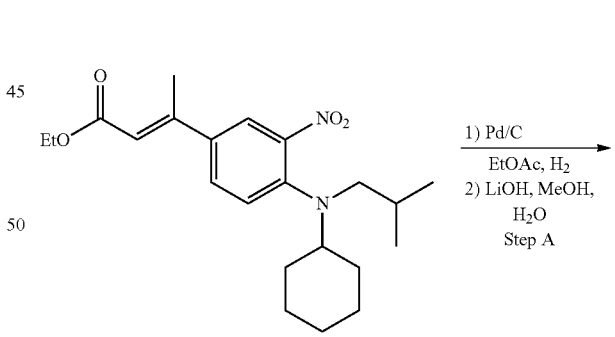

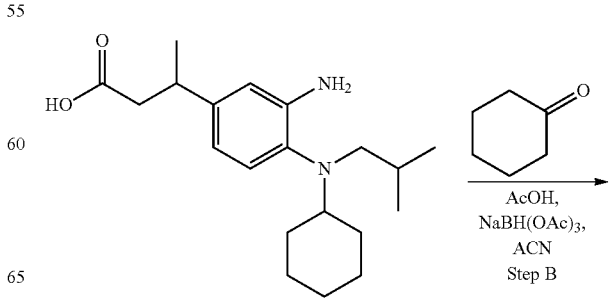

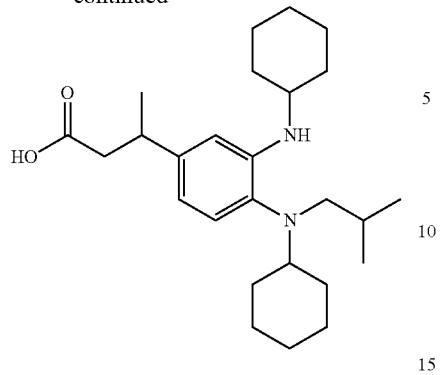

Step A

3-(3-Amino-4-(cyclohexyl(isobutyl)amino)phenyl)butanoic Acid

A suspension of (E)-ethyl 3-(4-(cyclohexyl(isobutyl)amino)-3-nitrophenyl)but-2-enoate (2.3 g, 5.92 mmol) and Pd/C (0.63 g, 0.592 mmol) in EtOAc was hydrogenated at 50 psi for 3 hours. The catalyst was filtered off through a plug of celite and the filtrate was concentrated to give a wine-red oil. This oil was dissolved in MeOH (40.0 mL) and treated with LiOH (4.85 g, 118 mmol) (in solution of 40 mL water) at room temperature for 4 hours. The reaction mixture was acidified to pH 4 with 1 M HCl, and most of the methanol was evaporated. EtOAc was added, the organics were separated, dried over magnesium sulfate and concentrated to give 3-(3-amino-4-(cyclohexyl(isobutyl)amino)phenyl)butanoic acid. LCMS ESI (M+H)+: m/z=333.4 $^1$H NMR (400 MHz, DMSO-$d_6$): δ ppm 7.23 (d, J=7.7 Hz, 1H), 6.72-6.90 (m, 2H), 2.90-3.14 (m, 3H), 2.46 (t, J=7.1 Hz, 2H), 1.91 (s, 2H), 1.72 (d, J=12.1 Hz, 2H), 1.33-1.61 (m, 4H), 0.98-1.21 (m, 7H), 0.70-0.84 (m, 6H).

Step B

3-(4-(Cyclohexyl(isobutyl)amino)-3-(cyclohexylamino)phenyl)butanoic Acid

A solution of 3-(3-amino-4-(cyclohexyl(isobutyl)amino)phenyl)butanoic acid (52 mg, 0.156 mmol) in MeCN (1.0 mL) was treated with cyclohexanone (18.42 mg, 0.188 mmol), acetic acid (0.018 mL, 0.313 mmol) and sodium triacetoxyborohydride (49.7 mg, 0.235 mmol) at room temperature for 30 minutes. The reaction mixture was purified directly via reverse phase chromatography to give 3-(4-(cyclohexyl(isobutyl)amino)-3-(cyclohexylamino)phenyl)butanoic acid (38 mg, 0.087 mmol, 55.7% yield). LCMS ESI (M+H)+: m/z=415.5 $^1$H NMR (400 MHz, DMSO-$d_6$): δ ppm 6.91 (d, J=8.1 Hz, 1H), 6.43 (s, 1H), 6.37 (d, J=8.1 Hz, 1H), 4.79 (d, J=8.4 Hz, 1H), 2.90-3.06 (m, 2H), 2.35-2.47 (m, 4H), 1.85-1.99 (m, 2H), 0.97-1.79 (m, 23H), 0.70-0.85 (m, 6H).

Example 20

3-(4-(Cyclohexyl(isobutyl)amino)-3-((thiophen-2-ylmethyl)amino)phenyl)butanoic Acid

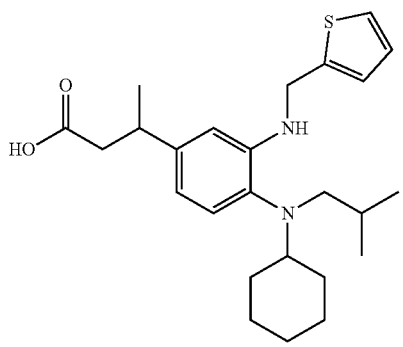

The title compound, 3-(4-(cyclohexyl(isobutyl)amino)-3-((thiophen-2-ylmethyl)amino)phenyl)butanoic acid, was made in a manner similar to example 19. 3-(4-(cyclohexyl(isobutyl)amino)-3-((thiophen-2-ylmethyl)amino)phenyl)butanoic acid was isolated (49 mg, 0.109 mmol, 72.2% yield). LCMS ESI (M+H)+: m/z=429.4. $^1$H NMR (400 MHz, DMSO-$d_6$): δ ppm 7.38 (d, J=4.9 Hz, 1H), 7.06 (d, J=2.9 Hz, 1H), 6.97 (dd, J=4.9, 3.5 Hz, 1H), 6.93 (d, J=8.1 Hz, 1H), 6.58 (s, 1H), 6.45 (d, J=7.9 Hz, 1H), 5.27 (t, J=6.1 Hz, 1H), 4.52 (dd, J=14.7, 5.5 Hz, 2H), 2.91-3.07 (m, 2H), 2.35-2.47 (m, 3H), 1.61-1.80 (m, 4H), 1.48-1.58 (m, 1H), 1.34-1.47 (m, 1H), 1.11-1.32 (m, 7H), 0.95-1.08 (m, 2H), 0.75 (d, J=6.4 Hz, 6H).

Example 21

3-(4-(Cyclohexyl(isobutyl)amino)-3-((thiazol-2-ylmethyl)amino)phenyl)butanoic Acid

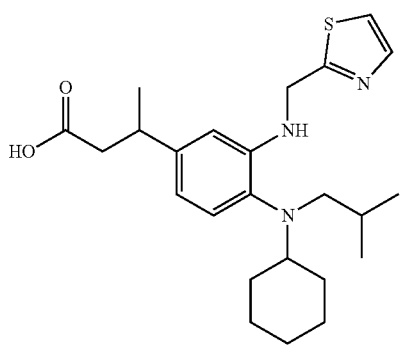

The title compound, 3-(4-(cyclohexyl(isobutyl)amino)-3-((thiazol-2-ylmethyl)amino)phenyl)butanoic acid, was made in a manner similar to example 19. 3-(4-(Cyclohexyl(isobutyl)amino)-3-((thiazol-2-ylmethyl)amino)phenyl)butanoic acid was isolated (36 mg, 0.080 mmol, 52.9% yield). LCMS ESI (M+H)+: m/z=430.4. $^1$H NMR (400 MHz, DMSO-$d_6$): δ ppm 7.74 (d, J=3.1 Hz, 1H), 7.58 (d, J=3.1 Hz, 1H), 6.95 (d, J=8.4 Hz, 1H), 6.41-6.53 (m, 2H), 5.76 (t, J=6.3 Hz, 1H), 4.69 (d, J=6.2 Hz, 2H), 2.91-3.04 (m, 2H), 2.29-2.47 (m, 3H), 1.85-1.97 (m, 1H), 1.62-1.80 (m, 3H), 1.49-1.60 (m, 1H), 1.37-1.47 (m, 1H), 0.96-1.35 (m, 9H), 0.72-0.85 (m, 6H).

Example 22

3-(4-(Cyclohexyl(isobutyl)amino)-3-((thiazol-5-ylmethyl)amino)phenyl)butanoic Acid

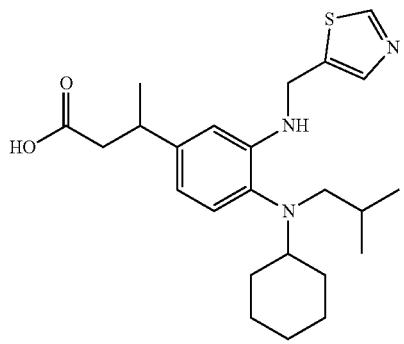

The title compound, 3-(4-(cyclohexyl(isobutyl)amino)-3-((thiazol-5-ylmethyl)amino)phenyl)butanoic acid, was made in a manner similar to example 19. 3-(4-(Cyclohexyl(isobutyl)amino)-3-((thiazol-5-ylmethyl)amino)phenyl)butanoic acid was isolated (36 mg, 0.080 mmol, 52.9% yield). LCMS ESI (M+H)$^+$: m/z=430.4. $^1$H NMR (400 MHz, DMSO-d$_6$) δ ppm 7.74 (d, J=3.1 Hz, 1H), 7.58 (d, J=3.1 Hz, 1H), 6.95 (d, J=8.4 Hz, 1H), 6.41-6.53 (m, 2H), 5.76 (t, J=6.3 Hz, 1H), 4.69 (d, J=6.2 Hz, 2H), 2.91-3.04 (m, 2H), 2.29-2.47 (m, 3H), 1.85-1.97 (m, 1H), 1.62-1.80 (m, 3H), 1.49-1.60 (m, 1H), 1.37-1.47 (m, 1H), 0.96-1.35 (m, 9H), 0.72-0.85 (m, 6H).

Example 23

3-(4-(Cyclohexyl(isobutyl)amino)-3-((2-methylbenzyl)amino)phenyl)butanoic Acid

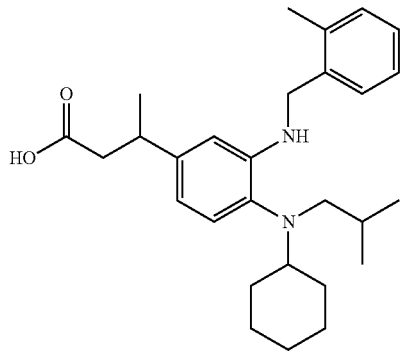 [SMILES: Cc1ccccc1CNc1cc(C(C)CC(=O)O)ccc1N(CC(C)C)C1CCCCC1]

The title compound, 3-(4-(cyclohexyl(isobutyl)amino)-3-((2-methylbenzyl)amino)phenyl)butanoic acid, was made in a manner similar to example 19. 3-(4-(Cyclohexyl(isobutyl)amino)-3-((2-methylbenzyl)amino)phenyl)butanoic acid was isolated (48 mg, 0.104 mmol, 69.4% yield). LCMS ESI (M+H)$^+$: m/z=437.14. $^1$H NMR (400 MHz, DMSO-d$_6$): δ ppm 7.23-7.31 (m, 1H), 7.09-7.23 (m, 3H), 6.94 (d, J=8.1 Hz, 1H), 6.40-6.52 (m, 2H), 5.03 (t, J=5.4 Hz, 1H), 4.14-4.35 (m, 2H), 2.92-3.06 (m, 2H), 2.31-2.48 (m, 6H), 1.47-1.80 (m, 5H), 0.93-1.46 (m, 10H), 0.74 (d, J=6.2 Hz, 6H).

Example 24

3-(4-(Diisobutylamino)-3-((4-methylthiazol-2-yl)amino)phenyl)butanoic Acid

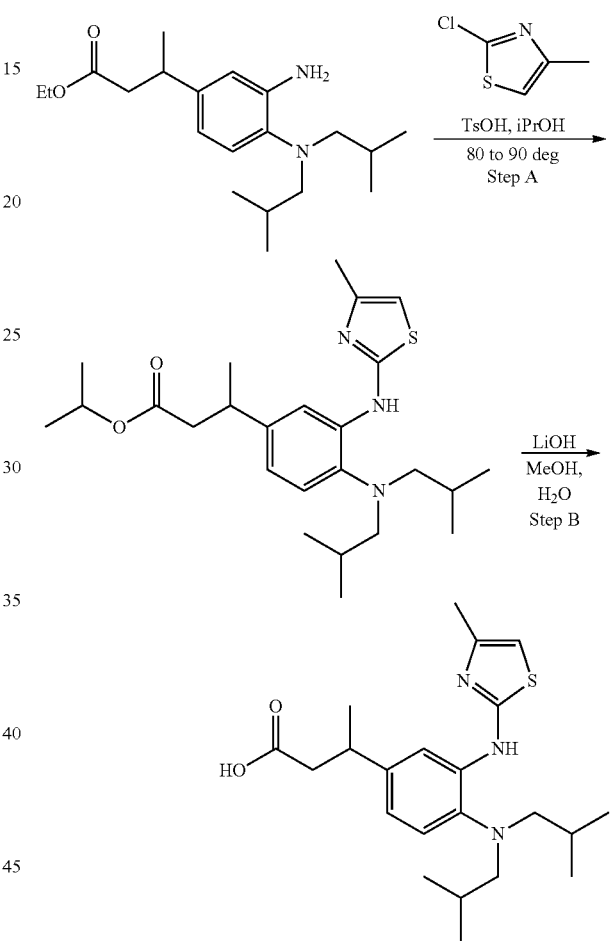

Step A

Isopropyl 3-(4-(diisobutylamino)-3-((4-methylthiazol-2-yl)amino)phenyl)butanoate A solution of ethyl 3-(3-amino-4-(diisobutylamino)phenyl)butanoate (0.100 g, 0.30 mmol), 2-chloro-4-methylthiazole (0.120 g, 0.90 mmol), and p-toluenesulfonic acid (0.057 g, 0.30 mmol) in iPrOH (1.5 mL) was heated at 80° C. for 3 d and 90° C. for 1 d. Saturated sodium bicarbonate solution was added and the reaction mixture was extracted with DCM. The organic layer was dried over Na$_2$SO$_4$, filtered, evaporated to give isopropyl 3-(4-(diisobutylamino)-3-((4-methylthiazol-2-yl)amino)phenyl)butanoate, which was used without further purification.

Step B

3-(4-(Diisobutylamino)-3-((4-methylthiazol-2-yl)amino)phenyl)butanoic Acid

The title compound, 3-(4-(diisobutylamino)-3-((4-methylthiazol-2-yl)amino)phenyl)butanoic acid, was made in a similar manner to Example 1, step B. 3-(4-(Diisobutylamino)-3-((4-methylthiazol-2-yl)amino)phenyl)butanoic acid was isolated (0.003 g, 2%) as a white solid. LCMS (M+H)+: m/z=404.4. $^1$H NMR (400 MHz, METHANOL-$d_4$) δ ppm 7.75 (s, 1H), 7.24 (d, J=8.28 Hz, 1H), 6.94 (d, J=8.03 Hz, 1H), 6.40 (s, 1H), 3.21-3.30 (m, 1H), 2.51-2.72 (m, 6H), 2.31 (s, 3H), 1.70 (m, 2H), 1.35 (d, J=7.03 Hz, 3H), 0.94 (d, J=6.53 Hz, 12H).

Example 25

3-(3-((3-Chloro-1,2,4-thiadiazol-5-yl)amino)-4-(diisobutylamino)phenyl)butanoic Acid

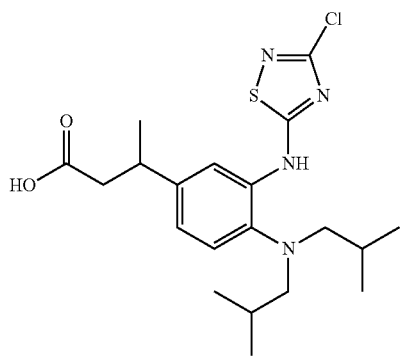

The title compound, 3-(3-((3-chloro-1,2,4-thiadiazol-5-yl)amino)-4-(diisobutylamino)phenyl)butanoic acid, was made in a similar manner to Example 1. In step A 3,5-dichloro-1,2,4-thiadiazole, DMF, and 90° C. were used. In step B, LiOH, THF, MeOH, and water were used. 3-(3-((3-Chloro-1,2,4-thiadiazol-5-yl)amino)-4-(diisobutylamino)phenyl)butanoic acid was isolated (35 mg, 73%) as a solid. $^1$H NMR (400 MHz, DMSO-$d_6$) δ ppm 0.80 (d, J=6.53 Hz, 12H) 1.21 (d, J=7.03 Hz, 3H) 1.67 (dt, J=13.18, 6.46 Hz, 2H) 2.72 (d, J=6.78 Hz, 5H) 3.02-3.21 (m, 2H) 7.07 (d, J=7.53 Hz, 1H) 7.18 (d, J=8.28 Hz, 1H) 7.50 (br. s., 1H) 10.05 (s, 1H) 11.98 (s, 1H).

Example 26

3-(3-((5-Cyclopropyl-1,3,4-thiadiazol-2-yl)amino)-4-(diisobutylamino)phenyl)butanoic Acid Trifluoroacetic Acid Salt

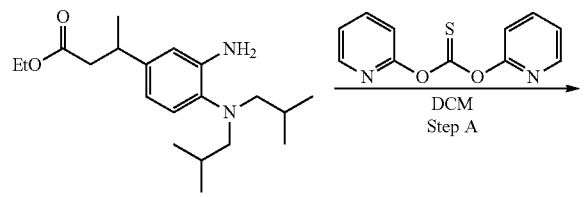

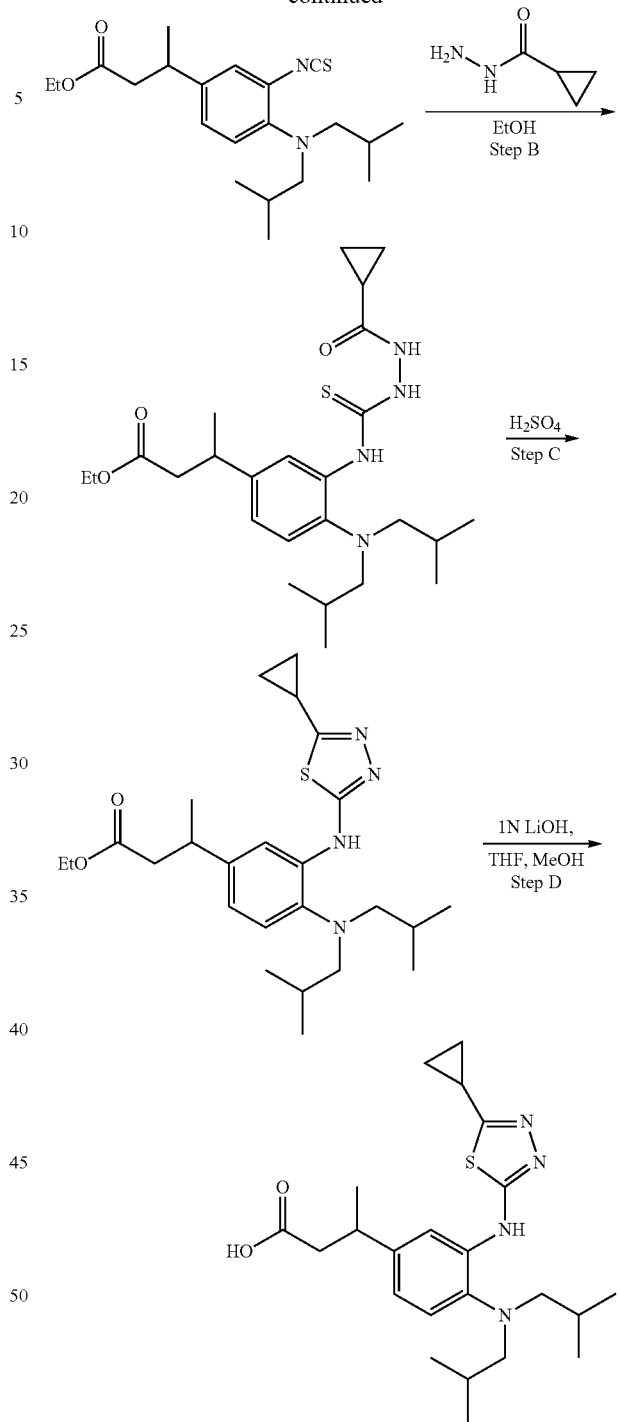

Step A

Ethyl 3-(4-(diisobutylamino)-3-isothiocyanatophenyl)butanoate

To ethyl 3-(3-amino-4-(diisobutylamino)phenyl)butanoate (100 mg, 0.299 mmol) in DCM (2 mL) was added O,O-di(pyridin-2-yl) carbonothioate (83 mg, 0.359 mmol) and stirred at room temperature for 1.5 h. The solvent was removed to give ethyl 3-(4-(diisobutylamino)-3-isothiocyanatophenyl)butanoate, which was used without further purification.

Step B

Ethyl 3-(3-(2-(cyclopropanecarbonyl)hydrazinecarbothioamido)-4-(diisobutylamino)phenyl)butanoate To ethyl 3-(4-(diisobutylamino)-3-isothiocyanatophenyl) butanoate in ethanol (2.00 mL) was added cyclopropanecarbohydrazide (35.9 mg, 0.359 mmol) and the mixture was stirred at 50° C. overnight. The reaction was cooled and the solvent was removed give ethyl 3-(3-(2-(cyclopropanecarbonyl)hydrazinecarbothioamido)-4-(diisobutylamino)phenyl)butanoate, which was used without further purification.

Step C

Ethyl 3-(3-((5-cyclopropyl-1,3,4-thiadiazol-2-yl)amino)-4-(diisobutylamino)phenyl)butanoate To ethyl 3-(3-(2-(cyclopropanecarbonyl)hydrazinecarbothioamido)-4-(diisobutylamino)phenyl)butanoate was added concentrated $H_2SO_4$ (0.319 mL, 5.98 mmol) dropwise and the mixture was stirred at room temperature for 30 min. The reaction mixture was poured into ice-water and extracted with EtOAc. Organic layer was separated, dried and purified by silica gel chromatography (0-10% EA in hexanes) to give ethyl 3-(3-((5-cyclopropyl-1,3,4-thiadiazol-2-yl)amino)-4-(diisobutylamino)phenyl)butanoate (57 mg, 0.117 mmol, 39.1% yield, three steps) as a colorless oil.

Step D 3-(3-((5-Cyclopropyl-1,3,4-thiadiazol-2-yl)amino)-4-(diisobutylamino)phenyl)butanoic Acid, Trifluoroacetic Acid Salt To ethyl 3-(3-((5-cyclopropyl-1,3,4-thiadiazol-2-yl) amino)-4-(diisobutylamino)phenyl)butanoatein (1 mL) was added 1N LiOH (1 mL) and MeOH (1 mL) and stirred at room temperature for 2 h. Solvents were evaporated and the reaction mixture was acidified with 1N HCl and was extracted with EtOAc. Organic layer was separated and dried to afford a residue that was purified by reverse phase chromatography (ACN/water 10-90%, 0.05% TFA) to obtain 3-(3-((5-cyclopropyl-1,3,4-thiadiazol-2-yl)amino)-4-(diisobutylamino)phenyl)butanoic acid, as the trifluoroacetic acid salt (46 mg, 0.084 mmol, 28.3% yield) as a white solid. LCMS (M+H)$^+$: m/z=431.5. $^1$H NMR (400 MHz, METHANOL-$d_4$) δ 7.50 (s, 1H), 7.43 (d, J=8.3 Hz, 1H), 7.10 (d, J=8.2 Hz, 1H), 3.30-3.25 (m, 1H), 3.08 (d, J=6.8 Hz, 4H), 2.61 (d, J=7.5 Hz, 2H), 2.22 (t, J=4.6 Hz, 1H), 1.70 (td, J=6.7, 13.4 Hz, 2H), 1.33 (d, J=7.0 Hz, 3H), 1.18-1.11 (m, 2H), 1.03-0.98 (m, 2H), 0.93 (d, J=6.6 Hz, 12H).

Example 27

3-(4-(Diisobutylamino)-3-((5-phenyl-1,3,4-thiadiazol-2-yl)amino)phenyl)butanoic Acid, Trifluoroacetic Acid Salt

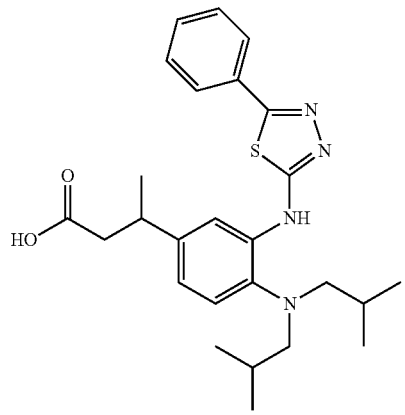 [SMILES: CC(C)CN(CC(C)C)c1ccc(C(C)CC(=O)O)cc1Nc1nnc(-c2ccccc2)s1]

The title compound, 3-(4-(diisobutylamino)-3-((5-phenyl-1,3,4-thiadiazol-2-yl)amino)phenyl)butanoic acid, was made in a similar manner to Example 26. 3-(4-(Diisobutylamino)-3-((5-phenyl-1,3,4-thiadiazol-2-yl)amino)phenyl) butanoic acid was isolated in 32% yield (four steps). LCMS (M+H)$^+$: m/z=467.4. $^1$H NMR (400 MHz, METHANOL-$d_4$) b=7.86-7.77 (m, 1H), 7.48-7.40 (m, 1H), 7.23 (d, J=8.0 Hz, 1H), 6.96 (d, J=8.2 Hz, 1H), 4.06 (q, J=7.2 Hz, 1H), 3.26-3.21 (m, 1H), 2.65 (d, J=6.8 Hz, 4H), 2.62-2.51 (m, J=7.6, 10.7 Hz, 1H), 1.97 (s, 2H), 1.66 (td, J=6.7, 13.4 Hz, 2H), 1.31 (d, J=7.0 Hz, 3H), 1.23-1.16 (m, 2H), 0.89 (d, J=6.6 Hz, 12H).

Example 28

3-(4-(Diisobutylamino)-3-((5-methyl-1,3,4-thiadiazol-2-yl)amino)phenyl)butanoic Acid

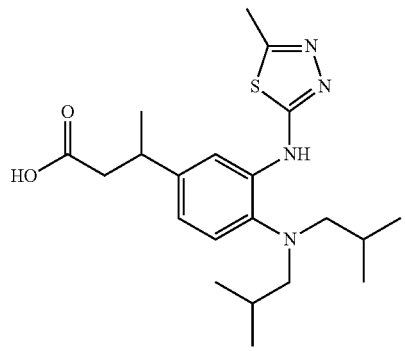

The title compound, 3-(4-(diisobutylamino)-3-((5-methyl-1,3,4-thiadiazol-2-yl)amino)phenyl)butanoic acid, was made in a similar manner to Example 26. 3-(4-(Diisobutylamino)-3-((5-methyl-1,3,4-thiadiazol-2-yl)amino) phenyl)butanoic acid was isolated in 16% yield (four steps). LCMS (M+H)$^+$: m/z=405.5. $^1$H NMR (400 MHz, METHANOL-$d_4$) δ 7.55 (s, 1H), 7.40 (d, J=8.2 Hz, 1H), 7.08 (dd, J=1.9, 8.3 Hz, 1H), 3.29-3.22 (m, 1H), 3.01 (d, J=7.0 Hz, 4H), 2.62 (s, 2H), 2.57 (s, 3H), 1.70 (td, J=6.8, 13.4 Hz, 2H), 1.33 (d, J=7.0 Hz, 3H), 0.93 (d, J=6.6 Hz, 12H).

Example 29

3-(4-(Cyclohexyl(isobutyl)amino)-3-((5-(trifluoromethyl)-1,3,4-thiadiazol-2-yl)amino)phenyl)butanoic Acid

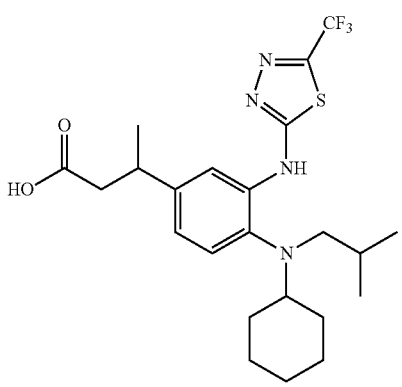 [SMILES: CC(C)CN(c1ccc(C(C)CC(=O)O)cc1Nc1nnc(C(F)(F)F)s1)C1CCCCC1]

The title compound, 3-(4-(cyclohexyl(isobutyl)amino)-3-((5-(trifluoromethyl)-1,3,4-thiadiazol-2-yl)amino)phenyl) butanoic acid, was made in a similar manner to Example 26. $^1$H NMR (400 MHz, METHANOL-$d_4$) δ ppm 0.77-1.03 (m, 6H) 1.00-1.42 (m, 10H) 1.61 (d, J=12.45 Hz, 1H) 1.80 (d, J=10.80 Hz, 3H) 2.00 (br. s., 2H) 2.63 (d, J=7.33 Hz, 4H) 7.20 (d, J=7.33 Hz, 1H) 7.36-7.54 (m, 1H) 7.58 (br. s., 1H).

Example 30

3-(3-((3-Cyclopropyl-1,2,4-thiadiazol-5-yl)amino)-4-(diisobutylamino)phenyl)butanoic Acid, Trifluoroacetic Acid Salt

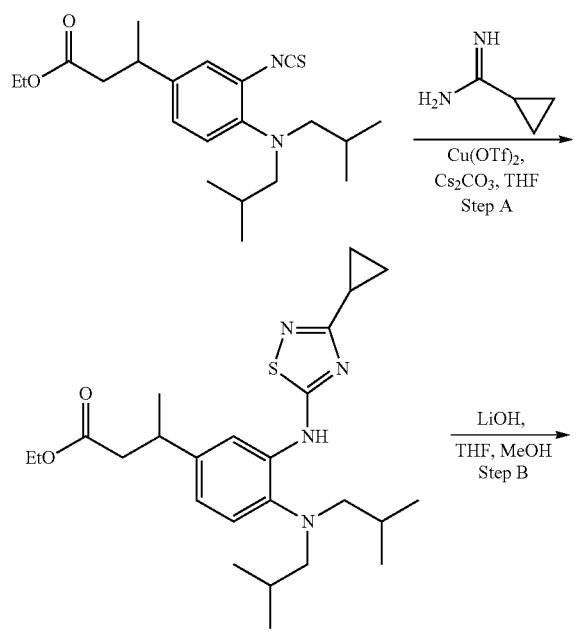

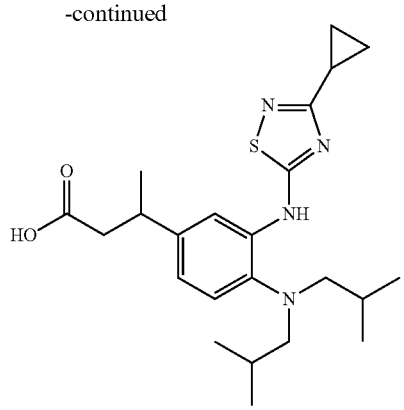

Step A

Ethyl 3-(3-((3-cyclopropyl-1,2,4-thiadiazol-5-yl)amino)-4-(diisobutylamino)phenyl)butanoate To ethyl 3-(4-(diisobutylamino)-3-isothiocyanatophenyl) butanoate was added THF (2 mL), cyclopropanecarboximidamide hydrochloride (39.7 mg, 0.329 mmol), Cs$_2$CO$_3$ (292 mg, 0.897 mmol) and under stirring was added copper(II) trifluoromethanesulfonate (5.41 mg, 0.015 mmol) (green color). The reaction was stirred open to air at 50° C. overnight. The solvents were removed to give ethyl 3-(3-((3-cyclopropyl-1,2,4-thiadiazol-5-yl)amino)-4-(diisobutylamino)phenyl)butanoate, which was used without purification.

Step B 3-(3-((3-cyclopropyl-1,2,4-thiadiazol-5-yl)amino)-4-(diisobutylamino)phenyl)butanoic Acid, Trifluoroacetic Acid Salt To ethyl 3-(3-((3-cyclopropyl-1,2,4-thiadiazol-5-yl) amino)-4-(diisobutylamino)phenyl)butanoate in THF (1 mL) was added 1N LiOH (1N, 1 mL) and MeOH (1 mL) and stirred at room temperature for 4 h. The solvent was removed and the mixture was acidified with 1N HCl and extracted with EtOAc. The solvents were removed and the residue was purified by reverse phase chromatography (ACN/water 10-90%, 0.05% TFA) to obtain 3-(3-((3-cyclopropyl-1,2,4-thiadiazol-5-yl)amino)-4-(diisobutylamino) phenyl)butanoic acid, trifluoroacetic acid salt (45 mg, 0.082 mmol, 27.4% yield) as a white solid. LCMS (M+H)$^+$: m/z=431.4. $^1$H NMR (400 MHz, METHANOL-$d_4$) δ 7.47 (d, J=1.2 Hz, 1H), 7.31 (d, J=8.2 Hz, 1H), 7.05 (dd, J=1.3, 8.2 Hz, 1H), 3.28-3.21 (m, 1H), 2.75 (d, J=6.8 Hz, 4H), 2.62-2.57 (m, 2H), 2.14-2.06 (m, 1H), 1.69 (td, J=6.7, 13.4 Hz, 2H), 1.33 (d, J=7.0 Hz, 3H), 1.10-0.98 (m, 4H), 0.91 (d, J=6.6 Hz, 12H).

Example 31

3-(4-(Diisobutylamino)-3-((3-methyl-1,2,4-thiadiazol-5-yl)amino)phenyl)butanoic Acid

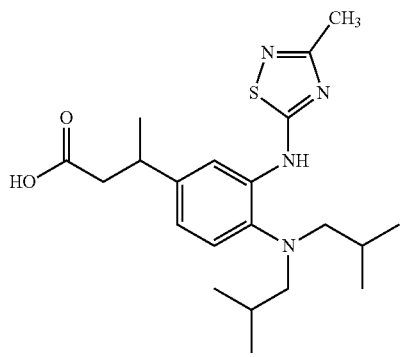

The title compound, 3-(4-(diisobutylamino)-3-((3-methyl-1,2,4-thiadiazol-5-yl)amino)phenyl)butanoic acid, was made in a manner similar to example 30. $^1$H NMR (400 MHz, DMSO-de) δ ppm 0.84 (d, J=6.53 Hz, 12H) 1.23 (d, J=6.27 Hz, 3H) 1.50-1.79 (m, 2H) 2.38 (s, 3H) 2.48 (br. s., 2H) 2.66 (d, J=7.03 Hz, 4H) 3.03-3.22 (m, 1H) 7.00 (d, J=8.03 Hz, 1H) 7.24 (d, J=8.03 Hz, 1H) 7.48 (s, 1H) 9.47 (br. s., 1H).

Example 32

3-(3-((3-Bromo-1,2,4-thiadiazol-5-yl)amino)-4-(diisobutylamino)phenyl)butanoic Acid

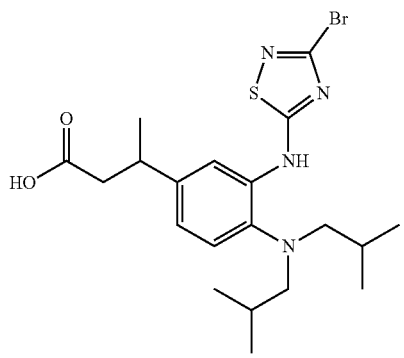 [SMILES: CC(C)CN(CC(C)C)c1ccc(C(C)CC(=O)O)cc1Nc1nc(Br)ns1]

The title compound, 3-(3-((3-bromo-1,2,4-thiadiazol-5-yl)amino)-4-(diisobutylamino)phenyl)butanoic acid, was made in a manner similar to example 30. $^1$H NMR (400 MHz, METHANOL-d$_4$) δ ppm 0.92 (d, J=6.53 Hz, 12H) 1.34 (d, J=5.77 Hz, 3H) 1.71 (dt, J=13.30, 6.65 Hz, 2H) 2.58 (br. s., 2H) 2.70 (d, J=7.03 Hz, 4H) 3.24-3.31 (m, 1H) 7.12 (d, J=8.03 Hz, 1H) 7.30 (d, J=8.03 Hz, 1H) 7.41 (s, 1H).

Example 33

3-(4-(Cyclohexyl(isobutyl)amino)-3-((3-(trifluoromethyl)-1,2,4-thiadiazol-5-yl)amino)phenyl)butanoic Acid

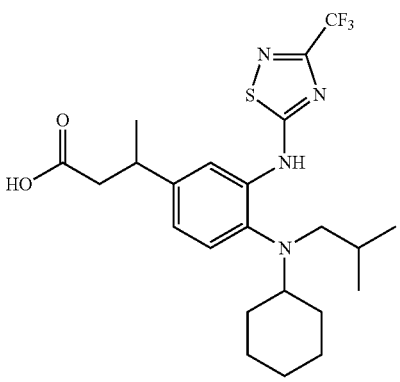

The title compound, compound 3-(4-(cyclohexyl(isobutyl)amino)-3-((3-(trifluoromethyl)-1,2,4-thiadiazol-5-yl)amino)phenyl)butanoic acid, was made in a manner similar to example 30. $^1$H NMR (400 MHz, METHANOL-d$_4$) δ ppm 0.85 (d, J=6.41 Hz, 6H) 0.95-1.22 (m, 3H) 1.21-1.51 (m, 7H) 1.57 (d, J=10.44 Hz, 1H) 1.74 (d, J=11.90 Hz, 2H) 1.89 (d, J=11.35 Hz, 2H) 2.50-2.72 (m, 3H) 2.87 (d, J=6.59 Hz, 2H) 7.08 (d, J=8.06 Hz, 1H) 7.27 (d, J=8.24 Hz, 1H) 7.63 (s, 1H).

Example 34

3-(4-(Diisobutylamino)-3-((3-(trifluoromethyl)-1,2,4-thiadiazol-5-yl)amino)phenyl)butanoic Acid

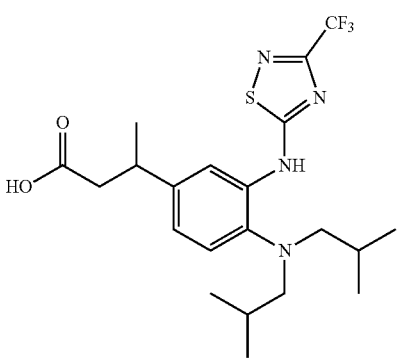

The title compound, 3-(4-(diisobutylamino)-3-((3-(trifluoromethyl)-1,2,4-thiadiazol-5-yl)amino)phenyl)butanoic acid, was made in a manner similar to example 30. $^1$H NMR (400 MHz, METHANOL-d$_4$) δ ppm 0.90 (d, J=6.59 Hz, 12H) 1.33 (d, J=6.04 Hz, 3H) 1.71 (dt, J=13.37, 6.68 Hz, 2H) 2.50-2.66 (m, 2H) 2.70 (d, J=7.14 Hz, 4H) 3.23-3.29 (m, 1H) 7.11 (d, J=8.06 Hz, 1H) 7.29 (d, J=8.06 Hz, 1H) 7.51 (s, 1H).

Synthesis of (E)-5-bromo-3-(but-2-en-1-yl)-2-propoxyaniline

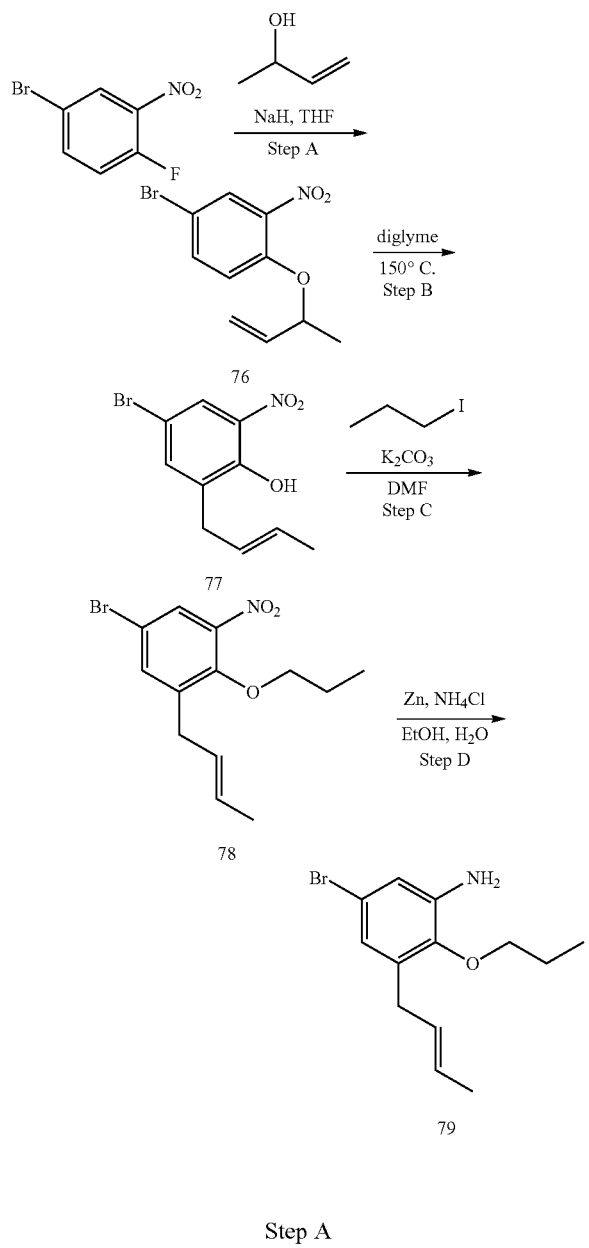

Step A

4-Bromo-1-(but-3-en-2-yloxy)-2-nitrobenzene

At 0° C., to a stirred solution of but-3-en-2-ol (24.5 g, 0.34 mol) in THF (300 mL) was added NaH (60%, 13.5 g, 0.34 mol). The mixture was stirred for 1 hr then treated with 4-bromo-1-fluoro-2-nitrobenzene (37 g, 0.17 mol) at 0° C. The reaction was stirred at 10° C. for 1 hr then acidified with 1 N HCl to ~pH 7 at −5° C. and extracted with EtOAc (3×50 mL). The combined organic layers were washed with brine (50 mL), dried over $Na_2SO_4$, and concentrated. The residue was purified by silica gel chromatography (5-15% EtOAc/PE) to give 4-bromo-1-(but-3-en-2-yloxy)-2-nitrobenzene (30 g, 67%) as a colorless oil. $^1$H NMR (400 MHz, $CDCl_3$) δ 7.91 (d, J=2.5 Hz, 1H), 7.55 (dd, J=9.0, 2.5 Hz, 1H), 6.97 (d, J=9.0 Hz, 1H), 5.89 (ddd, J=17.1, 10.6, 6.2 Hz, 1H), 5.27 (dd, J=27.1, 14.0 Hz, 2H), 4.87 (p, J=6.3 Hz, 1H), 1.49 (d, J=6.4 Hz, 3H).

Step B

(E)-4-Bromo-2-(but-2-en-1-yl)-6-nitrophenol

A solution of 4-bromo-1-(but-3-en-2-yloxy)-2-nitrobenzene (30 g, 0.11 mol) in diglyme (160 mL) was stirred at 150° C. overnight, then cooled to room temperature and partitioned between DCM (300 mL) and water (100 mL). The layers were separated and the organic layer was washed with brine (100 mL), dried over $Na_2SO_4$, and concentrated. The residue was purified by silica gel chromatography (5-15% EtOAc/PE) to give (E)-4-bromo-2-(but-2-en-1-yl)-6-nitrophenol (27 g, 90%) as a yellow oil. LCMS $(M+H)^+$: m/z=272.1.

Step C

(E)-5-Bromo-1-(but-2-en-1-yl)-3-nitro-2-propoxybenzene

To a solution of (E)-4-bromo-2-(but-2-en-1-yl)-6-nitrophenol (27 g, 0.099 mol) in DMF (270 mL) were added $K_2CO_3$ (30.2 g, 0.21 mol) and 1-iodopropane (22.7 g, 0.2 mol) at room temperature in one portion. The resulting mixture was stirred at 50° C. for 5 hrs before it was concentrated under reduced pressure. The residue was partitioned between EtOAc (250 mL) and water (80 mL). The layers were separated and the organic layer was washed with brine (80 mL), dried over $Na_2SO_4$, and concentrated. The crude product was purified by silica gel chromatography (100% PE) to give (E)-5-bromo-1-(but-2-en-1-yl)-3-nitro-2-propoxybenzene (21 g, 68%) as a yellow oil. LCMS $(M+H)^+$: m/z=314.0. $^1$H NMR (400 MHz, $CDCl_3$) δ 7.78 (d, J=2.5 Hz, 1H), 7.52 (d, J=2.5 Hz, 1H), 5.63-5.46 (m, 2H), 3.88 (t, J=6.6 Hz, 2H), 3.38 (d, J=5.8 Hz, 2H), 1.87-1.77 (m, 2H), 1.72 (dd, J=5.9, 1.0 Hz, 3H), 1.07-1.00 (m, 3H).

Step D

(E)-5-Bromo-3-(but-2-en-1-yl)-2-propoxyaniline

To a solution of (E)-5-bromo-1-(but-2-en-1-yl)-3-nitro-2-propoxybenzene (8.0 g, 0.025 mol) in EtOH (160 mL) and $H_2O$ (20 mL) was added $NH_4Cl$ (20.0 g, 0.38 mol) and zinc powder (25.0 g 0.38 mol) at 0° C. The resulting suspension was stirred at 25° C. for 8 hrs before it was filtered to remove excess zinc powder. The filtrate was concentrated and the residue was partitioned between EtOAc (200 mL) and water (60 mL). The layers were separated and the organic layer was washed with brine, dried over $Na_2SO_4$, and concentrated. The residue was purified by silica gel chromatography (10-50% EtOAa/PE) to give (E)-5-bromo-3-(but-2-en-1-yl)-2-propoxyaniline (6.15 g, 85%) as a red oil. LCMS $(M+H)^+$: m/z=284.1. $^1$H NMR (400 MHz, $CDCl_3$) δ 6.73 (d, J=2.4 Hz, 1H), 6.68 (d, J=2.4 Hz, 1H), 5.52 (dt, J=5.1, 2.7 Hz, 2H), 3.80 (s, 2H), 3.73 (t, J=6.6 Hz, 2H), 3.26 (d, J=2.1 Hz, 2H), 1.85-1.74 (m, 2H), 1.73-1.65 (m, 3H), 1.06 (t, J=7.4 Hz, 3H).

Example 35

3-(3-(Benzo[d]oxazol-2-ylamino)-5-butyl-4-propoxyphenyl) butanoic Acid

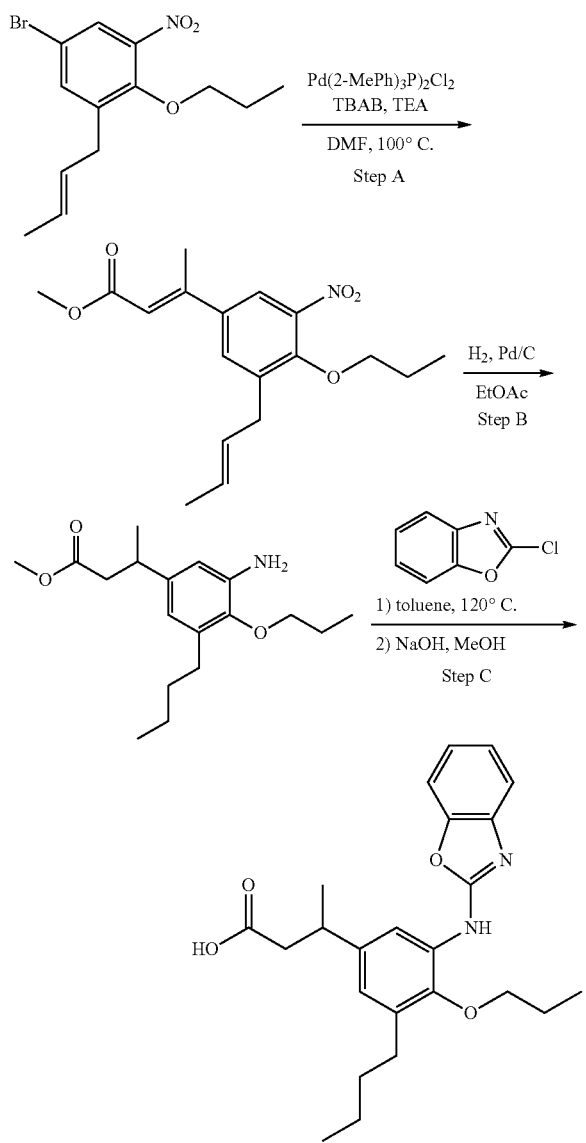

Step A

Methyl (E)-3-(3-((E)-but-2-en-1-yl)-5-nitro-4-propoxyphenyl)but-2-enoate

To a solution of (E)-5-bromo-1-(but-2-en-1-yl)-3-nitro-2-propoxybenzene (500 mg, 1.59 mmol), tetrabutylammonium bromide (103 mg, 0.32 mmol), methyl (E)-but-2-enoate (478 mg, 4.77 mmol), TEA (324 mg, 3.18 mmol) in DMF (6 mL) was added dichlorobis(tris(2-tolyl)phosphine) palladium (62 mg, 0.08 mmol) in one portion. The resulting mixture was purged with $N_2$ (3×) and stirred at 110° C. for 4 hrs. After the reaction was cooled to room temperature, the solids were filtered, and the filtrate was concentrated. The residue was partitioned between EtOAc (10 mL) and water (5 mL). The layers were separated and the organic layer was washed with brine (5 mL), dried over $Na_2SO_4$, and concentrated. The residue was purified by silica gel chromatography (100% PE) to give (E)-methyl 3-(3-((E)-but-2-en-1-yl)-5-nitro-4-propoxyphenyl)but-2-enoate (193 mg, 36%) as a yellow oil. $^1$H NMR (400 MHz, $CDCl_3$) δ 7.75 (d, J=2.4 Hz, 1H), 7.50 (d, J=2.4 Hz, 1H), 6.13 (d, J=1.3 Hz, 1H), 5.59-5.52 (m, 2H), 3.91 (t, J=6.6 Hz, 2H), 3.77 (s, 3H), 3.41 (d, J=1.7 Hz, 2H), 2.55 (d, J=1.3 Hz, 3H), 1.83 (dd, J=14.1, 6.8 Hz, 2H), 1.74-1.69 (m, 3H), 1.04 (t, J=7.4 Hz, 3H).

Step B

Methyl 3-(3-amino-5-butyl-4-propoxyphenyl)butanoate

To a solution of (E)-methyl 3-(3-((E)-but-2-en-1-yl)-5-nitro-4-propoxyphenyl)but-2-enoate (193 mg, 0.58 mmol) in EtOAc (6 mL) was added 10% palladium on carbon (40 mg). The resulting mixture was purged with $N_2$ (3×) and stirred at $H_2$ atmosphere at 50° C. for 1 hr. After filtration to remove the palladium catalyst, the filtrate was concentrated to give methyl 3-(3-amino-5-butyl-4-propoxyphenyl)butanoate (164 mg, 93%) as a yellow oil. LCMS $(M+H)^+$: m/z=308.1.

Step C

3-(3-(Benzo[d]oxazol-2-ylamino)-5-butyl-4-propoxyphenyl)butanoic Acid

The title compound, compound 3-(3-(benzo[d]oxazol-2-ylamino)-5-butyl-4-propoxyphenyl)butanoic acid, was prepared in a manner similar to Example 1. 3-(3-(benzo[d]oxazol-2-ylamino)-5-butyl-4-propoxyphenyl)butanoic acid (46 mg, 40% over two steps). LCMS $(M+H)^+$: m/z=411.2. $^1$H NMR (400 MHz, $CDCl_3$) δ 8.02 (d, J=2.1 Hz, 1H), 7.52 (dd, J=5.6, 2.3 Hz, 1H), 7.35 (d, J=7.6 Hz, 1H), 7.23 (dd, J=7.7, 1.1 Hz, 1H), 7.13 (td, J=7.8, 1.2 Hz, 1H), 6.77 (d, J=2.1 Hz, 1H), 3.80 (t, J=6.6 Hz, 2H), 3.38-3.27 (m, 1H), 2.73 (dd, J=15.4, 6.1 Hz, 1H), 2.68-2.58 (m, 3H), 1.93-1.82 (m, 2H), 1.60 (tt, J=7.9, 6.5 Hz, 2H), 1.45-1.33 (m, 5H), 1.11 (t, J=7.4 Hz, 3H), 0.95 (t, J=7.3 Hz, 3H).

Example 36

3-(3-Butyl-5-((3-chloro-1,2,4-thiadiazol-5-yl)amino)-4-propoxyphenyl)butanoic Acid, Trifluoroacetic Acid Salt

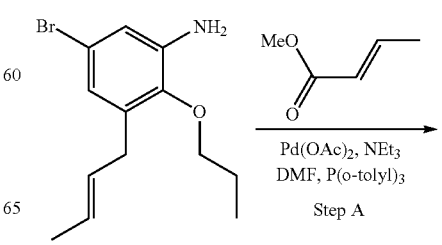

Step A

123
-continued

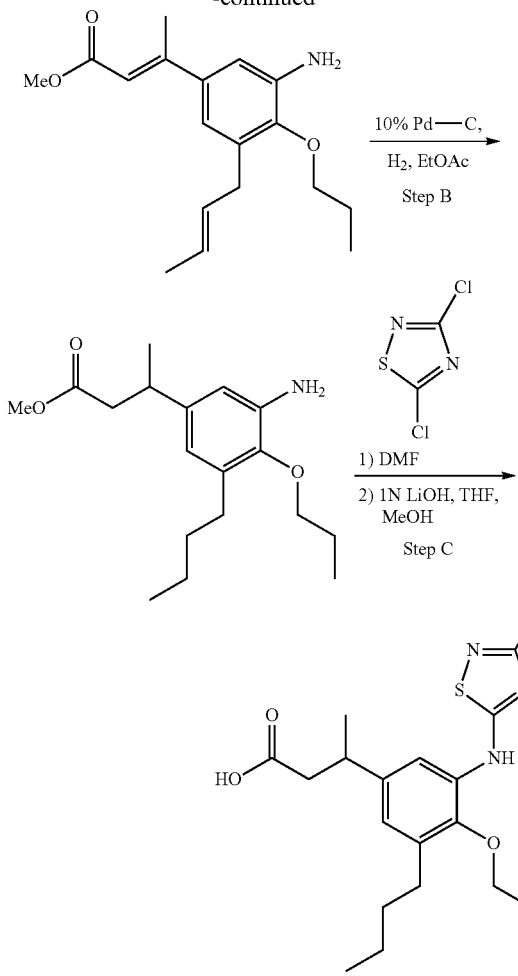

Step A (E)-methyl 3-(3-amino-5-((E)-but-2-en-1-yl)-4-propoxyphenyl)but-2-enoate

To (E)-5-bromo-3-(but-2-en-1-yl)-2-propoxyaniline (1000 mg, 3.52 mmol) and (E)-methyl but-2-enoate (1.238 mL, 17.59 mmol) in DMF (20 mL) was added TEA (1.471 mL, 10.56 mmol) and the mixture was degassed for 5 min. Then palladium(II) acetate (39.5 mg, 0.176 mmol) and tri-o-tolylphosphine (75.0 mg, 0.246 mmol) were added and degassed once and stirred at 110° C. for 2 h. Reaction mixture was acidified to pH 4.0 with 1N HCl and was extracted with EtOAc (2×20 ml). The organic layer was separated, dried and purified by silica gel chromatography (5-20% EtOAc/hexanes) to give (E)-methyl 3-(3-amino-5-((E)-but-2-en-1-yl)-4-propoxyphenyl)but-2-enoate (276 mg, 0.910 mmol, 25.9% yield). LCMS (M+H)⁺: m/z=304.3. ¹H NMR (400 MHz, CHLOROFORM-d) δ 6.75-6.68 (m, 2H), 6.07 (s, 1H), 5.62-5.46 (m, 2H), 4.12 (d, J=7.1 Hz, 1H), 3.90-3.70 (m, 4H), 3.31 (d, J=5.2 Hz, 2H), 2.51 (s, 3H), 2.04 (s, 1H), 1.88-1.76 (m, 2H), 1.68 (d, J=5.4 Hz, 3H), 1.26 (t, J=7.1 Hz, 1H), 1.07 (t, J=7.4 Hz, 3H).

124
Step B

Methyl 3-(3-amino-5-butyl-4-propoxyphenyl)butanoate

To (E)-methyl 3-(3-amino-5-((E)-but-2-en-1-yl)-4-propoxyphenyl)but-2-enoate (275 mg, 0.906 mmol) in EtOAc (20 mL) was added 10% Pd—C (135 mg, 0.127 mmol) and stirred under H₂ atmosphere at room temperature for 2 h. The reaction mixture was filtered and dried to give methyl 3-(3-amino-5-butyl-4-propoxyphenyl)butanoate (255 mg, 0.771 mmol, 85% yield) as a brown oil. LCMS (M+H)⁺: m/z=308.3. ¹H NMR (400 MHz, CHLOROFORM-d) δ 6.43 (d, J=8.1 Hz, 2H), 3.75 (t, J=6.6 Hz, 2H), 3.63 (s, 3H), 3.15-3.08 (m, 1H), 2.61-2.42 (m, 4H), 1.86-1.74 (m, 2H), 1.57 (quin, J=7.6 Hz, 2H), 1.43-1.31 (m, 2H), 1.28-1.20 (m, 3H), 1.06 (t, J=7.4 Hz, 3H), 0.93 (t, J=7.3 Hz, 3H).

Step C 3-(3-Butyl-5-((3-chloro-1,2,4-thiadiazol-5-yl)amino)-4-propoxyphenyl)butanoic Acid, Trifluoroacetic Acid Salt To methyl 3-(3-amino-5-butyl-4-propoxyphenyl)butanoate (50 mg, 0.163 mmol) in DMF (1 ml) was added 3,5-dichloro-1,2,4-thiadiazole (0.018 ml, 0.195 mmol) and stirred at 90° C. for 2 h. The reaction mixture was diluted with 2 mL water and extracted with EtOAc (2×2 mL). The organic layer was separated and dried to afford crude ester intermediate. To this intermediate was added THF (1.000 ml), LiOH (1.626 ml, 1.626 mmol) and MeOH (0.5 ml) and the mixture was stirred at room temperature overnight. The reaction mixture was purified using reverse phase column chromatography (ACN/water 10-90%, 0.05% TFA) to provide 3-(3-butyl-5-((3-chloro-1,2,4-thiadiazol-5-yl)amino)-4-propoxyphenyl)butanoic acid, trifluoroacetic acid salt (28 mg, 0.049 mmol, 29.9% yield) as a white solid. LCMS (M+H)⁺: m/z=412.3. ¹H NMR (400 MHz, METHANOL-d₄) δ 7.51 (d, J=1.3 Hz, 1H), 6.97 (d, J=1.9 Hz, 1H), 3.74 (t, J=6.6 Hz, 2H), 3.24-3.17 (m, 1H), 2.69-2.62 (m, 2H), 2.56 (dd, J=4.0, 7.5 Hz, 2H), 1.85-1.74 (m, 2H), 1.65-1.56 (m, 2H), 1.44-1.34 (m, 2H), 1.29 (d, J=7.0 Hz, 3H), 1.05-0.99 (m, 3H), 0.96 (t, J=7.3 Hz, 3H).

Synthesis of (S)-ethyl 3-(3-amino-4-(cyclohexyl(isobutyl)amino)phenyl)butanoate

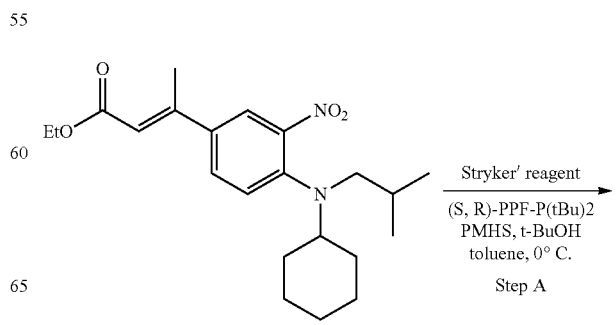

Stryker' reagent
(S, R)-PPF-P(tBu)2
PMHS, t-BuOH
toluene, 0° C.

Step A

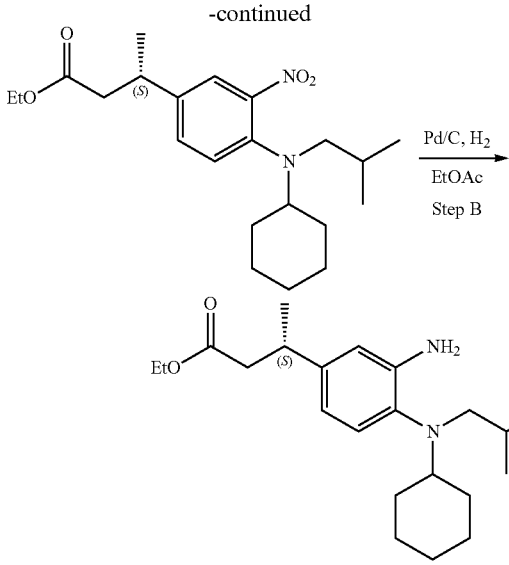

Step A

Ethyl (S)-3-(4-(cyclohexyl(isobutyl)amino)-3-nitrophenyl)butanoate

To a solution of (Ph₃P)CuH (18 mg, 0.054 mmol) and (R, S)-PPF-P(ᵗBu)₂ (CAS: 277306-29-3) (8 mg, 0.0154 mmol) in toluene (5 mL) was added PMHS (102 μL, 1.54 mmol) at 0° C., followed by addition of t-BuOH (81 μL, 0.85 mmol) and (E)-ethyl 3-(4-(cyclohexyl(isobutyl)amino)-3-nitrophenyl)but-2-enoate (300 mg, 0.77 mmol) in toluene (5 mL). The resulting mixture was stirred at 0° C. for 4 hr. The reaction was then quenched with sat. NaHCO₃ (10 mL) and diluted with EtOAc (20 mL) and H₂O (10 mL). The mixture was stirred for 2 hrs. The layers were separated and the aqueous layer was extracted with EtOAc (15 mL×3). The combined organic layers were washed with brine (30 mL), dried over Na₂SO₄, filtered, and concentrated. The residue was purified by silica gel chromatography (2% EtOAc/PE) to give (S)-ethyl 3-(4-(cyclohexyl(isobutyl)amino)-3-nitrophenyl)butanoate (260 mg, 86%) as an orange oil. LCMS (M+H)⁺: m/z=391.0. ¹H NMR (400 MHz, CDCl₃) δ 7.48 (d, J=2.2 Hz, 1H), 7.24 (d, J=2.2 Hz, 1H), 7.11 (d, J=8.5 Hz, 1H), 4.08 (q, J=7.1 Hz, 2H), 3.24 (dt, J=14.2, 7.1 Hz, 1H), 2.90-2.78 (m, 3H), 2.61-2.48 (m, 2H), 1.78 (dd, J=28.1, 12.1 Hz, 4H), 1.59 (s, 1H), 1.42-1.26 (m, 8H), 1.17 (t, J=7.1 Hz, 3H), 1.08-1.01 (m, 1H), 0.84 (d, J=6.6 Hz, 6H).

Step B

Ethyl (S)-3-(3-amino-4-(cyclohexyl(isobutyl)amino)phenyl)butanoate

To a solution of (S)-ethyl 3-(4-(cyclohexyl(isobutyl)amino)-3-nitrophenyl)butanoate (260 mg, 0.67 mol) in EtOAc (10 mL) was added 10% palladium on carbon (52 mg). The resulting mixture was purged with N₂ (3×) and stirred under a H₂ atmosphere for 2 hrs. The catalyst was filtered off. The filtrate was concentrated to give (S)-ethyl 3-(3-amino-4-(cyclohexyl(isobutyl)amino)phenyl)butanoate (240 mg, quantitative) as an orange oil. LCMS (M+H)⁺: m/z=361.0. ¹H NMR (400 MHz, CDCl₃) δ 6.94 (d, J=8.1 Hz, 1H), 6.59 (d, J=2.0 Hz, 1H), 6.53 (dd, J=8.1, 2.0 Hz, 1H), 4.24-3.71 (m, 4H), 3.18-3.08 (m, 1H), 2.93-2.39 (m, 5H), 1.82 (d, J=11.6 Hz, 2H), 1.73 (d, J=12.2 Hz, 2H), 1.57 (d, J=12.1 Hz, 1H), 1.47-1.14 (m, 11H), 1.05 (ddd, J=12.7, 8.0, 3.2 Hz, 1H), 0.81 (d, J=6.6 Hz, 6H).

Synthesis of (R)-ethyl 3-(3-amino-4-(cyclohexyl(isobutyl)amino)phenyl)butanoate

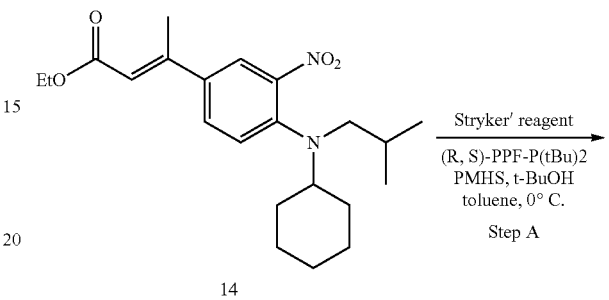

14

98

99

The title intermediate, (R)-ethyl 3-(3-amino-4-(cyclohexyl(isobutyl)amino)phenyl)butanoate, was prepared in a manner similar to (S)-ethyl 3-(3-amino-4-(cyclohexyl(isobutyl)amino)phenyl)butanoate. (R)-ethyl 3-(3-amino-4-(cyclohexyl(isobutyl)amino)phenyl)butanoate (800 mg, 96% yield over two steps) was obtained as an orange oil from (Ph₃P)CuH (54 mg, 0.16 mmol) and (R, S)-PPF-P(tBu)₂ (CAS: 155830-69-6) (24 mg, 0.045 mmol), PMHS (306 μL, 4.62 mmol), t-BuOH (243 μL, 2.55 mmol) and (E)-ethyl 3-(4-(cyclohexyl(isobutyl)amino)-3-nitrophenyl)but-2-enoate (900 mg, 2.31 mmol). LCMS (M+H)⁺: m/z=361.0. ¹H NMR (400 MHz, CDCl₃) δ 6.94 (d, J=8.1 Hz, 1H), 6.59 (d, J=2.0 Hz, 1H), 6.53 (dd, J=8.1, 2.0 Hz, 1H), 4.24-3.71 (m, 4H), 3.18-3.08 (m, 1H), 2.93-2.39 (m, 5H), 1.82 (d, J=11.6 Hz, 2H), 1.73 (d, J=12.2 Hz, 2H), 1.57 (d, J=12.1 Hz, 1H), 1.47-1.14 (m, 11H), 1.05 (ddd, J=12.7, 8.0, 3.2 Hz, 1H), 0.81 (d, J=6.6 Hz, 6H).

Example 37

(S)-3-(4-(Cyclohexyl(isobutyl)amino)-3-((3-(trifluoromethyl)-1,2,4-thiadiazol-5-yl)amino)phenyl)butanoic Acid

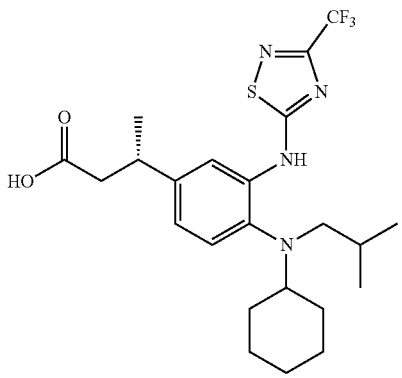 [SMILES: CC(C)CN(c1ccc([C@@H](C)CC(=O)O)cc1Nc1nc(C(F)(F)F)ns1)C1CCCCC1]

The title compound, (S)-3-(4-(cyclohexyl(isobutyl) amino)-3-((3-(trifluoromethyl)-1,2,4-thiadiazol-5-yl)amino) phenyl)butanoic acid, was made in a similar manner to Example 1. In step A (S)-ethyl 3-(3-amino-4-(cyclohexyl (isobutyl)amino)phenyl)butanoate, DMF, and 90° C. were used. In step B, LiOH, THF, MeOH, and water were used. $^1$H NMR (400 MHz, METHANOL-$d_4$) δ ppm 0.85 (d, J=6.41 Hz, 6H) 0.95-1.22 (m, 3H) 1.21-1.51 (m, 7H) 1.57 (d, J=10.44 Hz, 1H) 1.74 (d, J=11.90 Hz, 2H) 1.89 (d, J=11.35 Hz, 2H) 2.50-2.72 (m, 3H) 2.87 (d, J=6.59 Hz, 2H) 7.08 (d, J=8.06 Hz, 1H) 7.27 (d, J=8.24 Hz, 1H) 7.63 (s, 1H).

Example 38

(R)-3-(4-(Cyclohexyl(isobutyl)amino)-3-((3-(trifluoromethyl)-1,2,4-thiadiazol-5-yl)amino)phenyl)butanoic Acid

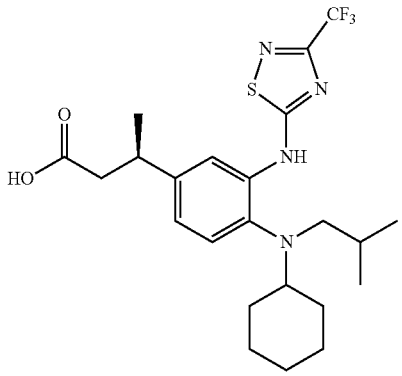 [SMILES: CC(C)CN(c1ccc([C@H](C)CC(=O)O)cc1Nc1nc(C(F)(F)F)ns1)C1CCCCC1]

The title compound, (R)-3-(4-(cyclohexyl(isobutyl) amino)-3-((3-(trifluoromethyl)-1,2,4-thiadiazol-5-yl)amino) phenyl)butanoic acid, was made in a similar manner to Example 1. In step A (R)-ethyl 3-(3-amino-4-(cyclohexyl (isobutyl)amino)phenyl)butanoate, DMF, and 90° C. were used. In step B, LiOH, THF, MeOH, and water were used. $^1$H NMR (400 MHz, METHANOL-$d_4$) δ ppm 0.85 (d, J=6.41 Hz, 6H) 0.95-1.22 (m, 3H) 1.21-1.51 (m, 7H) 1.57 (d, J=10.44 Hz, 1H) 1.74 (d, J=11.90 Hz, 2H) 1.89 (d, J=11.35 Hz, 2H) 2.50-2.72 (m, 3H) 2.87 (d, J=6.59 Hz, 2H) 7.08 (d, J=8.06 Hz, 1H) 7.27 (d, J=8.24 Hz, 1H) 7.63 (s, 1H).

Example 39

(S)-3-(3-((3-Chloro-1,2,4-thiadiazol-5-yl)amino)-4-(cyclohexyl(isobutyl)amino)phenyl)butanoic Acid

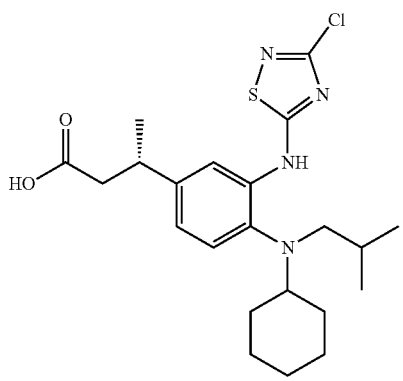

The title compound, (S)-3-(3-((3-chloro-1,2,4-thiadiazol-5-yl)amino)-4-(cyclohexyl(isobutyl)amino)phenyl)butanoic acid, was made in a similar manner to Example 1. In step A (S)-ethyl 3-(3-amino-4-(cyclohexyl(isobutyl)amino)phenyl) butanoate, DMF, and 90° C. were used. In step B, LiOH, THF, MeOH, and water were used. $^1$H NMR (400 MHz, METHANOL-$d_4$) δ ppm 0.84 (d, J=6.59 Hz, 6H) 0.97-1.22 (m, 4H) 1.22-1.44 (m, 5H) 1.58 (d, J=11.17 Hz, 2H) 1.75 (d, J=11.72 Hz, 2H) 1.88 (d, J=11.17 Hz, 2H) 2.60 (dquin, J=14.33, 7.45, 7.45, 7.45, 7.45 Hz, 3H) 2.86 (d, J=6.41 Hz, 2H) 7.08 (d, J=7.69 Hz, 1H) 7.26 (d, J=8.06 Hz, 1H) 7.49 (s, 1H).

Example 40

(R)-3-(3-((3-Chloro-1,2,4-thiadiazol-5-yl)amino)-4-(cyclohexyl(isobutyl)amino)phenyl)butanoic Acid

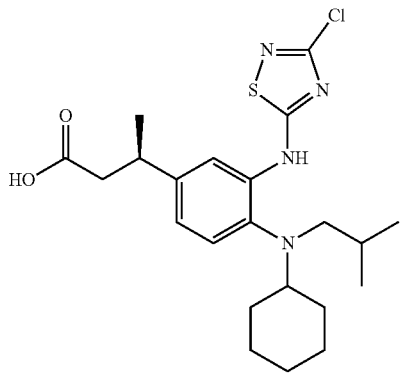

The title compound, (R)-3-(3-((3-chloro-1,2,4-thiadiazol-5-yl)amino)-4-(cyclohexyl(isobutyl)amino)phenyl)butanoic acid, was made in a similar manner to Example 1. In step A (R)-ethyl 3-(3-amino-4-(cyclohexyl(isobutyl)amino)phenyl)butanoate, DMF, and 90° C. were used. $^1$H NMR (400

MHz, METHANOL-d₄) δ ppm 0.84 (d, J=6.59 Hz, 6H) 0.98-1.24 (m, 3H) 1.24-1.51 (m, 7H) 1.57 (d, J=10.99 Hz, 1H) 1.75 (d, J=12.27 Hz, 2H) 1.88 (d, J=11.54 Hz, 2H) 2.49-2.70 (m, 3H) 2.86 (d, J=6.78 Hz, 2H) 7.07 (d, J=7.33 Hz, 1H) 7.26 (d, J=8.24 Hz, 1H) 7.49 (s, 1H).

Example 41

(S)-3-(3-((3-Chloro-1,2,4-thiadiazol-5-yl)amino)-4-(diisobutylamino)phenyl)butanoic Acid

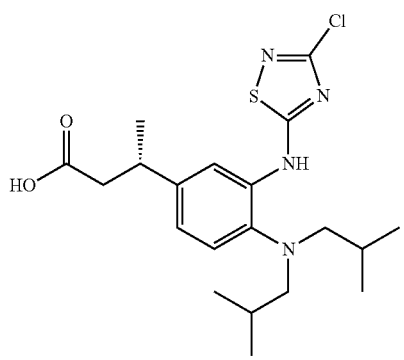 [SMILES: CC(C)CN(CC(C)C)c1ccc([C@@H](C)CC(=O)O)cc1Nc1nc(Cl)ns1]

The title compound, (S)-3-(3-((3-chloro-1,2,4-thiadiazol-5-yl)amino)-4-(diisobutylamino)phenyl)butanoic acid, was made in a manner similar to example 39. ¹H NMR (400 MHz, METHANOL-d₄) δ ppm 0.90 (d, J=6.41 Hz, 12H) 1.33 (d, J=5.86 Hz, 3H) 1.70 (dt, J=13.23, 6.66 Hz, 2H) 2.59 (br. s., 2H) 2.69 (d, J=6.96 Hz, 4H) 3.22-3.29 (m, 1H) 7.09 (d, J=7.87 Hz, 1H) 7.28 (d, J=8.06 Hz, 1H) 7.41 (s, 1H).

Example 42

(R)-3-(3-((3-Chloro-1,2,4-thiadiazol-5-yl)amino)-4-(diisobutylamino)phenyl)butanoic Acid

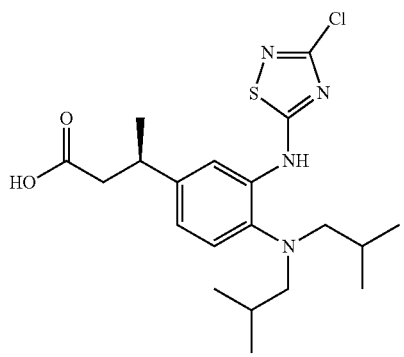 [SMILES: CC(C)CN(CC(C)C)c1ccc([C@H](C)CC(=O)O)cc1Nc1nc(Cl)ns1]

The title compound, compound (R)-3-(3-((3-chloro-1,2,4-thiadiazol-5-yl)amino)-4-(diisobutylamino)phenyl)butanoic acid, was made in a manner similar to example 40. ¹H NMR (400 MHz, METHANOL-d₄) δ ppm 0.90 (d, J=6.59 Hz, 12H) 1.30 (d, J=6.96 Hz, 3H) 1.69 (dt, J=13.37, 6.68 Hz, 2H) 2.29-2.42 (m, 1H) 2.42-2.54 (m, 1H) 2.67 (d, J=6.96 Hz, 4H) 3.20-3.29 (m, 1H) 7.11 (dd, J=8.24, 1.65 Hz, 1H) 7.27 (d, J=8.24 Hz, 1H) 7.35 (s, 1H).

Example 43

3-(4-(Diisobutylamino)-3-((4,5-dimethylthiazol-2-yl)amino)phenyl)butanoic Acid

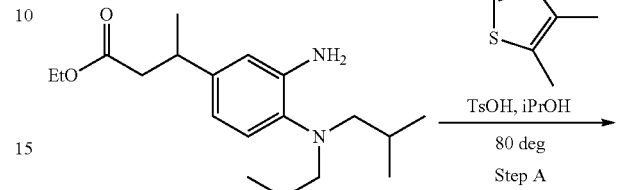

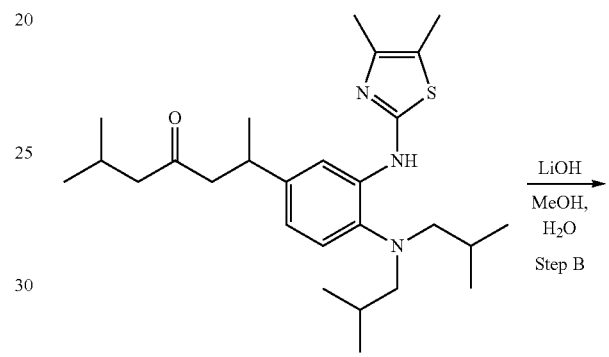

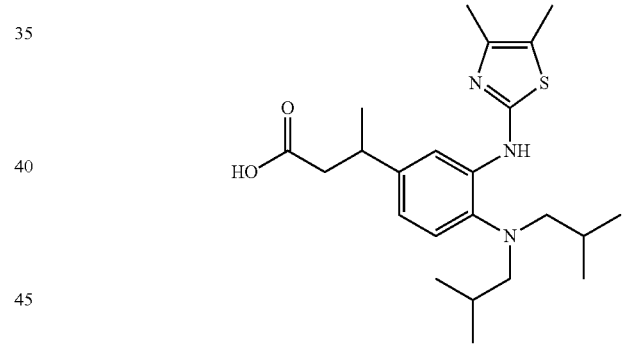

Step A

Isopropyl 3-(4-(diisobutylamino)-3-((4,5-dimethylthiazol-2-yl)amino)phenyl)butanoate A solution of ethyl 3-(3-amino-4-(diisobutylamino)phenyl)butanoate (0.100 g, 0.30 mmol), 2-bromo-4,5-dimethylthiazole (0.172 g, 0.90 mmol), and p-toluenesulfonic acid (0.057 g, 0.30 mmol) in iPrOH (1.5 mL) was heated at 80° C. for 2 d. Saturated NaHCO₃ was added and the reaction mixture was extracted with DCM. The organic layer was dried over Na₂SO₄, filtered, evaporated and purified by reverse phase chromatography (5-95% CH₃CN/H₂O (0.1% formic acid)) to obtain isopropyl 3-(4-(diisobutylamino)-3-((4,5-dimethylthiazol-2-yl)amino)phenyl)butanoate (0.0185 g, 13%). LCMS (M+H)⁺: m/z=460.5.

Step B

3-(4-(Diisobutylamino)-3-((4,5-dimethylthiazol-2-yl)amino)phenyl)butanoic Acid Isopropyl 3-(4-(diisobutylamino)-3-((4,5-dimethylthiazol-2-yl)amino)phenyl)butanoate (0.0185 g, 0.04 mmol) was subjected to base hydrolysis as previously described and purified by reverse phase chromatography (0-70% $CH_3CN$/$H_2O$ (0.1% formic acid)) to afford 3-(4-(diisobutylamino)-3-((4,5-dimethylthiazol-2-yl)amino)phenyl)butanoic acid (0.0125 g, 74%) as a white solid. LCMS (M+H)$^+$: m/z=418.4. $^1$H NMR (400 MHz, METHANOL-$d_4$) δ ppm 7.66 (s, 1H), 7.22 (d, J=8.28 Hz, 1H), 6.91 (d, J=8.28 Hz, 1H), 3.15-3.29 (m, 1H), 2.49-2.70 (m, 6H), 2.29 (s, 3H), 2.21 (s, 3H), 1.69 (s, 2H), 1.34 (d, J=6.78 Hz, 3H), 0.93 (d, J=6.53 Hz, 12H).

Example 44

3-(4-(Diisobutylamino)-3-((4-(trifluoromethyl)thiazol-2-yl)amino)phenyl)butanoic Acid

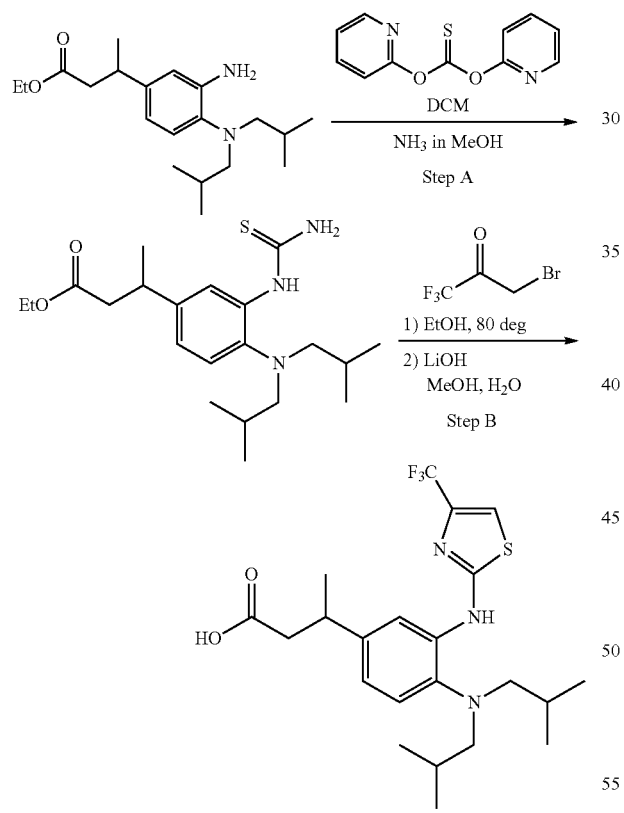

Step A

Ethyl 3-(4-(diisobutylamino)-3-thioureidophenyl)butanoate

O,O-di(pyridin-2-yl) carbonothioate (0.298 g, 1.28 mmol) was added to a solution of ethyl 3-(3-amino-4-(diisobutylamino)phenyl)butanoate (0.358 g, 1.07 mmol) in DCM (7 mL) and the reaction mixture was stirred for 2 h. 7N $NH_3$ in MeOH (3 mL) was added and the solution was stirred overnight and evaporated to dryness. The residue was purified by silica gel chromatography (EtOAc/hexanes) to afford ethyl 3-(4-(diisobutylamino)-3-thioureidophenyl)butanoate (0.38 g, 90%) as a clear oil. LCMS (M+H)$^+$: m/z=394.4.

Step B

3-(4-(Diisobutylamino)-3-((4-(trifluoromethyl)thiazol-2-yl)amino)phenyl)butanoic Acid A solution of ethyl 3-(4-(diisobutylamino)-3-thioureidophenyl)butanoate (0.064 g, 0.16 mmol) and 3-bromo-1,1,1-trifluoropropan-2-one (0.062 g, 0.33 mmol) in ethanol (1.6 mL) was stirred at 80° C. for 1 h 45 mins. The reaction mixture was evaporated to dryness and used without further purification. The residue (0.16 mmol) was subjected to base hydrolysis as previously described and purified by reverse phase chromatography (5-95% $CH_3CN$/$H_2O$ (0.1% formic acid)) to afford 3-(4-(diisobutylamino)-3-((4-(trifluoromethyl)thiazol-2-yl)amino)phenyl)butanoic acid (0.056 g, 76%) as a white solid. LCMS (M+H)$^+$: m/z=458.4. $^1$H NMR (400 MHz, METHANOL-$d_4$) δ ppm 7.87 (d, J=1.37 Hz, 1H), 7.34 (s, 1H), 7.22 (d, J=8.20 Hz, 1H), 6.94 (dd, J=8.20, 1.76 Hz, 1H), 3.16-3.25 (m, 1H), 2.47-2.65 (m, 6H), 1.59-1.72 (m, 2H), 1.29 (d, J=6.84 Hz, 3H), 0.89 (d, J=6.64 Hz, 12H).

Example 45

3-(4-(Diisobutylamino)-3-((5-methyl-4-(trifluoromethyl)thiazol-1-yl)amino)phenyl)butanoic Acid

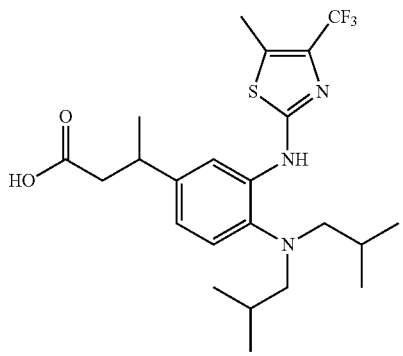

The title compound, 3-(4-(diisobutylamino)-3-((5-methyl-4-(trifluoromethyl)thiazol-2-yl)amino)phenyl)butanoic acid, was made in a manner similar to example 44. In step B, part 1, 3-bromo-1,1,1-trifluorobutan-2-one was used. 3-(4-(Diisobutylamino)-3-((5-methyl-4-(trifluoromethyl)thiazol-2-yl)amino)phenyl)butanoic acid (0.049 g, 81%) was isolated as a white solid. LCMS (M+H)$^+$: m/z=472.4. $^1$H NMR (400 MHz, METHANOL-$d_4$) δ ppm 7.82 (d, J=1.76 Hz, 1H), 7.19 (d, J=8.20 Hz, 1H), 6.91 (dd, J=8.10, 1.66 Hz, 1H), 3.12-3.23 (m, 1H), 2.46-2.65 (m, 6H), 2.43 (d, J=1.95 Hz, 3H), 1.59-1.72 (m, 2H), 1.28 (d, J=7.03 Hz, 3H), 0.89 (d, J=6.64 Hz, 12H).

Example 46

3-(4-(Diisobutylamino)-3-((4-isopropylthiazol-2-yl)amino)phenyl)butanoic Acid

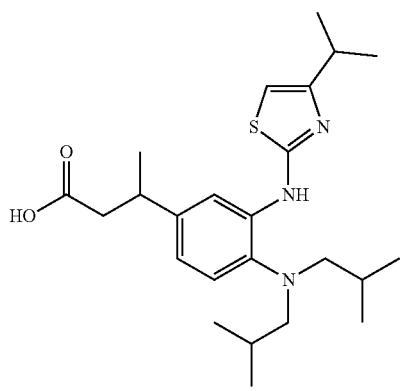 [SMILES: CC(C)CN(CC(C)C)c1ccc(C(C)CC(=O)O)cc1Nc1nc(C(C)C)cs1]

The title compound, 3-(4-(diisobutylamino)-3-((4-isopropylthiazol-2-yl)amino)phenyl)butanoic acid, was made in a manner similar to example 55. In step B, part 1, 1-bromo-3-methylbutan-2-one was used. 3-(4-(Diisobutylamino)-3-((4-isopropylthiazol-2-yl)amino)phenyl)butanoic acid (0.048 g, 82%) was isolated as a white solid. LCMS (M+H)$^+$: m/z=432.4. $^1$H NMR (400 MHz, METHANOL-d$_4$) δ ppm 7.86 (s, 1H), 7.17 (d, J=8.20 Hz, 1H), 6.87 (d, J=8.01 Hz, 1H), 6.32 (s, 1H), 3.14-3.25 (m, 1H), 2.83-2.95 (m, 1H), 2.46-2.64 (m, 6H), 1.59-1.72 (m, 2H), 1.21-1.33 (m, 9H), 0.89 (d, J=6.44 Hz, 12H).

Example 47

3-(4-(Diisobutylamino)-3-((5-methyl-4H-1,2,4-triazol-3-yl)amino)phenyl)butanoic Acid

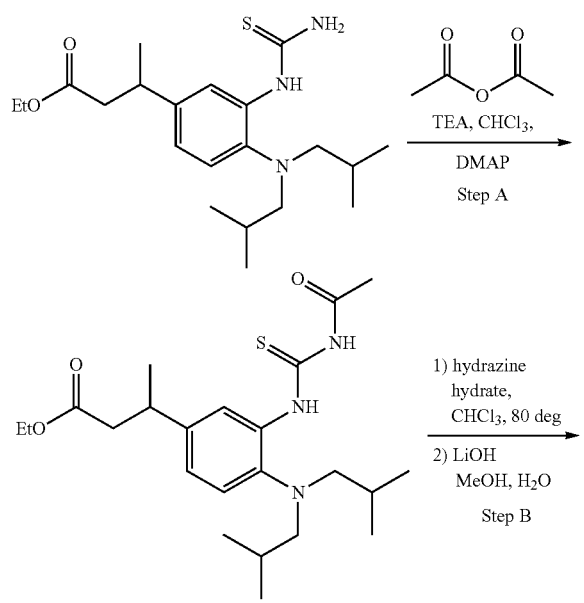

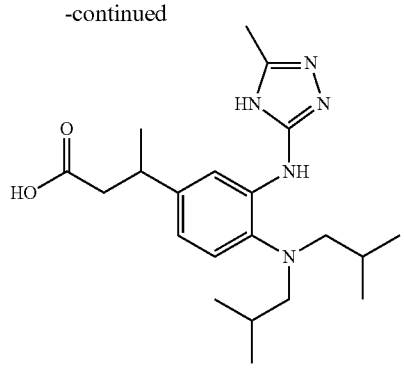

Step A

Ethyl 3-(3-(3-acetylthioureido)-4-(diisobutylamino)phenyl)butanoate

Acetic anhydride (0.022 mL, 0.24 mmol) was added to a solution of ethyl 3-(4-(diisobutylamino)-3-thioureidophenyl)butanoate (0.0462 g, 0.117 mmol) and TEA (0.033 ml, 0.235 mmol) in CHCl$_3$ (1.2 mL). The reaction mixture was stirred overnight, DMAP (catalytic) was added and stirring was continued for 2 h. The solution was evaporated to dryness and the residue was purified by silica gel chromatography (EtOAc/hexanes) to afford ethyl 3-(3-(3-acetylthioureido)-4-(diisobutylamino)phenyl)butanoate (0.026 g, 50%) as a light yellow oil. LCMS (M+H)$^+$: m/z=436.5. $^1$H NMR (400 MHz, CHLOROFORM-d) δ ppm 12.22 (s, 1H), 9.02 (br. s., 1H), 8.28 (s, 1H), 6.94-7.14 (m, 2H), 4.09 (q, J=7.14 Hz, 2H), 3.20-3.35 (m, 1H), 2.46-2.76 (m, 6H), 2.20 (s, 3H), 1.68-1.81 (m, 2H), 1.27-1.36 (m, 3H), 1.13-1.23 (m, 3H), 0.77-0.93 (m, 12H).

Step B 3-(4-(Diisobutylamino)-3-((5-methyl-4H-1,2,4-triazol-3-yl)amino)phenyl)butanoic Acid A solution of ethyl 3-(3-(3-acetylthioureido)-4-(diisobutylamino)phenyl)butanoate (0.0257 g, 0.06 mmol) and hydrazine hydrate (0.059 g, 1.18 mmol) in CHCl$_3$ (1 mL) was heated at 80° C. for 3 h. The reaction mixture was diluted with saturated sodium bicarbonate solution and extracted with EtOAc. The organic layer was dried over Na$_2$SO$_4$, filtered, and evaporated to a residue that was taken onto the next step without further purification. The residue (0.06 mmol) was subjected to base hydrolysis as previously described and purified by reverse phase chromatography (5-95% CH$_3$CN/H$_2$O (0.1% formic acid)) to afford 3-(4-(diisobutylamino)-3-((5-methyl-4H-1,2,4-triazol-3-yl)amino)phenyl)butanoic acid (0.002 g, 8%) as a white solid. LCMS (M+H)$^+$: m/z=388.4. $^1$H NMR (400 MHz, METHANOL-d$_4$) δ ppm 7.91 (br. s., 1H), 7.15 (d, J=8.06 Hz, 1H), 6.79 (d, J=7.33 Hz, 1H), 3.15-3.26 (m, 1H), 2.45-2.69 (m, 6H), 2.38 (s, 3H), 1.64-1.76 (m, 2H), 1.31 (d, J=6.78 Hz, 3H), 0.90-0.97 (m, 12H).

Example 48

3-(3-((5-Cyclopropyl-4H-1,2,4-triazol-3-yl)amino)-4-(diisobutylamino)phenyl)butanoic Acid

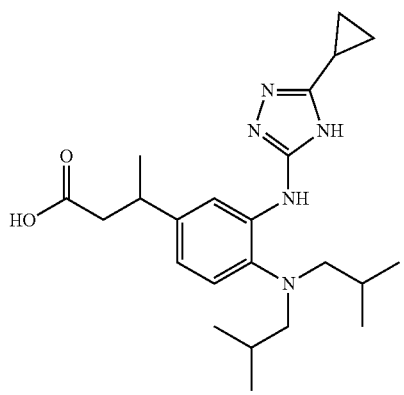 [SMILES: CC(C)CN(CC(C)C)c1ccc(C(C)CC(=O)O)cc1Nc1nnc(C2CC2)[nH]1]

The title compound, 3-(3-((5-cyclopropyl-4H-1,2,4-triazol-3-yl)amino)-4-(diisobutylamino)phenyl)butanoic acid, was made in a manner similar to example 47. In step A, cyclopropanecarbonyl chloride, TEA, and catalytic DMAP was used. 3-(3-((5-Cyclopropyl-4H-1,2,4-triazol-3-yl)amino)-4-(diisobutylamino)phenyl)butanoic acid (0.015 g, 72%) was isolated as a white solid. LCMS (M+H)$^+$: m/z=414.5. $^1$H NMR (400 MHz, METHANOL-$d_4$) δ ppm 7.91 (d, J=1.10 Hz, 1H), 7.14 (d, J=8.06 Hz, 1H), 6.77 (dd, J=8.24, 1.65 Hz, 1H), 3.12-3.27 (m, 1H), 2.45-2.69 (m, 6H), 1.93-2.06 (m, 1H), 1.59-1.75 (m, 2H), 1.30 (d, J=6.96 Hz, 3H), 0.97-1.09 (m, 4H), 0.92 (d, J=6.59 Hz, 12H).

Example 49

(R)-3-(4-(Cyclohexyl(isobutyl)amino)-3-((4-(trifluoromethyl)thiazol-2-yl)amino)phenyl)butanoic Acid

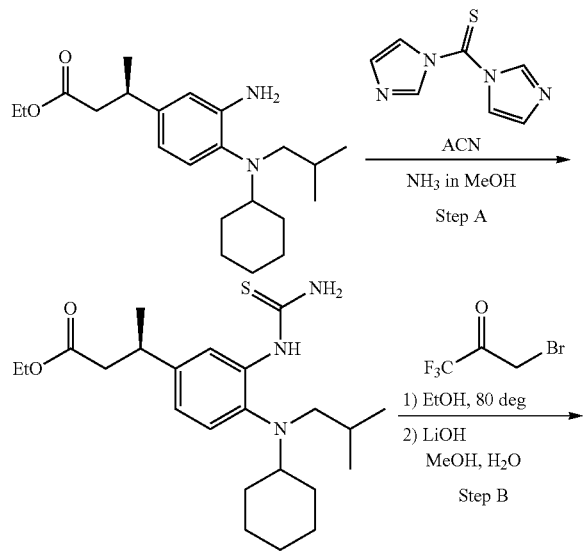

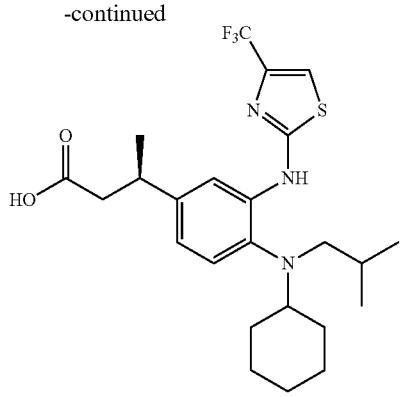

Step A

(R)-Ethyl 3-(4-(cyclohexyl(isobutyl)amino)-3-thioureidophenyl)butanoate

Di(1H-imidazol-1-yl)methanethione (0.289 g, 1.62 mmol) was added to a solution of (R)-ethyl 3-(3-amino-4-(cyclohexyl(isobutyl)amino)phenyl)butanoate (0.292 g, 0.81 mmol) in ACN (4 mL) and the reaction mixture was stirred for 1 h. 7N NH$_3$ in MeOH (3 mL) was added and the solution was stirred overnight and evaporated to dryness. The residue was purified by silica gel chromatography (EtOAc/hexanes) to afford (R)-ethyl 3-(4-(cyclohexyl(isobutyl)amino)-3-thioureidophenyl)butanoate (0.324 g, 95%) as a white solid. LCMS (M+H)$^+$: m/z=420.5. $^1$H NMR (400 MHz, CHLOROFORM-d) δ ppm 8.07 (br. s., 1H), 7.23 (br. s., 1H), 7.09-7.15 (m, 1H), 6.97-7.02 (m, 1H), 6.29 (br. s., 1H), 4.03 (q, J=7.14 Hz, 2H), 3.16-3.31 (m, 1H), 2.80 (s, 2H), 2.43-2.64 (m, 3H), 1.89 (br. s., 2H), 1.72-1.82 (m, 2H), 0.98-1.45 (m, 13H), 0.83 (d, J=6.59 Hz, 6H).

Step B

(R)-3-(4-(Cyclohexyl(isobutyl)amino)-3-((4-(trifluoromethyl)thiazol-2-yl)amino)phenyl)butanoic Acid A solution of (R)-ethyl 3-(4-(cyclohexyl(isobutyl)amino)-3-thioureidophenyl)butanoate (0.0544 g, 0.13 mmol) and 3-bromo-1,1,1-trifluoropropan-2-one (0.050 g, 0.26 mmol) in EtOH (1.3 mL) was stirred at 80° C. for 1 h 45 mins. The reaction mixture was evaporated to give a residue. The residue (0.13 mmol) was subjected to base hydrolysis as previously described and purified by reverse phase chromatography (10-100% CH$_3$CN/H$_2$O+0.1% formic acid) to afford (R)-3-(4-(cyclohexyl(isobutyl)amino)-3-((4-(trifluoromethyl)thiazol-2-yl)amino)phenyl)butanoic acid (0.0069 g, 11%) as a white solid. LCMS (M+H)$^+$: m/z=484.4. $^1$H NMR (400 MHz, METHANOL-$d_4$) δ ppm 7.77 (d, J=1.65 Hz, 1H), 7.37 (s, 1H), 7.23 (d, J=8.06 Hz, 1H), 6.97 (dd, J=8.15, 1.74 Hz, 1H), 3.19-3.29 (m, 1H), 2.86 (d, J=6.78 Hz, 2H), 2.50-2.68 (m, 3H), 1.90 (d, J=11.35 Hz, 2H), 1.75 (d, J=12.45 Hz, 2H), 1.57 (d, J=10.99 Hz, 1H), 1.24-1.46 (m, 6H), 1.03-1.23 (m, 3H), 0.86 (d, J=6.59 Hz, 6H).

Example 50

(R)-3-(4-(Cyclohexyl(isobutyl)amino)-3-((5-cyclopropyl-4H-1,2,4-triazol-3-yl)amino)phenyl)butanoic Acid

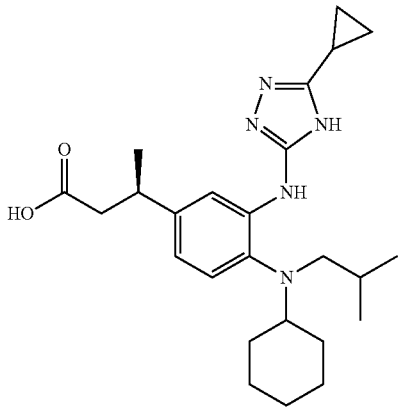 [SMILES: CC(C)CN(c1ccc([C@H](C)CC(=O)O)cc1Nc1nnc(C2CC2)[nH]1)C1CCCCC1]

The title compound, (R)-3-(4-(cyclohexyl(isobutyl)amino)-3-((5-cyclopropyl-4H-1,2,4-triazol-3-yl)amino)phenyl)butanoic acid, was made in a manner similar to example 47. In step A, (R)-ethyl 3-(4-(cyclohexyl(isobutyl)amino)-3-thioureidophenyl)butanoate, cyclopropanecarbonyl chloride, TEA, and catalytic DMAP were used. (R)-3-(4-(cyclohexyl(isobutyl)amino)-3-((5-cyclopropyl-4H-1,2,4-triazol-3-yl)amino)phenyl)butanoic acid (0.022 g, 75%) was isolated as an off-white solid. LCMS (M+H)$^+$: m/z=440.5. $^1$H NMR (400 MHz, METHANOL-d$_4$) δ ppm 7.93 (d, J=1.10 Hz, 1H), 7.11 (d, J=8.06 Hz, 1H), 6.76 (dd, J=8.06, 1.65 Hz, 1H), 3.14-3.27 (m, 1H), 2.45-2.96 (m, 5H), 1.90-2.04 (m, 3H), 1.75 (d, J=12.27 Hz, 2H), 1.58 (d, J=11.35 Hz, 1H), 0.97-1.47 (m, 13H), 0.85 (d, J=6.41 Hz, 6H).

Example 51

3-(4-(Diisobutylamino)-3-((3-phenyl-1,2,4-oxadiazol-5-yl)amino)phenyl)butanoic Acid

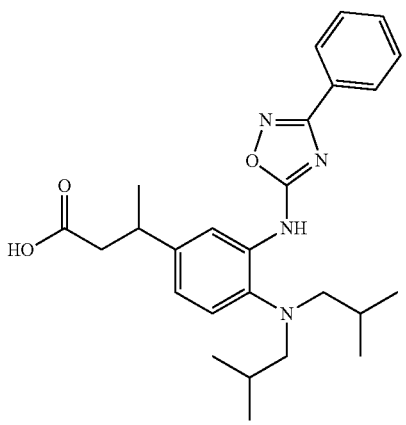 [SMILES: CC(C)CN(CC(C)C)c1ccc(C(C)CC(=O)O)cc1Nc1nc(-c2ccccc2)no1]

The title compound, 3-(4-(diisobutylamino)-3-((3-phenyl-1,2,4-oxadiazol-5-yl)amino)phenyl)butanoic acid, was made in a manner similar to Example 1. $^1$H NMR (400 MHz, METHANOL-d$_4$) δ ppm 0.98 (d, J=6.78 Hz, 12H) 1.39 (d, J=6.27 Hz, 3H) 1.74 (dt, J=13.43, 6.59 Hz, 2H) 2.54-2.73 (m, 6H) 3.37 (s, 1H) 7.07 (d, J=8.03 Hz, 1H) 7.32 (d, J=8.28 Hz, 1H) 7.48-7.64 (m, 3H) 8.03-8.16 (m, 2H) 8.20 (s, 1H).

Example 52

3-(3-((3-Bromo-1,2,4-thiadiazol-5-yl)amino)-4-(cyclohexyl(isobutyl)amino)phenyl)butanoic Acid

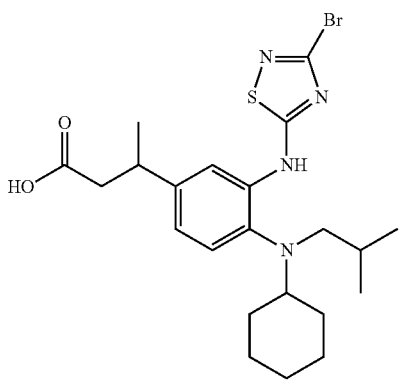

The title compound, 3-(3-((3-bromo-1,2,4-thiadiazol-5-yl)amino)-4-(cyclohexyl(isobutyl)amino)phenyl)butanoic acid, was made in a manner similar to Example 1. $^1$H NMR (400 MHz, METHANOL-d$_4$) δ ppm 0.84 (d, J=6.41 Hz, 6H) 1.03-1.21 (m, 3H) 1.21-1.46 (m, 8H) 1.57 (d, J=11.72 Hz, 1H) 1.74 (d, J=12.27 Hz, 2H) 1.88 (d, J=11.35 Hz, 2H) 2.35-2.69 (m, 3H) 2.85 (d, J=6.78 Hz, 2H) 7.09 (d, J=8.06 Hz, 1H) 7.25 (d, J=8.24 Hz, 1H) 7.42 (s, 1H).

Example 53

(S)-3-(4-(Diisobutylamino)-3-((3-(trifluoromethyl)-1,2,4-thiadiazol-5-yl)amino)phenyl)butanoic Acid

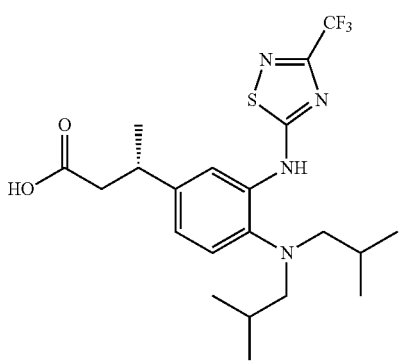 [SMILES: CC(C)CN(CC(C)C)c1ccc([C@@H](C)CC(=O)O)cc1Nc1nc(C(F)(F)F)ns1]

The title compound, (S)-3-(4-(diisobutylamino)-3-((3-(trifluoromethyl)-1,2,4-thiadiazol-5-yl)amino)phenyl)butanoic acid, was made in a manner similar to Example 1. $^1$H NMR (400 MHz, METHANOL-d$_4$) δ ppm 0.90 (d, J=6.59 Hz, 12H) 1.33 (d, J=6.59 Hz, 3H) 1.70 (dt, J=13.32, 6.62 Hz, 2H) 1.85-1.88 (m, 1H) 2.54 (dd, J=12.27, 7.69 Hz, 2H) 2.70 (d, J=6.96 Hz, 4H) 7.11 (d, J=8.06 Hz, 1H) 7.29 (d, J=8.24 Hz, 1H) 7.48 (s, 1H).

Example 54

(R)-3-(4-(Diisobutylamino)-3-((3-(trifluoromethyl)-1,2,4-thiadiazol-5-yl)amino)phenyl)butanoic Acid

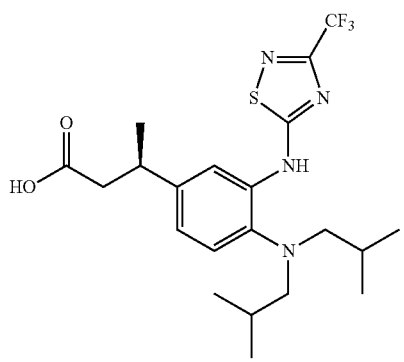 [SMILES: CC(C)CN(CC(C)C)c1ccc([C@H](C)CC(=O)O)cc1Nc1nc(C(F)(F)F)ns1]

The title compound, (R)-3-(4-(diisobutylamino)-3-((3-(trifluoromethyl)-1,2,4-thiadiazol-5-yl)amino)phenyl)butanoic acid, was made in a manner similar to Example 1. $^1$H NMR (400 MHz, DMSO-$d_6$) δ ppm 0.79 (d, J=6.23 Hz, 12H) 1.17 (d, J=6.59 Hz, 3H) 1.56-1.75 (m, 2H) 2.11-2.40 (m, 2H) 2.74 (d, J=6.41 Hz, 4H) 3.08 (d, J=6.41 Hz, 1H) 6.97 (br. s., 1H) 7.08 (d, J=7.69 Hz, 1H) 7.37 (br. s., 1H).

Example 55

3-(4-(Diisobutylamino)-3-((5-(trifluoromethyl)-1,3,4-thiadiazol-2-yl)amino)phenyl)butanoic Acid, 2,2,2-trifluoroacetic Acid Salt

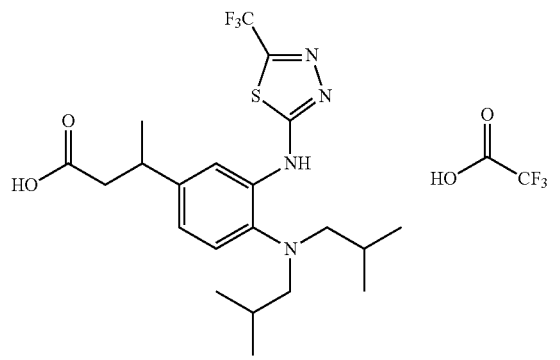 [SMILES: CC(C)CN(CC(C)C)c1ccc(C(C)CC(=O)O)cc1Nc1nnc(C(F)(F)F)s1 ; O=C(O)C(F)(F)F]

The title compound, 3-(4-(diisobutylamino)-3-((5-(trifluoromethyl)-1,3,4-thiadiazol-2-yl)amino)phenyl)butanoic acid 2,2,2-trifluoroacetic acid salt, was made in a manner similar to Example 26. $^1$H NMR (400 MHz, METHANOL-$d_4$) δ ppm 0.87 (d, J=6.64 Hz, 12H) 1.30 (d, J=7.03 Hz, 3H) 1.68 (dt, J=13.43, 6.66 Hz, 2H) 2.58 (dd, J=7.42, 3.12 Hz, 2H) 2.82 (br. s., 4H) 3.19-3.26 (m, 1H) 7.10 (d, J=7.62 Hz, 1H) 7.31 (d, J=8.20 Hz, 1H) 7.64 (br. s., 1H).

Example 56

(R)-3-(4-(cyclohexyl(isobutyl)amino)-3-((5-cyclopropyl-1,3,4-thiadiazol-2-yl)amino)phenyl)butanoic Acid

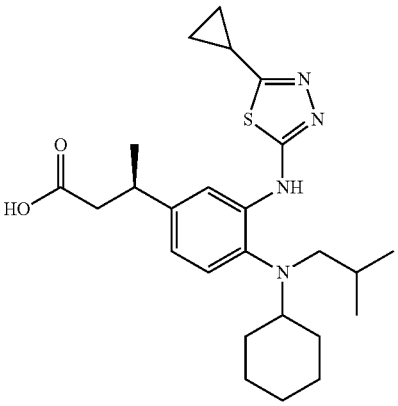 [SMILES: CC(C)CN(c1ccc([C@H](C)CC(=O)O)cc1Nc1nnc(C2CC2)s1)C1CCCCC1]

The title compound, (R)-3-(4-(cyclohexyl(isobutyl)amino)-3-((5-cyclopropyl-1,3,4-thiadiazol-2-yl)amino)phenyl)butanoic acid, was made in a manner similar to Example 26. $^1$H NMR (400 MHz, METHANOL-d4) δ 7.62 (d, J=2.0 Hz, 1H), 7.19 (s, 1H), 6.93 (d, J=2.0 Hz, 1H), 3.24-3.17 (m, 1H), 2.82 (d, J=6.6 Hz, 2H), 2.63-2.48 (m, 3H), 2.28 (tt, J=5.0, 8.3 Hz, 1H), 1.85 (d, J=10.9 Hz, 2H), 1.71 (d, J=13.5 Hz, 2H), 1.54 (d, J=10.7 Hz, 1H), 1.34 (dd, J=6.5, 13.4 Hz, 1H), 1.28 (s, 4H), 1.27-1.20 (m, 1H), 1.18-1.12 (m, 3H), 1.12-1.03 (m, 2H), 1.03-0.98 (m, 2H), 0.82 (d, J=6.6 Hz, 6H).

Example 57

(S)-3-(4-(Cyclohexyl(isobutyl)amino)-3-((5-cyclopropyl-1,3,4-thiadiazol-2-yl)amino)phenyl)butanoic Acid

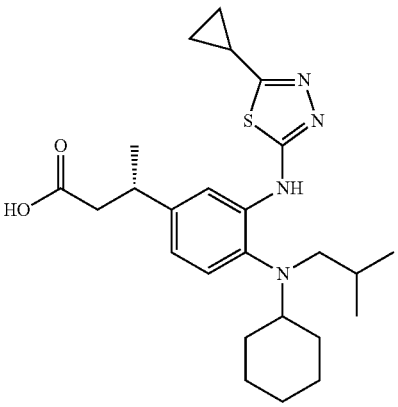 [SMILES: CC(C)CN(c1ccc([C@@H](C)CC(=O)O)cc1Nc1nnc(C2CC2)s1)C1CCCCC1]

The title compound, (S)-3-(4-(cyclohexyl(isobutyl)amino)-3-((5-cyclopropyl-1,3,4-thiadiazol-2-yl)amino)phenyl)butanoic acid, was made in a manner similar to Example 26. H NMR (400 MHz, METHANOL-d4) δ 8.22 (s, 1H), 7.66 (d, J=2.0 Hz, 1H), 7.21 (d, J=8.2 Hz, 1H), 6.97-6.92 (m, 1H), 3.28-3.19 (m, 1H), 2.85 (d, J=6.8 Hz, 2H), 2.66-2.51 (m, 3H), 2.35-2.26 (m, 1H), 1.89 (d, J=10.8 Hz, 2H), 1.74 (d, J=12.6 Hz, 2H), 1.57 (d, J=11.7 Hz, 1H), 1.38 (s, 1H), 1.34-1.23 (m, 5H), 1.22-1.00 (m, 7H), 0.84 (d, J=6.6 Hz, 6H).

Example 58

3-(4-(Diisobutylamino)-3-(pyrazin-2-ylamino)phenyl)butanoic Acid

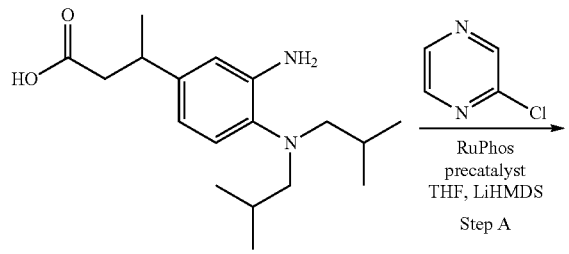

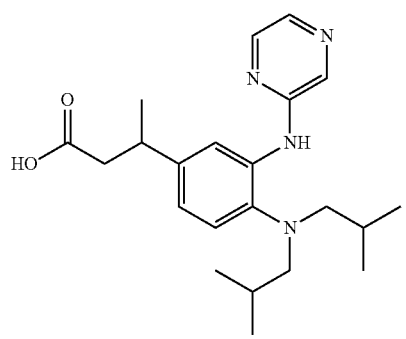

Step A 3-(4-(Diisobutylamino)-3-(pyrazin-2-ylamino)phenyl)butanoic Acid

To a solution of 3-(3-amino-4-(diisobutylamino)phenyl)butanoic acid (80 mg, 0.261 mmol), 2-chloropyrazine (44.8 mg, 0.392 mmol) and chloro-(2-dicyclohexylphosphino-2',6'-diisopropoxy-1,1'-biphenyl)[2-(2-aminoethyl)phenyl]palladium(II)-methyl-t-butyl ether adduct (RuPhos precatalyst) (64.0 mg, 0.078 mmol) in THF (5.0 ml) at room temperature was added LiHMDS (1.044 ml, 1.044 mmol). The reaction mixture was stirred at room temperature for 5 minutes. The reaction mixture was purified directly via reverse phase chromatography to give 3-(4-(diisobutylamino)-3-(pyrazin-2-ylamino)phenyl)butanoic acid (23 mg, 0.057 mmol, 21.77% yield). LCMS ESI (M+H)$^+$: m/z=385.4. $^1$H NMR (400 MHz, DMSO-d$_6$): δ ppm 8.44 (s, 1H), 8.18-8.26 (m, 2H), 8.14 (d, J=1.8 Hz, 1H), 7.97 (d, J=2.7 Hz, 1H), 7.23 (d, J=8.0 Hz, 1H), 6.89 (dd, J=8.2, 1.8 Hz, 1H), 3.05-3.18 (m, 1H), 2.60 (d, J=7.2 Hz, 4H), 2.41-2.51 (m, 2H), 1.65 (dt, J=13.3, 6.7 Hz, 2H), 1.22 (d, J=7.0 Hz, 3H), 0.87 (d, J=6.6 Hz, 12H).

Example 59

3-(4-(Cyclohexyl(isobutyl)amino)-3-((furan-2-ylmethyl)amino)phenyl)butanoic Acid

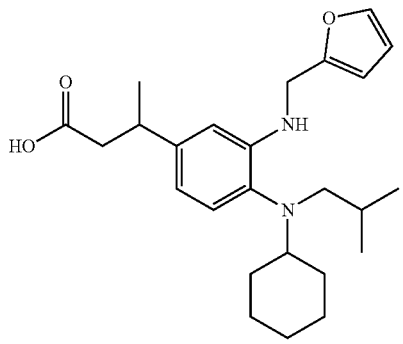

The title compound, 3-(4-(cyclohexyl(isobutyl)amino)-3-((furan-2-ylmethyl)amino)phenyl)butanoic acid, was made in a manner similar to Example 19. 3-(4-(Cyclohexyl(isobutyl)amino)-3-((furan-2-ylmethyl)amino)phenyl)butanoic acid was isolated (37 mg, 0.085 mmol, 56.7% yield). LCMS ESI (M+H)$^+$: m/z=413.4. $^1$H NMR (400 MHz, DMSO-d$_6$): δ ppm 7.56 (s, 1H), 6.92 (d, J=8.1 Hz, 1H), 6.59 (d, J=1.5 Hz, 1H), 6.45 (d, J=7.9 Hz, 1H), 6.37 (dd, J=2.9, 1.8 Hz, 1H), 6.24 (d, J=2.9 Hz, 1H), 5.23 (t, J=6.3 Hz, 1H), 4.33 (dd, J=11.7, 5.9 Hz, 2H), 2.91-3.08 (m, 2H), 2.34-2.46 (m, 3H), 1.72 (d, J=11.0 Hz, 5H), 1.45-1.57 (m, 1H), 1.11-1.32 (m, 7H), 0.95-1.05 (m, 2H), 0.76 0.70-0.85 (m, 6H).

Example 60

3-(4-(Diisobutylamino)-3-((4-methyl-2-(trifluoromethyl)thiazol-5-yl)amino)phenyl)butanoic Acid

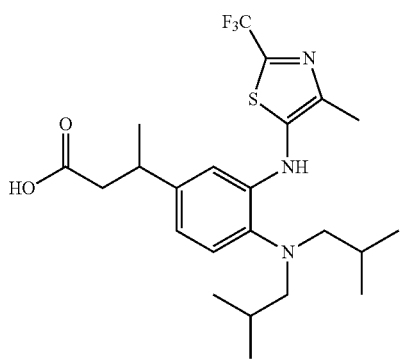 [SMILES: Cc1nc(C(F)(F)F)sc1Nc1cc(C(C)CC(=O)O)ccc1N(CC(C)C)CC(C)C]

The title compound, 3-(4-(diisobutylamino)-3-((4-methyl-2-(trifluoromethyl)thiazol-5-yl)amino)phenyl)butanoic acid, was made in a manner similar to Example 17. 3-(4-(Diisobutylamino)-3-((4-methyl-2-(trifluoromethyl)thiazol-5-yl)amino)phenyl)butanoic acid was isolated (32 mg, 0.067 mmol, 61.3% yield) as a thick yellowish residue. LCMS (M+H)$^+$: m/z=472 $^1$H NMR (400 MHz, DMSO-d) δ ppm 0.85 (d, J=6.41 Hz, 12H), 1.16 (d, J=6.78 Hz, 3H), 1.64 (dt, J=13.19, 6.59 Hz, 2H), 2.29 (s, 3H), 2.40-2.47 (m, 2H), 2.64 (d, J=6.96 Hz, 4H), 2.99-3.14 (m, 1H), 6.74-6.87 (m, 2H), 7.20 (d, J=8.06 Hz, 1H), 7.44 (s, 1H), 12.03 (s, 1H).

Example 61

3-(3-((2-Cyclopropylthiazol-5-yl)amino)-4-(diisobutylamino)phenyl)butanoic Acid

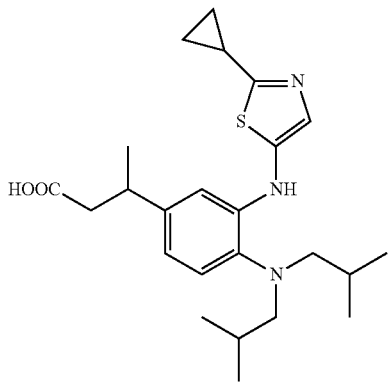 [SMILES: CC(C)CN(CC(C)C)c1ccc(C(C)CC(=O)O)cc1Nc1cnc(C2CC2)s1]

The title compound, 3-(3-((2-cyclopropylthiazol-5-yl)amino)-4-(diisobutylamino)phenyl)butanoic acid, was made in a manner similar to Example 17. 3-(3-((2-Cyclopropylthiazol-5-yl)amino)-4-(diisobutylamino)phenyl)butanoic acid was isolated (33.2 mg, 0.077 mmol, 36.4% yield) as thick oil. LCMS (M+H)$^+$: m/z=430. $^1$H NMR (400 MHz, DMSO-d$_6$) δ ppm 0.85 (d, J=6.44 Hz, 12H), 0.90-0.96 (m, 2H), 1.00-1.08 (m, 2H), 1.15 (d, J=6.84 Hz, 3H), 1.55-1.69 (m, 2H), 2.23-2.34 (m, 1H), 2.35-2.47 (m, 2H), 2.56 (d, J=7.23 Hz, 4H), 2.96-3.08 (m, 1H), 6.71 (d, J=8.20 Hz, 1H), 6.77 (s, 1H), 7.11-7.18 (m, 2H), 7.29 (s, 1H), 12.06 (br. s., 1H).

Example 62

(S)-3-(3-((2-Chloropyrimidin-4-yl)amino)-4-(cyclohexyl(isobutyl)amino)phenyl)butanoic Acid

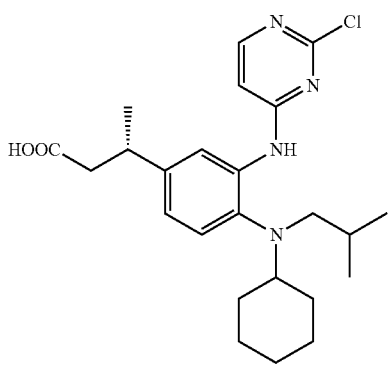 [SMILES: CC(C)CN(c1ccc([C@@H](C)CC(=O)O)cc1Nc1ccnc(Cl)n1)C1CCCCC1]

The title compound, (S)-3-(3-((2-chloropyrimidin-4-yl)amino)-4-(cyclohexyl(isobutyl)amino)phenyl)butanoic acid, was made in a manner similar to Example 11 using (S)-ethyl 3-(3-amino-4-(cyclohexyl(isobutyl)amino)phenyl)butanoate. (S)-3-(3-((2-Chloropyrimidin-4-yl)amino)-4-(cyclohexyl(isobutyl)amino)phenyl)butanoic acid was isolated (44.7 mg, 0.100 mmol, 33.3% yield) as yellowish solid foam. LCMS (M+H)$^+$: m/z=445. $^1$H NMR (400 MHz, DMSO-d$_6$) δ ppm 0.79 (d, J=6.64 Hz, 6H), 0.90-1.03 (m, 3H), 1.15-1.41 (m, 7H), 1.58-1.76 (m, 4H), 2.4-2.6 (m, 3H), 2.76 (d, J=6.44 Hz, 2H), 3.05-3.19 (m, 1H), 6.74 (br. s., 1H), 7.02 (d, J=8.20 Hz, 1H), 7.14 (d, J=8.40 Hz, 1H), 7.60 (br. s., 1H), 8.11 (d, J=5.86 Hz, 1H), 8.81 (s, 1H), 12.09 (s, 1H).

Example 63

(R)-3-(3-((2-Chloropyrimidin-4-yl)amino)-4-(cyclohexyl(isobutyl)amino)phenyl)butanoic Acid

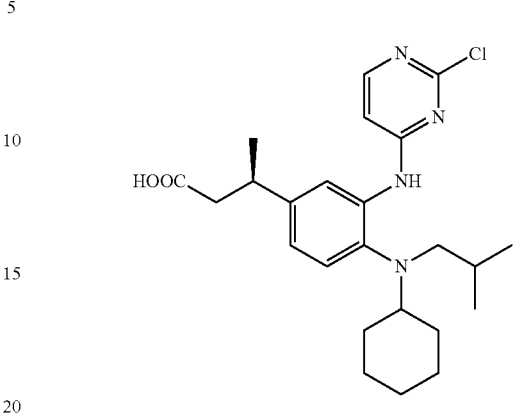

The title compound, (R)-3-(3-((2-chloropyrimidin-4-yl)amino)-4-(cyclohexyl(isobutyl)amino)phenyl)butanoic acid, was made in a manner similar to Example 11 (R)-ethyl 3-(3-amino-4-(cyclohexyl(isobutyl)amino)phenyl)butanoate. (R)-3-(3-((2-Chloropyrimidin-4-yl)amino)-4-(cyclohexyl(isobutyl)amino)phenyl)butanoic acid was isolated (44.7 mg, 0.100 mmol, 33.3% yield) as a yellowish solid. LCMS (M+H)$^+$: m/z=445. $^1$H NMR (400 MHz, DMSO-d$_6$) δ ppm 0.79 (d, J=6.64 Hz, 6H), 0.90-1.03 (m, 3H), 1.15-1.41 (m, 7H), 1.58-1.76 (m, 4H), 2.4-2.6 (m, 3H), 2.76 (d, J=6.44 Hz, 2H), 3.05-3.19 (m, 1H), 6.74 (br. s., 1H), 7.02 (d, J=8.20 Hz, 1H), 7.14 (d, J=8.40 Hz, 1H), 7.60 (br. s., 1H), 8.11 (d, J=5.86 Hz, 1H), 8.81 (s, 1H), 12.09 (s, 1H).

Example 64

3-((R)-3-(4-(Cyclohexyl(isobutyl)amino)-3-(cyclohexylamino)phenyl)butanoic Acid

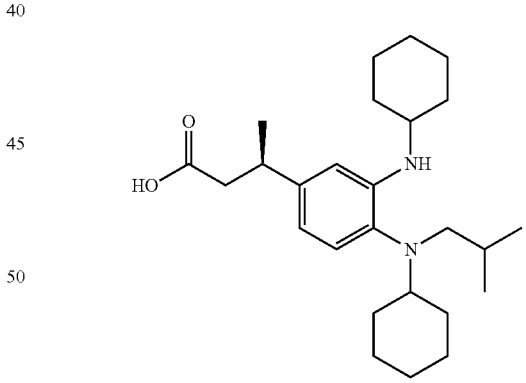

A solution of (R)-3-(3-amino-4-(cyclohexyl(isobutyl)amino)phenyl)butanoic acid (52 mg, 0.156 mmol) in MeCN (1.0 mL) was treated with cyclohexanone (15.35 mg, 0.156 mmol), acetic acid (0.018 mL, 0.313 mmol) and sodium triacetoxyborohydride (49.7 mg, 0.235 mmol) and stirred at room temperature for 30 minutes. The reaction mixture was purified directly via reverse phase chromatography to give 3-((R)-3-(4-(cyclohexyl(isobutyl)amino)-3-(cyclohexylamino)phenyl)butanoic acid (28 mg, 0.064 mmol, 41.0% yield). LCMS ESI (M+H)$^+$: m/z=415.1 $^1$H NMR (400 MHz, DMSO-d$_6$) δ ppm $^1$H NMR (400 MHz, DMSO-d$_6$) δ ppm 6.91 (d, J=8.1 Hz, 1H), 6.43 (s, 1H), 6.37 (d, J=7.9 Hz, 1H), 4.79 (d, J=8.2 Hz, 1H), 2.90-3.08 (m, 2H), 2.35-2.48 (m, 4H), 1.91 (m, 2H), 0.95-1.81 (m, 23H), 0.78 (dd, J=14.6, 6.3 Hz, 6H).

Example 65

3-(4-(Cyclohexyl(isobutyl)amino)-3-((3-(trifluoromethyl)phenyl)amino)phenyl)butanoic Acid

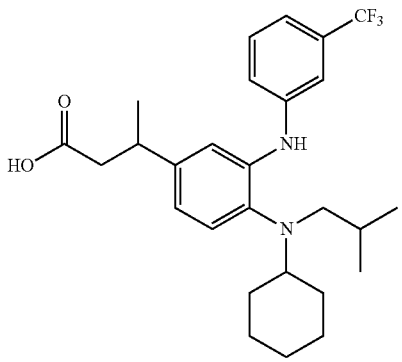 [SMILES: CC(C)CN(c1ccc(C(C)CC(=O)O)cc1Nc1cccc(C(F)(F)F)c1)C1CCCCC1]

A suspension of 3-(3-amino-4-(cyclohexyl(isobutyl)amino)phenyl)butanoic acid (170 mg, 0.511 mmol), (3-(trifluoromethyl)phenyl)boronic acid (291 mg, 1.534 mmol), copper (II) acetate (150 mg, 0.826 mmol), 4A MS (1600 mg, 0.511 mmol), and TEA (5.11 mL, 5.11 mmol) in DCM (4.0 mL) was stirred at room temperature for 2 hours. The suspension was filtered through celite, diluted with EtOAc, and washed with 1N HCl. The organics were separate, concentrated, and purified via reverse phase chromatography to give 3-(4-(cyclohexyl(isobutyl)amino)-3-((3-(trifluoromethyl)phenyl)amino)phenyl)butanoic acid (8.6 mg, 0.017 mmol, 3.35% yield). LCMS ESI (M+H)+: m/z=477.0. $^1$H NMR (400 MHz, DMSO-d$_6$) 5 ppm $^1$H NMR (400 MHz, DMSO-d$_6$) δ ppm 7.37-7.44 (m, 1H), 7.26-7.36 (m, 2H), 7.19 (s, 1H), 7.05-7.15 (m, 3H), 6.85 (d, J=8.1 Hz, 1H), 3.08 (q, J=7.0 Hz, 1H), 2.76 (d, J=6.6 Hz, 2H), 2.40-2.49 (m, 3H), 1.72 (d, J=11.4 Hz, 2H), 1.61 (d, J=12.3 Hz, 2H), 1.15-1.47 (m, 7H), 0.75-1.03 (m, 9H).

Example 66

3-(4-(Cyclohexyl(isobutyl)amino)-3-((4-(trifluoromethyl)phenyl)amino)phenyl)butanoic Acid

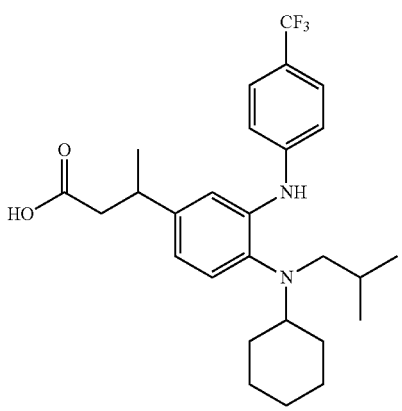 [SMILES: CC(C)CN(c1ccc(C(C)CC(=O)O)cc1Nc1ccc(C(F)(F)F)cc1)C1CCCCC1]

A suspension of 3-(3-amino-4-(cyclohexyl(isobutyl)amino)phenyl)butanoic acid (170 mg, 0.511 mmol), (4-(trifluoromethyl)phenyl)boronic acid (291 mg, 1.534 mmol), copper (II) acetate (150 mg, 0.826 mmol), 4A MS (1600 mg, 0.511 mmol), and TEA (5.11 mL, 5.11 mmol) in DCM (4.0 mL) was stirred at room temperature for 2 hours. The suspension was filtered through celite, diluted with EtOAc, and washed with 1N HCl. The organics were separate, concentrated and purified via reverse phase chromatography to give 3-(4-(cyclohexyl(isobutyl)amino)-3-((4-(trifluoromethyl)phenyl)amino)phenyl)butanoic acid (13 mg, 0.026 mmol, 5.07% yield). LCMS ESI (M+H)+: m/z=477.4. $^1$H NMR (400 MHz, DMSO-d$_6$) 5 ppm $^1$H NMR (400 MHz, DMSO-d$_6$) δ ppm 12.05 (br. s., 1H), 7.51 (d, J=8.4 Hz, 2H), 7.35 (s, 1H), 7.01-7.21 (m, 4H), 6.88 (d, J=8.1 Hz, 1H), 3.10 (q, J=7.1 Hz, 1H), 2.77 (d, J=6.6 Hz, 2H), 4.48-2.55 (m, 3H), 1.56-1.82 (m, 4H), 1.17-1.51 (m, 7H), 0.75-1.07 (m, 9H).

Example 67

3-(3-((4-Cyanophenyl)amino)-4-(cyclohexyl(isobutyl)amino)phenyl)butanoic Acid

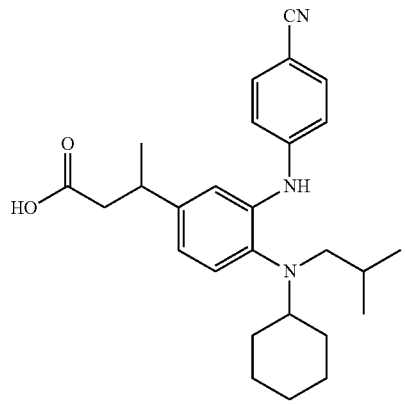

A suspension of 3-(3-amino-4-(cyclohexyl(isobutyl)amino)phenyl)butanoic acid (170 mg, 0.511 mmol), (4-cyanophenyl)boronic acid (225 mg, 1.534 mmol), copper (II) acetate (150 mg, 0.826 mmol), 4A MS (1600 mg, 0.511 mmol), and TEA (5.11 mL, 5.11 mmol) in DCM (4.0 mL) was stirred at room temperature for 2 hours. The suspension was filtered through celite, diluted with EtOAc, and washed with 1N HCl. The organics were separate, concentrated and purified via reverse phase chromatography to give 3-(3-((4-cyanophenyl)amino)-4-(cyclohexyl(isobutyl)amino)phenyl)butanoic acid (7 mg, 0.015 mmol, 3.00% yield). LCMS ESI (M+H)+: m/z=434.0. $^1$H NMR (400 MHz, DMSO-d$_6$) δ ppm $^1$H NMR (400 MHz, DMSO-d$_6$) δ ppm 7.53-7.59 (m, 3H), 7.14 (d, J=1.5 Hz, 1H), 7.10 (d, J=8.2 Hz, 1H), 7.04 (d, J=8.8 Hz, 2H), 6.94 (d, J=8.2 Hz, 1H), 3.05-3.16 (m, 1H), 2.75 (d, J=6.6 Hz, 2H), 2.41-2.48 (m, 3H), 1.56-1.70 (m, 4H), 1.14-1.48 (m, 7H), 0.76-0.99 (m, 9H).

Example 68

3-(4-(Cyclohexyl(isobutyl)amino)-3-(phenylamino)phenyl)butanoic Acid

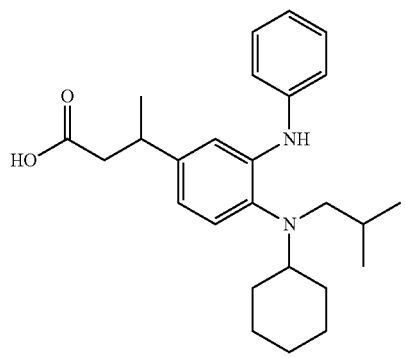

A suspension of 3-(3-amino-4-(cyclohexyl(isobutyl)amino)phenyl)butanoic acid (170 mg, 0.511 mmol), phenylboronic acid (187 mg, 1.534 mmol), copper (II) acetate (150 mg, 0.826 mmol), TEA (0.713 mL, 5.11 mmol) and 4A MS (1600 mg) in DCM (5.0 mL) was stirred at room temperature for 2 hours. The reaction mixture was filtered over celite, diluted with EtOAc, and washed with 1 N HCl. The organics were concentrated and purified via silica gel chromatography (5-40% EtOAc/Hex) to give 3-(4-(cyclohexyl(isobutyl)amino)-3-(phenylamino)phenyl)butanoic acid (29 mg, 0.071 mmol, 13.88% yield). LCMS ESI (M+H)$^+$: m/z=409.0. $^1$H NMR (400 MHz, DMSO-d$_6$) δ ppm 12.05 (s, 1H), 7.23-7.29 (m, 2H), 7.07-7.14 (m, 4H), 7.01 (s, 1H), 6.86 (t, J=7.3 Hz, 1H), 6.72 (d, J=8.1 Hz, 1H), 3.02-3.12 (m, 1H), 2.78 (d, J=6.6 Hz, 2H), 2.40-2.48 (m, 3H), 1.76 (d, J=11.7 Hz, 2H), 1.65 (m, 2H), 1.47 (m, 1H), 1.16-1.41 (m, 6H), 0.91-1.06 (m, 3H), 0.82 (d, J=6.6 Hz, 6H).

Example 69

3-(3-(Benzylamino)-4-(cyclohexyl(isobutyl)amino)phenyl)butanoic Acid

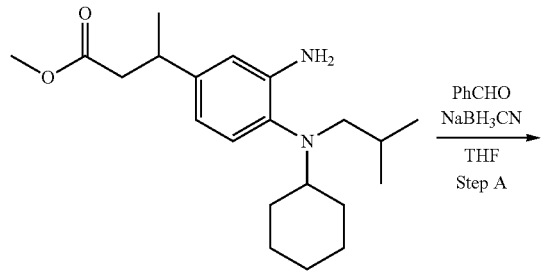

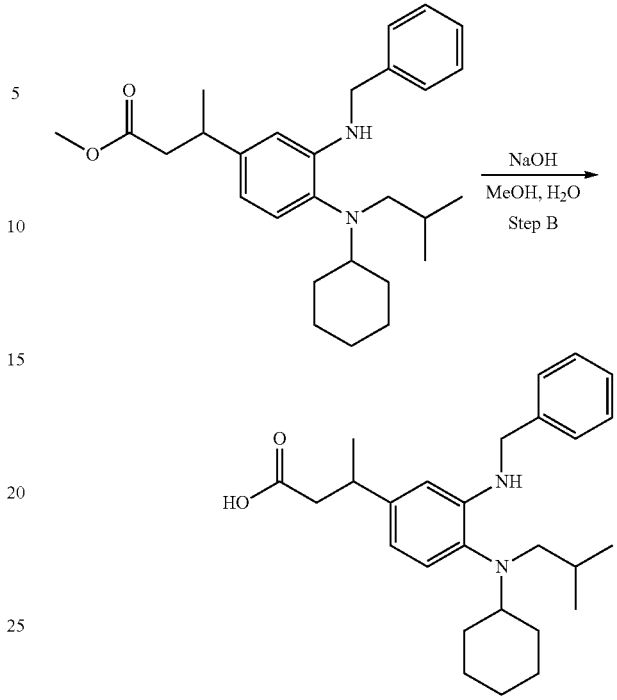

Step A

Methyl 3-(3-(benzylamino)-4-(cyclohexyl(isobutyl)amino)phenyl)butanoate

To a solution of methyl 3-(3-amino-4-(cyclohexyl(isobutyl)amino)phenyl)butanoate (100 mg, 0.29 mmol) and benzaldehyde (61 mg, 0.58 mmol) in THF was added 2 drops of AcOH following by the addition of NaBH$_3$CN (18 mg, 0.29 mmol) in one portion. The resulting mixture was stirred for 2 hrs at room temperature before partitioned between EtOAc (15 mL) and water (7 mL). The combined organic layers was washed with brine (10 mL), dried over Na$_2$SO$_4$ and concentrated. The crude product was purified by prep TLC (silica gel, 5-15% EtOAc in petroleum ether) to give methyl 3-(3-(benzylamino)-4-(cyclohexyl(isobutyl)amino)phenyl)butanoate (126 mg, quantitative). LCMS (M+H)$^+$: m/z=437.3.

Step B

3-(3-(Benzylamino)-4-(cyclohexyl(isobutyl)amino)phenyl)butanoic Acid

To a solution of methyl 3-(3-(benzylamino)-4-(cyclohexyl(isobutyl)amino)phenyl) butanoate (63 mg, 0.144 mmol) in MeOH (5 mL) obtained above was added NaOH (1 N, 2.0 mL, 20 mmol). The resulting mixture was stirred at 50° C. for 1 hr before acidified with 1 N HCl to ~pH 7. The reaction mixture was purified by reverse phase chromatography (40-100% acetonitrile in water, 0.1% formic acid) to give the title compound (28 mg, 46%) as a white solid. LCMS (M−H)$^+$: m/z=421.6. $^1$H NMR (400 MHz, DMSO) δ 7.40-7.29 (m, 4H), 7.25 (dd, J=9.5, 4.3 Hz, 1H), 6.92 (d, J=8.0 Hz, 1H), 6.48 (d, J=1.8 Hz, 1H), 6.42 (dd, J=8.0, 1.8 Hz, 1H), 5.27 (t, J=6.1 Hz, 1H), 4.32 (dd, J=16.1, 5.0 Hz, 2H), 2.98 (dd, J=15.0, 6.4 Hz, 2H), 2.42 (dd, J=15.2, 5.9 Hz, 2H), 2.33 (dd, J=15.1, 8.8 Hz, 1H), 1.72 (d, J=10.4 Hz, 4H), 1.53 (s, 1H), 1.45-1.18 (m, 4H), 1.12 (d, J=6.9 Hz, 3H), 1.02 (s, 2H), 0.77 (s, 6H).

Example 70

3-(4-(Cyclohexyl(isobutyl)amino)-3-((tetrahydro-2H-pyran-4-yl)amino)phenyl)butanoic Acid

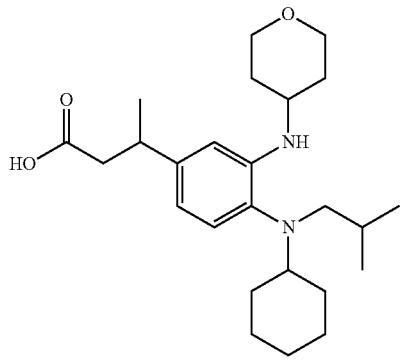 [SMILES: CC(C)CN(c1ccc(C(C)CC(=O)O)cc1NC1CCOCC1)C1CCCCC1]

The title compound, 3-(4-(cyclohexyl(isobutyl)amino)-3-((tetrahydro-2H-pyran-4-yl)amino)phenyl)butanoic acid, was made in a manner similar to Example 69. In step A: tetrahydro-4H-pyran-4-one and NaBH(OAc)$_3$ were used. 3-(4-(cyclohexyl(isobutyl)amino)-3-((tetrahydro-2H-pyran-4-yl)amino)phenyl)butanoic acid (40 mg, 57%) was isolated. LCMS (M+H)$^+$: m/z=417.6. $^1$H NMR (400 MHz, CDCl$_3$) δ 6.92-6.87 (m, 1H), 6.38 (dd, J=5.0, 1.9 Hz, 2H), 4.94 (s, 1H), 3.92 (t, J=13.9 Hz, 2H), 3.45 (tt, J=9.7, 7.7 Hz, 3H), 3.11 (dq, J=13.3, 6.6 Hz, 1H), 2.90 (d, J=9.4 Hz, 1H), 2.61 (dd, J=15.4, 5.9 Hz, 1H), 2.43 (ddd, J=18.7, 13.5, 8.8 Hz, 3H), 1.97 (s, 2H), 1.72 (dd, J=51.1, 17.5 Hz, 4H), 1.56-1.29 (m, 5H), 1.26-1.12 (m, 5H), 1.08-0.93 (m, 2H), 0.74 (dd, J=17.7, 6.4 Hz, 6H).

Synthesis of 4-(cyclohexyl(isobutyl)amino)-3-nitrobenzaldehyde

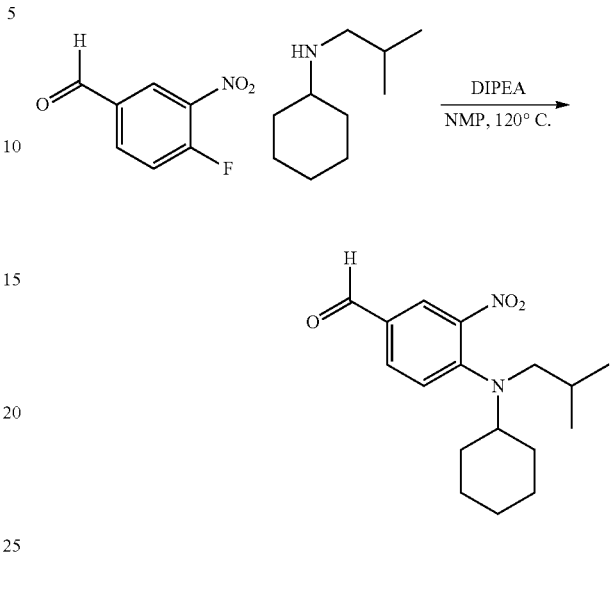

A mixture of 4-fluoro-3-nitrobenzaldehyde (13.0 g, 77.4 mmol), N-isobutylcyclohexanamine (24.0 g, 154.8 mmol) and DIEA (30 g, 232 mmol) in NMP (30 mL) was stirred at 120° C. for 3 hr under N$_2$ then cooled to room temperature and partitioned between EtOAc (50 mL) and water (20 mL). The combined organic layers was washed with brine (10 mL), dried over Na$_2$SO$_4$ and concentrated. The crude product was purified by silica gel chromatography (1-5% EtOAc/PE) to give 4-(cyclohexyl(isobutyl)amino)-3-nitrobenzaldehyde (17.2 g, 74%) as an orange solid. LCMS (M+H)$^+$: m/z=305.0.

Example 71

3-(3-((3-Chloro-1,2,4-thiadiazol-5-yl)amino)-4-(cyclohexyl(isobutyl)amino)phenyl)-4,4,4-trifluorobutanoic Acid

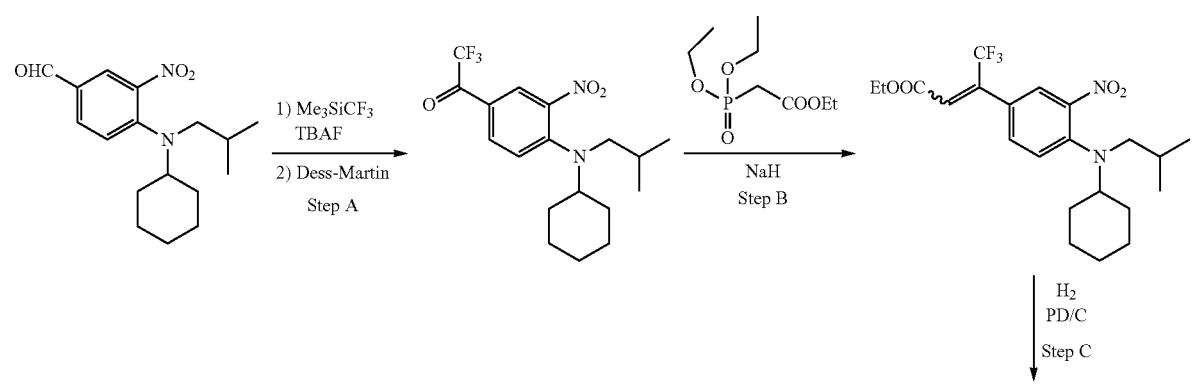

-continued

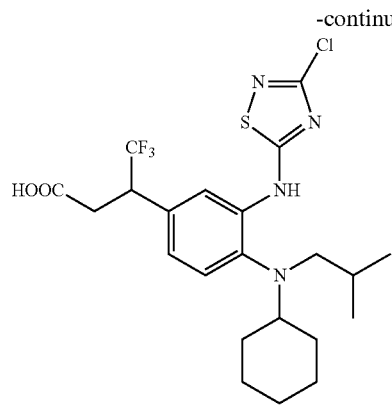

1)

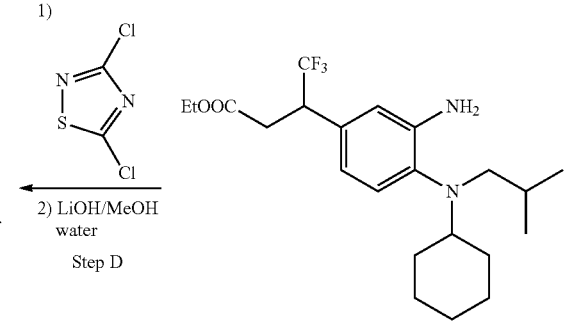

2) LiOH/MeOH
water

Step D

Step A

1-(4-(Cyclohexyl(isobutyl)amino)-3-nitrophenyl)-2,2,2-trifluoroethanone

To a solution of 4-(cyclohexyl(isobutyl)amino)-3-nitrobenzaldehyde (650 mg, 2.114 mmol) in THF (10 mL) at 0° C. under nitrogen atmosphere was added trimethyl(trifluoromethyl)silane (1.586 mL, 3.17 mmol) (2M/THF) followed by TBAF (0.050 mL, 0.050 mmol) (1M/THF) and the mixture was warmed to ambient temperature and stirred for 50 min, then 1N HCl/water (2.5 mL, 2.5 mmol) was added and stirring at ambient temperature continued for 20 min. The mixture was diluted with EtOAc and washed with water. The organic phase was dried over $Na_2SO_4$, concentrated to provide 1-(4-(cyclohexyl(isobutyl)amino)-3-nitrophenyl)-2,2,2-trifluoroethanol (824 mg, 2.179 mmol, 103% yield). LCMS $(M+H)^+$: m/z=375. $^1$H NMR (400 MHz, CHLOROFORM-d) δ ppm 0.89 (d, J=6.59 Hz, 6H), 0.99-1.14 (m, 1H), 1.15-1.32 (m, 3H), 1.36-1.53 (m, 2H), 1.56-1.73 (m, 2H), 1.74-1.91 (m, 3H), 2.86-3.02 (m, 3H), 4.13 (q, J=7.14 Hz, 1H), 5.01 (q, J=6.53 Hz, 1H), 7.23 (br. s., 1H), 7.50 (d, J=8.61 Hz, 1H), 7.81 (d, J=1.47 Hz, 1H). To a solution of 1-(4-(cyclohexyl(isobutyl)amino)-3-nitrophenyl)-2,2,2-trifluoroethanol (795 mg, 2.123 mmol) in DCM (25 mL) was added dess-martin periodinane (1351 mg, 3.19 mmol) and the mixture was stirred at room temperature for 1 h then 20% $Na_2S_2O_3$/water and saturated $NaHCO_3$/water was added and the mixture was stirred for 1.5 h. The org. phase was dried over $Na_2SO_4$, concentrated, and coevaporated with MeCN (2×) and dried in vac. to provide 1-(4-(cyclohexyl(isobutyl)amino)-3-nitrophenyl)-2,2,2-trifluoroethanone (23.7 mg, 0.064 mmol, 92% yield) as a yellow oil. LCMS $(M+H)^+$: m/z=373. $^1$H NMR (400 MHz, CHLOROFORM-d) δ ppm 0.91 (d, J=6.64 Hz, 6H), 1.01-1.17 (m, 1H), 1.18-1.35 (m, 2H), 1.41-1.57 (m, 2H), 1.64 (d, J=12.89 Hz, 1H), 1.76-1.94 (m, 5H), 3.05 (d, J=7.42 Hz, 2H), 3.08-3.19 (m, 1H), 7.10 (d, J=9.18 Hz, 1H), 7.96-8.06 (m, 1H), 8.40 (d, J=0.98 Hz, 1H).

Step B

Ethyl 3-(4-(cyclohexyl(isobutyl)amino)-3-nitrophenyl)-4,4,4-trifluorobut-2-enoate To a suspension of sodium hydride (113 mg, 2.82 mmol) (60%/mineral oil) in THF (20 mL) at −8° C. and under nitrogen atmosphere was add dropwise triethyl phosphonoacetate (0.564 mL, 2.82 mmol) followed by dropwise addition in −10 min of a solution of 1-(4-(cyclohexyl(isobutyl) amino)-3-nitrophenyl)-2,2,2-trifluoroethanone (750 mg, 2.014 mmol)/(THF, 10 mL). After 5 min the mixture was warmed to ambient temperature. After 20 min, the mixture was diluted with EtOAc and washed with water and saturated $NH_4Cl$/water (5:1). The organic phase was dried over $Na_2SO_4$, concentrated, purified on silica (EtOAc/hexanes 0-5%) to provide (Z)-ethyl 3-(4-(cyclohexyl(isobutyl) amino)-3-nitrophenyl)-4,4,4-trifluorobut-2-enoate (465 mg, 1.051 mmol, 52.2% yield) and (E)-ethyl 3-(4-(cyclohexyl(isobutyl)amino)-3-nitrophenyl)-4,4,4-trifluorobut-2-enoate (222 mg, 0.502 mmol, 24.91% yield) as orange oils. LCMS $(M+H)^+$: m/z=443.

Step C

Ethyl 3-(3-amino-4-(cyclohexyl(isobutyl)amino)phenyl)-4,4,4-trifluorobutanoate To a solution of (E)-ethyl 3-(4-(cyclohexyl(isobutyl) amino)-3-nitrophenyl)-4,4,4-trifluorobut-2-enoate (218 mg, 0.493 mmol) in MeOH (10 mL) under nitrogen was added Pd—C (130 mg, 0.122 mmol) (10% wt., wet, Degussa type E101 NE/W) and the mixture was stirred under hydrogen atmosphere at 50 psi for 1.5 h. The mixture was filtered (fiber glass filter) and the filtrate concentrated, coevaporated with MeCN, dried in vacuo to provide ethyl 3-(3-amino-4-(cyclohexyl(isobutyl)amino)phenyl)-4,4,4-trifluorobutanoate (193 mg, 0.456 mmol, 93% yield) as an dark orange oil. LCMS $(M+H)^+$: m/z=415. $^1$H NMR (400 MHz, CHLOROFORM-d) δ ppm 0.72-0.92 (m, 6H), 0.95-1.28 (m, 7H), 1.40 (dd, J=13.19, 6.59 Hz, 2H), 1.49-1.65 (m, 4H), 1.68-1.91 (m, 4H), 2.61 (br. s., 1H), 2.74-2.89 (m, 1H), 2.90-3.03 (m, 1H), 3.70-3.88 (m, 1H), 4.08 (q, J=6.96 Hz, 3H), 6.62 (d, J=7.69 Hz, 1H), 6.67 (s, 1H), 6.98 (d, J=8.06 Hz, 1H).

Step D

3-(3-((3-Chloro-1,2,4-thiadiazol-5-yl)amino)-4-(cyclohexyl(isobutyl)amino)phenyl)-4,4,4-trifluorobutanoic Acid To a solution of ethyl 3-(3-amino-4-(cyclohexyl(isobutyl) amino)phenyl)-4,4,4-trifluorobutanoate (185 mg, 0.446 mmol) in DMF (2 mL) was added 3,5-dichloro-1,2,4-thiadiazole (83 mg, 0.536 mmol) and the mixture was stirred at 90° C. under nitrogen atmosphere for 4.5 h. Additional 3,5-dichloro-1,2,4-thiadiazole (83 mg, 0.536 mmol) was added and stirring at 90° C. continued for 3 h. The mixture was cooled to ambient temperature and water was added, extracted with EtOAc. The organic phase was washed with water and brine and the organic phase was dried over Na$_2$SO$_4$, concentrated to provide ethyl 3-(3-((3-chloro-1,2,4-thiadiazol-5-yl)amino)-4-(cyclohexyl(isobutyl)amino)phenyl)-4,4,4-trifluorobutanoate. This residue was dissolved in MeOH (1 mL) and 1M LiOH/water (0.8 mL) was added and the mixture was heated to 55° C. for 30 min. The mixture was acidified to pH-3 with 1N HCl/water then extracted with EtOAc. The organic phase was dried over Na$_2$SO$_4$ concentrated, purified by reverse phase chromatography (MeCN/water 10-100%, 0.05% TFA) to provide 3-(3-((3-chloro-1,2,4-thiadiazol-5-yl)amino)-4-(cyclohexyl(isobutyl)amino)phenyl)-4,4,4-trifluorobutanoic acid (75 mg, 0.149 mmol, 33.3% yield) as a pale yellow solid foam. LCMS (M+H)$^+$: m/z=505. $^1$H NMR (400 MHz, DMSO-d$_6$) δ ppm 0.79 (d, J=6.64 Hz, 6H), 0.92-1.09 (m, 3H), 1.20-1.43 (m, 3H), 1.50 (br. s., 1H), 1.66 (br. s., 2H), 1.78 (d, J=10.74 Hz, 2H), 2.60-2.72 (m, 1H), 2.80 (d, J=6.64 Hz, 2H), 2.83-3.01 (m, 2H), 3.89-4.06 (m, 1H), 7.13-7.27 (m, 2H), 7.81-7.89 (m, 1H), 10.12 (s, 1H), 12.56 (br. s., 1H).

Example 72

3-(4-(Cyclohexyl(isobutyl)amino)-3-(((R)-4-phenyl-4,5-dihydrooxazol-2-yl)amino)phenyl)butanoic Acid

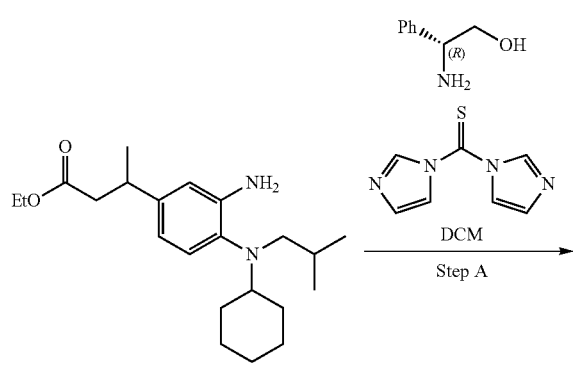

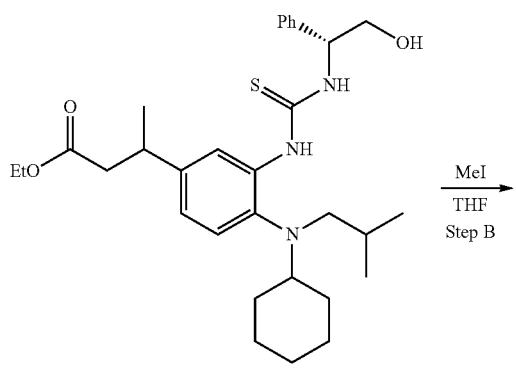

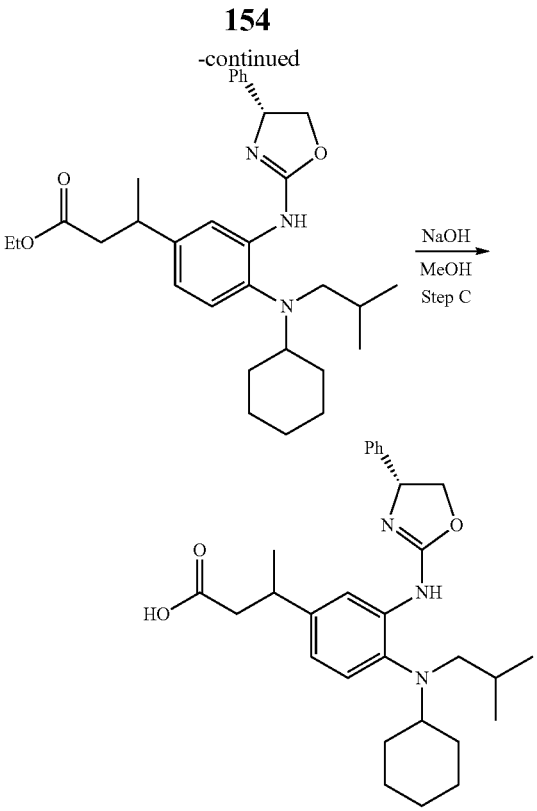

Step A

Ethyl 3-(4-(cyclohexyl(isobutyl)amino)-3-(3-((R)-2-hydroxy-1-phenylethyl)thioureido)phenyl)butanoate At 0° C., a stirred solution of ethyl 3-(3-amino-4-(cyclohexyl(isobutyl)amino)phenyl) butanoate (200 mg, 0.55 mmol) in DCM was treated with di(1H-imidazol-1-yl)methanethione (196 mg, 1.1 mmol) in one portion. The mixture was stirred at room temperature for 4 hrs then treated with (R)-2-amino-2-phenylethan-1-ol (152 mg, 1.11 mmol). The resulting mixture was stirred overnight and partitioned between EtOAc (30 mL) and water (15 mL). The combined organic layers was washed with brine (15 mL), dried over Na$_2$SO$_4$ and concentrated. The residue was purified by silica gel chromatography (5-15% EtOAc/PE) to give ethyl 3-(4-(cyclohexyl(isobutyl)amino)-3-(3-((R)-2-hydroxy-1-phenylethyl)thioureido)phenyl)butanoate (180 mg, 55%) as an oil. LCMS (M+H)$^+$: m/z=540.6.

Step B

Ethyl 3-(4-(cyclohexyl(isobutyl)amino)-3-(((R)-4-phenyl-4,5-dihydrooxazol-2-yl)amino)phenyl)butanoate A mixture of ethyl 3-(4-(cyclohexyl(isobutyl)amino)-3-(3-((R)-2-hydroxy-1-phenylethyl)thioureido)phenyl)butanoate (50 mg, 0.092 mmol) and MeI (13 mg, 0.92 mmol) was stirred in THF at room temperature overnight. The reaction was then partitioned between EtOAc (15 mL) and water (5 mL). The combined organic layers was washed with brine (5 mL), dried over Na$_2$SO$_4$ and concentrated. The residue was purified by prep TLC (silica gel, 5-15% EtOAc/PE) to give ethyl 3-(4-(cyclohexyl(isobutyl)amino)-3-(((R)-

4-phenyl-4,5-dihydrooxazol-2-yl)amino)phenyl)butanoate (20 mg, 43%) as an oil. LCMS (M+H)⁺: m/z=506.4.

Step C 3-(4-(Cyclohexyl(isobutyl)amino)-(((R)-4-phenyl-4,5-dihydrooxazol-2-yl)amino)phenyl)butanoic Acid To a solution of ethyl 3-(4-(cyclohexyl(isobutyl)amino)-3-(((R)-4-phenyl-4,5-dihydrooxazol-2-yl)amino)phenyl)butanoate (20 mg, 0.04 mmol) in MeOH (5 mL) was added NaOH (1 N, 2.0 mL, 20 mmol). The resulting mixture was stirred at room temperature for 3 hrs before acidified with 1 N HCl to ~pH 7. The reaction mixture was directly purified by reverse phase chromatography (40-100% ACN/water, 0.1% formic acid) to give 3-(4-(cyclohexyl(isobutyl)amino)-3-(((R)-4-phenyl-4,5-dihydrooxazol-2-yl)amino)phenyl)butanoic acid (7.2 mg, 39%) as a white solid. LCMS (M–H)⁺: m/z=476.5. ¹H NMR (400 MHz, CDCl₃) δ 7.81 (d, J=20.9 Hz, 1H), 7.28 (dd, J=8.2, 4.9 Hz, 5H), 7.00 (dd, J=8.1, 1.9 Hz, 1H), 6.72 (t, J=6.5 Hz, 1H), 5.47-5.39 (m, 1H), 4.60 (t, J=7.9 Hz, 1H), 4.12-4.04 (m, 1H), 3.14 (d, J=6.0 Hz, 1H), 2.71-2.41 (m, 5H), 1.79 (s, 2H), 1.67 (s, 2H), 1.52 (d, J=12.3 Hz, 1H), 1.38-0.95 (m, 9H), 0.77 (d, J=6.5 Hz, 6H).

Example 73

3-(4-(Cyclohexyl(isobutyl)amino)-3-(((R)-4-phenyl-4,5-dihydrooxazol-2-yl)amino)phenyl)butanoic

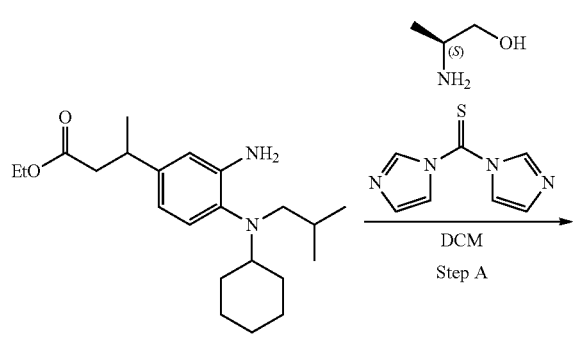

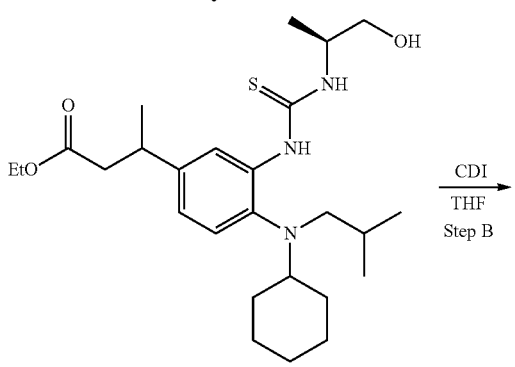

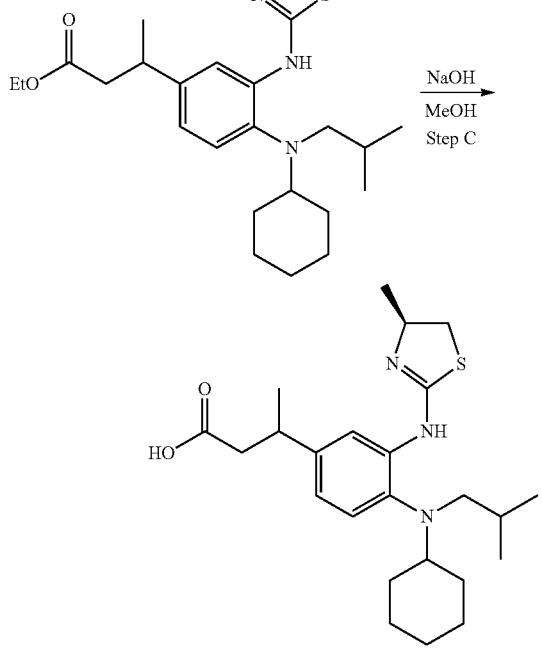

Step A

Ethyl 3-(4-(cyclohexyl(isobutyl)amino)-3-(3-((S)-1-hydroxypropan-2-yl)thioureido)phenyl)butanoate At 0° C., a solution of ethyl 3-(3-amino-4-(cyclohexyl(isobutyl)amino)phenyl) butanoate (200 mg, 0.55 mmol) in DCM was treated with di(1H-imidazol-1-yl)methanethione (196 mg, 1.1 mmol) in one portion. The mixture was stirred at room temperature for 4 hrs then treated with with (S)-2-aminopropan-1-ol (103 mg, 1.38 mmol). The resulting mixture was stirred overnight and partitioned between EtOAc (30 mL) and water (15 mL). The combined organic layers was washed with brine (15 mL), dried over Na₂SO₄ and concentrated. The residue was purified by silica gel chromatography (5-15% EtOAc/PE) to give ethyl 3-(4-(cyclohexyl(isobutyl)amino)-3-(3-((S)-1-hydroxypropan-2-yl)thioureido)phenyl)butanoate (260 mg, 98%) as an oil.

Step B

Ethyl 3-(4-(cyclohexyl(isobutyl)amino)-3-(((S)-4-methyl-4,5-dihydrothiazol-2-yl)amino)phenyl)butanoate A mixture of ethyl 3-(4-(cyclohexyl(isobutyl)amino)-3-(3-((S)-1-hydroxypropan-2-yl)thioureido)phenyl)butanoate (78 mg, 0.163 mmol) and di(1H-imidazol-1-yl)methanone (40 mg, 0.245 mmol) in THF was stirred at room temperature overnight. The reaction was then partitioned between EtOAc (15 mL) and water (5 mL). The combined organic layers was washed with brine (5 mL), dried over Na₂SO₄ and concentrated. The residue was purified by prep TLC (silica gel, 5-15% EtOAc/PE) to give ethyl 3-(4-(cyclohexyl (isobutyl)amino)-3-(((S)-4-methyl-4,5-dihydrothiazol-2-yl) amino)phenyl)butanoate (50 mg, 67%) as an oil. LCMS (M+H)+: m/z=460.1.

Step C 3-(4-(Cyclohexyl(isobutyl)amino)-3-(((R)-4-phenyl-4,5-dihydrooxazol-2-yl)amino)phenyl)butanoic Acid The title compound, 3-(4-(cyclohexyl(isobutyl)amino)-3-(((S)-4-methyl-4,5-dihydrothiazol-2-yl)amino)phenyl) butanoic acid (24.7 mg, 53%) was obtained as white powder from ethyl 3-(4-(cyclohexyl(isobutyl)amino)-3-(((S)-4-methyl-4,5-dihydrothiazol-2-yl)amino)phenyl)butanoate (50 mg, 0.10 mmol) and NaOH (1 N), following a similar procedure outlined in the preparation of 3-(4-(cyclohexyl (isobutyl)amino)-3-(((R)-4-phenyl-4,5-dihydrooxazol-2-yl) amino)phenyl)butanoic acid (Step 3). LCMS (M−H)+: m/z=430.7. 1H NMR (400 MHz, CDCl3) δ 7.68 (s, 1H), 7.01 (d, J=8.2 Hz, 1H), 6.88 (d, J=7.5 Hz, 1H), 4.50 (dd, J=12.3, 6.7 Hz, 1H), 3.40 (dd, J=10.6, 7.2 Hz, 1H), 3.22 (dd, J=13.1, 6.4 Hz, 1H), 2.93 (ddd, J=10.5, 7.0, 1.4 Hz, 1H), 2.75 (d, J=6.8 Hz, 2H), 2.67-2.58 (m, 2H), 2.57-2.45 (m, 1H), 1.77 (dd, J=34.3, 11.7 Hz, 4H), 1.57 (d, J=12.2 Hz, 1H), 1.49-1.36 (m, 4H), 1.36-0.99 (m, 8H), 0.84 (d, J=6.6 Hz, 6H).

Example 74

3-(4-(Cyclohexyl(isobutyl)amino)-3-(((R)-4-methyl-4,5-dihydrothiazol-2-yl)amino)phenyl)butanoic Acid

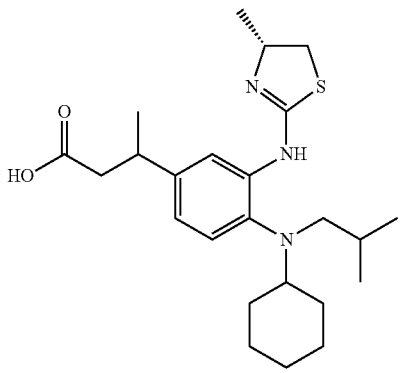 [SMILES: CC(C)CN(c1ccc(C(C)CC(=O)O)cc1NC1=N[C@H](C)CS1)C1CCCCC1]

The title compound, 3-(4-(cyclohexyl(isobutyl)amino)-3-(((R)-4-methyl-4,5-dihydrothiazol-2-yl)amino)phenyl)butanoic acid, was made in a manner similar to Example 73. 3-(4-(cyclohexyl(isobutyl)amino)-3-(((R)-4-methyl-4,5-dihydrothiazol-2-yl)amino)phenyl)butanoic acid (33.2 mg, 71%) was isolated. 1H NMR (400 MHz, CDCl3) δ 7.65 (s, 1H), 6.95 (d, J=8.2 Hz, 1H), 6.81 (d, J=8.1 Hz, 1H), 4.48-4.41 (m, 1H), 3.35 (dd, J=10.5, 7.2 Hz, 1H), 3.16 (dd, J=13.1, 6.5 Hz, 1H), 2.87 (ddd, J=10.6, 7.0, 1.5 Hz, 1H), 2.69 (d, J=6.8 Hz, 2H), 2.57 (dd, J=15.2, 6.4 Hz, 2H), 2.47 (dd, J=15.9, 7.6 Hz, 2H), 1.75 (d, J=11.1 Hz, 2H), 1.66 (d, J=12.4 Hz, 2H), 1.50 (d, J=12.2 Hz, 1H), 1.42-1.06 (m, 11H), 1.02-0.92 (m, 1H), 0.78 (t, J=10.4 Hz, 6H).

Example 75

3-(4-(Cyclohexyl(isobutyl)amino)-3-(((R)-4-(trifluoromethyl)-4,5-dihydrothiazol-2-yl)amino)phenyl) butanoic Acid

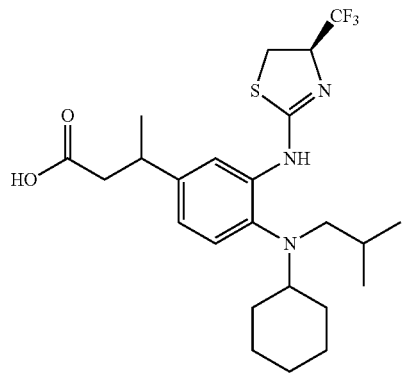 [SMILES: CC(C)CN(c1ccc(C(C)CC(=O)O)cc1NC1=N[C@H](C(F)(F)F)CS1)C1CCCCC1]

The title compound, 3-(4-(cyclohexyl(isobutyl)amino)-3-(((R)-4-(trifluoromethyl)-4,5-dihydrothiazol-2-yl)amino) phenyl)butanoic acid prepared in a manner similar to Example 73. 3-(4-(cyclohexyl(isobutyl)amino)-3-(((R)-4-(trifluoromethyl)-4,5-dihydrothiazol-2-yl)amino)phenyl) butanoic acid (3.2 mg, 23%) was isolated. LCMS (M−H)+: m/z=486.8. 1H NMR (400 MHz, CDCl3) δ 8.12 (s, 1H), 7.00 (d, J=8.1 Hz, 1H), 6.75 (dd, J=8.1, 2.0 Hz, 1H), 4.84 (ddd, J=15.3, 7.7, 3.1 Hz, 1H), 3.50-3.36 (m, 2H), 3.18 (dd, J=14.5, 7.1 Hz, 1H), 2.86-2.36 (m, 5H), 1.71 (dd, J=32.7, 10.3 Hz, 4H), 1.51 (d, J=12.4 Hz, 1H), 1.38-1.22 (m, 5H), 1.19-1.05 (m, 3H), 1.03-0.92 (m, 1H), 0.76 (d, J=6.6 Hz, 6H).

Example 76

3-(4-(Cyclohexyl(isobutyl)amino)-3-(((R)-4-(trifluoromethyl)-4,5-dihydrooxazol-2-yl)amino)phenyl) butanoic acid

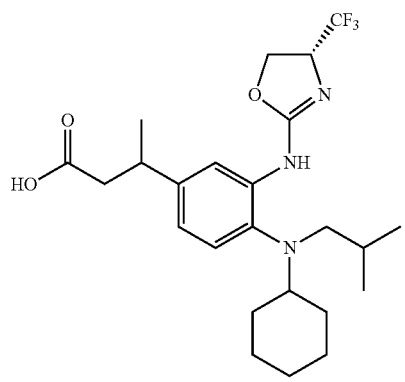 [SMILES: CC(C)CN(c1ccc(C(C)CC(=O)O)cc1NC1=N[C@@H](C(F)(F)F)CO1)C1CCCCC1]

The title compound, 3-(4-(cyclohexyl(isobutyl)amino)-3-(((R)-4-(trifluoromethyl)-4,5-dihydrooxazol-2-yl)amino) phenyl)butanoic acid, was prepared in a manner similar to Example 72. 3-(4-(Cyclohexyl(isobutyl)amino)-3-(((R)-4-

(trifluoromethyl)-4,5-dihydrooxazol-2-yl)amino)phenyl)butanoic acid (13 mg, 46%) was obtained as a white powder. LCMS (M+H)$^+$: m/z=470.4 $^1$H NMR (400 MHz, CDCl$_3$) δ 8.13 (s, 1H), 7.93 (s, 1H), 7.08 (dd, J=8.1, 4.6 Hz, 1H), 6.84 (d, J=8.1 Hz, 1H), 4.85 (dd, J=14.3, 7.4 Hz, 1H), 4.42 (p, J=9.1 Hz, 2H), 3.28 (dd, J=15.1, 6.9 Hz, 1H), 2.84-2.47 (m, 5H), 1.79 (dd, J=37.4, 11.5 Hz, 4H), 1.58 (d, J=12.8 Hz, 1H), 1.42-1.01 (m, 9H), 0.82 (d, J=6.5 Hz, 6H).

Administration and Formulation

In another embodiment, there is provided a pharmaceutical composition comprising a pharmaceutically acceptable diluent and a therapeutically effective amount of a compound of Formula I or a pharmaceutically acceptable salt thereof.

The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formula I may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, Na$_2$CO$_3$, K$_2$CO$_3$, NaH, and potassium-t-butoxide.

Salts derived from pharmaceutically acceptable organic non-toxic bases include salts of primary, secondary, and tertiary amines, including in part, trimethylamine, diethylamine, N, N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences*, 17th ed., Mack Publishing Company, Easton, Pa., 1985, p. 1418, the disclosure of which is hereby incorporated by reference only with regards to the lists of suitable salts.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. D$_2$O, d$_6$-acetone, d$_6$-DMSO.

Compounds of Formula I containing one or more asymmetric carbon atoms can exist as two or more stereoisomers. Where a compound of Formula I contains an amidoxime or alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope in some embodiments or alternate embodiments of the claimed compounds in the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where in some embodiments or alternate embodiments the compounds of Formula I contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula I, for example, those incorporating a radioactive isotope, are useful in drug and/or substrate tissue distribution studies. The radioactive isotopes tritium, ie. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labelled compounds of Formula I can generally be prepared by conventional techniques known to those skilled in the art or by processes analogous to those described in the accompanying Examples and Preparations using an appropriate isotopically-labelled reagent in place of the non-labelled reagent previously employed.

The compounds of the present invention may be administered as prodrugs. Thus, certain derivatives of compounds of Formula I, which may have little or no pharmacological activity themselves can, when administered into or onto the body, be converted into compounds of Formula I as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 7-3500 mg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %.

Compound Data

Human indoleamine 2,3-dioxgenase (IDO) cellular data is presented in Table 2 below. Brief descriptions of the cellular assays are provided following the table.

TABLE 2

| Example No. | Structure | pEC50 Hela | pEC$_{50}$ PBMC |
|---|---|---|---|
| 1 | 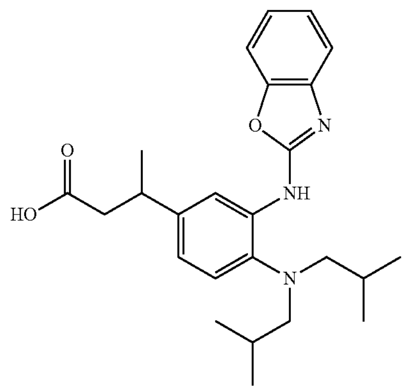 [SMILES: CC(C)CN(CC(C)C)c1ccc(C(C)CC(=O)O)cc1Nc1nc2ccccc2o1] | 6.4 | 6.2 |
| 2 | 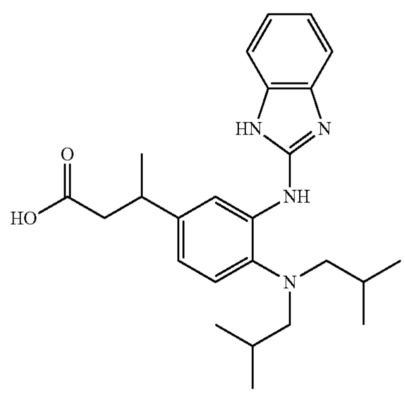 | 8.4 | N/A |
| 3 | 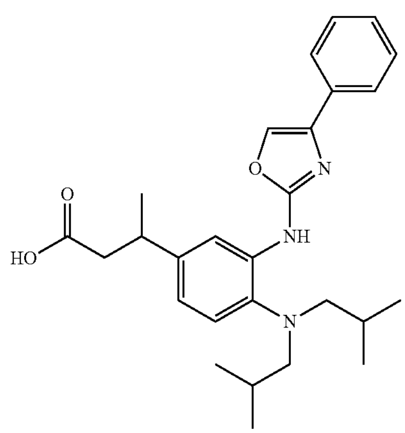 [SMILES: CC(C)CN(CC(C)C)c1ccc(C(C)CC(=O)O)cc1Nc1nc(-c2ccccc2)co1] | 6.3 | N/A |
| 4 | 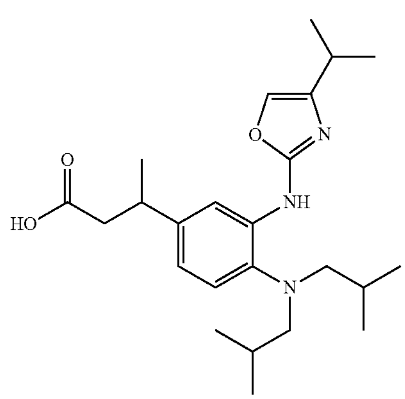 [SMILES: CC(C)CN(CC(C)C)c1ccc(C(C)CC(=O)O)cc1Nc1nc(C(C)C)co1] | 6.2 | N/A |

TABLE 2-continued

| Example No. | Structure | pEC50 Hela | pEC$_{50}$ PBMC |
|---|---|---|---|
| 5 | 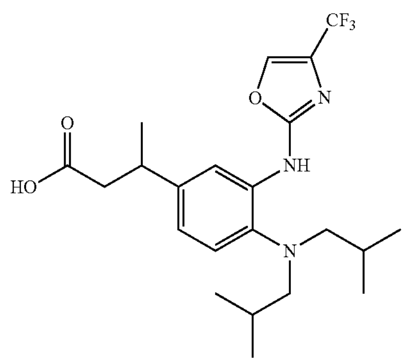 [SMILES: CC(C)CN(CC(C)C)c1ccc(C(C)CC(=O)O)cc1Nc1nc(C(F)(F)F)co1] | 7.7 | N/A |
| 6 | 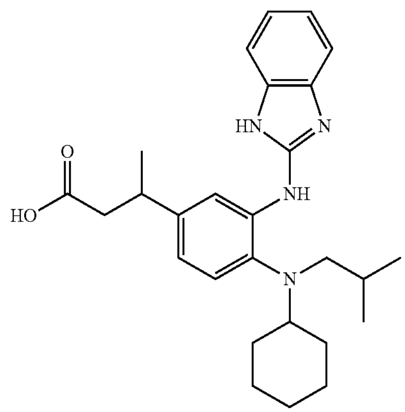 | 8.6 | N/A |
| 7 | 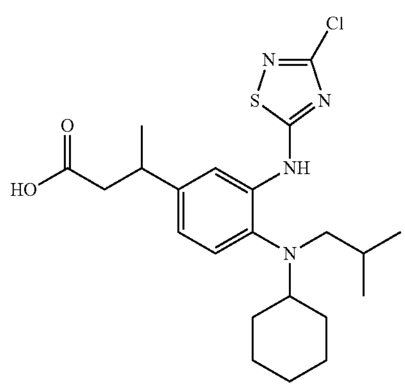 | 8.3 | N/A |
| 8 | 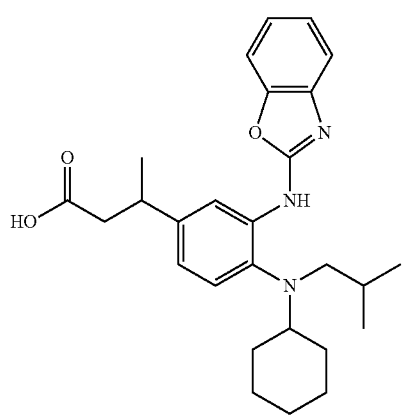 [SMILES: CC(C)CN(c1ccc(C(C)CC(=O)O)cc1Nc1nc2ccccc2o1)C1CCCCC1] | 7.5 | N/A |

TABLE 2-continued

| Example No. | Structure | pEC50 Hela | pEC$_{50}$ PBMC |
|---|---|---|---|
| 9 | 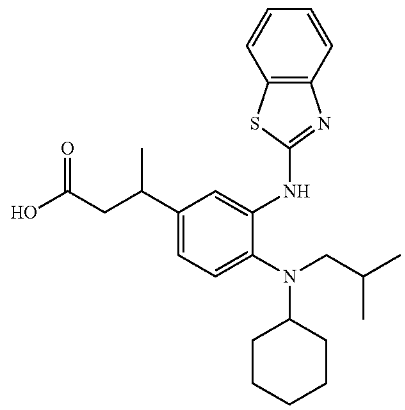 | 8.4 | N/A |
| 10 | 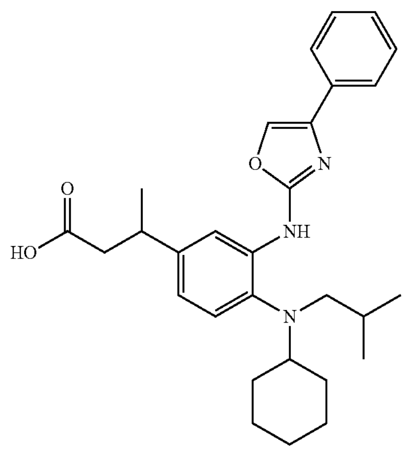 [SMILES: CC(C)CN(c1ccc(C(C)CC(=O)O)cc1Nc1nc(-c2ccccc2)co1)C1CCCCC1] | 7.0 | N/A |
| 11 | 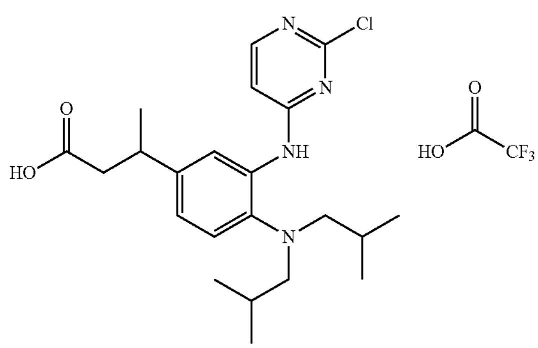 [SMILES: CC(C)CN(CC(C)C)c1ccc(C(C)CC(=O)O)cc1Nc1ccnc(Cl)n1 ; O=C(O)C(F)(F)F] | 7.0 | N/A |
| 12 | 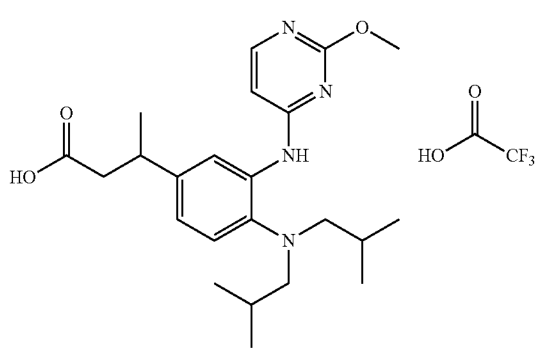 [SMILES: COc1nccc(Nc2cc(C(C)CC(=O)O)ccc2N(CC(C)C)CC(C)C)n1 ; O=C(O)C(F)(F)F] | 6.9 | 6.8 |

TABLE 2-continued

| Example No. | Structure | pEC50 Hela | pEC$_{50}$ PBMC |
|---|---|---|---|
| 13 | 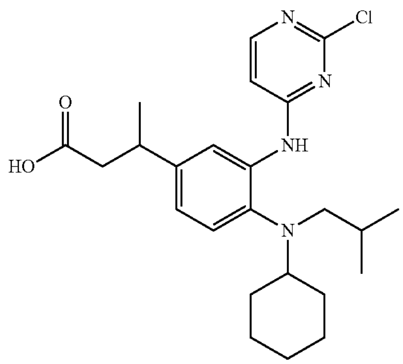 [SMILES: CC(C)CN(c1ccc(C(C)CC(=O)O)cc1Nc1ccnc(Cl)n1)C1CCCCC1] | 7.9 | N/A |
| 14 | 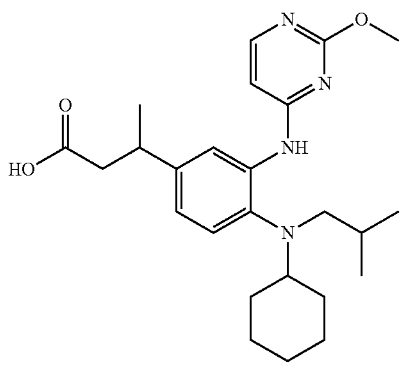 [SMILES: COc1nccc(Nc2cc(C(C)CC(=O)O)ccc2N(CC(C)C)C2CCCCC2)n1] | 7.4 | N/A |
| 15 | 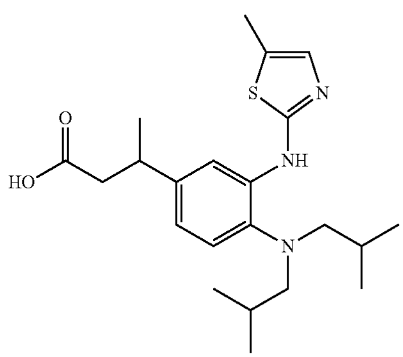 | 6.8 | N/A |
| 16 | 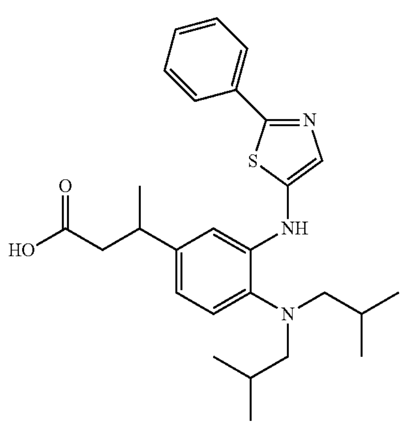 | 6.9 | N/A |

TABLE 2-continued

| Example No. | Structure | pEC50 Hela | pEC$_{50}$ PBMC |
|---|---|---|---|
| 17 | 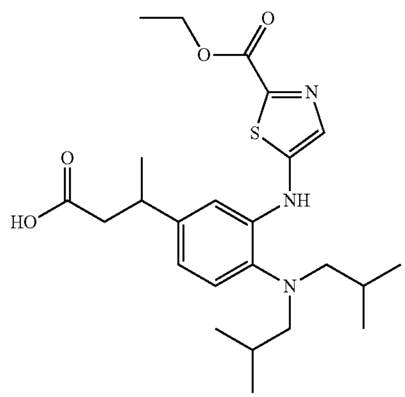 [SMILES: CCOC(=O)c1ncc(Nc2cc(C(C)CC(=O)O)ccc2N(CC(C)C)CC(C)C)s1] | 7.6 | N/A |
| 18 | 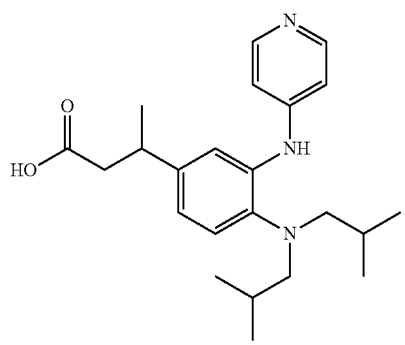 [SMILES: CC(C)CN(CC(C)C)c1ccc(C(C)CC(=O)O)cc1Nc1ccncc1] | 6.5 | 6.7 |
| 19 | 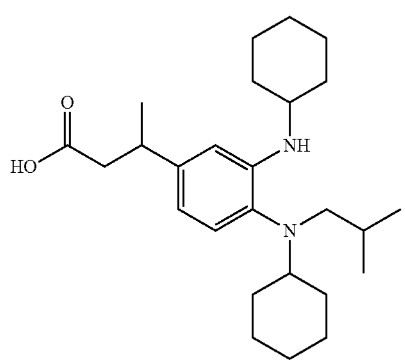 [SMILES: CC(C)CN(c1ccc(C(C)CC(=O)O)cc1NC1CCCCC1)C1CCCCC1] | 7.0 | 7.3 |
| 20 | 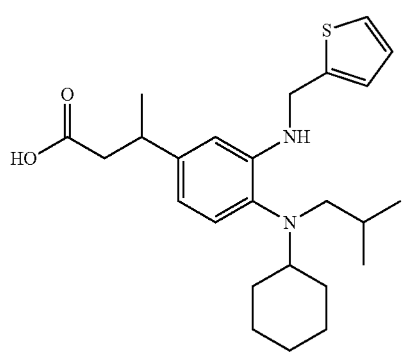 [SMILES: CC(C)CN(c1ccc(C(C)CC(=O)O)cc1NCc1cccs1)C1CCCCC1] | 6.9 | 7.3 |

TABLE 2-continued

| Example No. | Structure | pEC50 Hela | pEC$_{50}$ PBMC |
|---|---|---|---|
| 21 | 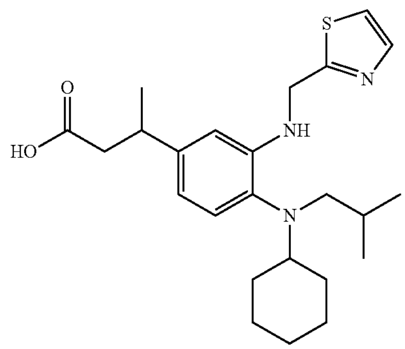 [SMILES: CC(C)CN(c1ccc(C(C)CC(=O)O)cc1NCc1nccs1)C1CCCCC1] | 6.3 | 6.6 |
| 22 | 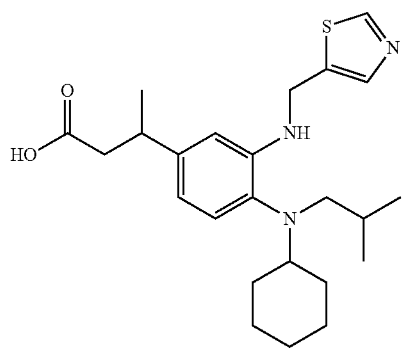 [SMILES: CC(C)CN(c1ccc(C(C)CC(=O)O)cc1NCc1cncs1)C1CCCCC1] | 6.7 | 7.0 |
| 23 | 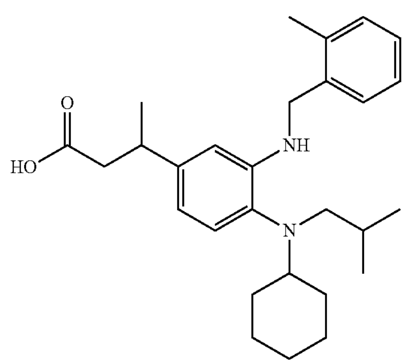 [SMILES: Cc1ccccc1CNc1cc(C(C)CC(=O)O)ccc1N(CC(C)C)C1CCCCC1] | 6.5 | 6.7 |
| 24 | 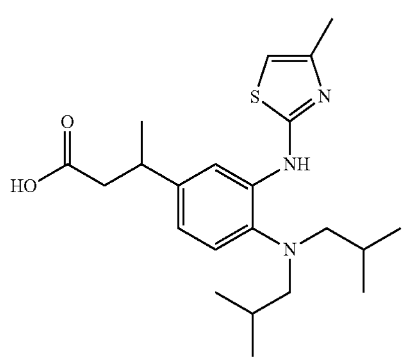 [SMILES: Cc1csc(Nc2cc(C(C)CC(=O)O)ccc2N(CC(C)C)CC(C)C)n1] | 6.5 | N/A |

TABLE 2-continued
| Example No. | Structure | pEC50 Hela | pEC$_{50}$ PBMC |
|---|---|---|---|
| 25 | 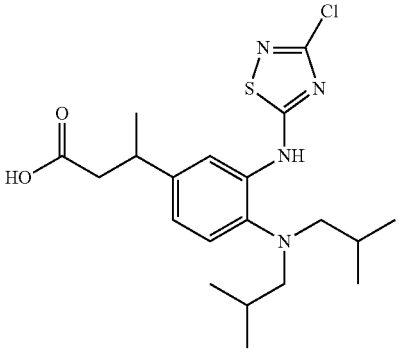 | 7.5 | 7.6 |
| 26 | 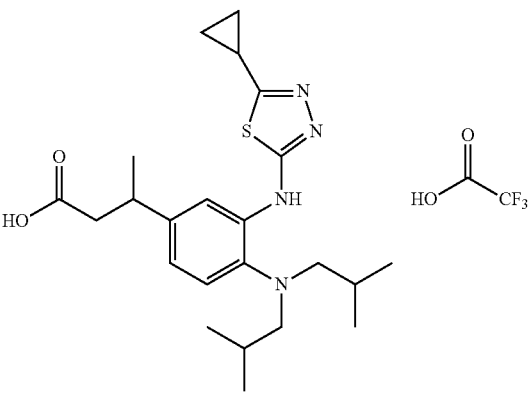 [SMILES: CC(C)CN(CC(C)C)c1ccc(C(C)CC(=O)O)cc1Nc1nnc(C2CC2)s1 ; O=C(O)C(F)(F)F] | 8.3 | N/A |
| 27 | 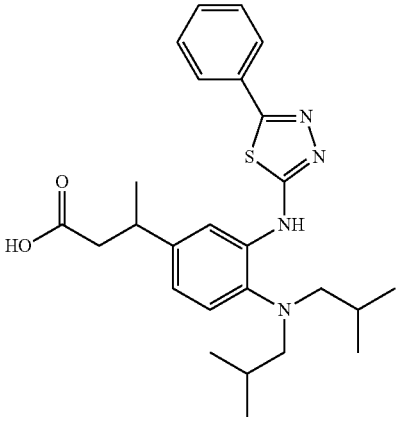 [SMILES: CC(C)CN(CC(C)C)c1ccc(C(C)CC(=O)O)cc1Nc1nnc(-c2ccccc2)s1] | 7.5 | N/A |
| 28 | 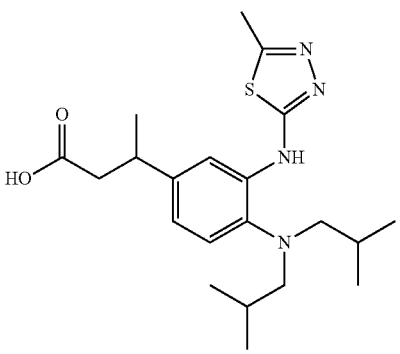 [SMILES: Cc1nnc(Nc2cc(C(C)CC(=O)O)ccc2N(CC(C)C)CC(C)C)s1] | 7.5 | N/A |

TABLE 2-continued

| Example No. | Structure | pEC50 Hela | pEC$_{50}$ PBMC |
|---|---|---|---|
| 29 | 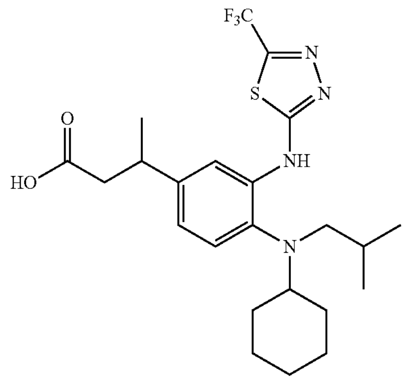 [SMILES: CC(C)CN(c1ccc(C(C)CC(=O)O)cc1Nc1nnc(C(F)(F)F)s1)C1CCCCC1] | 8.5 | 9.5 |
| 30 | 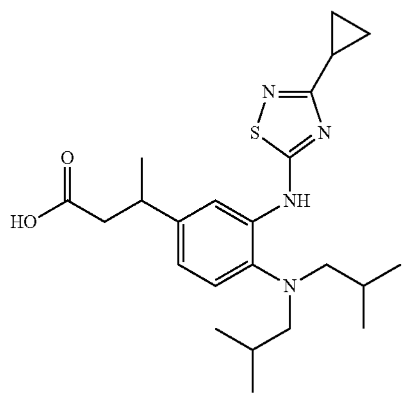 [SMILES: CC(C)CN(CC(C)C)c1ccc(C(C)CC(=O)O)cc1Nc1nc(C2CC2)ns1] | 7.3 | N/A |
| 31 | 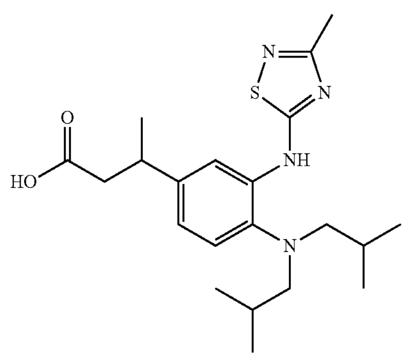 | 7.1 | N/A |
| 32 | 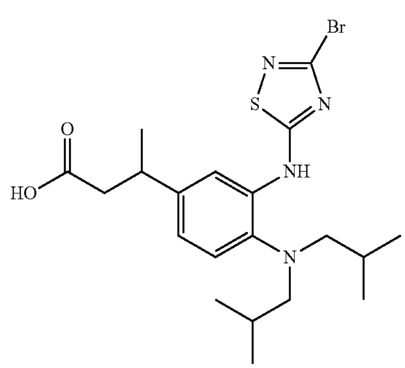 | 6.7 | N/A |

TABLE 2-continued

| Example No. | Structure | pEC50 Hela | pEC$_{50}$ PBMC |
|---|---|---|---|
| 33 | 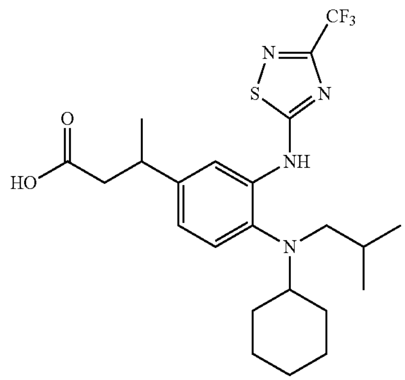 | 8.6 | N/A |
| 34 | 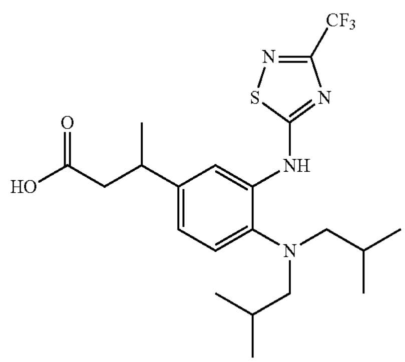 | 8.4 | 8.3 |
| 35 | 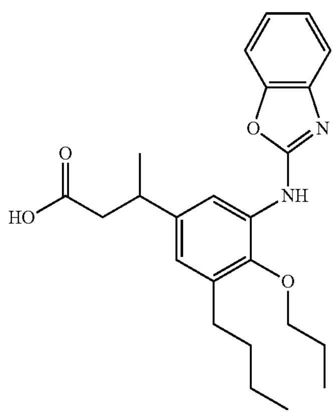 [SMILES: CCCCc1cc(C(C)CC(=O)O)cc(Nc2nc3ccccc3o2)c1OCCC] | 6.7 | N/A |
| 36 | 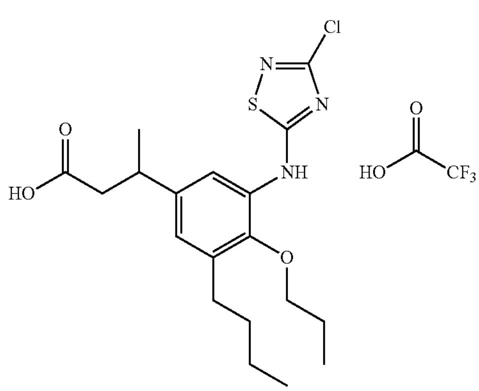 [SMILES: CCCCc1cc(C(C)CC(=O)O)cc(Nc2nc(Cl)ns2)c1OCCC ; O=C(O)C(F)(F)F] | 6.8 | N/A |

TABLE 2-continued
| Example No. | Structure | pEC50 Hela | pEC$_{50}$ PBMC |
|---|---|---|---|
| 37 | 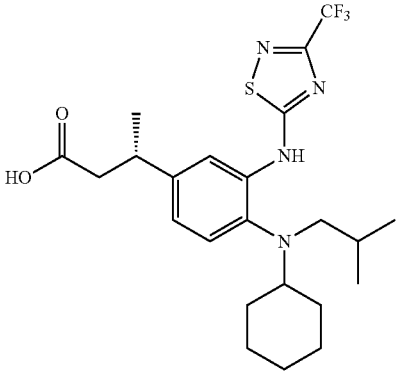 | 8.7 | 9.0 |
| 38 | 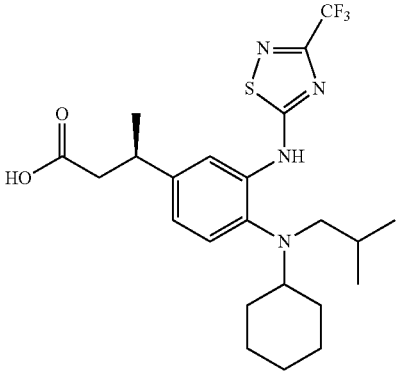 [SMILES: CC(C)CN(c1ccc([C@H](C)CC(=O)O)cc1Nc1nc(Cl)ns1)C1CCCCC1] | 8.4 | 9.0 |
| 39 | 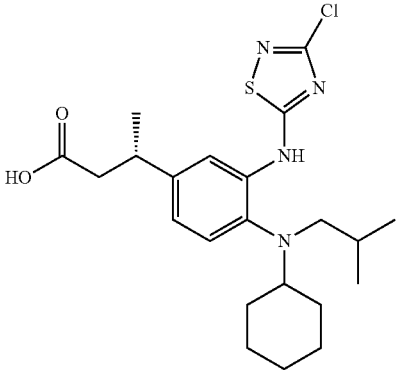 | 7.9 | 8.9 |
| 40 | 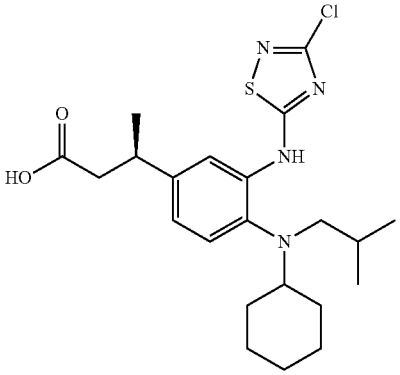 | 8.2 | 9.2 |

TABLE 2-continued

| Example No. | Structure | pEC50 Hela | pEC$_{50}$ PBMC |
|---|---|---|---|
| 41 | 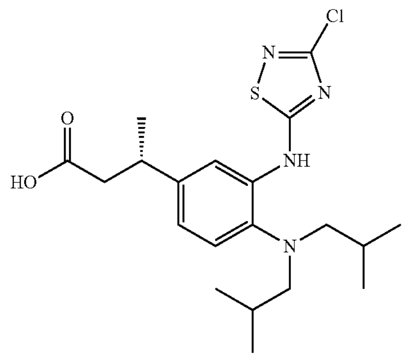 | 7.2 | 8.0 |
| 42 | 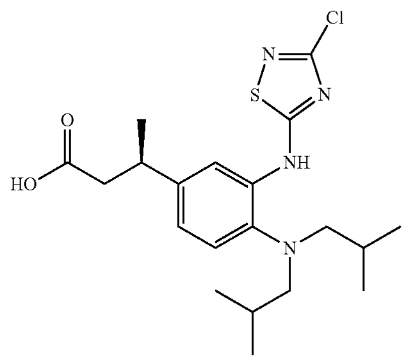 | 7.4 | 8.1 |
| 43 | 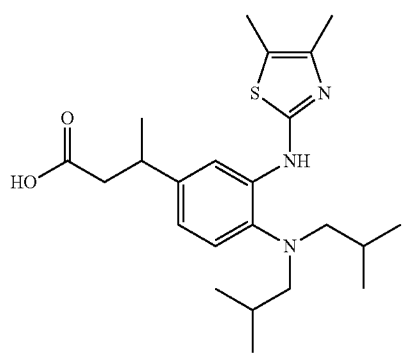 | 6.5 | N/A |
| 44 | 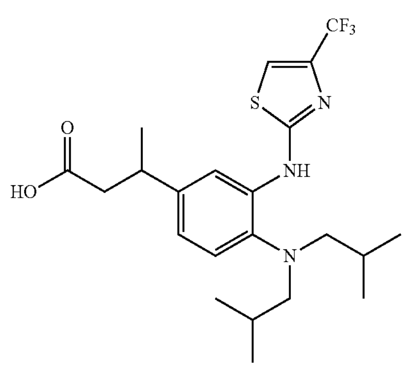 | 7.7 | N/A |

TABLE 2-continued
| Example No. | Structure | pEC50 Hela | pEC$_{50}$ PBMC |
|---|---|---|---|
| 45 | 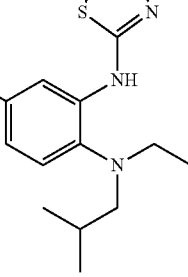 | 7.1 | N/A |
| 46 | 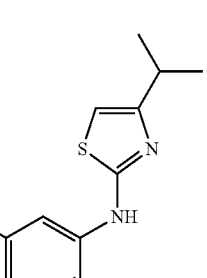 | 6.9 | N/A |
| 47 | 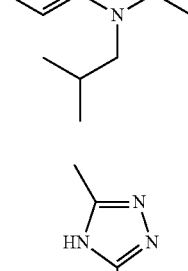 | 6.8 | 6.7 |
| 48 | 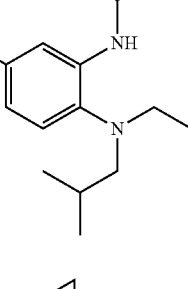 | 7.2 | 7.6 |

TABLE 2-continued

| Example No. | Structure | pEC50 Hela | pEC$_{50}$ PBMC |
|---|---|---|---|
| 49 | 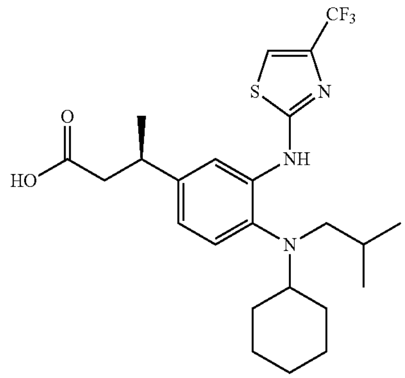 | 8.5 | 9.1 |
| 50 | 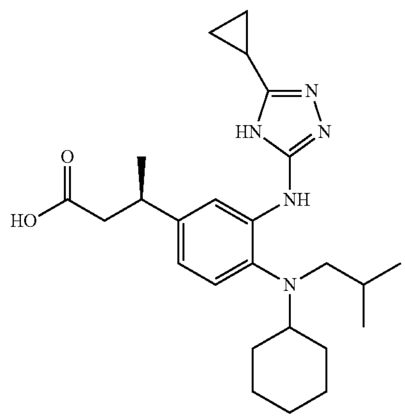 | 8.0 | 8.6 |
| 51 | 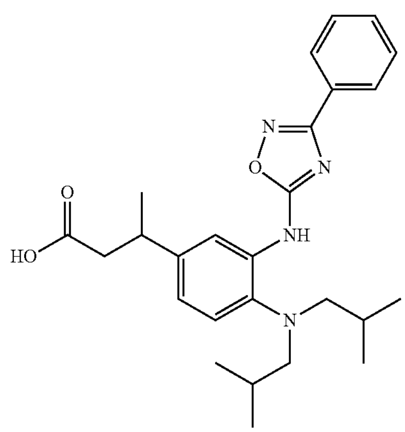 [SMILES: CC(C)CN(CC(C)C)c1ccc(C(C)CC(=O)O)cc1Nc1nc(-c2ccccc2)no1] | 6.4 | N/A |
| 52 | 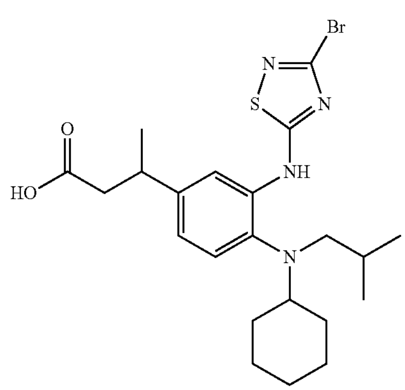 | 7.1 | N/A |

TABLE 2-continued

| Example No. | Structure | pEC50 Hela | pEC$_{50}$ PBMC |
|---|---|---|---|
| 53 | 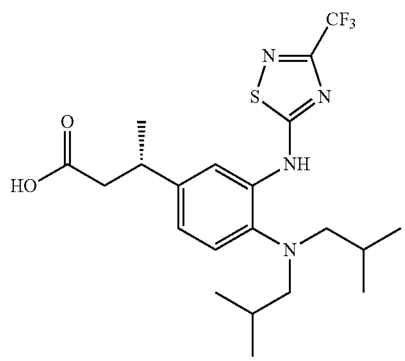 [SMILES: CC(C)CN(CC(C)C)c1ccc([C@@H](C)CC(=O)O)cc1Nc1nc(C(F)(F)F)ns1] | 8.0 | 8.5 |
| 54 | 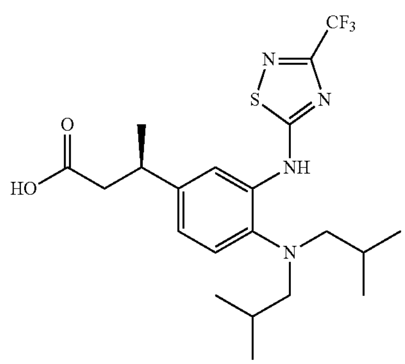 [SMILES: CC(C)CN(CC(C)C)c1ccc([C@H](C)CC(=O)O)cc1Nc1nc(C(F)(F)F)ns1] | 8.2 | 8.7 |
| 55 | 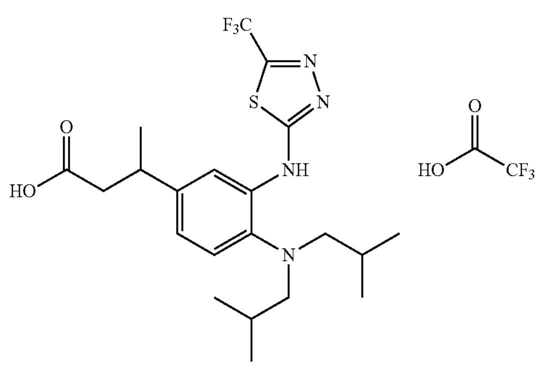 [SMILES: CC(C)CN(CC(C)C)c1ccc(C(C)CC(=O)O)cc1Nc1nnc(C(F)(F)F)s1 ; O=C(O)C(F)(F)F] | 8.5 | 9.2 |
| 56 | 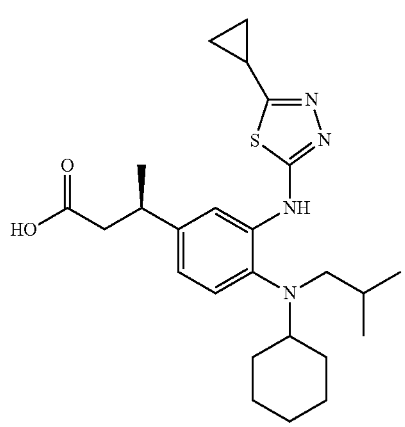 [SMILES: CC(C)CN(c1ccc([C@H](C)CC(=O)O)cc1Nc1nnc(C2CC2)s1)C1CCCCC1] | 8.5 | 9.6 |

TABLE 2-continued

| Example No. | Structure | pEC50 Hela | pEC$_{50}$ PBMC |
|---|---|---|---|
| 57 | 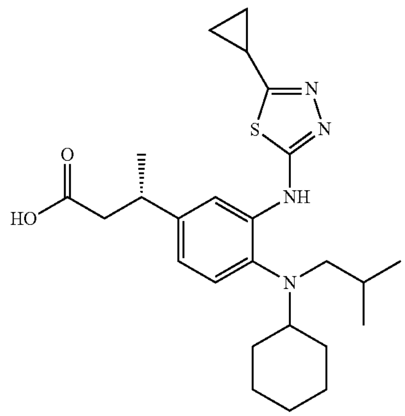 [SMILES: CC(C)CN(c1ccc([C@@H](C)CC(=O)O)cc1Nc1nnc(C2CC2)s1)C1CCCCC1] | 8.7 | 9.2 |
| 58 | 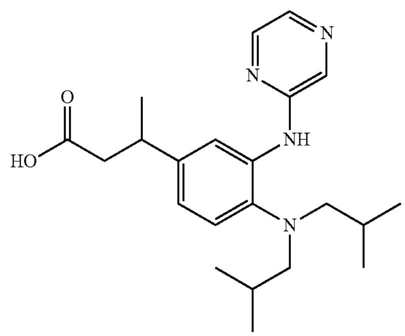 [SMILES: CC(C)CN(CC(C)C)c1ccc(C(C)CC(=O)O)cc1Nc1cnccn1] | 6.5 | 6.8 |
| 59 | 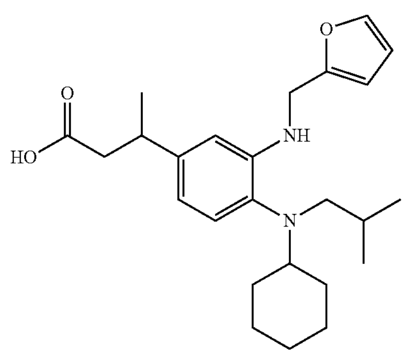 | 6.3 | 6.7 |
| 60 | 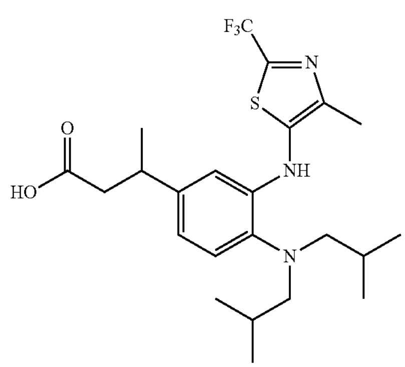 [SMILES: Cc1nc(C(F)(F)F)sc1Nc1cc(C(C)CC(=O)O)ccc1N(CC(C)C)CC(C)C] | 6.3 | 6.4 |

TABLE 2-continued
| Example No. | Structure | pEC50 Hela | pEC$_{50}$ PBMC |
|---|---|---|---|
| 61 | 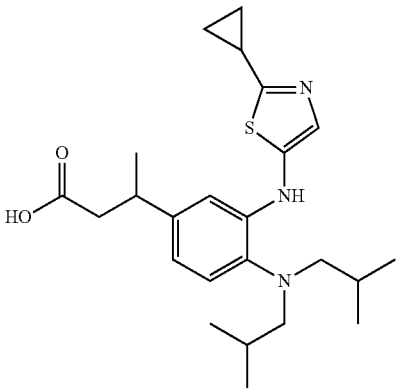 [SMILES: CC(C)CN(CC(C)C)c1ccc(C(C)CC(=O)O)cc1Nc1cnc(C2CC2)s1] | 7.2 | 7.5 |
| 62 | 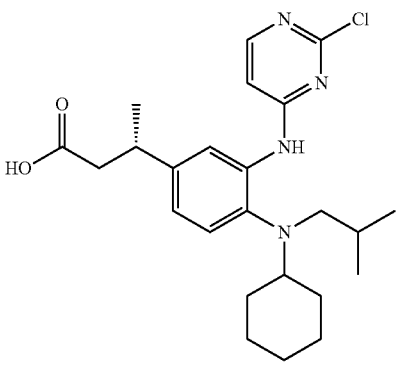 [SMILES: CC(C)CN(c1ccc([C@@H](C)CC(=O)O)cc1Nc1ccnc(Cl)n1)C1CCCCC1] | 8.4 | 8.6 |
| 63 | 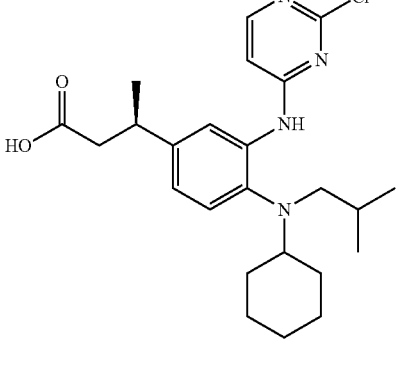 | 7.5 | 7.7 |
| 64 | 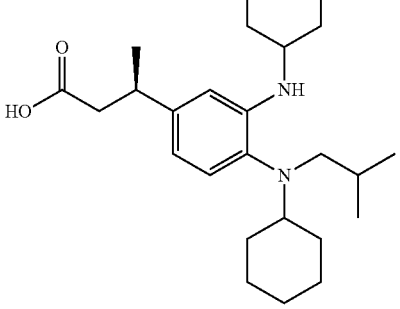 | N/A | 7.2 |

TABLE 2-continued
| Example No. | Structure | pEC50 Hela | pEC$_{50}$ PBMC |
|---|---|---|---|
| 65 | 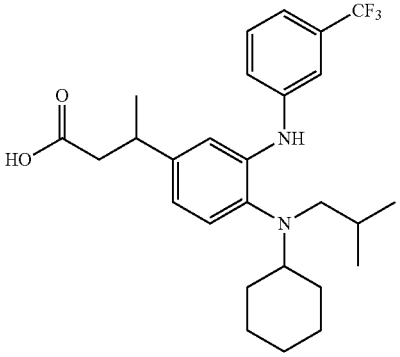 [SMILES: CC(C)CN(c1ccc(C(C)CC(=O)O)cc1Nc1cccc(C(F)(F)F)c1)C1CCCCC1] | N/A | 7.8 |
| 66 | 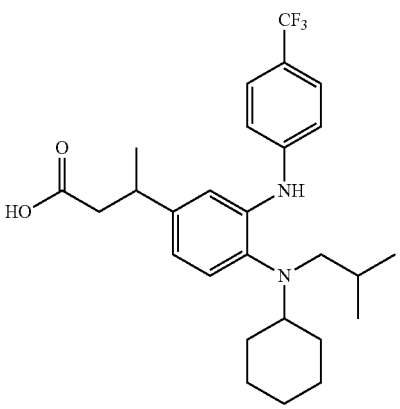 | N/A | 8.9 |
| 67 | 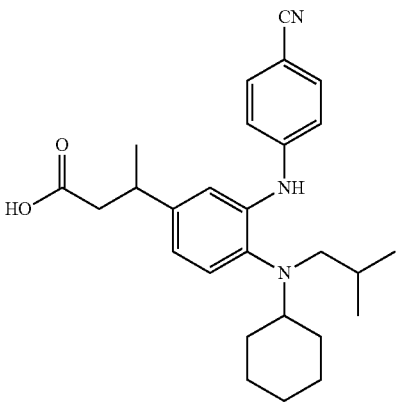 | N/A | 9.1 |
| 68 | 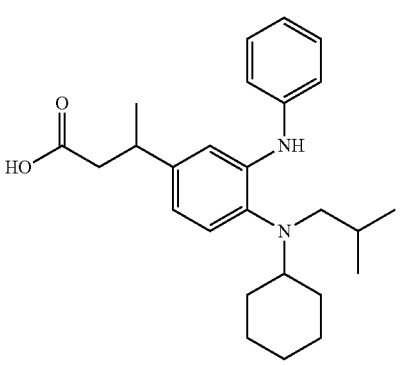 [SMILES: CC(C)CN(c1ccc(C(C)CC(=O)O)cc1Nc1ccccc1)C1CCCCC1] | N/A | 8.5 |

TABLE 2-continued

| Example No. | Structure | pEC50 Hela | pEC$_{50}$ PBMC |
|---|---|---|---|
| 69 | 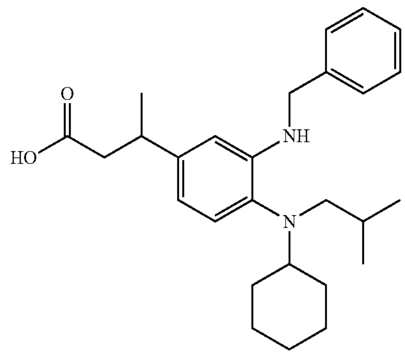 | 6.8 | N/A |
| 70 | 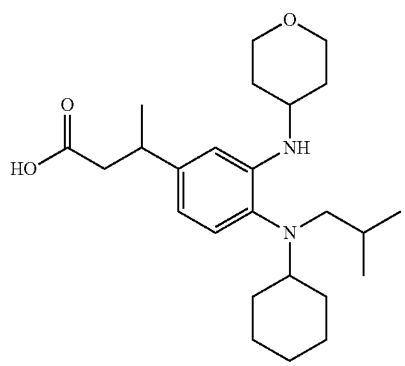 [SMILES: CC(C)CN(c1ccc(C(C)CC(=O)O)cc1NC1CCOCC1)C1CCCCC1] | 6.9 | N/A |
| 71 | 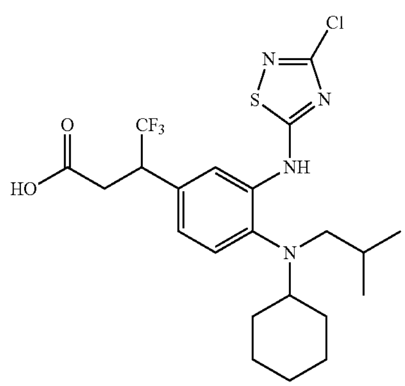 | 8.2 | 9.1 |
| 72 | 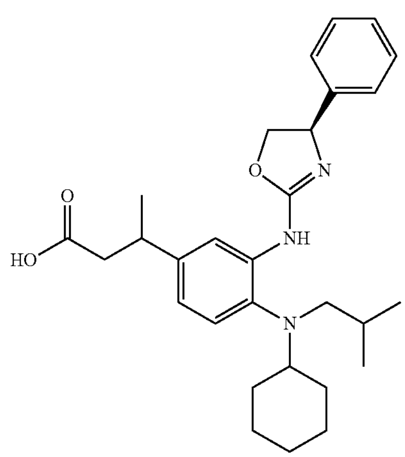 [SMILES: CC(C)CN(c1ccc(C(C)CC(=O)O)cc1NC1=N[C@H](c2ccccc2)CO1)C1CCCCC1] | 6.5 | N/A |

TABLE 2-continued
| Example No. | Structure | pEC50 Hela | pEC50 PBMC |
|---|---|---|---|
| 73 | 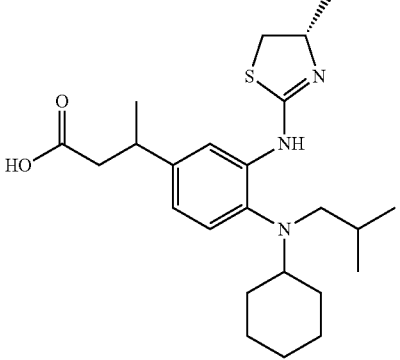 | 6.4 | N/A |
| 74 | 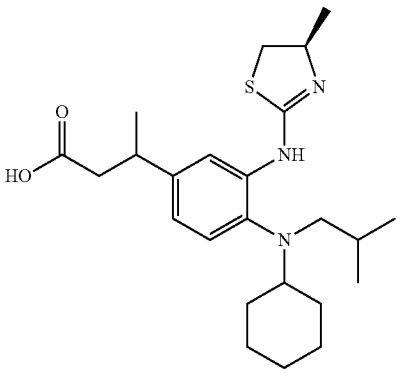 [SMILES: CC(C)CN(c1ccc(C(C)CC(=O)O)cc1NC1=N[C@H](C)CS1)C1CCCCC1] | 6.4 | N/A |
| 75 | 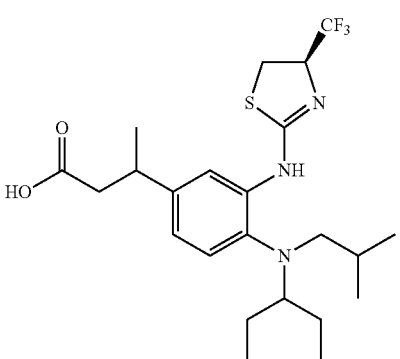 | 7.5 | 7.2 |
| 76 | 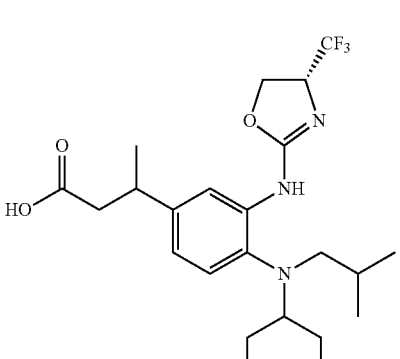 | 7.5 | 7.7 |

Example 77

HeLa IDOi Assay:

Data shown in Table 2. Compounds of the present invention were tested via high-throughput cellular assays utilizing detection of kynurenine via mass spectrometry and cytotoxicity as end-points. For the mass spectrometry and cytotoxicity assays, human epithelial HeLa cells (CCL-2; ATCC®, Manassas, Va.) were stimulated with human interferon-γ (IFN-γ) (Sigma-Aldrich Corporation, St. Louis, Mo.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (–IFN-γ) HeLa cells for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ) HeLa cells for both the mass spectrometry and cytotoxicity assays.

Frozen stocks of HeLa cells were washed and recovered in DMEM high glucose medium with HEPES (Thermo Fisher Scientific, Inc., Waltham, Mass.) supplemented with 10% v/v certified fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 100,000 cells/mL in the supplemented DMEM medium. 50 µL of either the cell suspension, for the mass spectrometry assay, or medium alone, for the cytotoxicity assay, were added to the low control wells, on the previously prepared 384-well compound plates, resulting in 5,000 cells/well or 0 cells/well respectively. IFN-γ was added to the remaining cell suspension at a final concentration of 10 nM, and 50 µL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 10 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula 100−(100*((U−C2)/(C1−C2))), where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula 100−(100*((U−C2)/(C1−C2))), where U was the unknown value, C1 was the average of the high (0% cytotoxicity) control wells and C2 was the average of the low (100% cytotoxicity) control wells.

Curve fitting was performed with the equation $y=A+((B-A)/(1+(10^Y/10^C)^D))$, where A was the minimum response, B was the maximum response, C was the $\log(XC_{50})$ and D was the Hill slope. The results for each test compound were recorded as pIC50 values for the mass spectrometry assay and as pCC50 values for the cytoxicity assay (−C in the above equation).

Example 78

PBMC IDOi Assay:

Data shown in Table 2. Compounds of the present invention were tested via high-throughput cellular assays utilizing detection of kynurenine via mass spectrometry and cytotoxicity as end-points. For the mass spectrometry and cytotoxicity assays, human peripheral blood mononuclear cells (PBMC) (PB003F; AllCells®, Alameda, Calif.) were stimulated with human interferon-γ (IFN-γ) (Sigma-Aldrich Corporation, St. Louis, Mo.) and lipopolysaccharide from *Salmonella minnesota* (LPS) (Invivogen, San Diego, Calif.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ/−LPS) PBMCs for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ/+LPS) PBMCs for both the mass spectrometry and cytotoxicity assays.

Frozen stocks of PBMCs were washed and recovered in RPMI 1640 medium (Thermo Fisher Scientific, Inc., Waltham, Mass.) supplemented with 10% v/v heat-inactivated fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 1,000,000 cells/mL in the supplemented RPMI 1640 medium. 50 μL of either the cell suspension, for the mass spectrometry assay, or medium alone, for the cytotoxicity assay, were added to the low control wells, on the previously prepared 384-well compound plates, resulting in 50,000 cells/well or 0 cells/well respectively. IFN-γ and LPS were added to the remaining cell suspension at final concentrations of 100 ng/ml and 50 ng/ml respectively, and 50 μL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 40 μL were added to each plate well. After a twenty minute incubation at room temperature, luminescence was read on an EnVision® Multilabel Reader (PerkinElmer Inc., Waltham, Mass.). For the mass spectrometry assay, 10 μL of supernatant from each well of the compound-treated plates were added to 40 μL of acetonitrile, containing 10 μM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 μL from each well of the acetonitrile extraction plates were added to 90 μL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula $100-(100*((U-C2)/(C1-C2)))$, where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula $100-(100*((U-C2)/(C1-C2)))$, where U was the unknown value, C1 was the average of the high (0% cytotoxicity) control wells and C2 was the average of the low (100% cytotoxicity) control wells.

Curve fitting was performed with the equation $y=A+((B-A)/(1+(10^x/10^C)^D))$, where A was the minimum response, B was the maximum response, C was the $\log(XC_{50})$ and D was the Hill slope. The results for each test compound were recorded as pIC50 values for the mass spectrometry assay and as pCC50 values for the cytoxicity assay (–C in the above equation).

Although the invention has been shown and described above with reference to some embodiments, those skilled in the art will readily appreciate that the specific experiments detailed are only illustrative of the invention. It should be understood that various modifications can be made without departing from the spirit of the invention.

For example, for claim construction purposes, it is not intended that the claims set forth hereinafter be construed in any way narrower than the literal language thereof, and it is thus not intended that exemplary embodiments from the specification be read into the claims.

Accordingly, it is to be understood that the present invention has been described by way of illustration and not limitations on the scope of the claims. Accordingly, the invention is limited only by the following claims. All publications, issued patents, patent applications, books and journal articles, cited in this application are each herein incorporated by reference in their entirety.

1) Lohse N, Hansen A B, Pedersen G, Kronborg G, Gerstoft J, Sørensen HT, Vaeth M, Obel N. Survival of persons with and without HIV infection in Denmark, 1995-2005. Ann Intern Med. 2007 Jan. 16; 146(2):87-95.
2) Deeks S G. HIV infection, inflammation, immunosenescence, and aging. Annu Rev Med. 2011; 62:141-55.
3) Hunt P W, Sinclair E, Rodriguez B, Shive C, Clagett B, Funderburg N, Robinson J, Huang Y, Epling L, Martin J N, Deeks S G, Meinert C L, Van Natta M L, Jabs D A, Lederman M M. Gut epithelial barrier dysfunction and innate immune activation predict mortality in treated HIV infection. J Infect Dis. 2014 Oct. 15; 210(8):1228-38.
4) Tenorio A R, Zheng Y, Bosch R J, Krishnan S, Rodriguez B, Hunt P W, Plants J, Seth A, Wilson C C, Deeks S G, Lederman M M, Landay A L. Soluble markers of inflammation and coagulation but not T-cell activation predict non-AIDS-defining morbid events during suppressive antiretroviral treatment. J Infect Dis. 2014 Oct. 15; 210 (8):1248-59.
5) Byakwaga H, Boum Y 2nd, Huang Y, Muzoora C, Kembabazi A, Weiser S D, Bennett J, Cao H, Haberer J E, Deeks S G, Bangsberg D R, McCune J M, Martin J N, Hunt P W. The kynurenine pathway of tryptophan catabolism, CD4+ T-cell recovery, and mortality among HIV-infected Ugandans initiating antiretroviral therapy. J Infect Dis. 2014 Aug. 1; 210(3):383-91.
6) Pearson J T, Siu S, Meininger D P, Wienkers L C, Rock D A. In vitro modulation of cytochrome P450 reductase supported indoleamine 2,3-dioxygenase activity by allosteric effectors cytochrome b(5) and methylene blue. Biochemistry 49, 2647-2656 (2010).

What is claimed is:
1. A compound having the structure of Formula I:

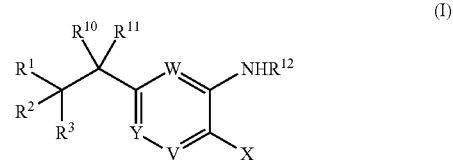

or a pharmaceutically acceptable salt thereof, wherein:

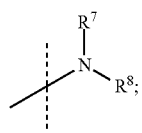

X is
W is $CR^4$;
Y is $CR^5$;
V is $CR^6$;
$R^1$ is selected from the group consisting of —$CO_2H$, tetrazol-5-yl, —$NHSO_2R^{13}$, and —$CONHSO_2R^{14}$;
$R^2$ is selected from the group consisting of —H, —OH, —Cl, —F, and —$OCH_3$;

$R^3$ is —H;

$R^4$ is selected from the group consisting of —H and —F;

$R^5$ is selected from the group consisting of —H and —F;

$R^6$ is selected from the group consisting of —H, —F, and —Cl;

$R^7$ and $P^8$ are independently selected from the group consisting of the following structures

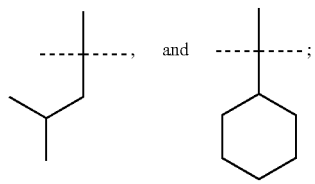

$R^{10}$ and $R^{11}$ are independently selected from the group consisting of —H, —$CH_3$, and —$CHF_2$;

$R^{12}$ is selected from the group consisting of the following structures:

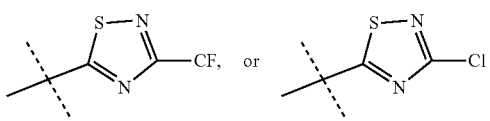

$R^{13}$ is —$CH_3$;

$R^{14}$ is selected from the group consisting of —$CH_3$, —$CF_3$, and -$cC_3H_5$.

2. The compound or salt of claim 1, wherein $R^1$ is selected from —$CO_2H$ or tetrazol-5-yl.

3. The compound or salt of claim 1, wherein $R^2$ is —H.

4. The compound or salt of claim 1, wherein $R^{10}$ is —H.

5. The compound or salt of claim 1, wherein $R^{11}$ is —$CH_3$.

6. The compound or salt of claim 1, wherein $R^{11}$ is —$CF_3$.

7. The compound or salt of claim 1, wherein

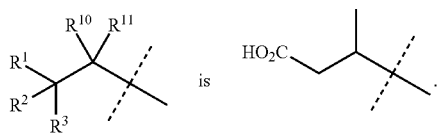

8. The compound or salt of claim 1, wherein

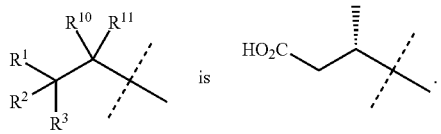

9. The compound or salt of claim 1, wherein

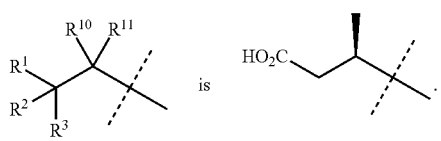

10. The compound or salt of claim 1, wherein $R^{12}$

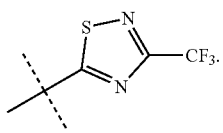

11. The compound or salt of claim 1, wherein $R^{12}$ is

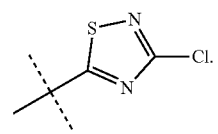

* * * * *